(12) United States Patent
    Colby

(10) Patent No.: US 10,722,191 B2
(45) Date of Patent: *Jul. 28, 2020

(54) DIGITAL X-RAY DIAGNOSIS AND EVALUATION OF DENTAL DISEASE

(71) Applicant: Oregon Dental, Inc., Eugene, OR (US)

(72) Inventor: Leigh E. Colby, Eugene, OR (US)

(73) Assignee: OREGON DENTAL, INC., Eugene, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 15/829,766

(22) Filed: Dec. 1, 2017

(65) Prior Publication Data
    US 2018/0085073 A1    Mar. 29, 2018

Related U.S. Application Data

(63) Continuation of application No. 15/156,271, filed on May 16, 2016, now Pat. No. 9,839,402, which is a
(Continued)

(51) Int. Cl.
    *A61B 6/14*    (2006.01)
    *A61B 6/00*    (2006.01)
    *G06T 7/00*    (2017.01)

(52) U.S. Cl.
    CPC .............. *A61B 6/14* (2013.01); *A61B 6/461* (2013.01); *A61B 6/463* (2013.01); *A61B 6/467* (2013.01);
(Continued)

(58) Field of Classification Search
    None
    See application file for complete search history.

(56) References Cited

U.S. PATENT DOCUMENTS

| 5,113,424 A | 5/1992 | Burdea et al. |
| 5,222,021 A | 6/1993 | Feldman et al. |
| (Continued) |

OTHER PUBLICATIONS

Kang, Byung-Cheol et al., "Computer-aided proximal caries diagnosis: correlation with clinical examination and histology," Korean Journal of Oral and Maxillofacial Radiology, 2002, 32 pp. 187-194.
(Continued)

*Primary Examiner* — Vikkram Bali
(74) *Attorney, Agent, or Firm* — Green, Howard & Mughal, LLP; Karen Dana Oster

(57) ABSTRACT

A method for diagnosis and evaluation of tooth decay comprises: locating in an x-ray image the contour of the dento-enamel junction (DEJ); measuring optical density along contours substantially parallel to and on either side of the DEJ contour; and calculating at least one decay value from the measured optical densities. A method for diagnosis and evaluation of periodontal disease comprises: measuring in an x-ray image a bone depth (BD) relative to the position of the cemento-enamel junctions (CEJs) of adjacent teeth; measuring bone density along a contour between the adjacent teeth; and calculating a crestal density (CD) value from the measured bone density. Calibration standards may be employed for facilitating calculation of the values. A dental digital x-ray imaging calibration method for at least partly correcting for variations of the optical densities of images acquired from the dental digital x-ray imaging system.

16 Claims, 113 Drawing Sheets

Related U.S. Application Data continuation of application No. 13/858,805, filed on Apr. 8, 2013, now Pat. No. 9,339,245, which is a continuation of application No. 11/652,822, filed on Jan. 12, 2007, now Pat. No. 8,417,010.

(60) Provisional application No. 60/758,829, filed on Jan. 12, 2006.

(52) U.S. Cl.
CPC ............ *A61B 6/505* (2013.01); *A61B 6/5217* (2013.01); *A61B 6/582* (2013.01); *G06T 7/0012* (2013.01); *A61B 6/583* (2013.01); *G06T 2207/30036* (2013.01)

(56) References Cited

U.S. PATENT DOCUMENTS

| | | | |
|---|---|---|---|
| 5,235,628 | A | 8/1993 | Kalender |
| 5,331,550 | A | 7/1994 | Stafford et al. |
| 5,335,260 | A | 8/1994 | Arnold |
| 5,493,601 | A | 2/1996 | Fivez et al. |
| 5,570,182 | A | 10/1996 | Nathel et al. |
| 5,742,700 | A | 4/1998 | Yoon et al. |
| 6,302,582 | B1 | 10/2001 | Nord et al. |
| 6,690,761 | B2 | 2/2004 | Lang et al. |
| 6,736,776 | B2 | 5/2004 | Miles |
| 6,811,310 | B2 | 11/2004 | Lang et al. |
| 6,868,172 | B2 | 3/2005 | Boland et al. |
| 6,904,123 | B2 | 6/2005 | Lang |
| 7,343,305 | B2 | 3/2008 | Benn et al. |
| 7,488,109 | B2 | 2/2009 | Hangartner et al. |
| 8,073,521 | B2 | 12/2011 | Liew et al. |
| 2002/0085673 | A1 | 7/2002 | Rinaldi et al. |
| 2003/0112921 | A1 | 6/2003 | Lang et al. |
| 2004/0062358 | A1 | 4/2004 | Lang et al. |
| 2004/0081287 | A1 | 4/2004 | Lang et al. |
| 2005/0010106 | A1 | 1/2005 | Lang et al. |
| 2005/0032720 | A1 | 2/2005 | Wingrove et al. |
| 2005/0078802 | A1 | 4/2005 | Lang et al. |
| 2005/0100866 | A1 | 5/2005 | Arnone et al. |
| 2005/0226374 | A1 | 10/2005 | Lang et al. |
| 2006/0263825 | A1 | 11/2006 | Denny et al. |
| 2007/0025607 | A1 | 2/2007 | Takaishi |
| 2010/0239689 | A1 | 9/2010 | Sekimoto et al. |

OTHER PUBLICATIONS

Smith, Kevin E., DMD, "Carries Detection: At Best an Inexact Science, Part One," The Global Dental News Journal, 1999, 9 pages, http://www.global-dental.com.

Smith, Kevin E., DMD, "Carries Detection: At Best an Inexact Science, Part II," The Global Dental News Journal, 2000, 13 pages, http://www.global-dental.com.

Umar, Hikmet, DMD, MSIS, "Capabilities of Computerized Clinical Decision Support Systems: The Implications for the Practicing Dental Professional," The Journal of Contemporary Dental Practice, vol. 3, No. 1, Feb. 15, 2002, 17 pages.

Zhero, Natalia Ivanivna, Abstract of Ukrainian Patent No. UA9186U entitled Method for Differential Diagnosis of Destructive Forms of Periodonitis, Sep. 15, 2005, 1 page.

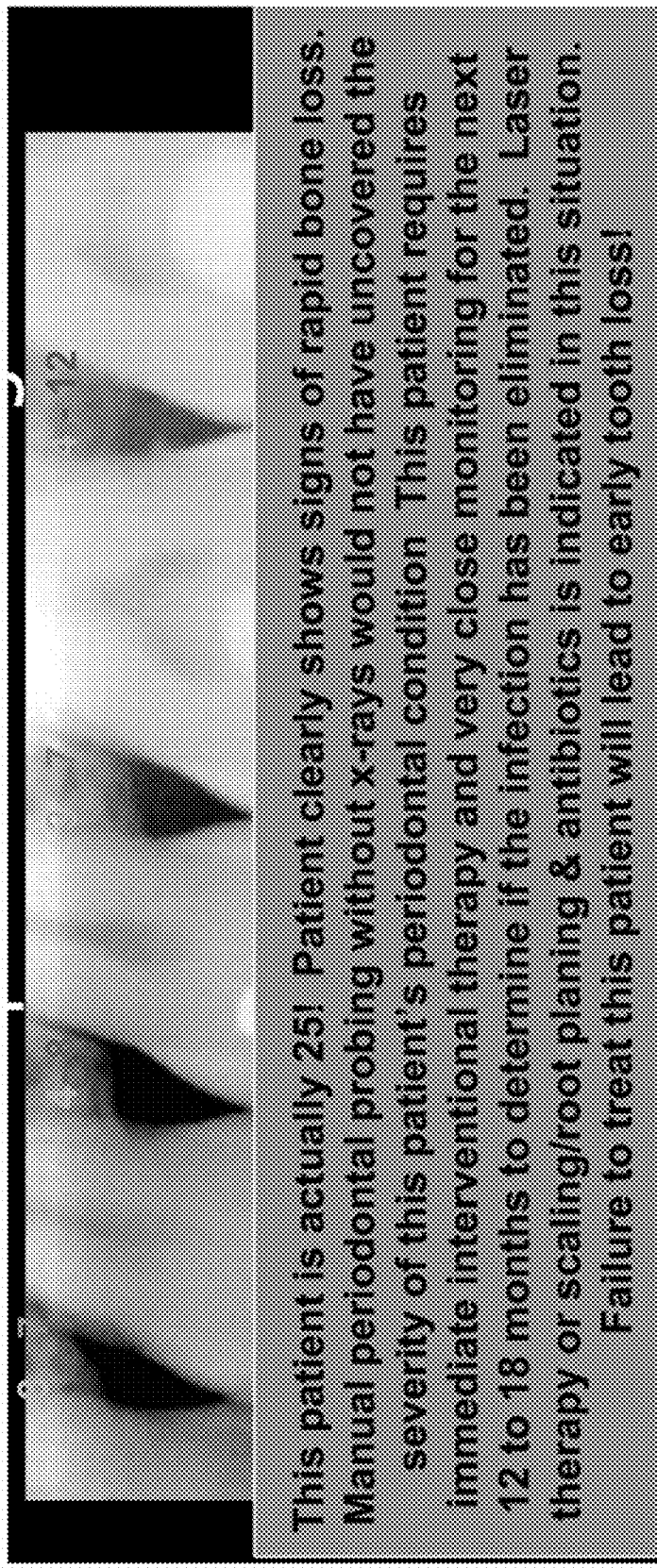
FIG. 111

DIGITAL X-RAY DIAGNOSIS AND EVALUATION OF DENTAL DISEASE

The present application is a continuation of U.S. patent application Ser. No. 15/156,871, filed May 16, 2016. U.S. patent application Ser. No. 15/156,871 is a continuation of U.S. patent application Ser. No. 13/858,805, filed Apr. 8, 2013, now U.S. Pat. No. 9,339,245. U.S. patent application Ser. No. 13/858,805 is a continuation of U.S. patent application Ser. No. 11/652,822, filed Jan. 12, 2007, now U.S. Pat. No. 8,417,010. U.S. patent application Ser. No. 11/652,822 is an application claiming the benefit under 35 USC Section 119(e) of U.S. Provisional Patent Application Ser. No. 60/758,829, filed Jan. 12, 2006. The present application is based on and claims priority from these applications, the disclosures of which are hereby expressly incorporated herein by reference in their entirety.

BACKGROUND OF INVENTION

The field of the present invention relates to diagnosis and evaluation of dental disease, including dental caries and periodontal disease. In particular, systems and methods are described herein for analysis of digital x-ray images for diagnosis and evaluation of dental caries or periodontal disease.

Diagnosis and evaluation of dental disease (such as dental caries, periodontal disease, or dental abscesses) based on visual inspection of x-rays (either film or digital) is hampered by variations among film, x-ray sources, imaging x-ray sensors, display devices, subjective interpretation by clinicians, and so on. At least one earlier attempt has been made to address such variations by analysis of digital x-ray images for detection of dental caries (i.e. tooth decay or cavities), and is described in U.S. Pat. No. 5,742,700 issued to Yoon et al. (said patent is hereby incorporated by reference as if fully set forth herein). However, a subsequent study indicates the earlier system may not be sufficiently reliable in its diagnosis and evaluation of decay (Kang et al., *Korean J Oral Maxillofacial Radiology* v32 pp187-194 (2002), which is hereby incorporated by reference as if fully set forth herein).

Therefore, a need exists for more reliable systems and methods for diagnosis and evaluation of dental or periodontal disease.

BRIEF SUMMARY OF THE INVENTION

A method for diagnosis and evaluation of tooth decay comprises: locating in an x-ray image the contour of the dento-enamel junction (DEJ); measuring optical density (relative to the absorption of x-rays in the electromagnetic spectrum used for radiographs—i.e. radiodensity) along contours substantially parallel to and on either side of the DEJ contour; and calculating at least one numerical decay value from the measured optical densities. A method for diagnosis and evaluation of periodontal disease comprises: measuring in an x-ray image a bone depth (BD) relative to the position of the cemento-enamel junctions (CEJs) of adjacent teeth; measuring bone density along a contour between the adjacent teeth; and calculating a numerical crestal density (CD) value from the measured bone density. Calibration standards may be employed for facilitating calculation of the numerical values.

The present invention is also directed to a dental digital x-ray imaging calibration method for at least partly correcting for variations of the optical densities of images acquired from the dental digital x-ray imaging system. The calibration method of the present invention may include five exemplary basic steps. The first step is providing at least one calibration block or standard that simulates dental tissues. The second step is acquiring an image of the calibration block or standard from the dental digital x-ray imaging system. The third step is calculating a calculated numerical decay value. The fourth step is comparing the known numerical decay value and the calculated numerical decay value. The fifth step is calibrating the dental digital x-ray imaging system by adjusting the dental digital x-ray imaging system so that the calculated numerical decay value approaches the known numerical decay value.

Objects and advantages pertaining to digital x-ray diagnosis and evaluation of dental or periodontal disease may become apparent upon referring to the exemplary embodiments illustrated in the drawings and disclosed in the following written description and/or claims.

BRIEF DESCRIPTION OF THE SEVERAL VIEWS OF THE DRAWINGS

FIGS. 109-111 are radiographs with displayed values for bone depth and bone density.

Figure 1:
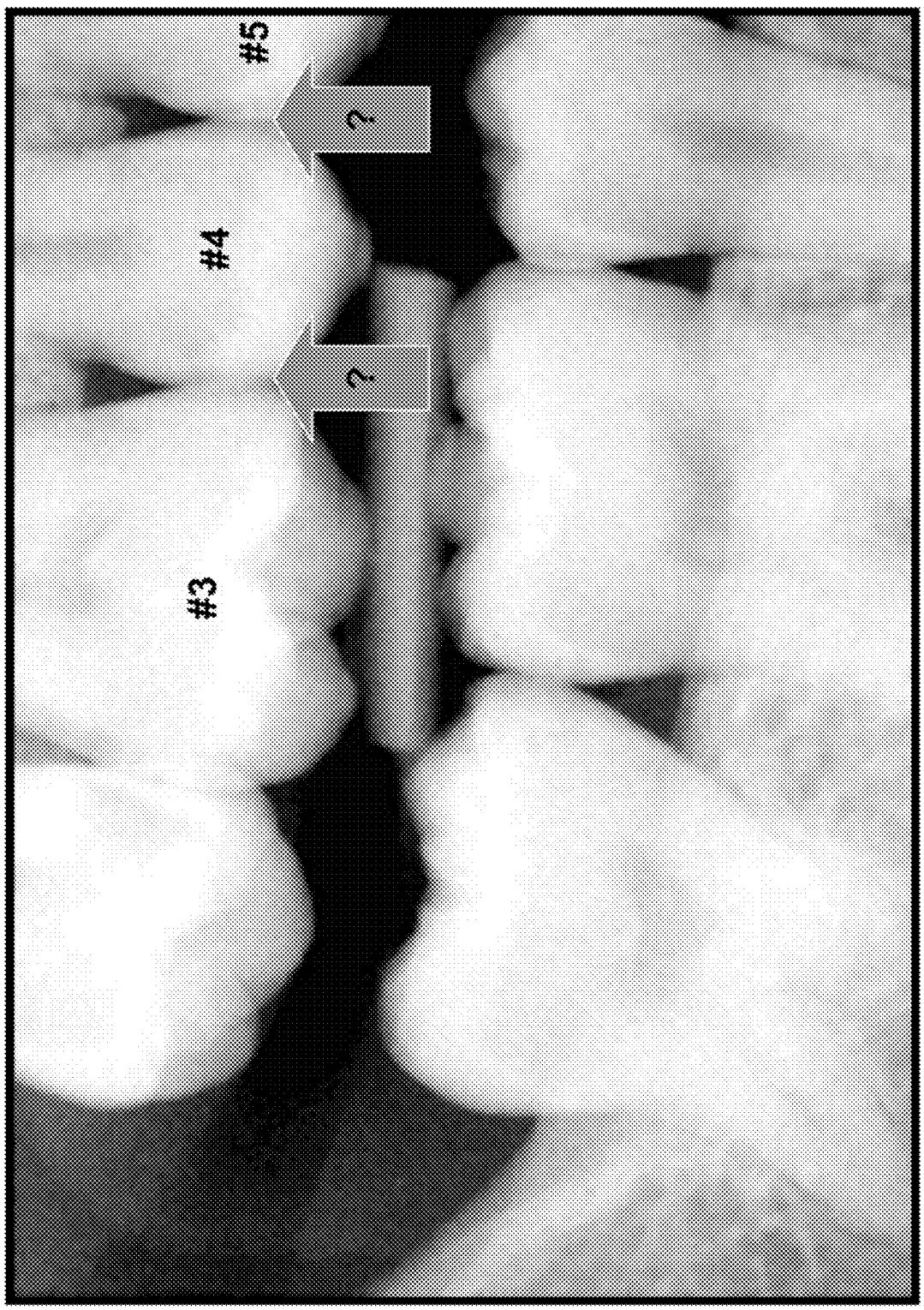
FIGS. 1-4 are dental x-ray images showing areas of suspected decay.

The embodiments shown in the figures are exemplary, and should not be construed as limiting the scope of the present disclosure and/or appended claims.

DETAILED DESCRIPTION OF THE INVENTION

The primary economic consideration when converting to digital dental imaging is the accurate diagnosis of primary decay, directly related secondary decay conditions, or other dental diseases such as periodontal disease or endodontic abscesses. A typical dental practice profile in the U.S. comprises one dentist or doctor (terms used interchangeably herein) and one hygienist generating around $500K or more. Approximately 60% or more of that revenue is derived from the diagnosis of decay or conditions secondary to decay. Any inability to accurately diagnose decay or any other dental disease using dental imaging therefore represents a significant opportunity for loss of revenue, and typically profit as well, in addition to putting the patient at risk for a missed (e.g., false negative) or inaccurate (e.g., false positive) diagnosis.

Conversion to digital dental x-ray imaging and analysis may be employed for improving the accuracy of dental disease diagnosis, and may offer other practical benefits as well. For example, the use of digital imaging and analysis may reduce the time required for making a diagnosis, benefiting both dentist and patient. Images may be retrieved electronically for viewing or analysis quickly and remotely without searching for x-ray films. Patient may be more accepting of a diagnosis made by digital methodologies because they can better visualize their own condition.

However, existing digital imaging and analysis systems have been demonstrated to be no more accurate than visual evaluation of traditional x-ray film images. (See for example U.S. Pat. No. 5,742,700 to Yoon, and Kang et al., "Computer-aided proximal caries diagnosis: correlation with clinical examination and histology," *Korean Journal of Oral and Maxillofacial Radiology* v32 pp187-194 (2002), both of which are hereby incorporated by reference as if fully set forth herein.) In another report (Smith, K.; "Caries Detection; At Best an Inexact Science"; *Global Dental Newsjournal*; www.global-dental.com/clinical.html and www.global-dental.com/clinical_2.html), significantly higher false-positive rates are found for visual evaluation of digital images (11% false positives) relative to visual evaluation of film images (7% false positives). As already stated above, any inability to accurately diagnose decay, whether arising from inaccurate visual evaluation of x-ray film or inaccurate analysis of digital x-ray images, represents a significant opportunity for loss of revenue, and typically profit as well. Furthermore, inaccurate diagnosis may undermine the patient's confidence in the doctor's skill or judgment, or lead to patient hesitation regarding the doctor's future diagnoses or treatment recommendations.

From a clinician's perspective, an accurate diagnosis of decay includes accurate "staging" of the decay. Stage I and Stage II decay exist only in the enamel of the affected tooth, with Stage I decay penetrating less than 50% through the enamel toward the dentin, and with Stage II decay penetrating more than 50% toward the dentin (but still not reaching the dentin). Stage III and Stage IV decay exist in both the enamel and the dentin, with Stage III penetrating less than 50% through the dentin toward the nerve space, and with Stage IV decay penetrating more than 50% through the dentin. The stage of the decay and the age and clinical history of the patient are considered together in determining the appropriate clinical course. For example, for a teenager with rapidly progressing or widespread Stage I, decay should be treated aggressively with fillings to prevent penetration of decay into the dentin. In contrast, an adult with radiographically detectable Stage II decay at a routine six-month exam may be appropriately treated by watching rather than filling. Stage III decay almost always requires fillings for treatment, and if not accurately diagnosed will likely progress to Stage IV decay. Stage IV decay may require even more extensive treatment, such as a root canal or a very deep filling with a pulp cap for reducing painful post-operative sensitivity. In each of these cases, an accurate diagnosis is necessary to inform the patient and to plan appropriate treatment.

Figure 2:
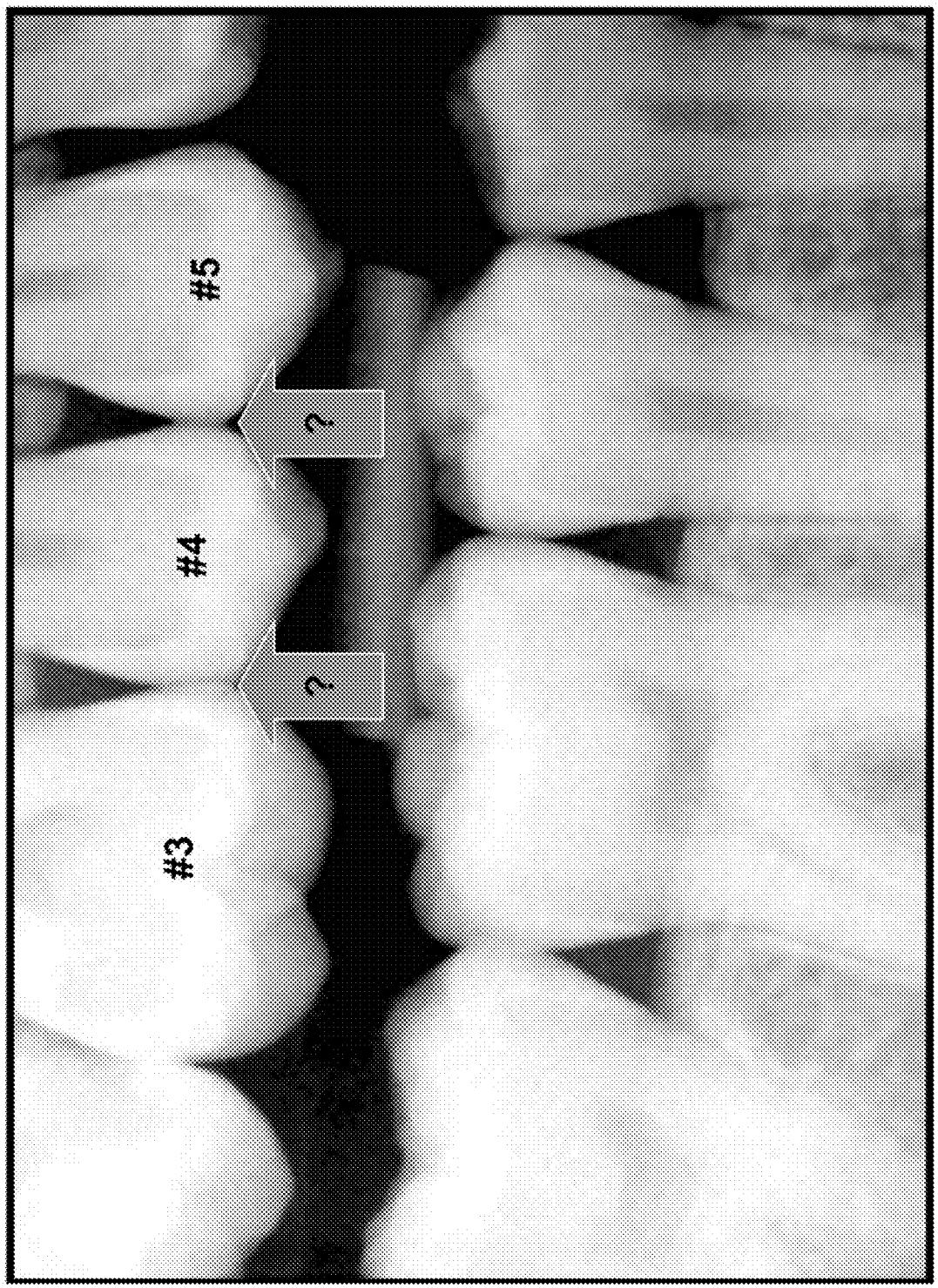
Figure 3:
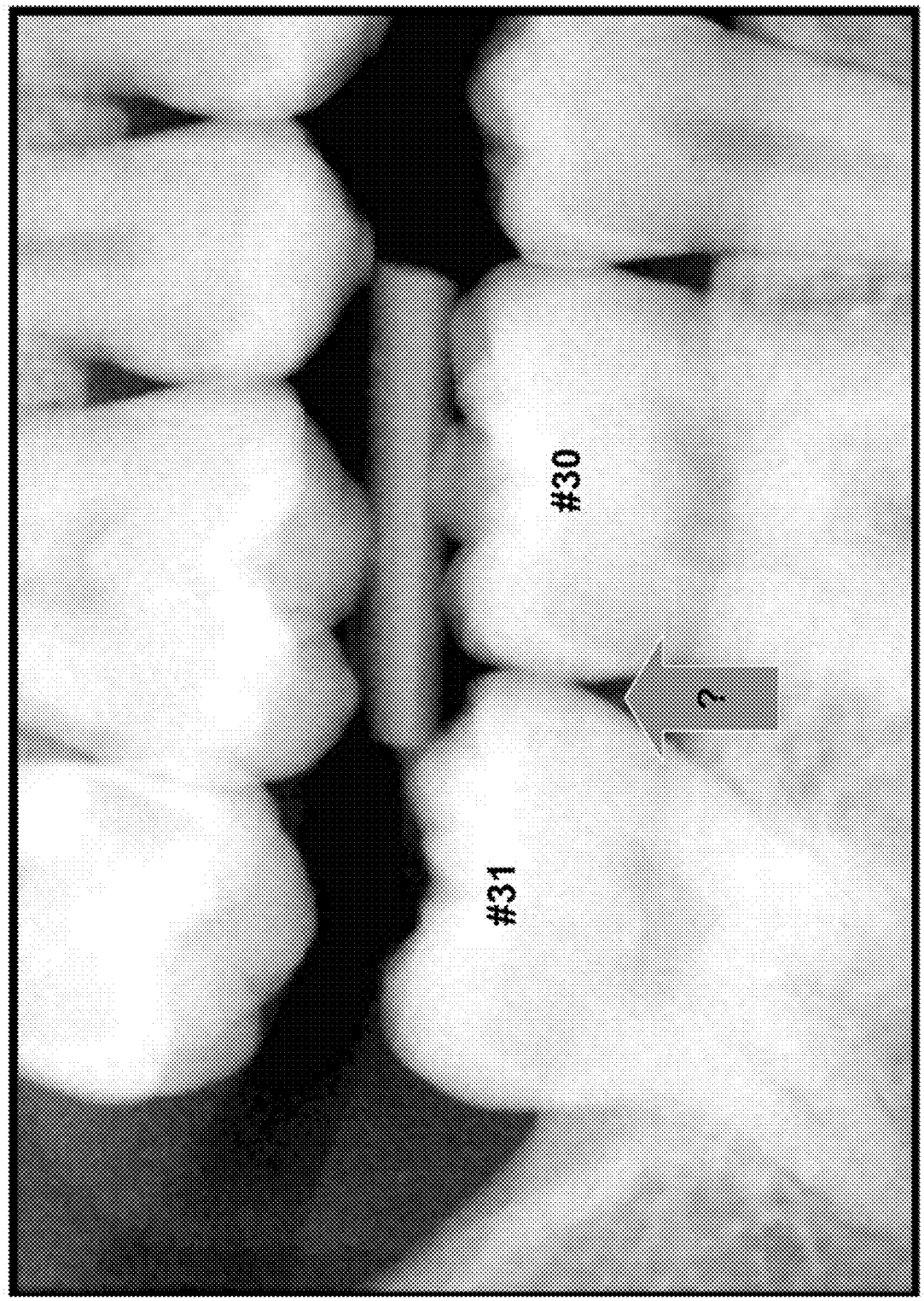
Figure 4:
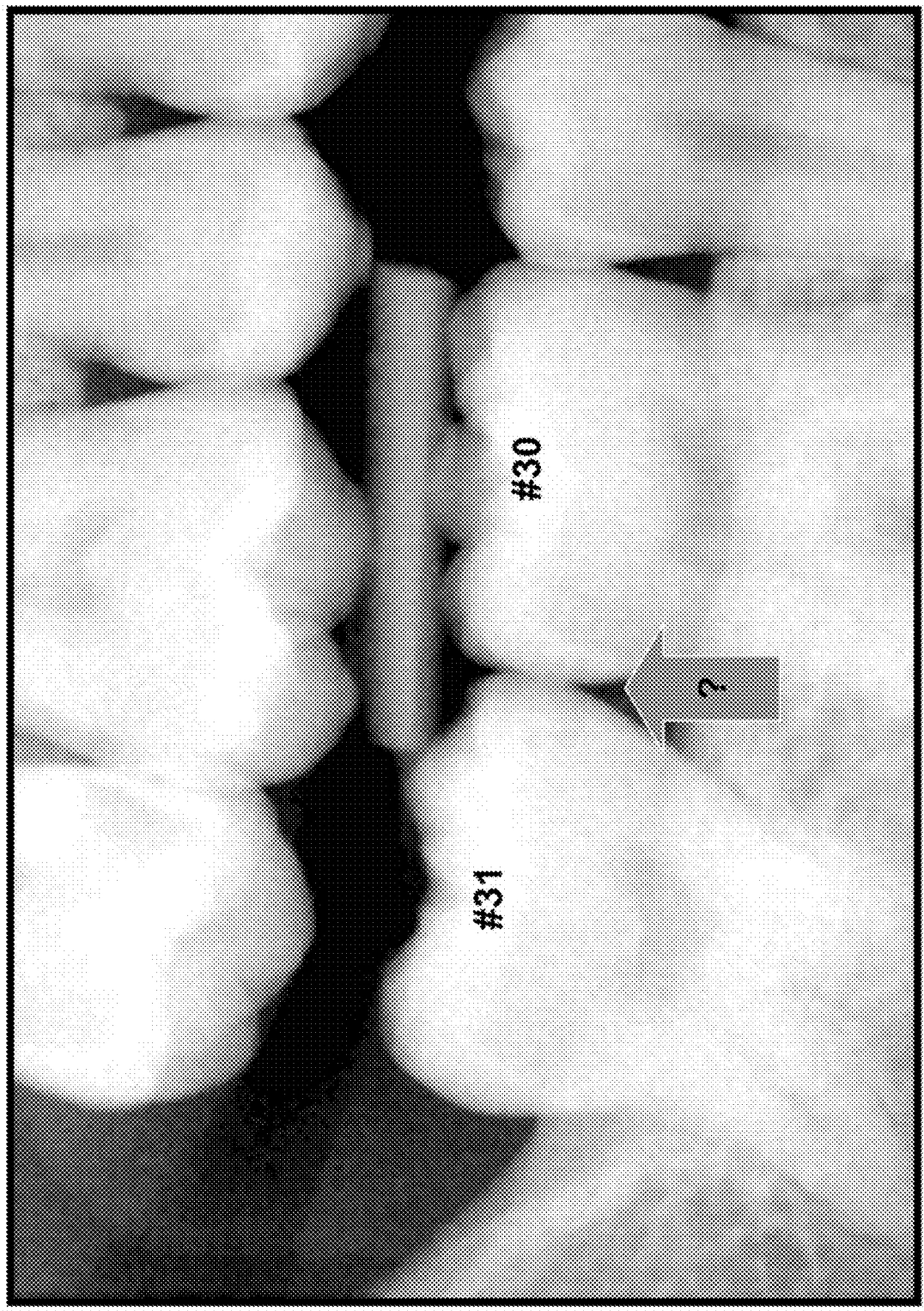
Figure 5:
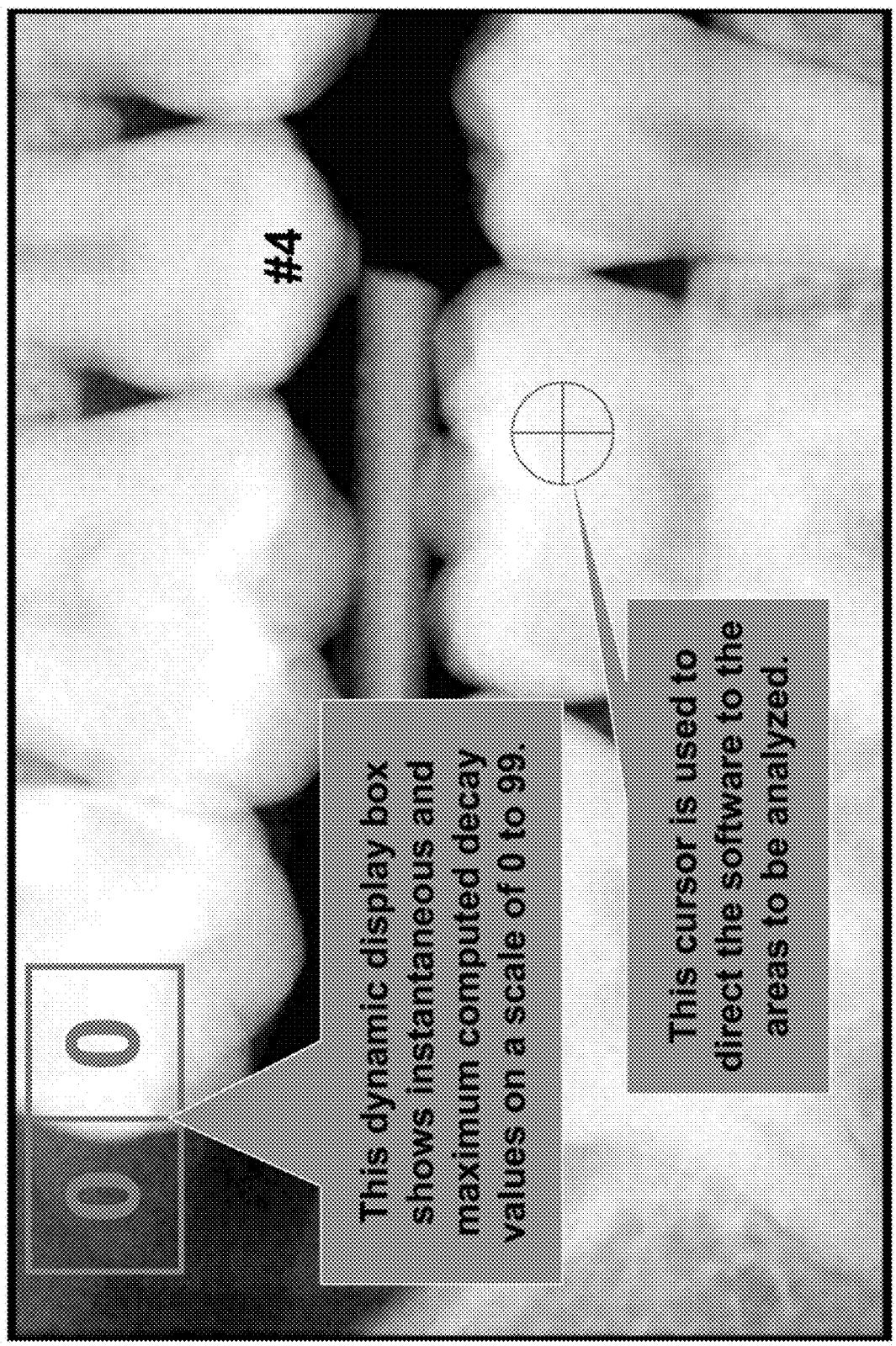
FIGS. 5-15 are images that illustrate use of a software algorithm for diagnosing and evaluating decay from the digital dental x-ray image.

Several exemplary dental x-ray images are shown in FIGS. 1-4, illustrating the difficulty of accurately diagnosing decay from such images. FIGS. 1 and 2 show teeth #3, #4, and #5 (specific teeth may be referred to hereinafter by number only). It is difficult to discern from these images the extent of interproximal decay between these teeth, or if decay is even present. Likewise, in FIGS. 3 and 4, it is difficult to evaluate interproximal decay (if any) between #30 and #31. These direct digital images were "enhanced" for visual interpretation on a display monitor. Critical data is often washed out by the x-ray capture and image display process, making decay difficult to detect or evaluate. Other difficulties arise from: i) lack of calibration of x-ray output, which typically degrades with the age of the instrument; ii) neither x-ray film nor digital x-ray imaging sensors are typically optimized relative to each x-ray machine (non-optimization of x-ray film or digital x-ray imaging sensors relative to each x-ray machine); iii) existing x-ray film chemical processing and x-ray image software processing are optimized for visual inspection, but not necessarily for decay detection (non-optimization of x-ray film chemical processing and x-ray image software processing for visual inspection, but not necessarily for decay detection); iv) degradation of image quality as the display monitor ages; and v) variation among different operators acquiring the images or different observers interpreting the images.

It may be preferable to develop a diagnostic procedure or protocol using the native data captured from film or digital sensors and pre-processed separately from the visual display for optimum dental disease detection. Such an approach might be designated for convenience as Computer Aided Dental Diagnostics (CADD). Such procedure or protocols might include: i) periodic (i.e. yearly) calibration of the x-ray source and digital x-ray imaging sensor; ii) including both normal and diseased tissue (i.e. normal tooth and decay) in the calibration procedure; iii) use of software algorithms to determine the presence or extent of decay; and iv) providing a numerical value (a numerical decay value calculated from the measured optical densities) that correlates with the extent of decay present to further assist the clinician in making an accurate diagnosis or appropriate treatment plan.

Figure 6:
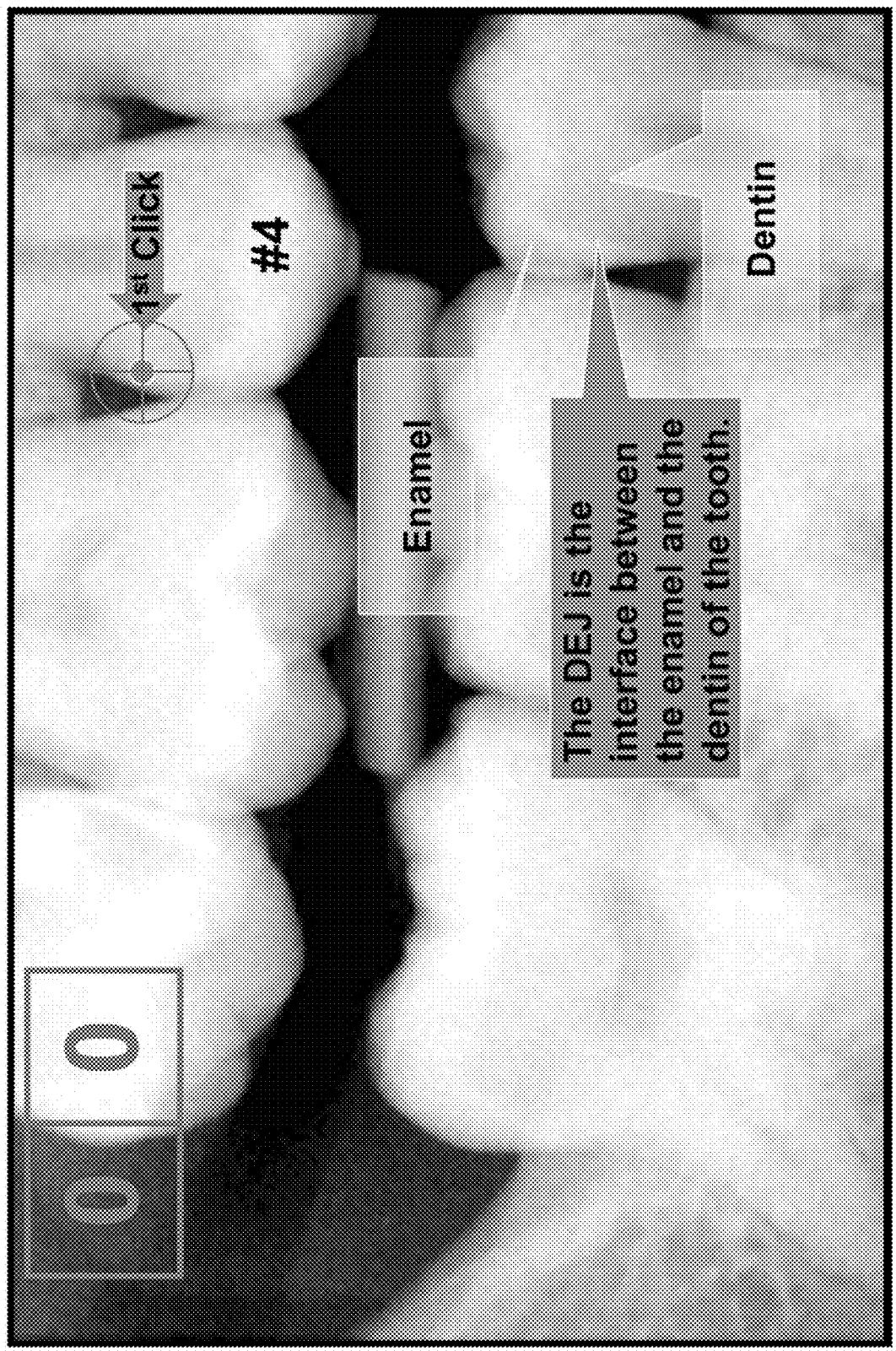
Figure 7:
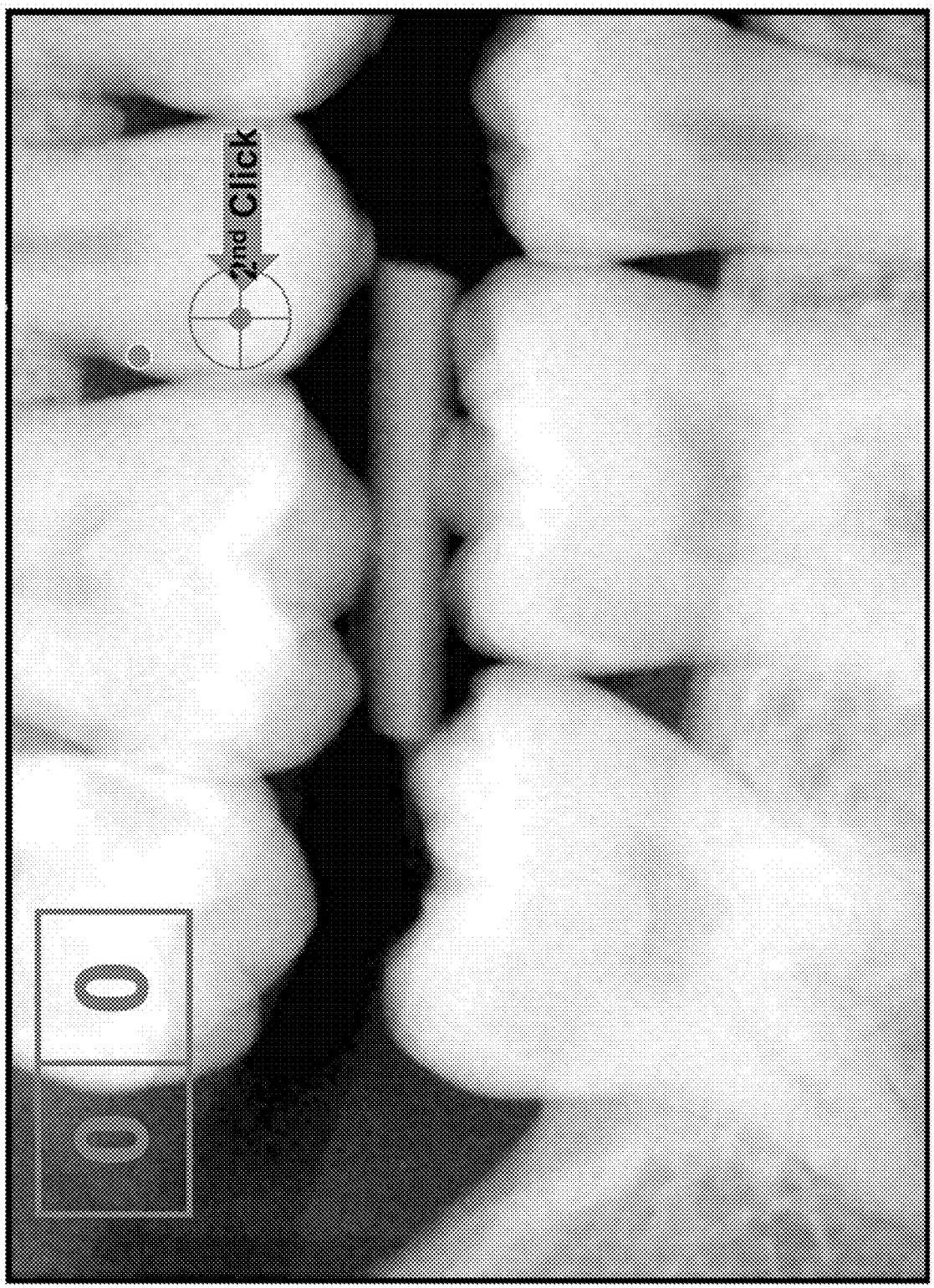
Figure 8:
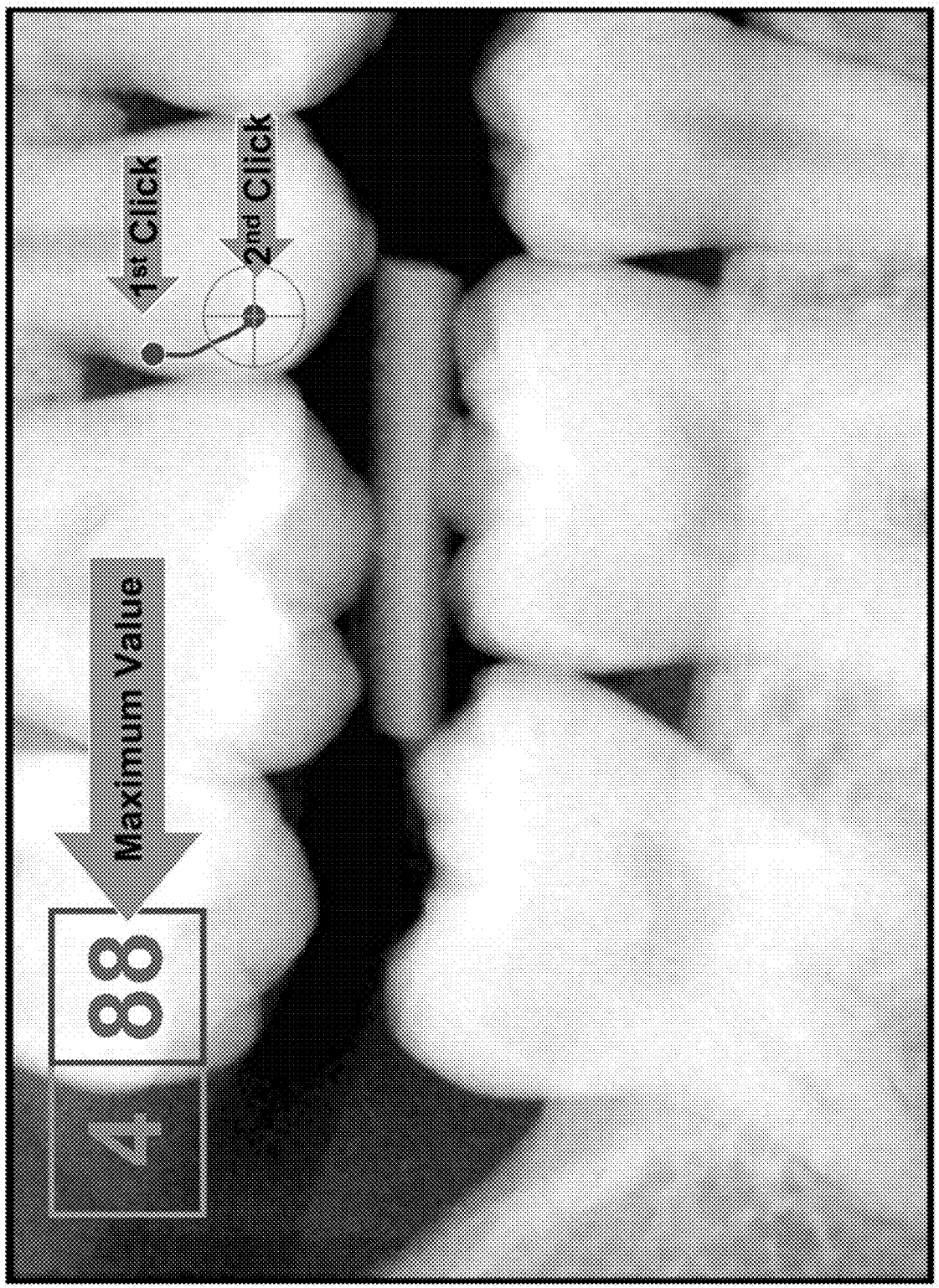
Figure 9:
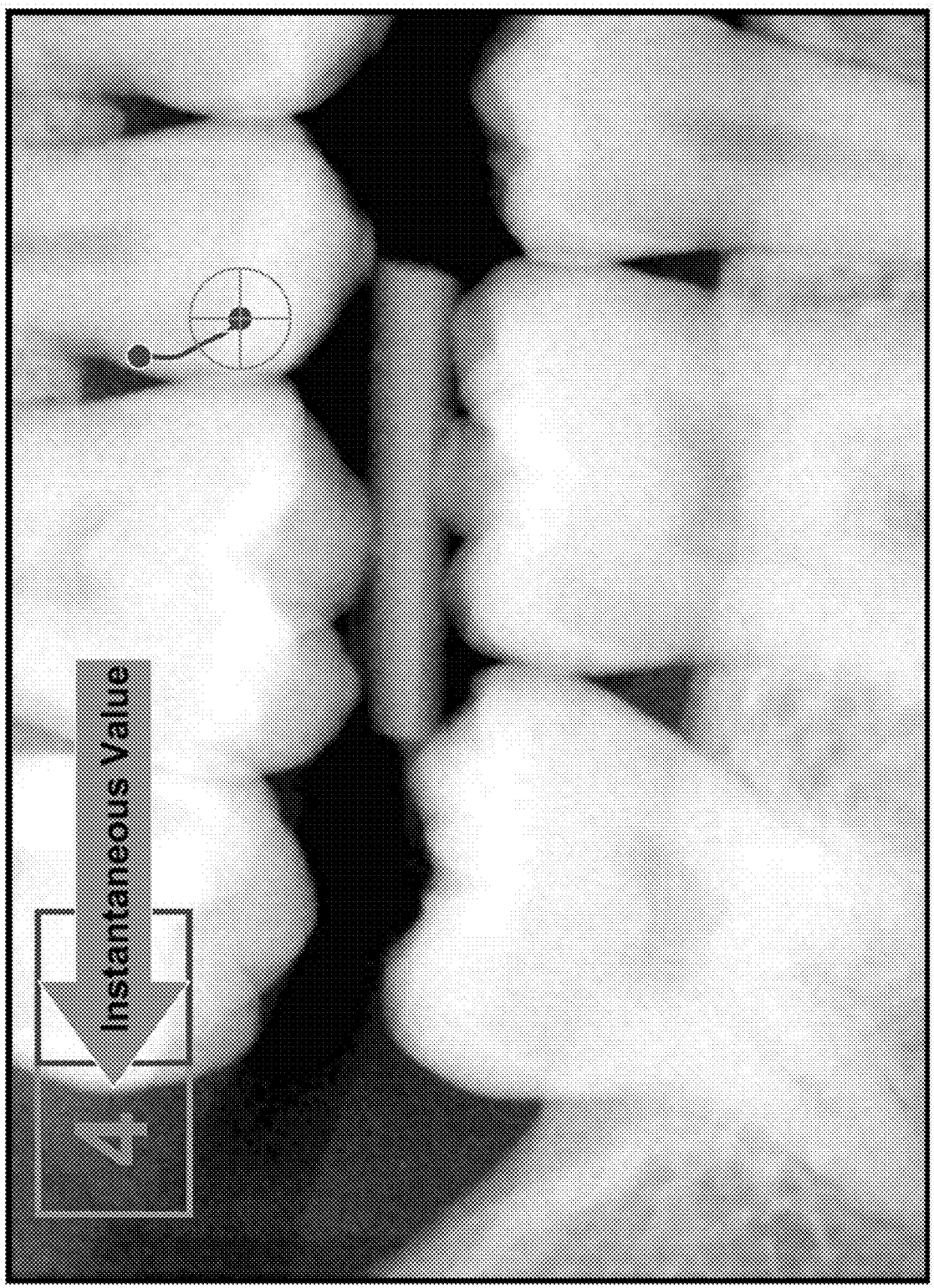
Figure 10:
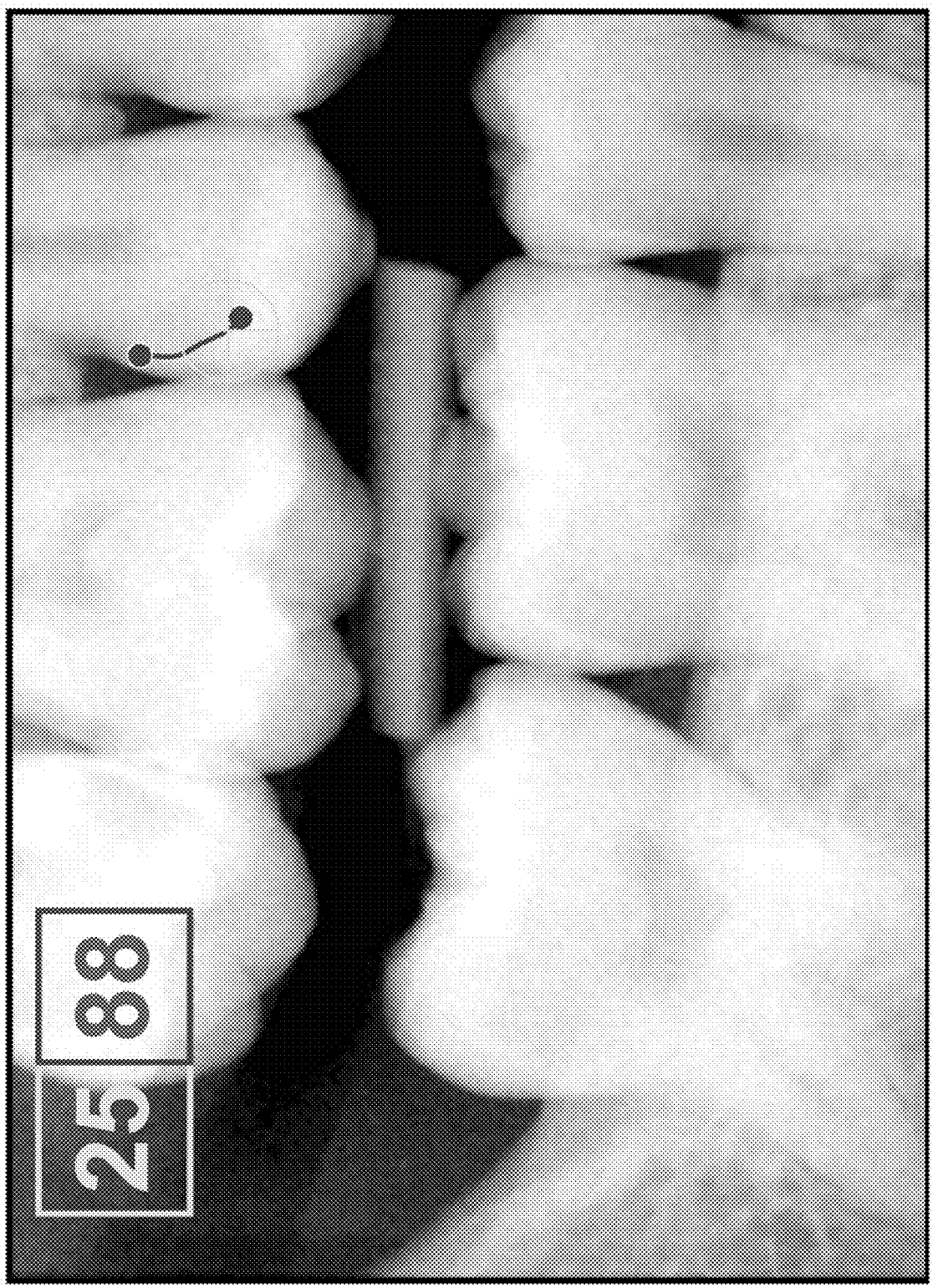
Figure 11:
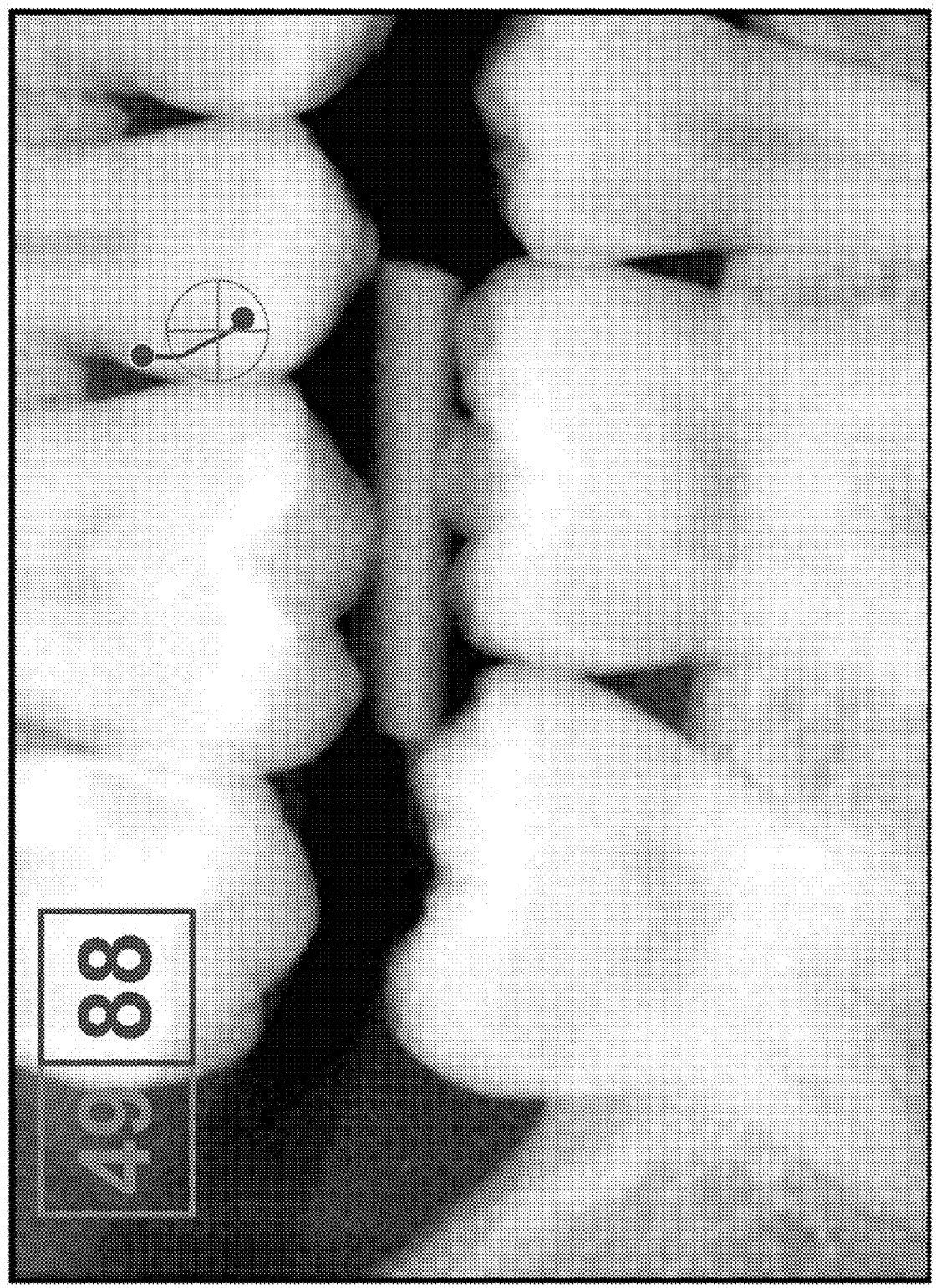
Figure 12:
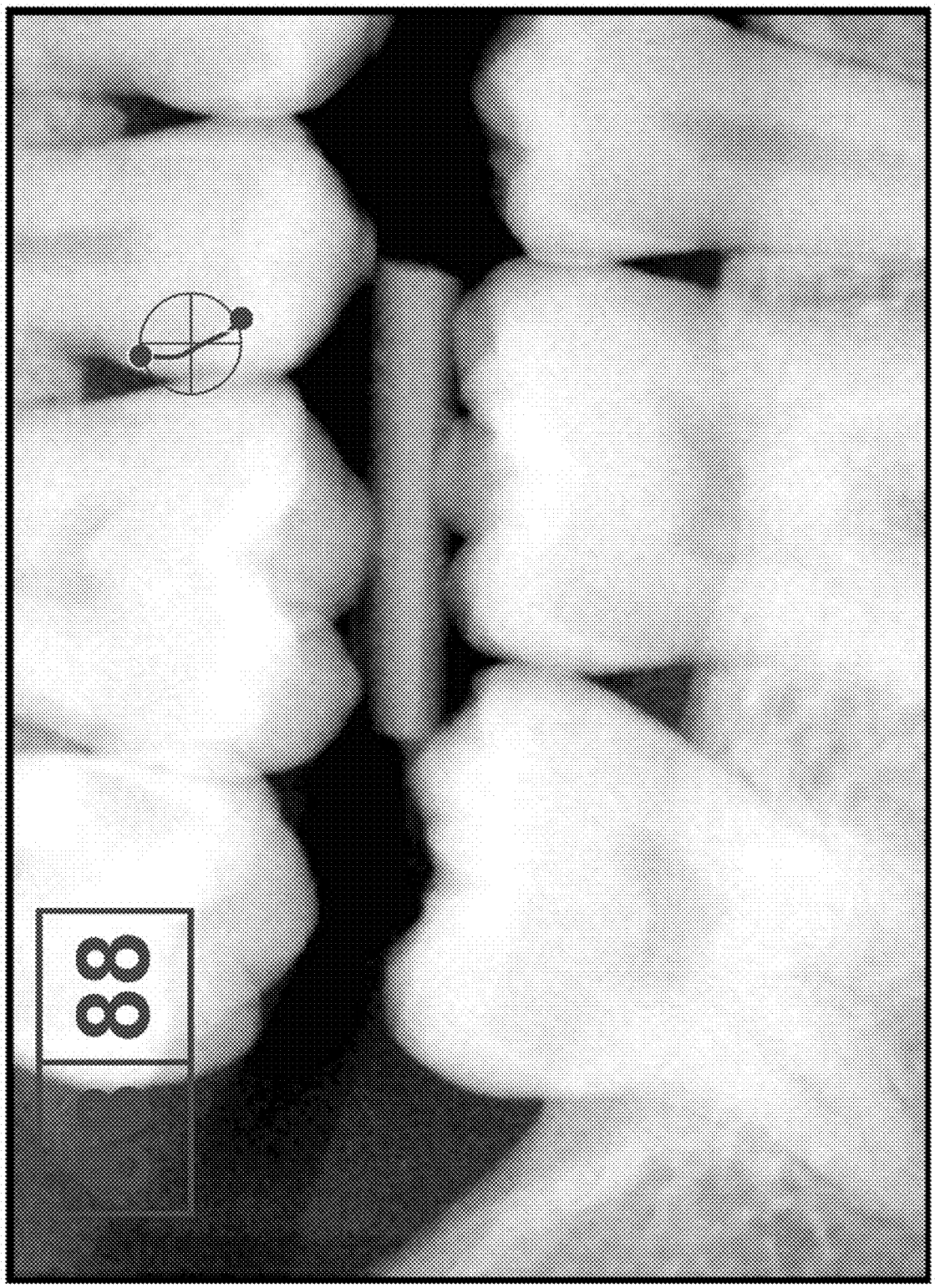
Figure 13:
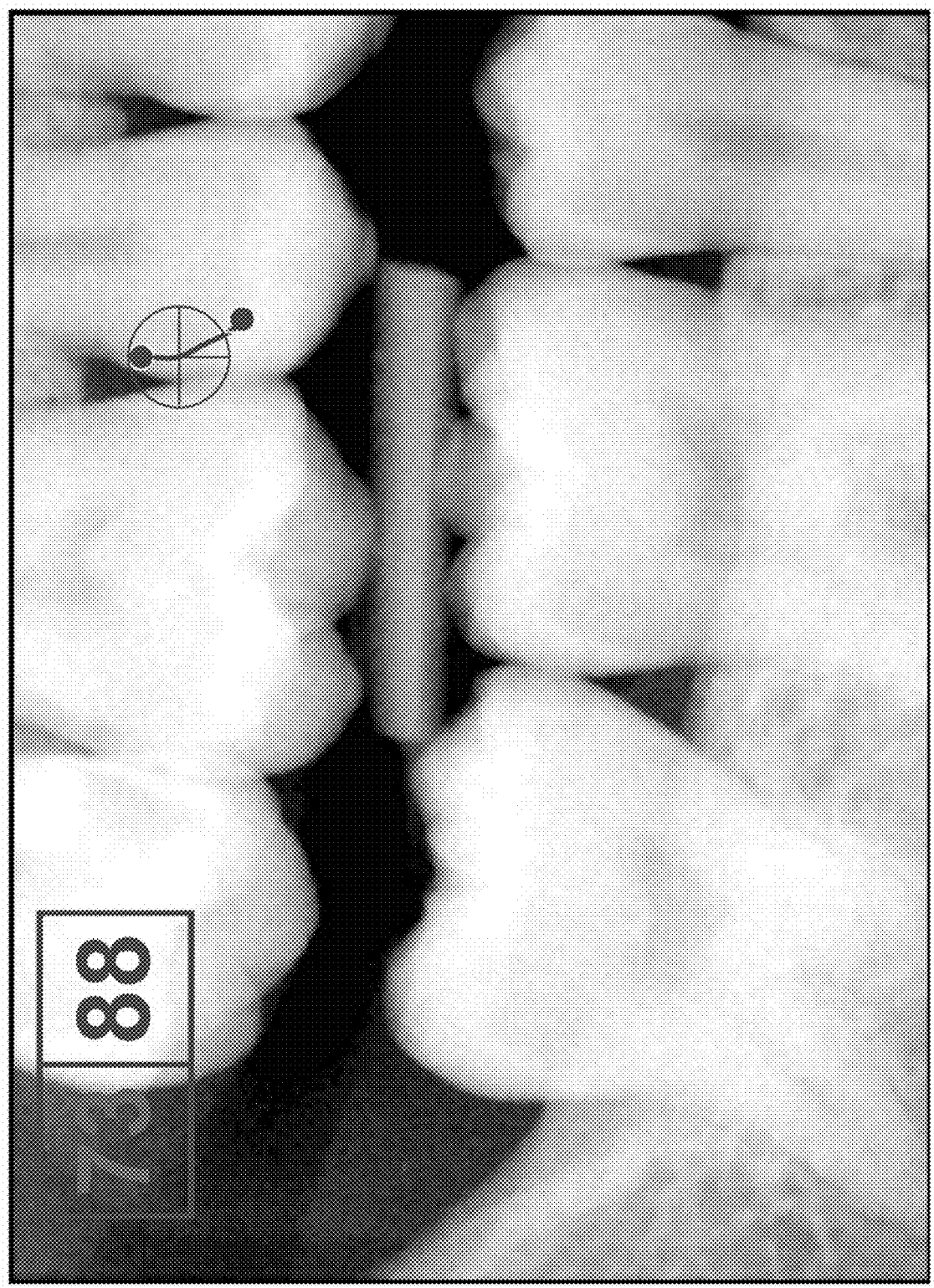
Figure 14:
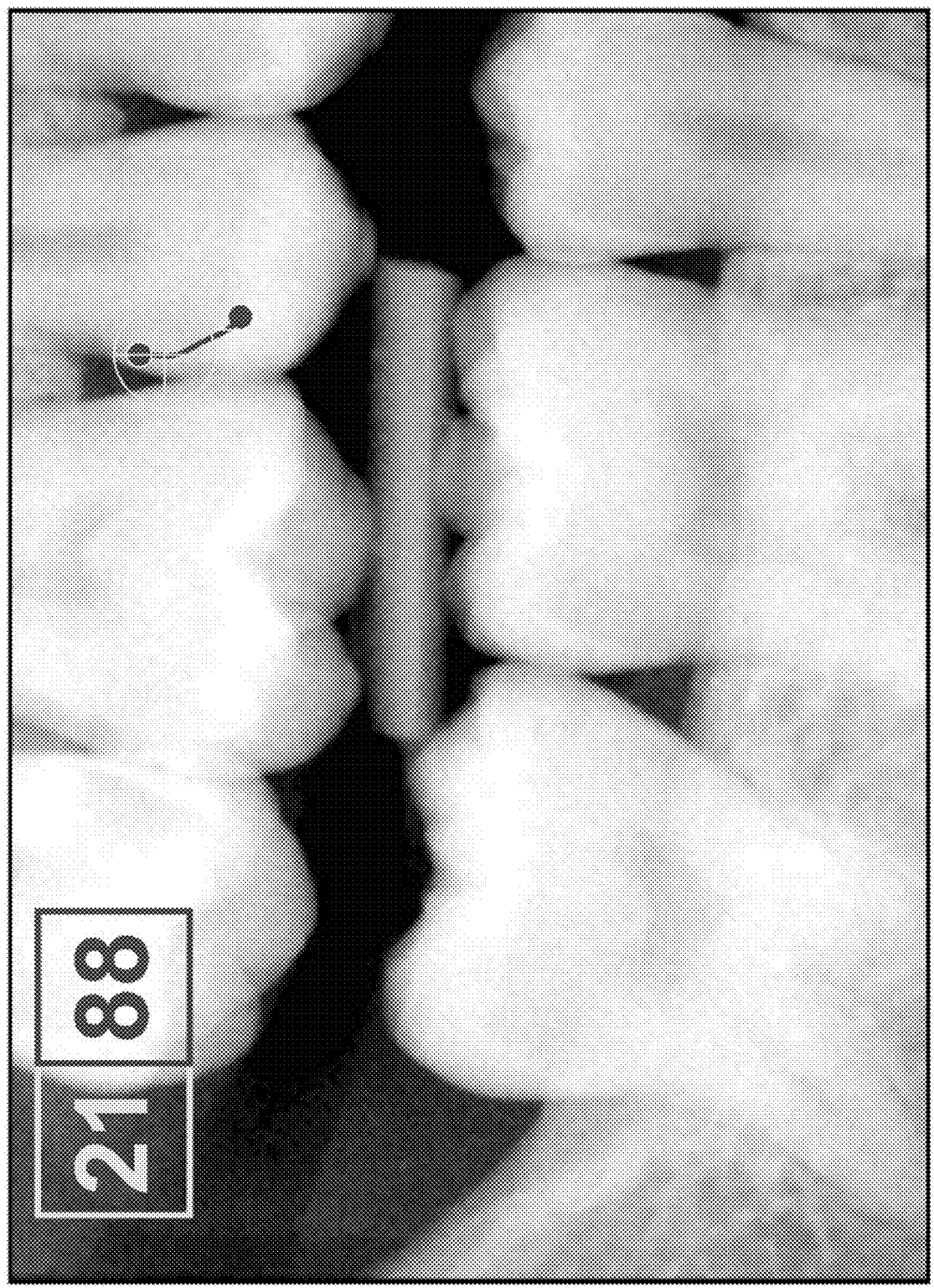
Figure 15:
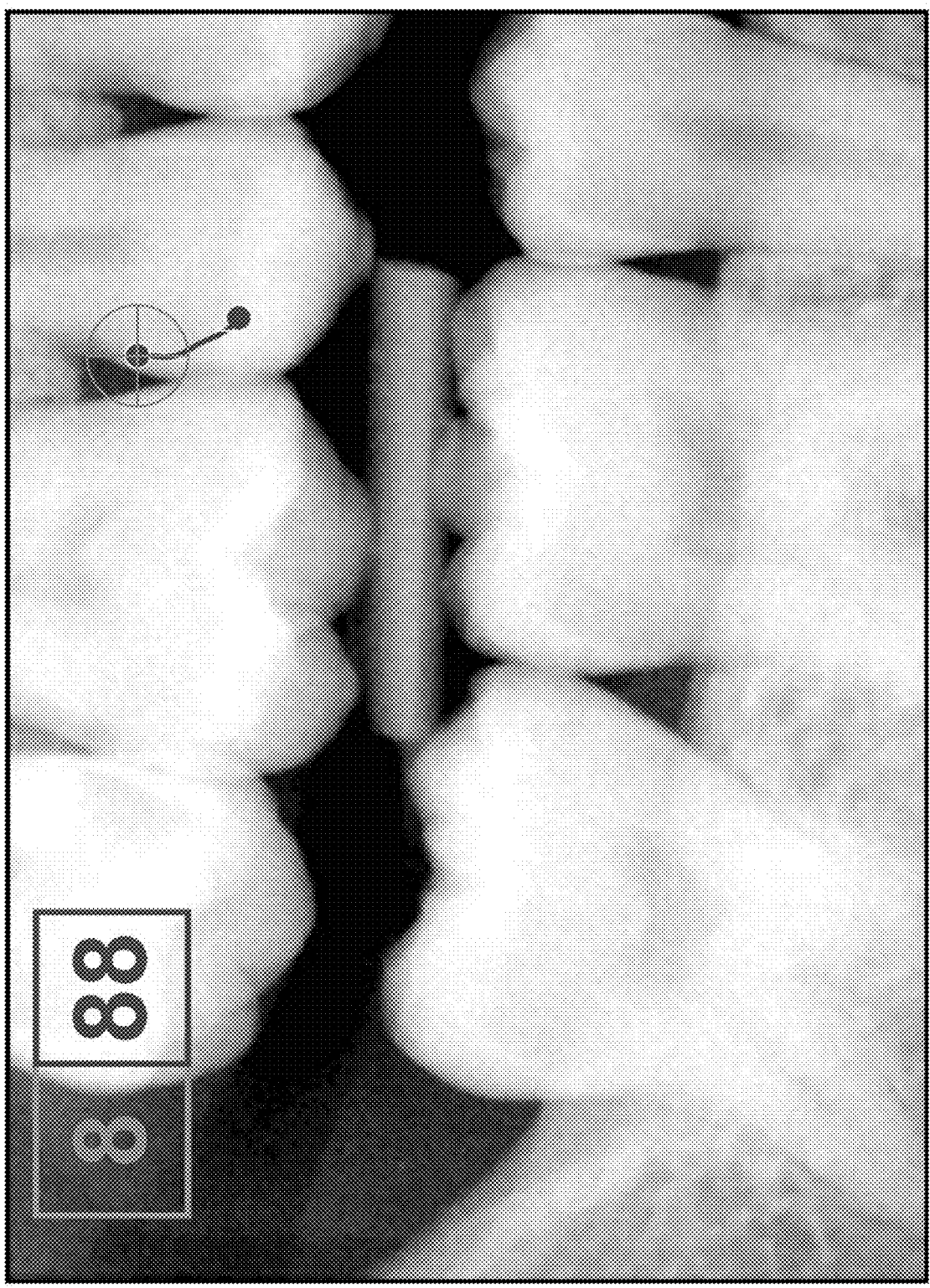

One exemplary software algorithm for detecting and evaluating tooth decay may be designated for convenience as CarieScan CADD. The algorithm uses the native x-ray image data for processing. The software analyzes the image to detect decay based upon algorithms which may utilize edge detection techniques, pattern recognition techniques, individual tooth geometry data, or other factors (including patient data). The results of the software analysis may be superimposed onto a dental x-ray image, but are obtained in a manner independent of any processing of the image for visual presentation or interpretation. FIGS. 5-15 illustrate use of the CarieScan algorithm. Upon activation (FIG. 5), a dental x-ray image is displayed, along with a user-movable cursor and a dynamic numerical display showing maximum and local values for a numerical decay value. Both displayed numerical values may be zeroed before any analysis occurs. As shown in FIGS. 6 and 7, a user uses the cursor to mark the ends of a segment of the dentin-enamel junction (DEJ). Once the ends are marked, the software analyzes the raw image data (not the processed version of the data used to generate the display) to locate the DEJ and to generate a numerical decay value that may vary with position along the DEJ (FIG. 8). A 0-100 scale is used in this example, with higher numerical values corresponding to greater extent of decay. Any scale, however, with any desired magnitude or directionality may be employed. Once the analysis is complete (described further herein below), the numerical display shows a local (at the cursor location) numerical decay value in one box (the left in this case) and a maximum numerical decay value for the marked portion of the DEJ in the other box. The cursor may be moved along the DEJ in the image while the user notes the location(s) of high numerical decay values (FIGS. 9-15).

Audible alarms, color-coded text or graphics in the display, or other suitable means may be employed for alerting the user to detected decay. These may be coded to correspond to varying numerical decay values, based on any suitable or desirable criteria. Many scaling options are possible and may be employed. For example, a scheme may be employed wherein: i) green indicates decay that has not yet penetrated through enamel; ii) yellow indicates decay that has penetrated through enamel into dentin less than about 0.5 mm or less than about 50% of the thickness of adjacent enamel; iii) orange indicates decay that has penetrated into dentin more than about 0.5 mm but less than about 1.0 mm, or more than about 50% but less than about 100% of the thickness of adjacent enamel; and iv) red indicates decay that has penetrated into the dentin more than about 1.0 mm or more than about 100% of the thickness of adjacent enamel.

Figure 16:
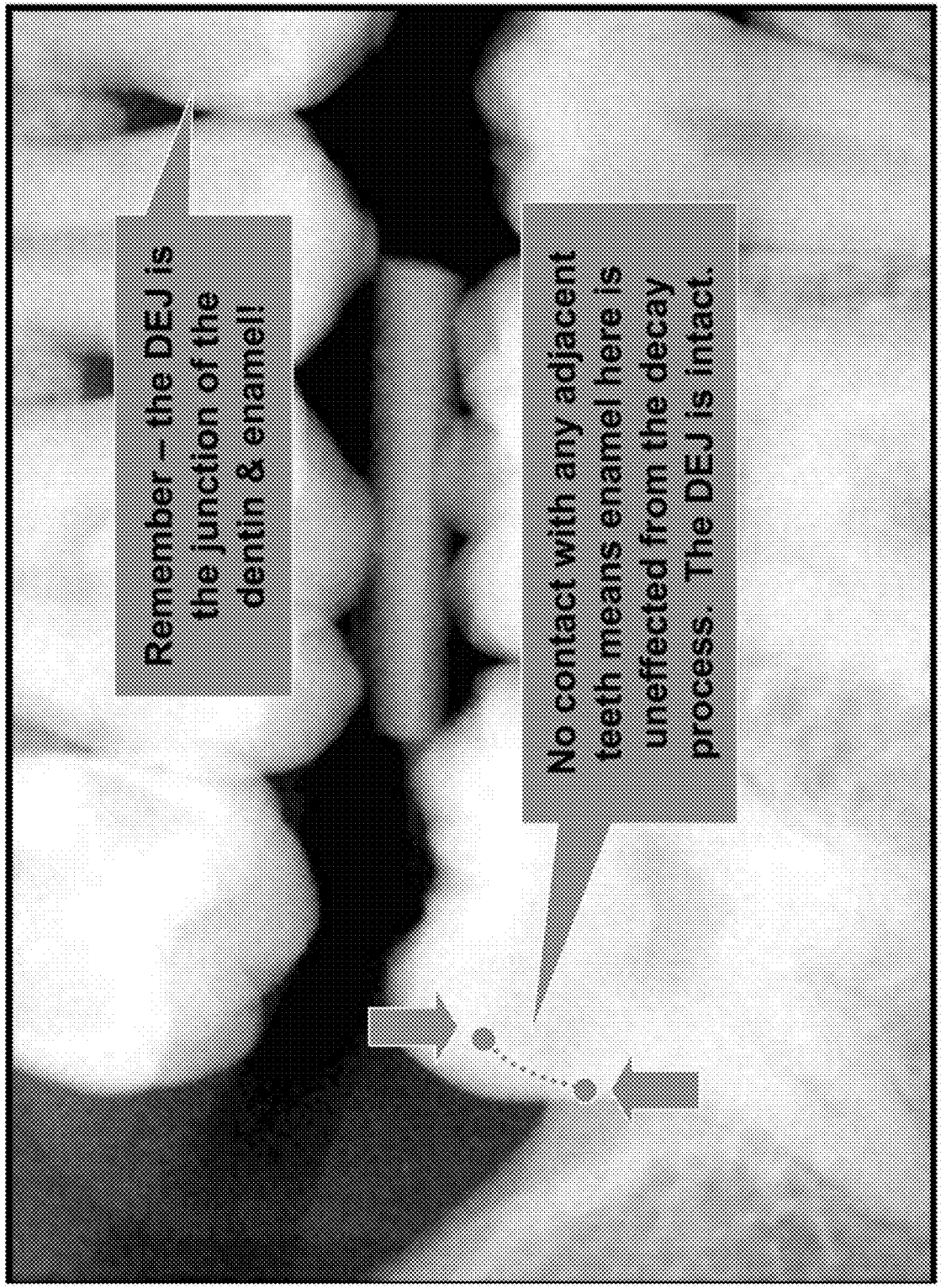
FIGS. 16-18 are dental x-ray images showing areas of suspected decay analyzed with the software algorithm.
Figure 17:
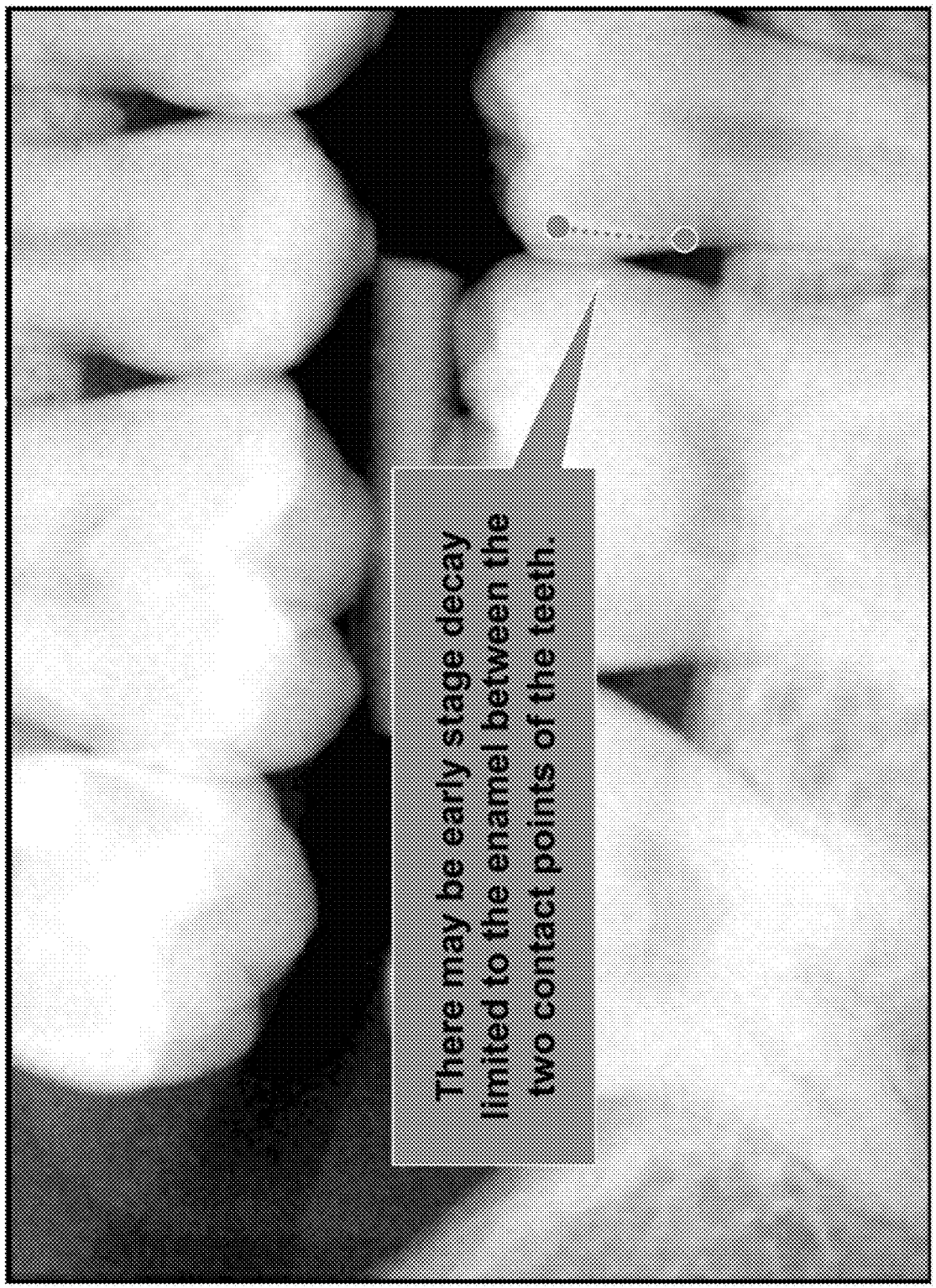
Figure 19:
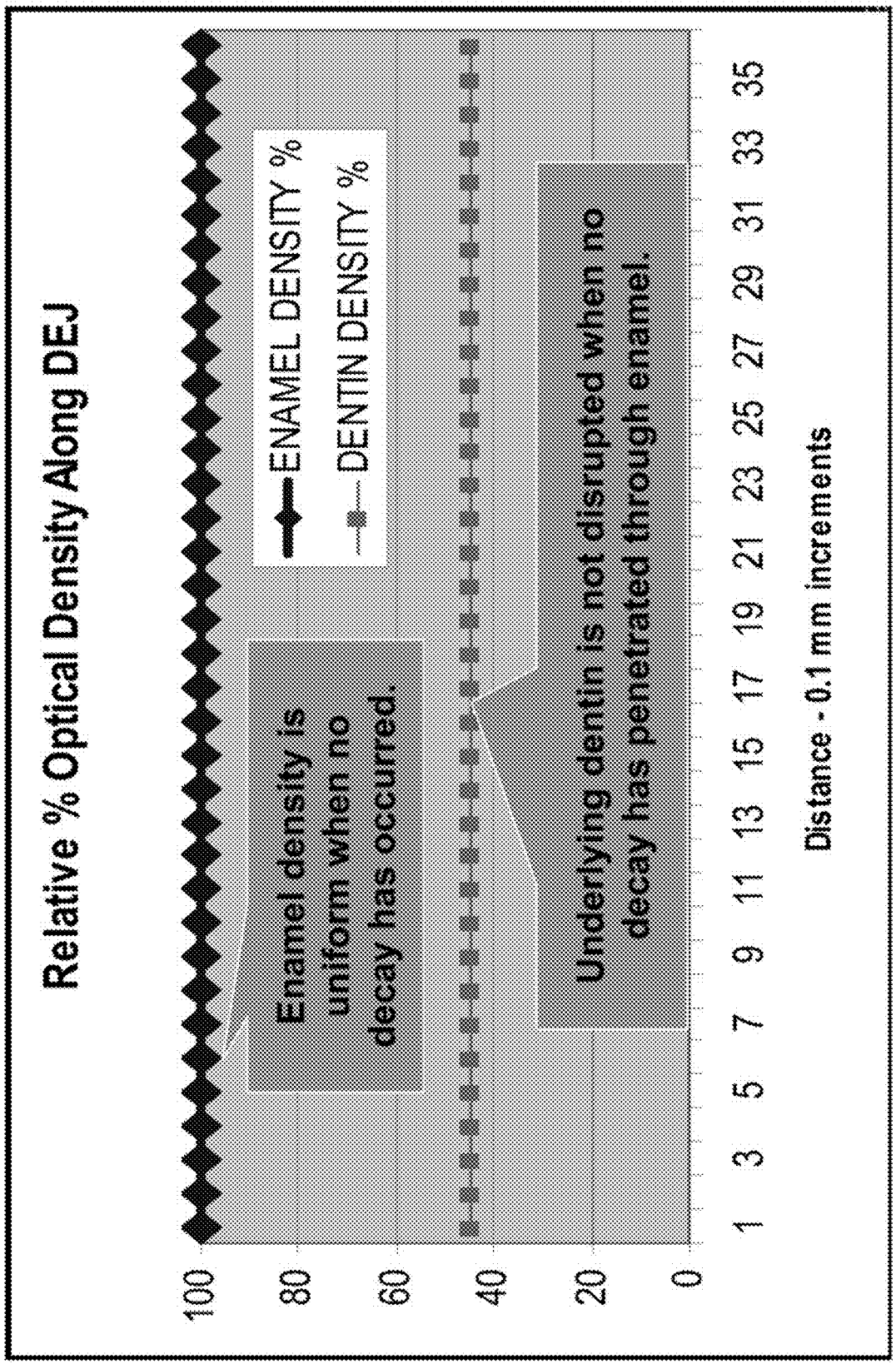
FIGS. 19-21 are charts that illustrate optical density plots along the DEJ corresponding to FIGS. 16-18, respectively.
Figure 20:
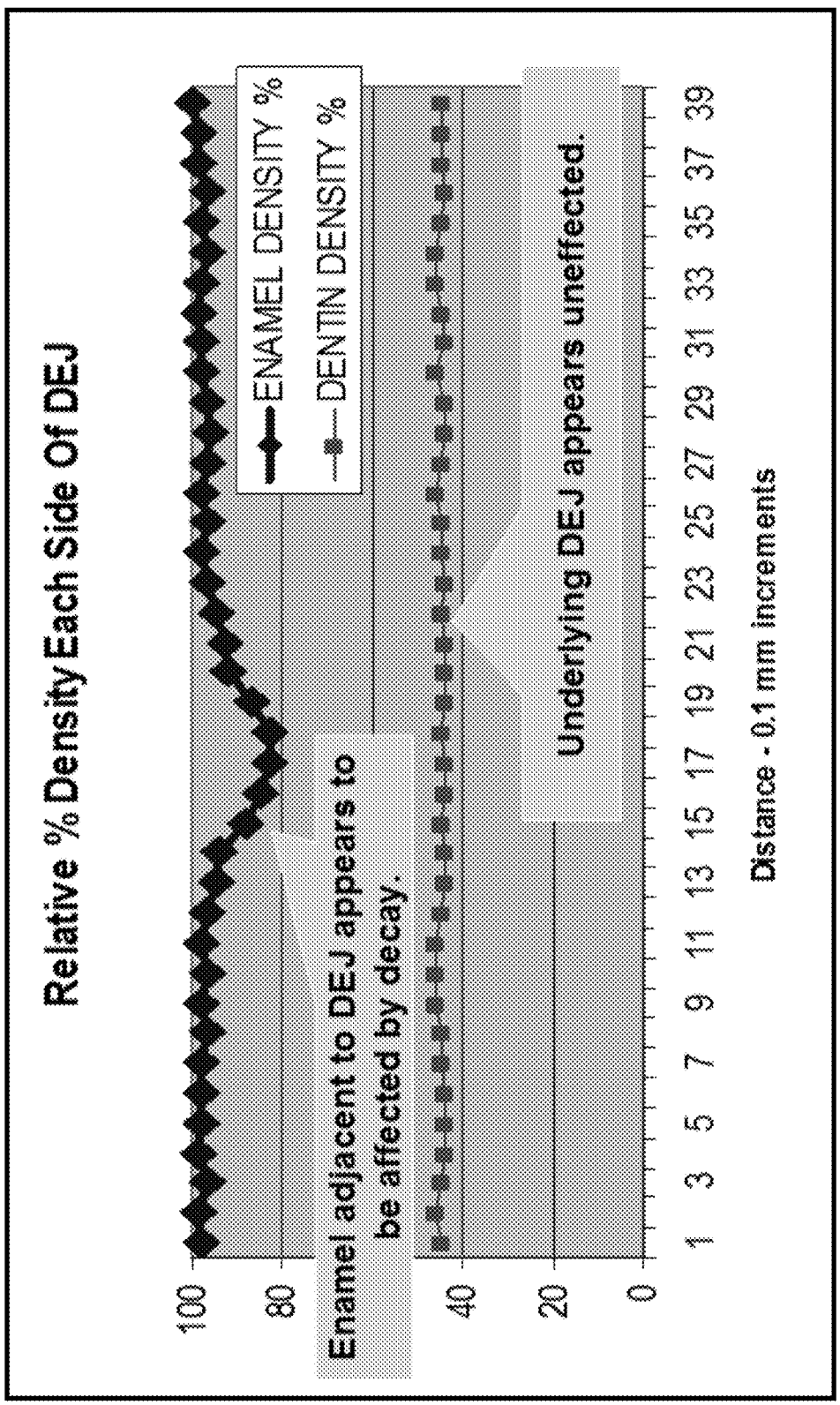

Analysis of the raw x-ray image data to yield numerical decay values focuses on the densities of enamel and dentin along the dentin-enamel junction (DEJ). In FIG. 16, a tooth is analyzed that is unaffected by decay, with the DEJ intact. Once the user clicks near the ends of the DEJ (as in FIGS. 6 and 7), the analysis algorithm first locates the contour of the DEJ. The optical density is then measured along substantially parallel contours, one just outside the DEJ in the enamel, the other just inside the DEJ in the dentin. The optical density (equivalently, radiodensity) is plotted as a function of distance along the DEJ in FIG. 19. In a tooth unaffected by decay, the two density curves are substantially flat (indicating substantially constant density), with the enamel density larger than the dentin density. The numerical density of intact enamel is arbitrarily normalized to 100% in this example. In FIG. 17, a tooth is analyzed that shows signs of only early-stage decay penetrating only partly into the enamel. Results of the corresponding analysis are shown in FIG. 20. The density curve for the dentin remains substantially flat, while a dip is seen in the density curve for the enamel, indicating that a portion of the enamel near the DEJ has been affected by decay. The curves are normalized, with the flat portions of the enamel density curve being set to 100%.

Figure 18:
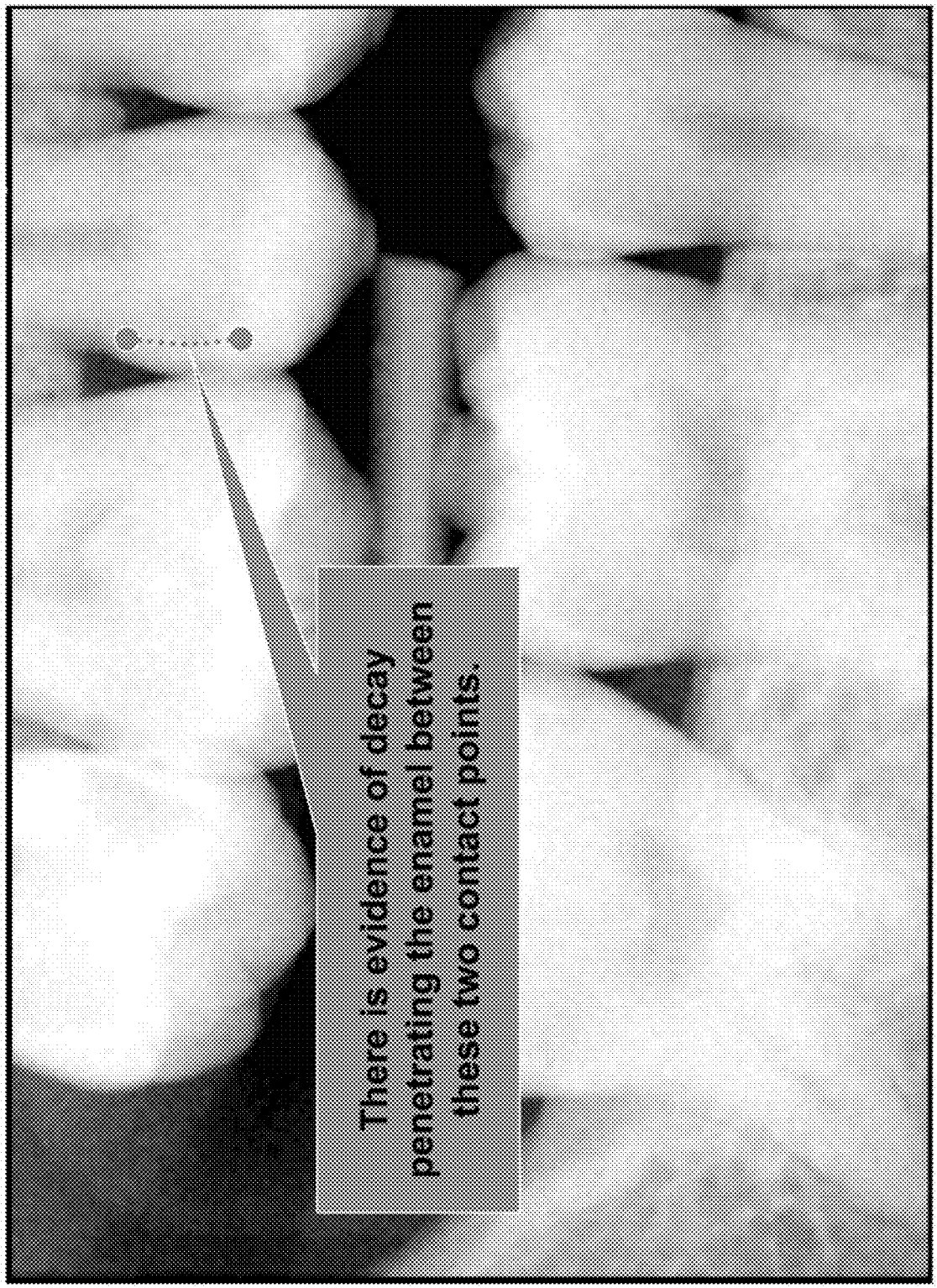

In FIG. 18, analysis of an area of more advanced decay is illustrated. The corresponding density curves in FIG. 21 exhibit extensive dips in both enamel and dentin density curves. The width of the affected area (i.e. the length of the dip along the DEJ) is larger in the dentin. This arises from differing pathophysiology of the respective decay processes in enamel and dentin. The decay process in enamel is diet-driven: bacteria rely on external nutrients (such as dietary sugars), and the acids produced by their metabolic activity drives the decay process. The decay "tunnels" through the enamel, often along developmental grooves on biting surfaces or at contact points between teeth where acids can accumulate; open areas of the enamel are typically less prone to decay. Dentin-based decay is not diet driven; dentin contains proteins that nourish bacteria independent of the patient's diet. The bacteria present in the dentin engage in a different breakdown process. Decay in dentin is essentially a surface process, which results in a substantially hemispherical geometry radiating into the dentin from the point of penetration through the enamel. The remaining enamel effectively shields the bacteria from the protective properties of saliva, thereby facilitating the decay process.

The density curves for enamel and dentin along the DEJ exhibit distinct qualitative features depending on the extent of the decay process. The curves are analyzed by the software algorithm to yield a numerical decay value. An exemplary analysis procedure includes: i) integration of the area of a dip in the normalized enamel density curve; ii) integration of the area of a dip in the normalized dentin density curve; iii) application of relative scaling factors to the two integrated values (typically weighting any dentinal decay more heavily; iv) adding together the integrated, scaled values; and v) multiplying by another scale factor to normalize to a desired scaling range.

Figure 21:
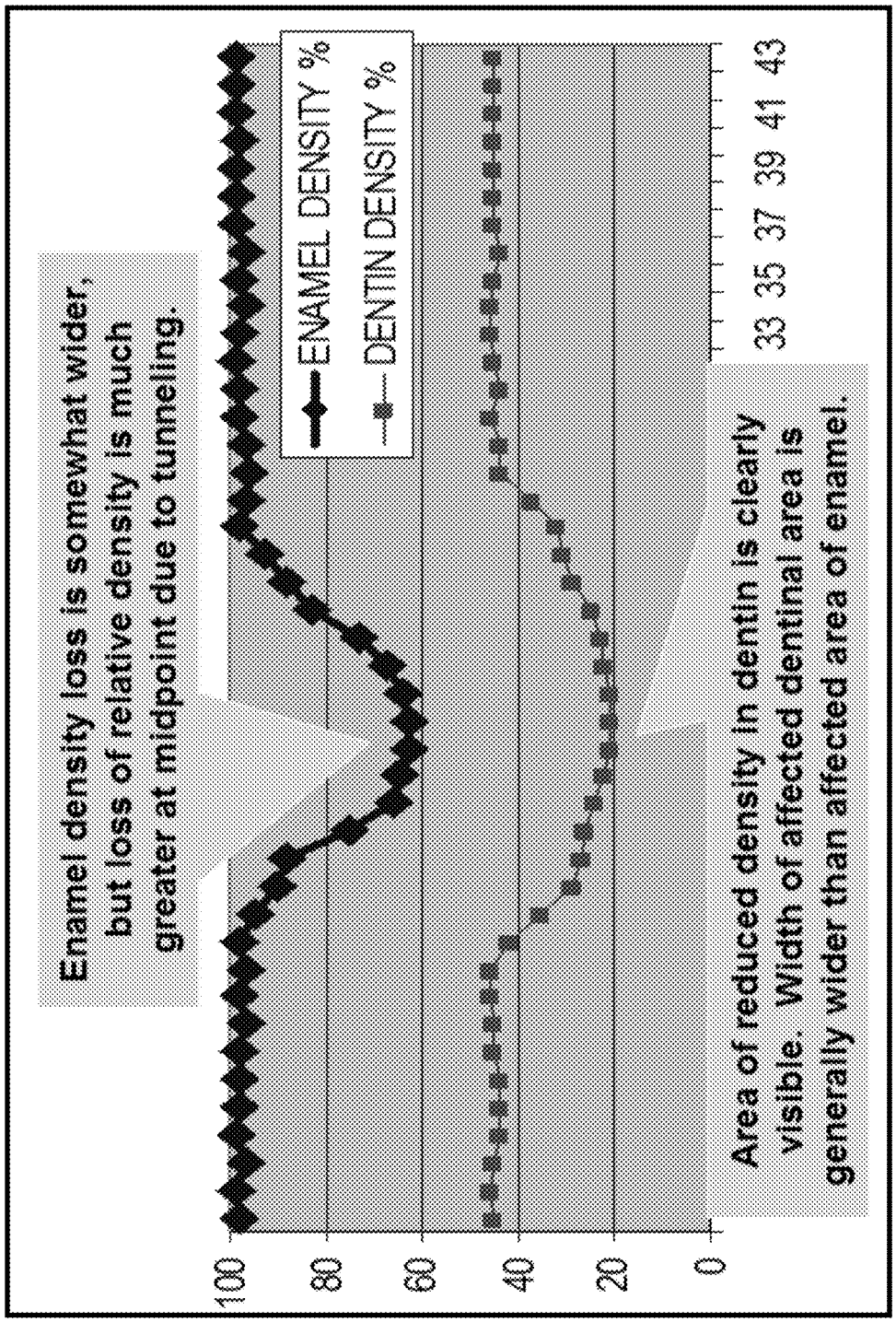
Figure 22:
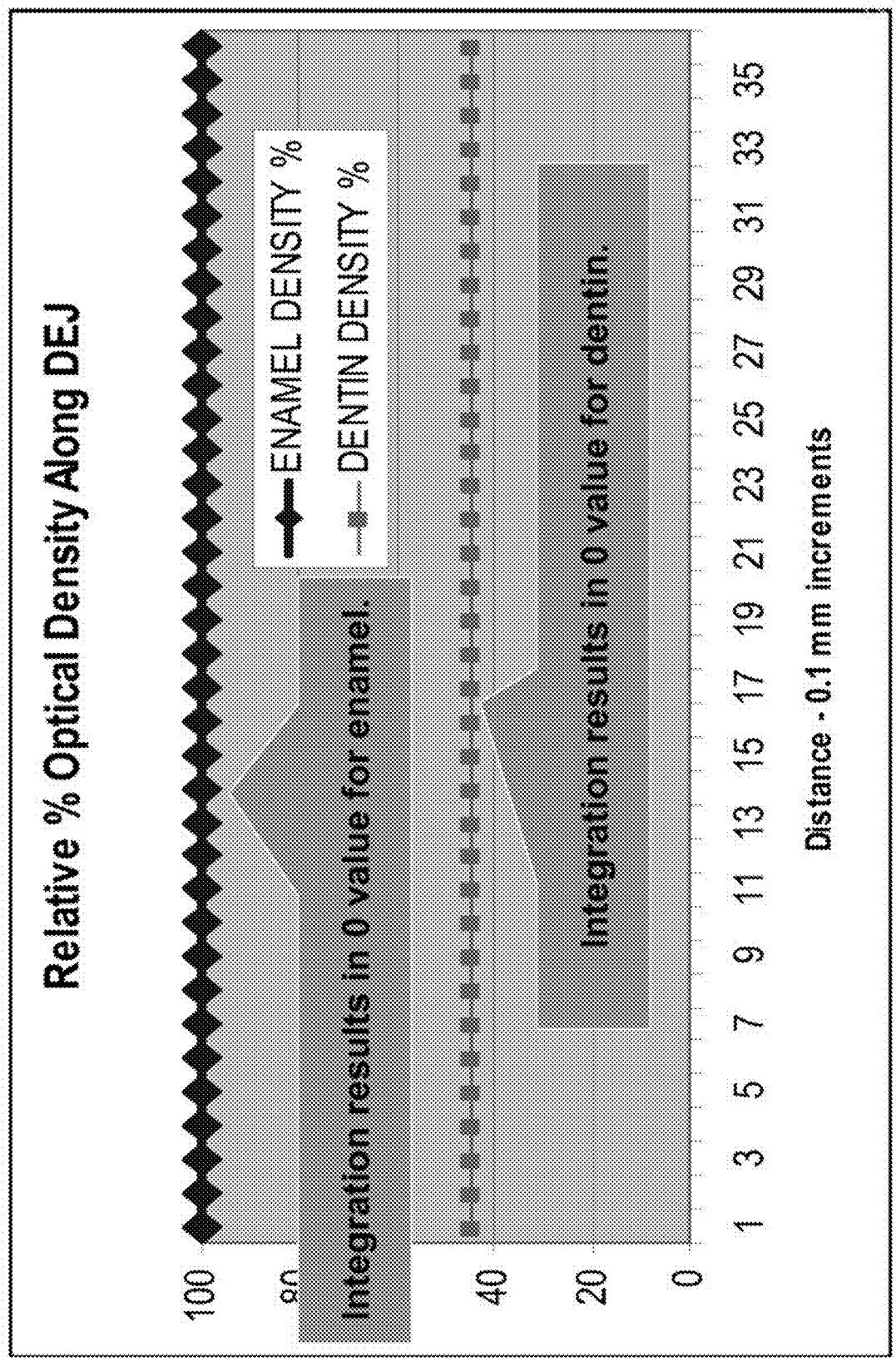
FIGS. 22-24 are charts that illustrate integration of areas of dips in the optical density plots of FIG. 19-21, respectively.
Figure 23:
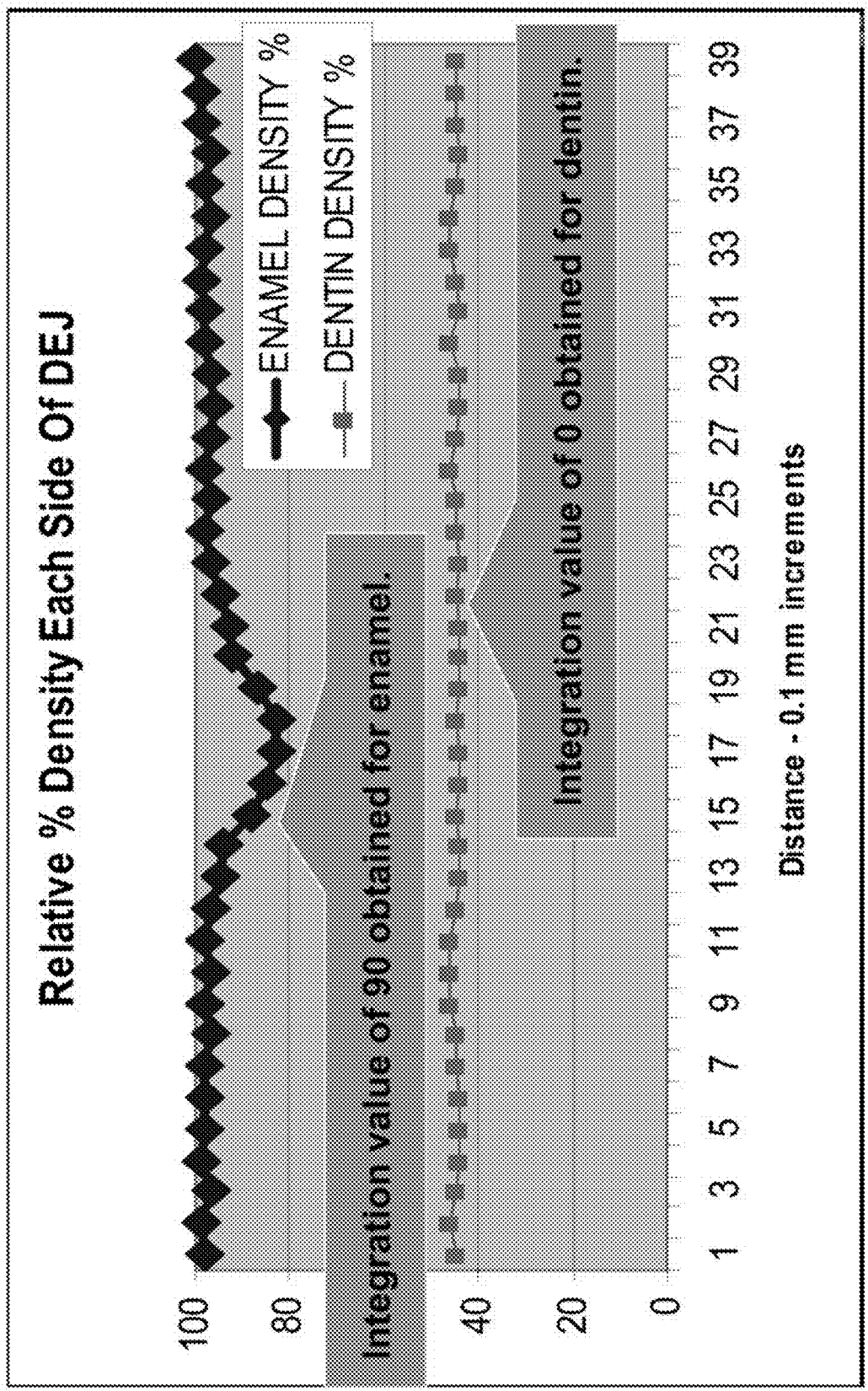
Figure 24:
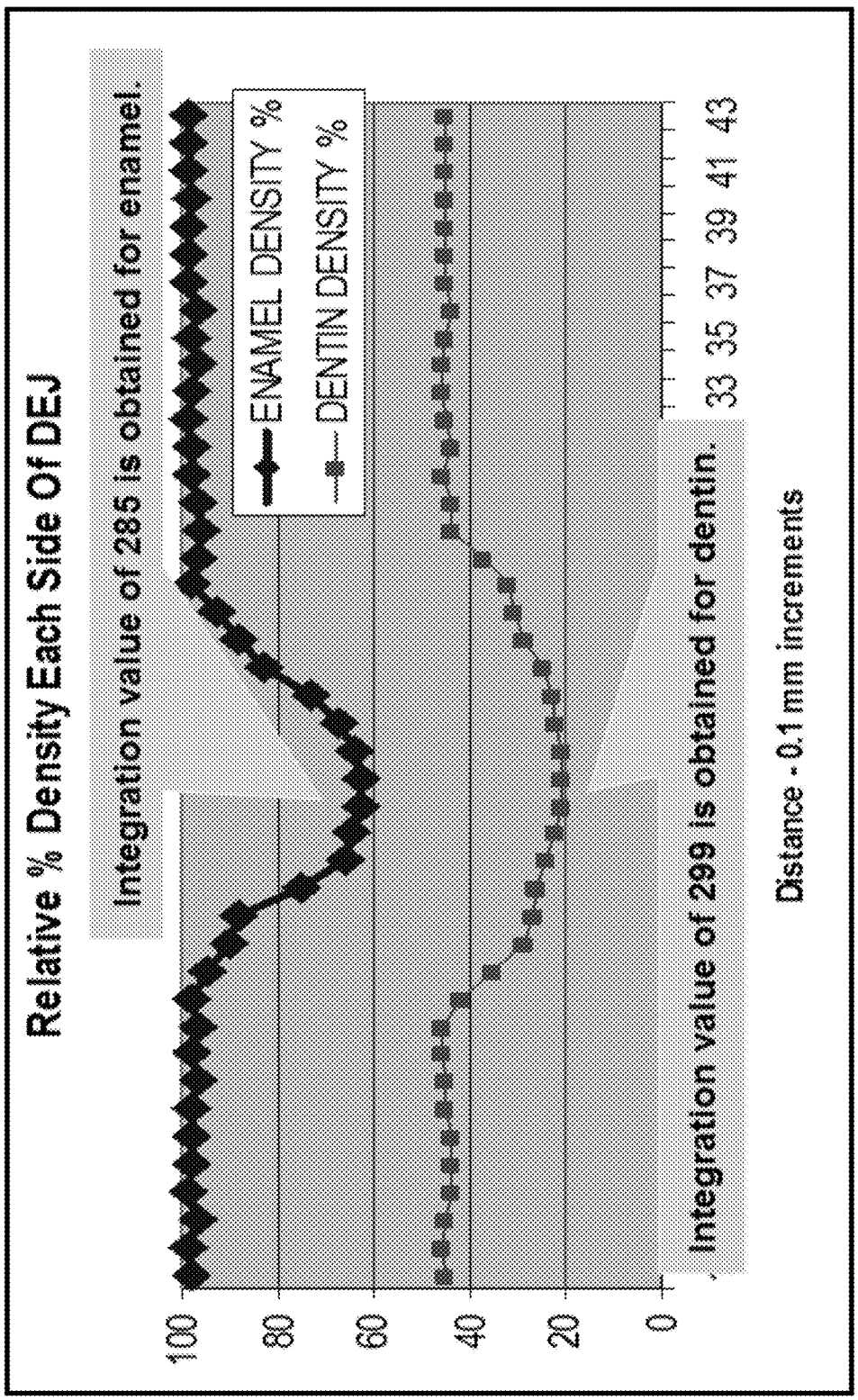
Figure 25:
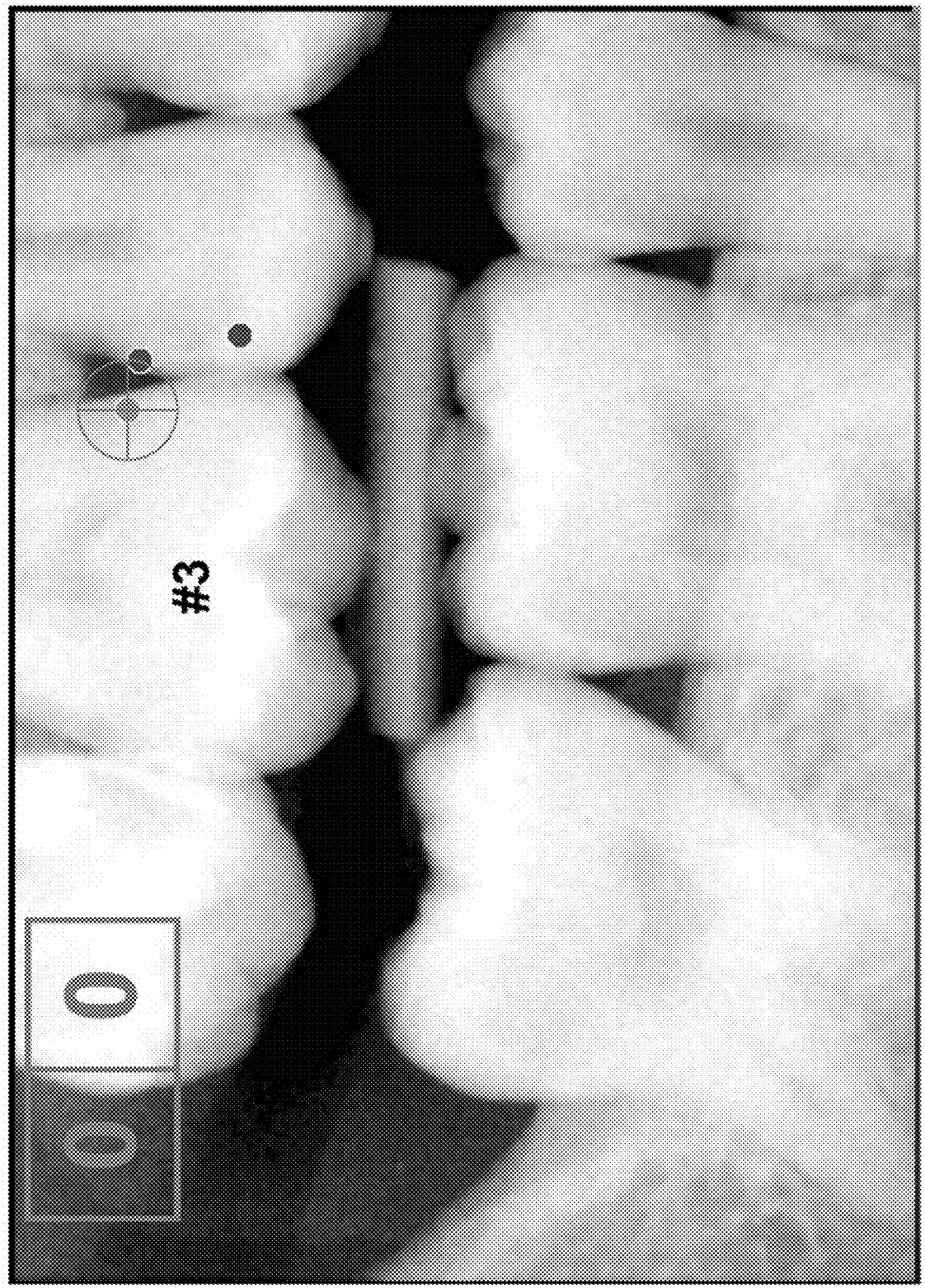
FIGS. 25-30 are images that illustrate selection of areas of a dental x-ray image for analysis.
Figure 26:
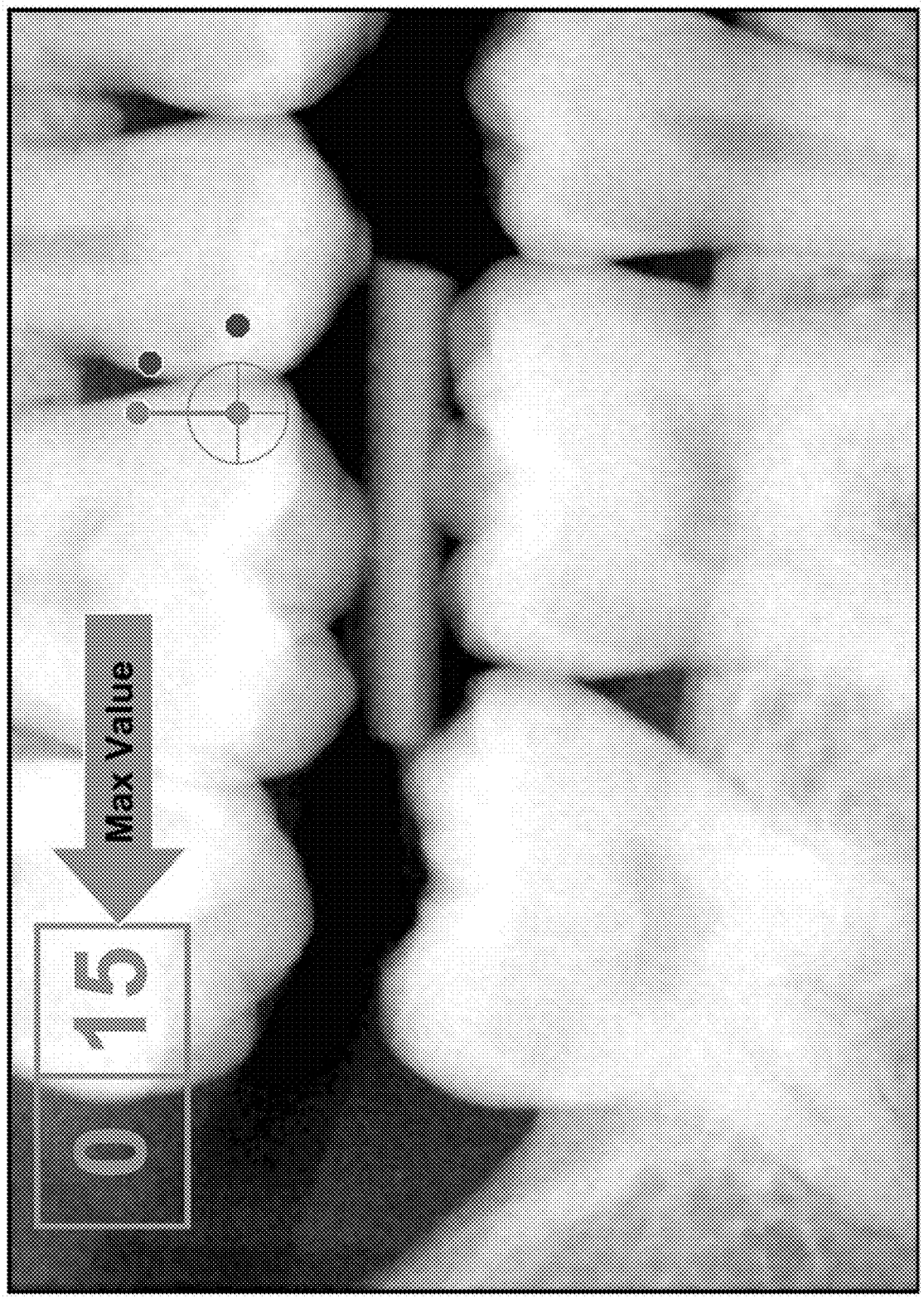
Figure 27:
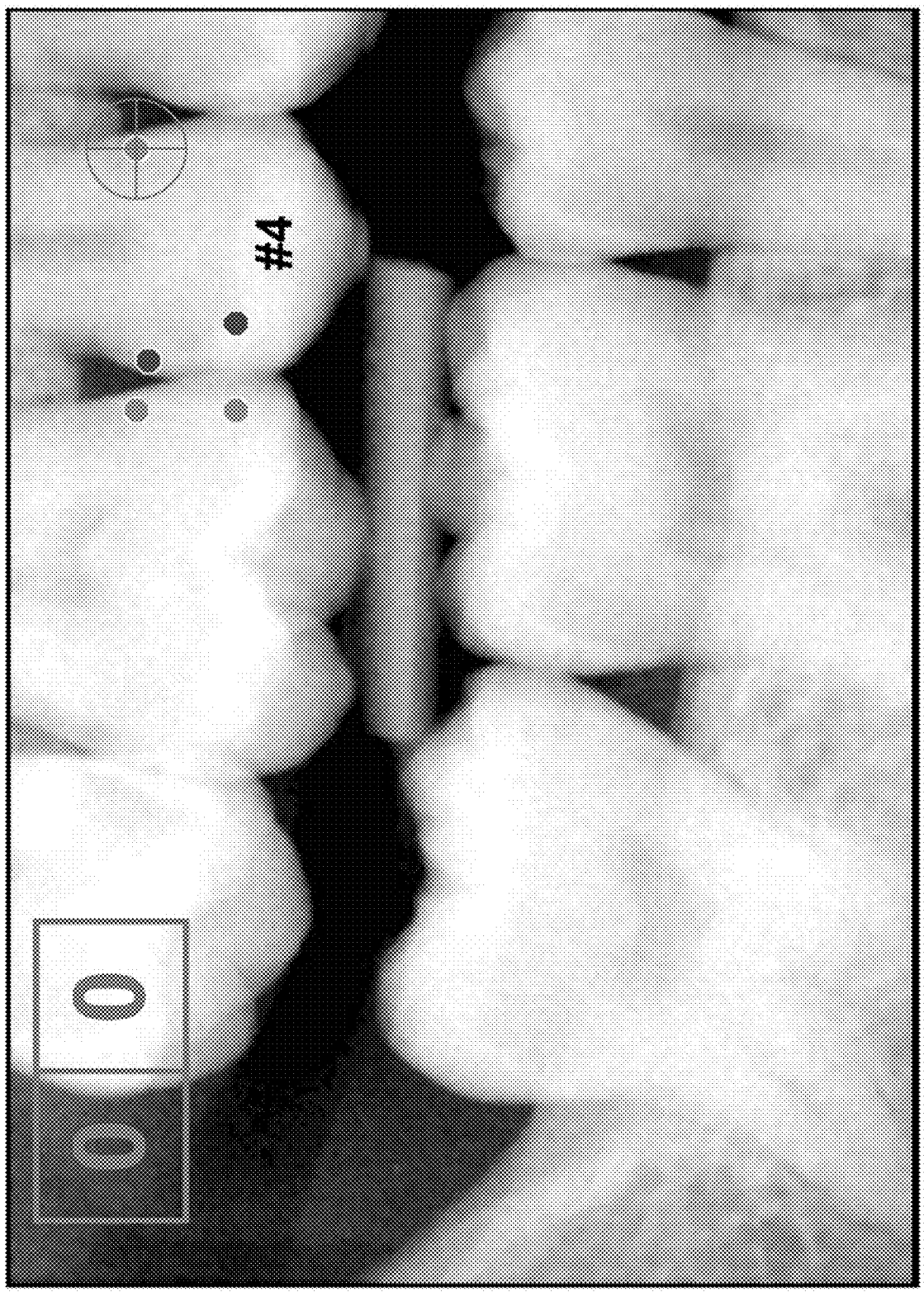
Figure 28:
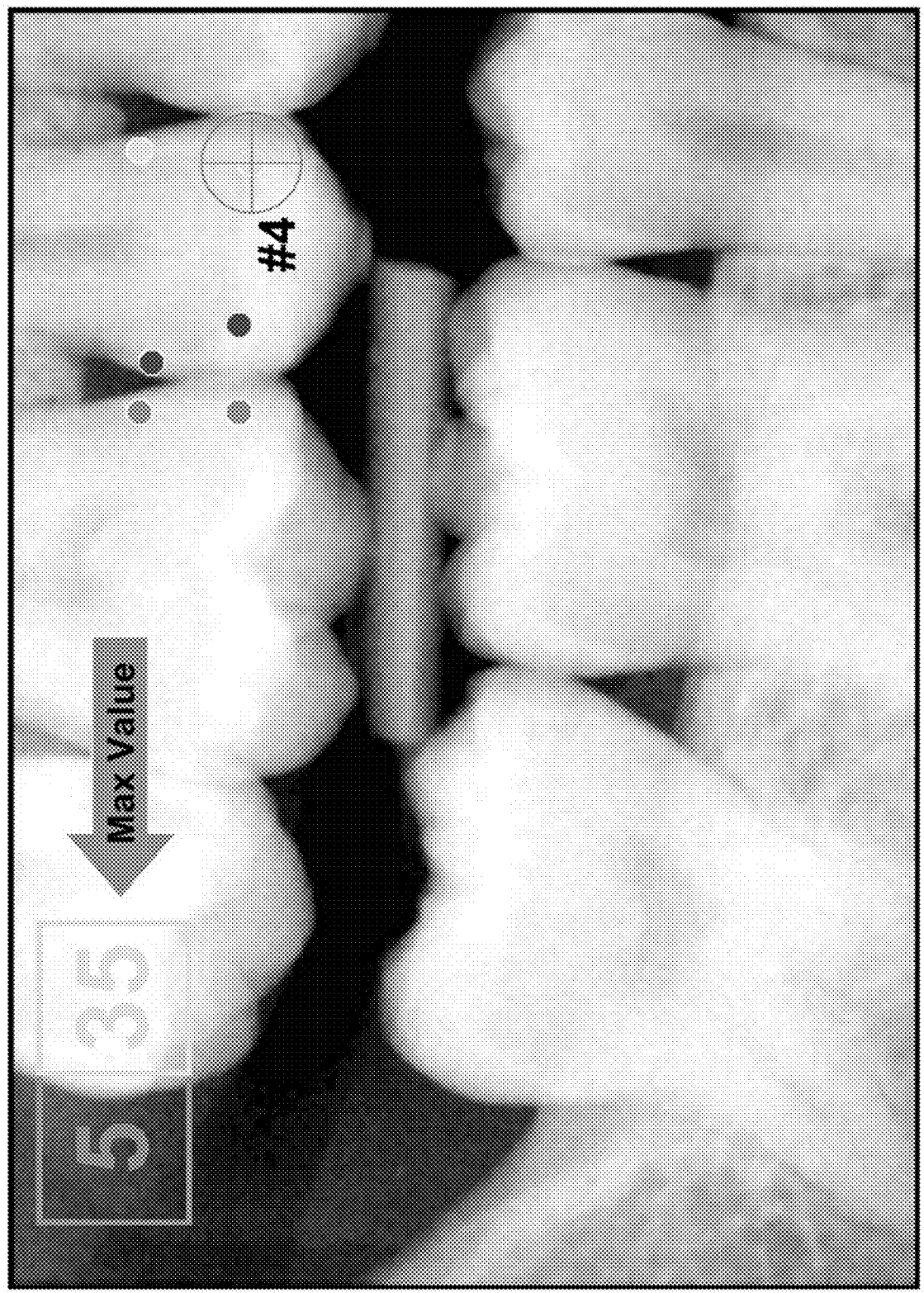
Figure 29:
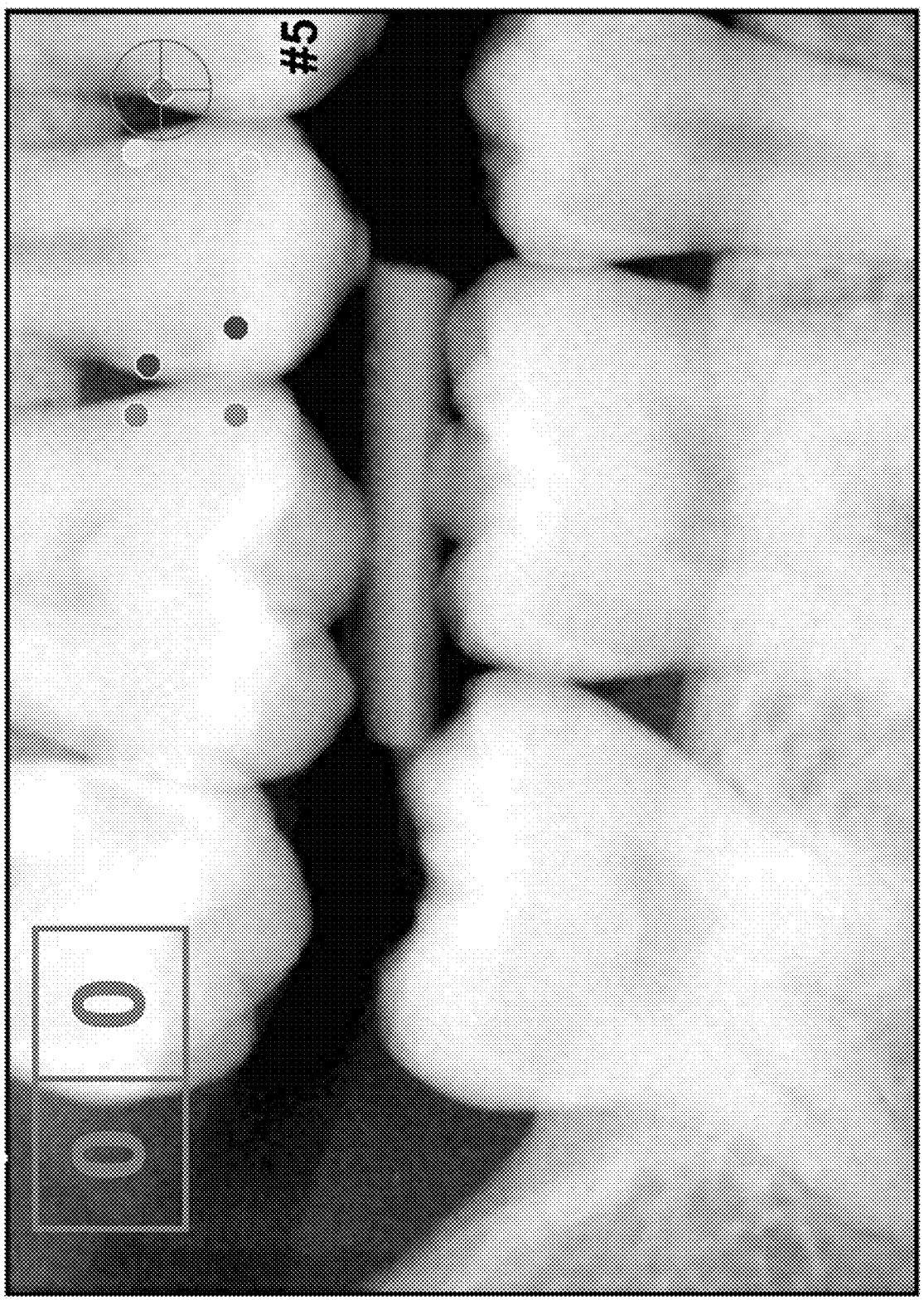
Figure 30:
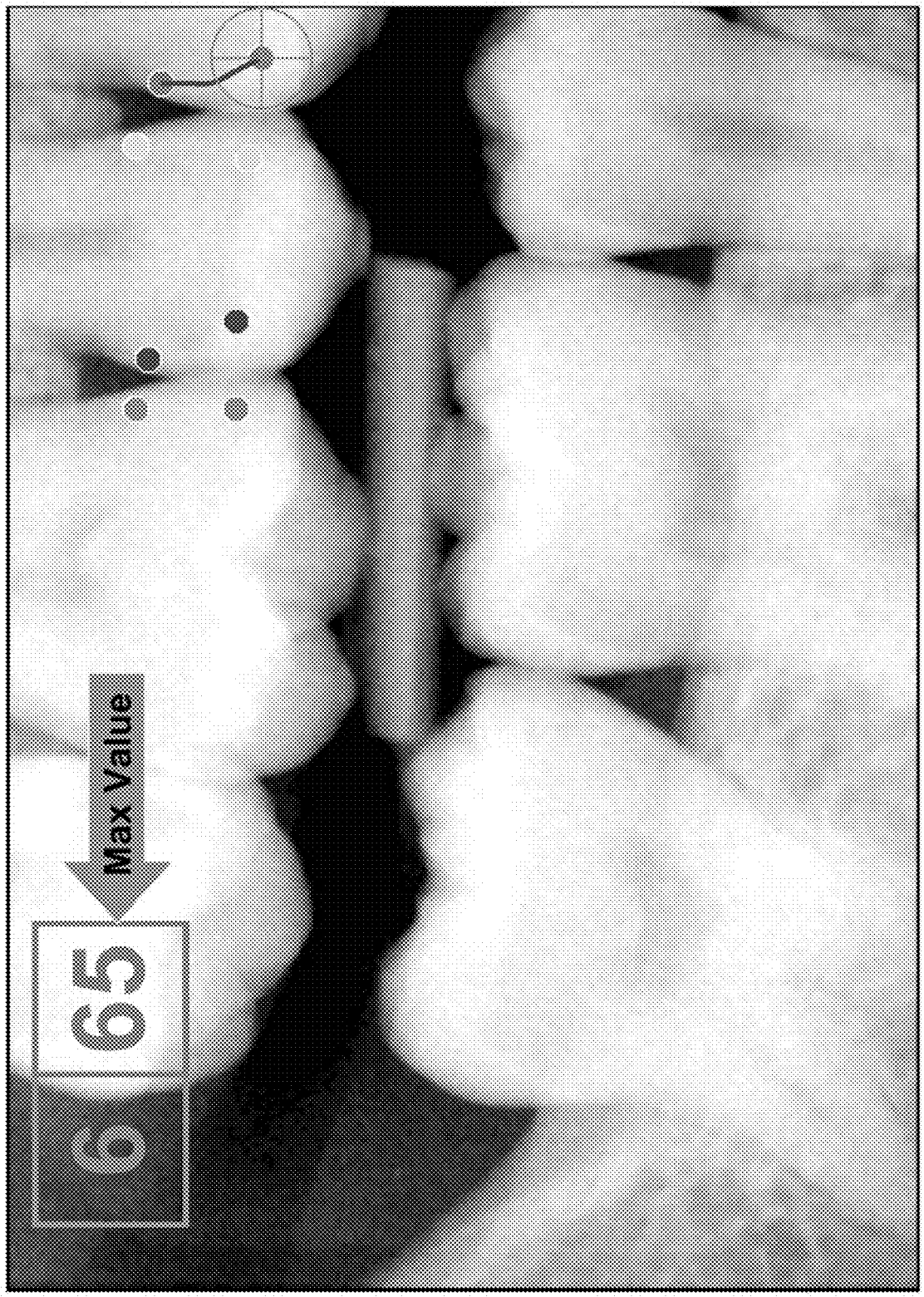
Figure 31:
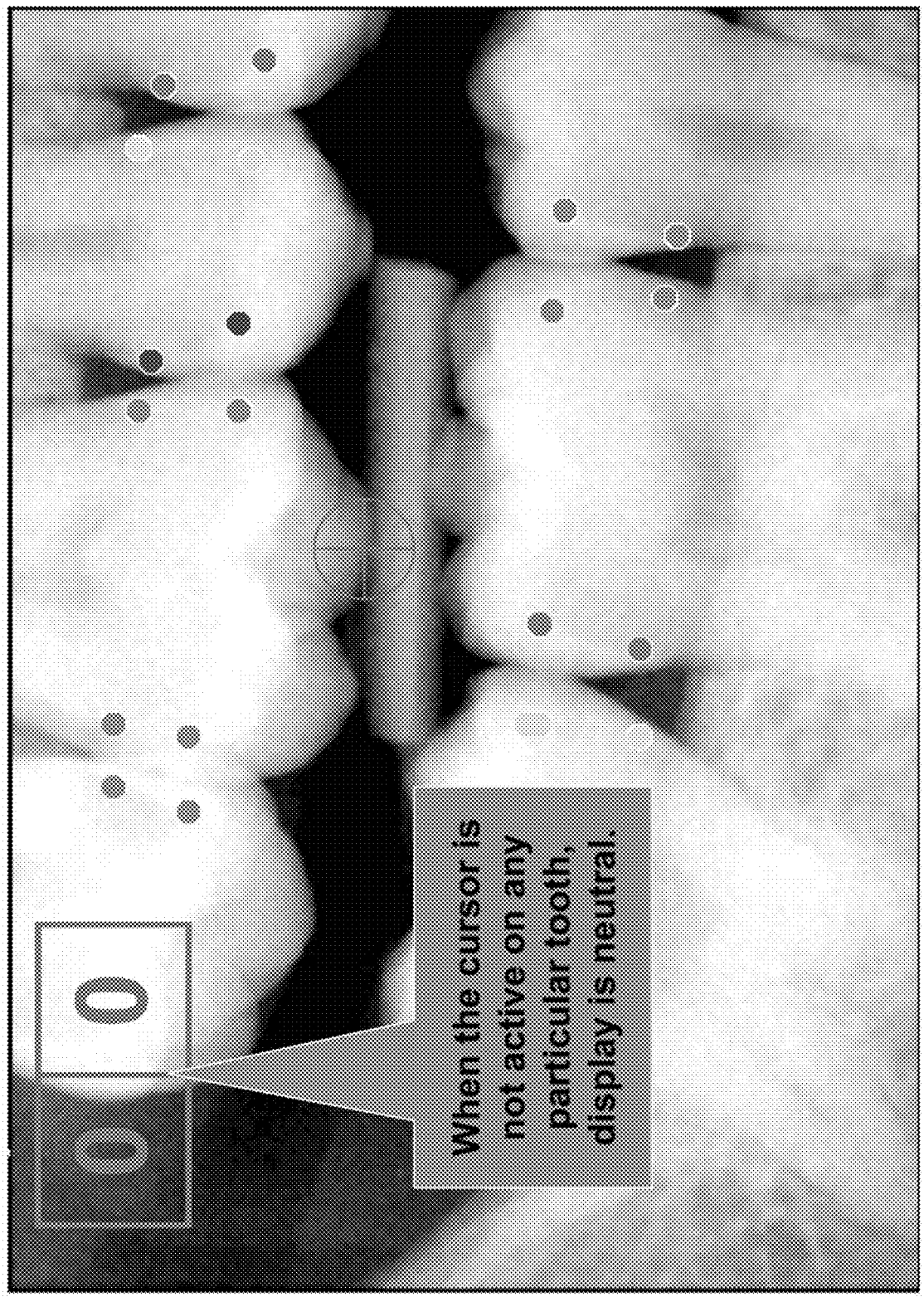
FIGS. 31-38 are images that illustrate results of the analysis indicated in FIGS. 25-30.
Figure 32:
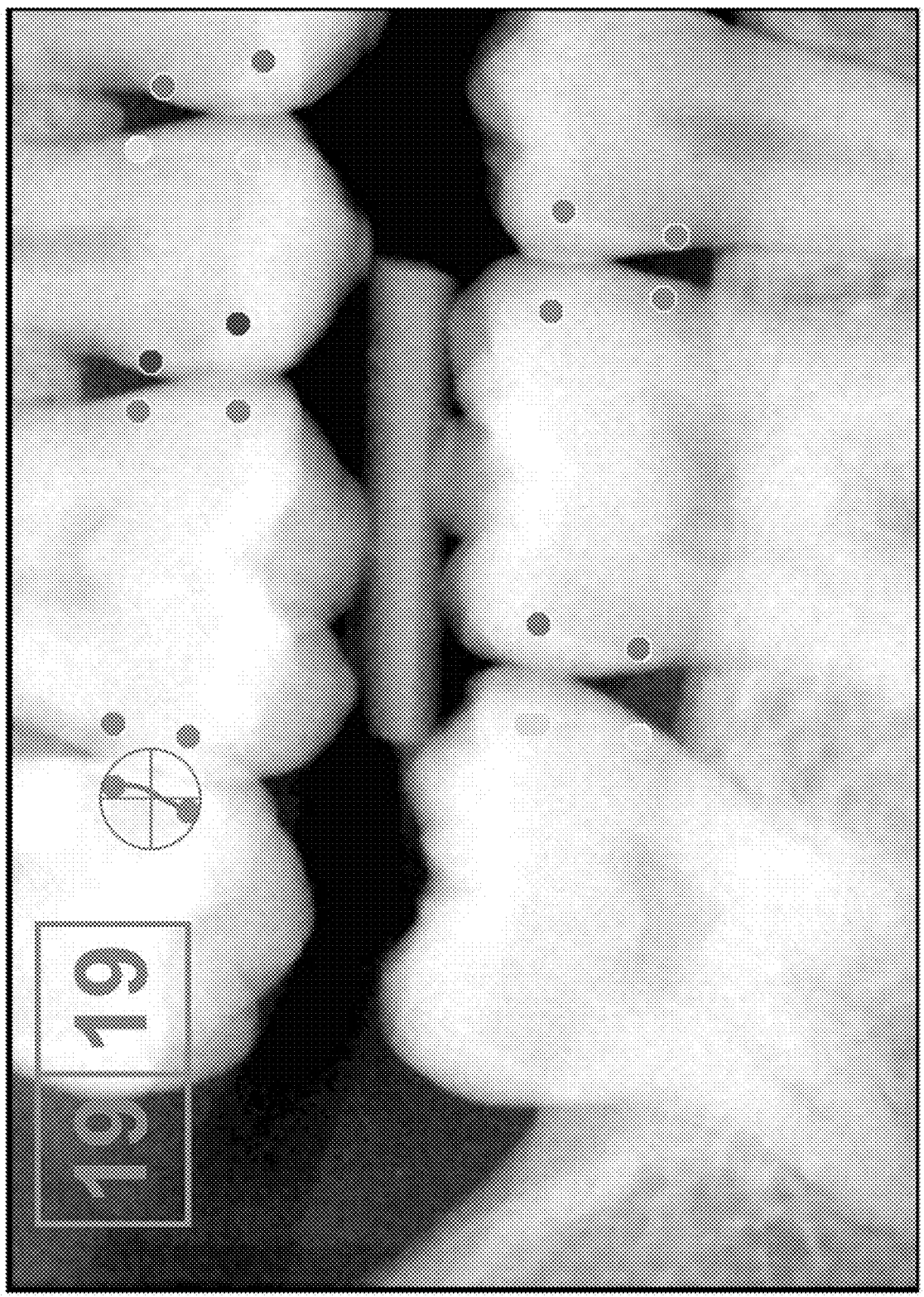
Figure 33:
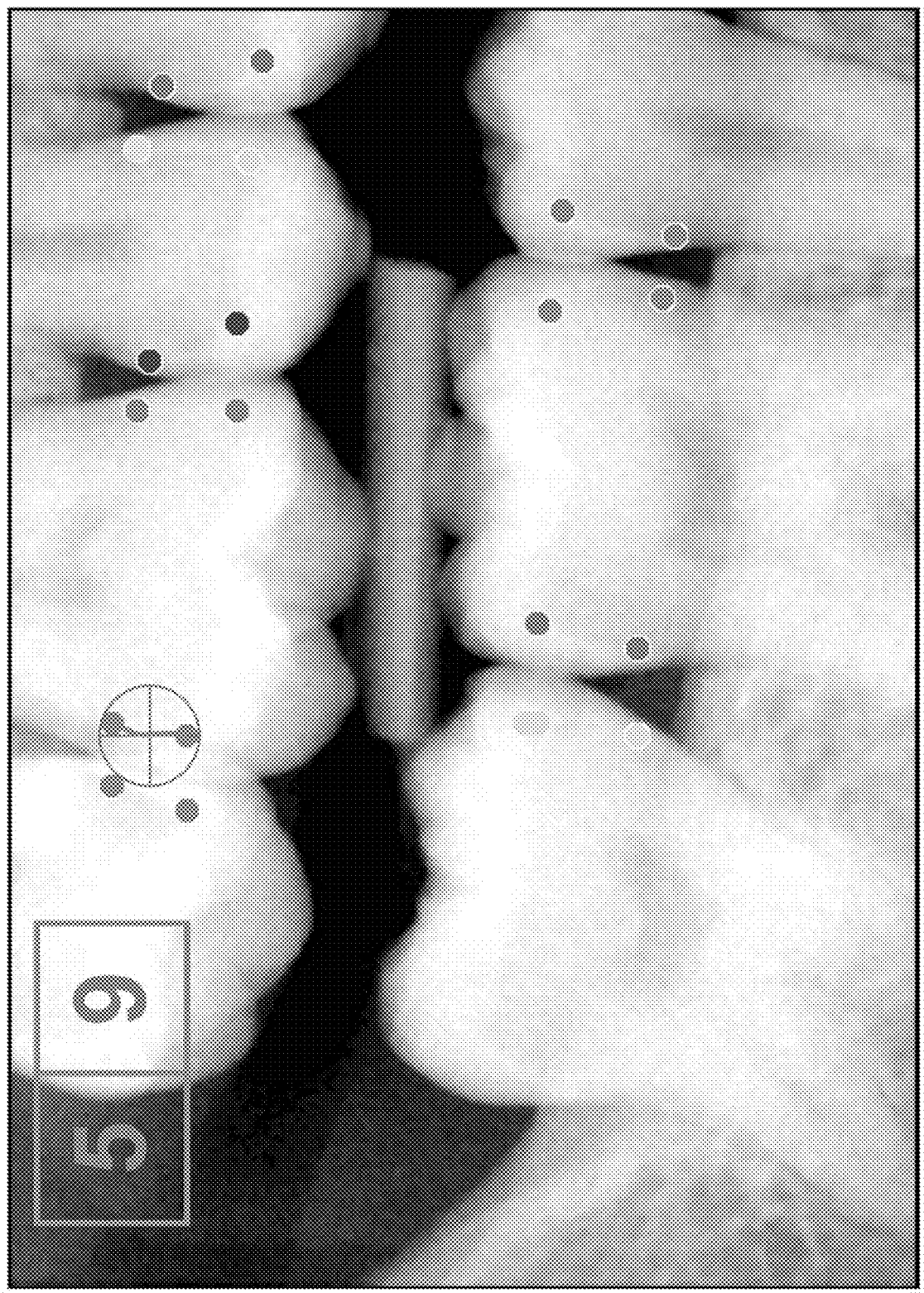
Figure 34:
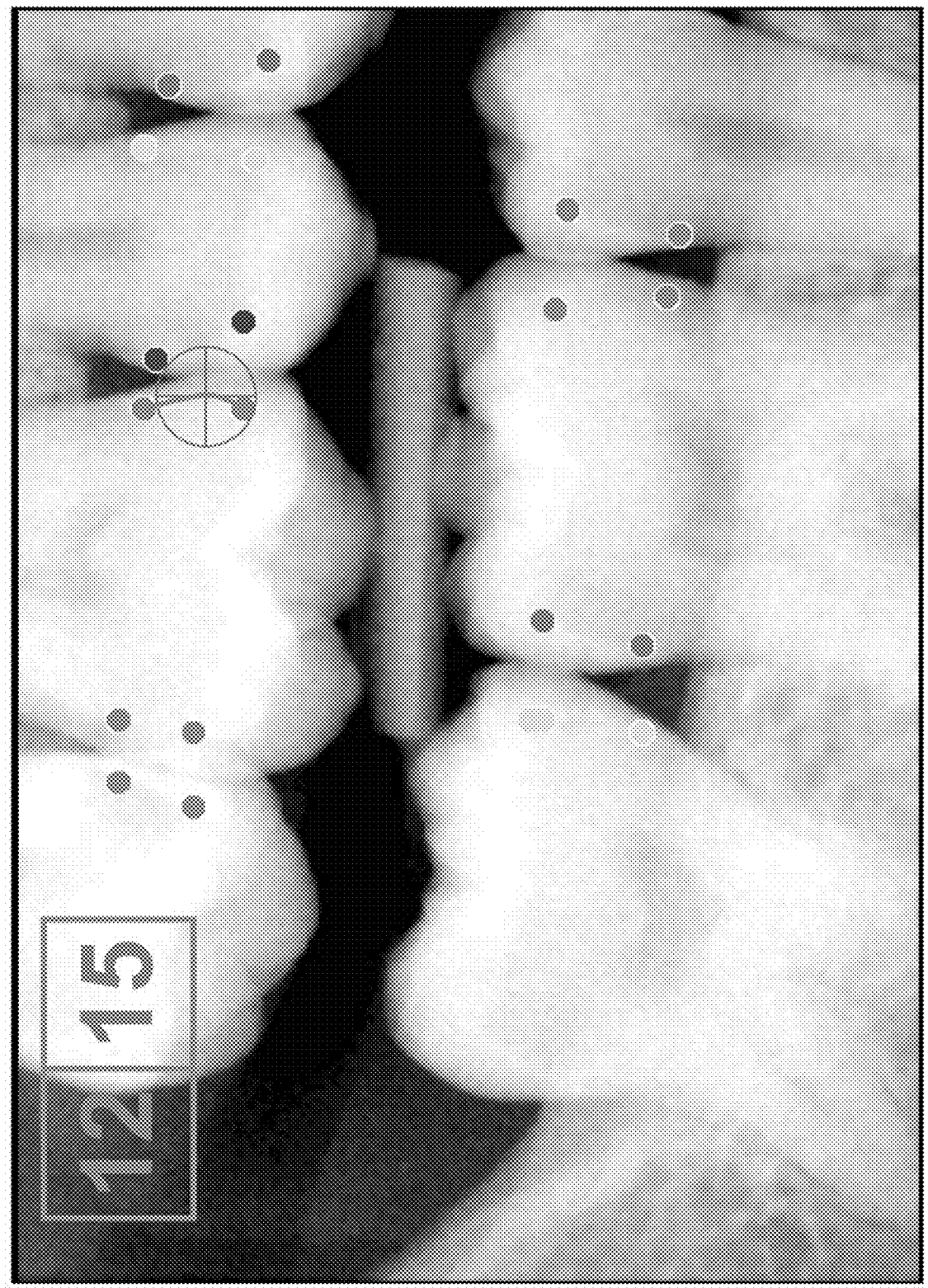
Figure 35:
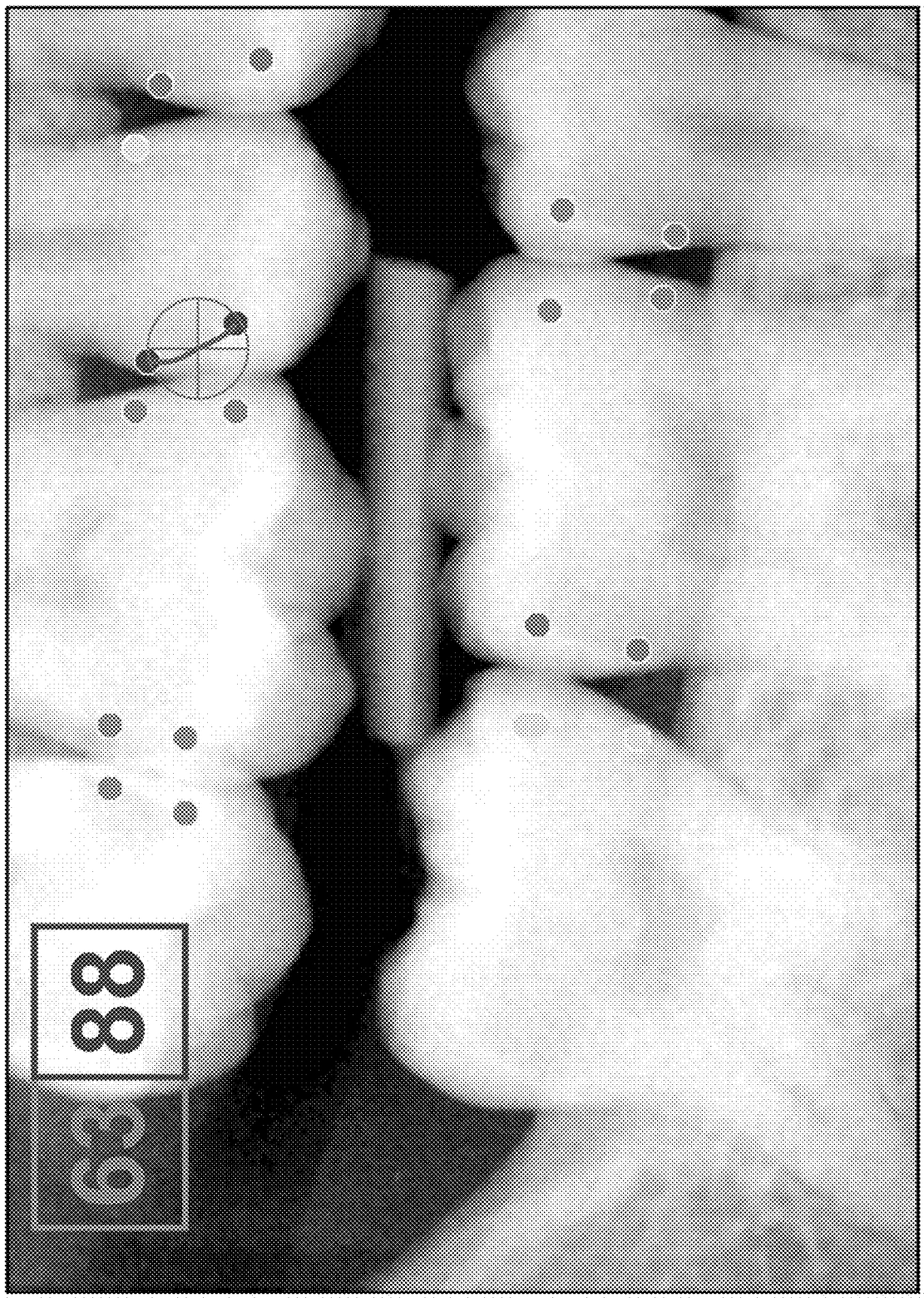
Figure 36:
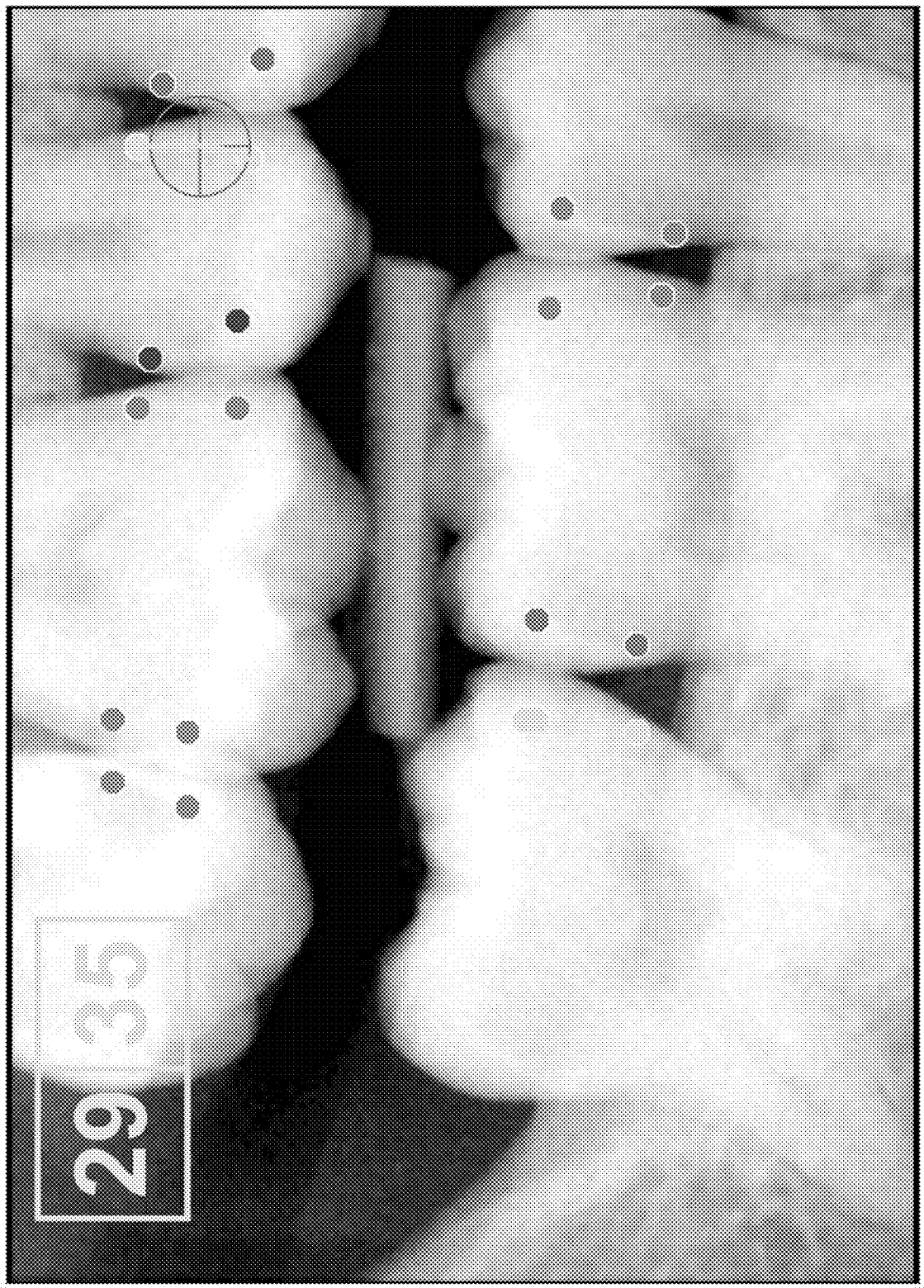
Figure 37:
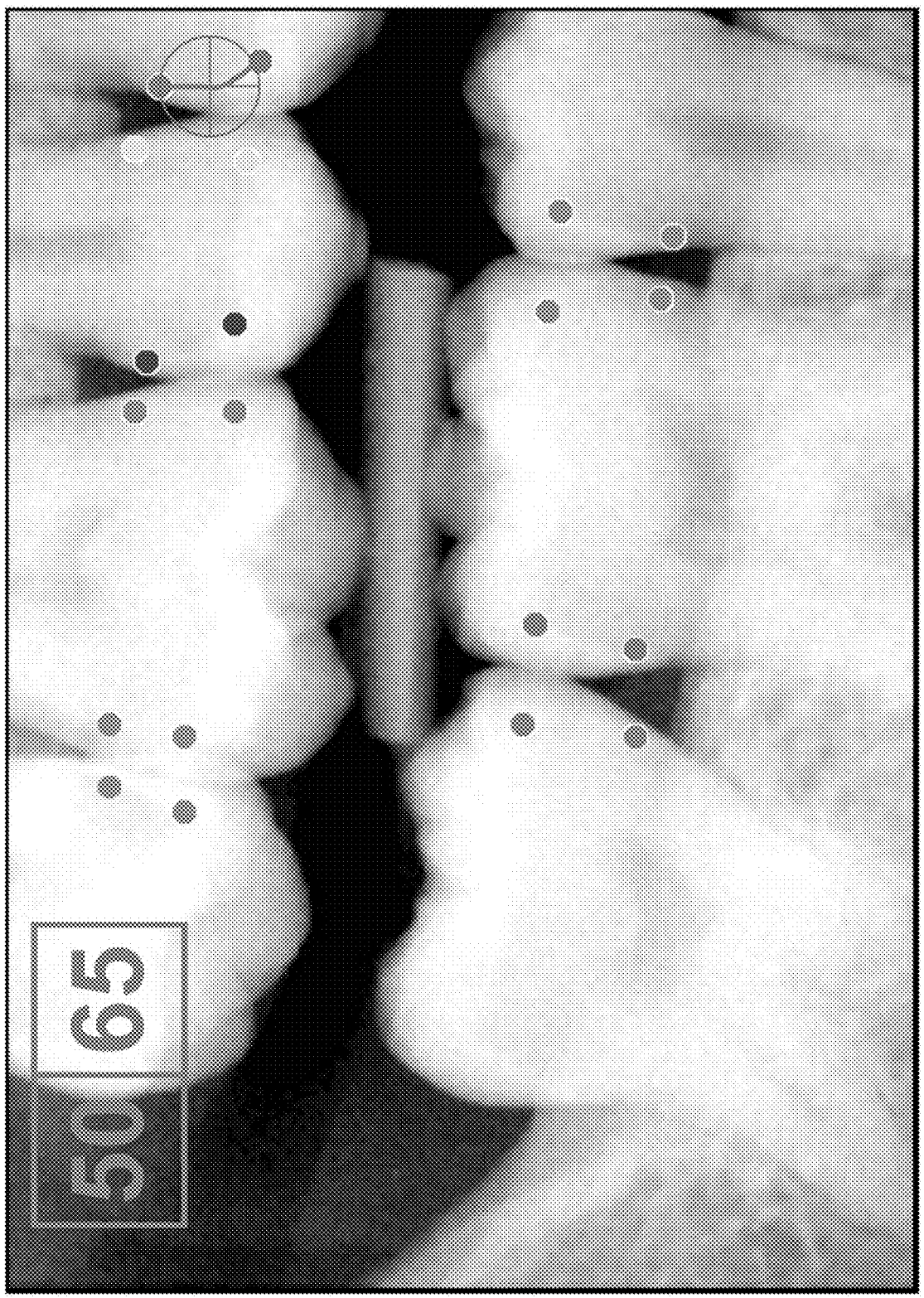

When this procedure is applied to the density curves from a tooth substantially free of decay (as in FIG. 19), integrated values of about zero are obtained (as in FIG. 22). A numerical decay value of zero would indicate that no decay is present. Application of the procedure is illustrated in FIG. 23 for the curves shown in FIG. 20. Integration of the enamel curve yields a value of 90, and integration of the dentin curve yields a value of 0. Dividing the sum of these two values by a scaling factor of 10 yields a numerical decay value of 9, indicating a low probability of decay requiring interventional treatment. Application of the analysis procedure to the density curves of FIG. 21 is illustrated in FIG. 24. An integrated value of 285 is obtained for enamel-borne decay adjacent to the DEJ, while an integration value of 299 is obtained for dentin-borne decay adjacent to DEJ, which is then multiplied by a relative scaling factor of 2 since dentin-borne decay is the more significant decay process. The sum 285+(299×2)=883 is divided by the scaling factor of 10 to obtain a numerical decay value of 88, which indicates highly active decay requiring treatment as soon as possible.

Figure 38:
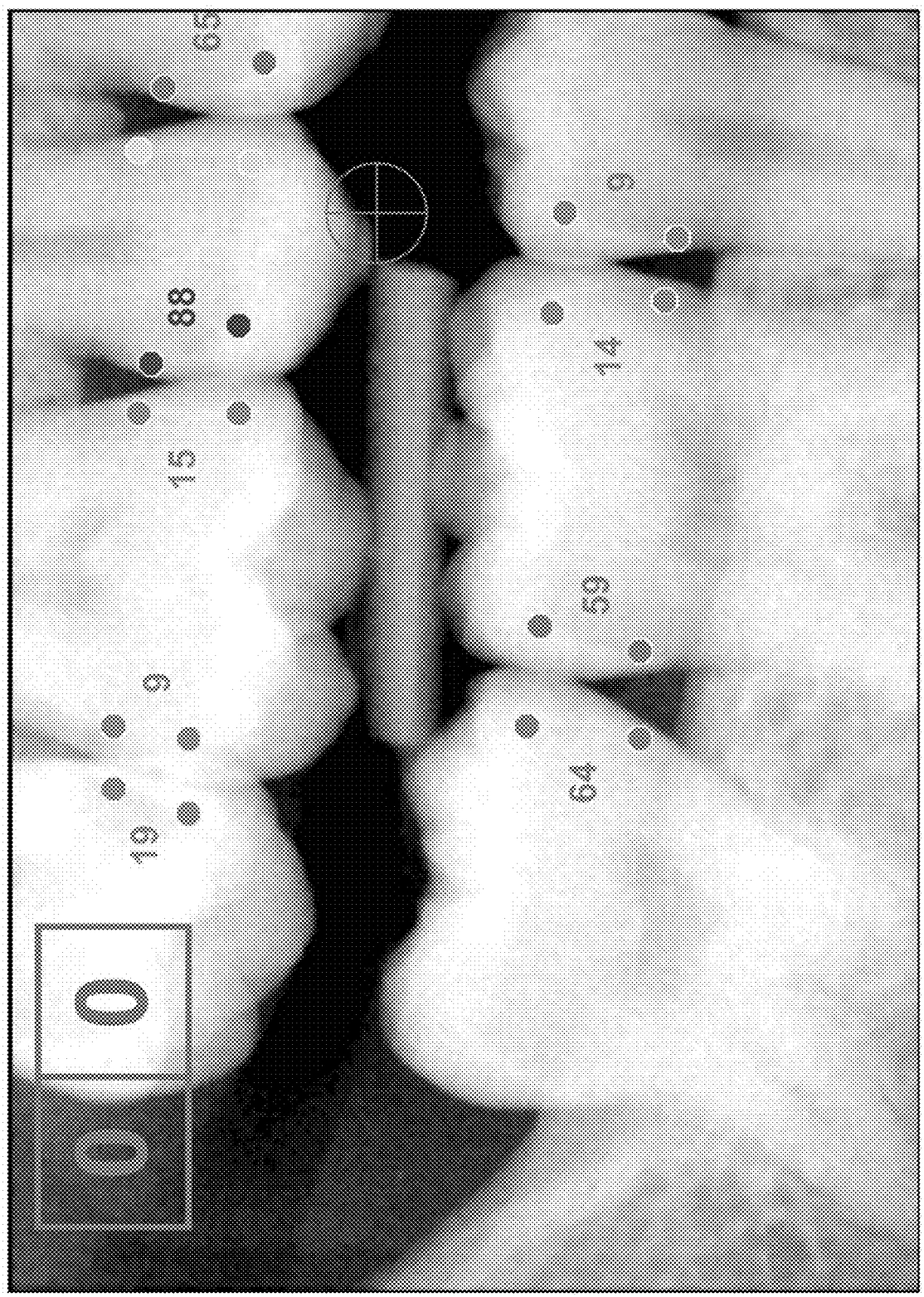
Figure 39:
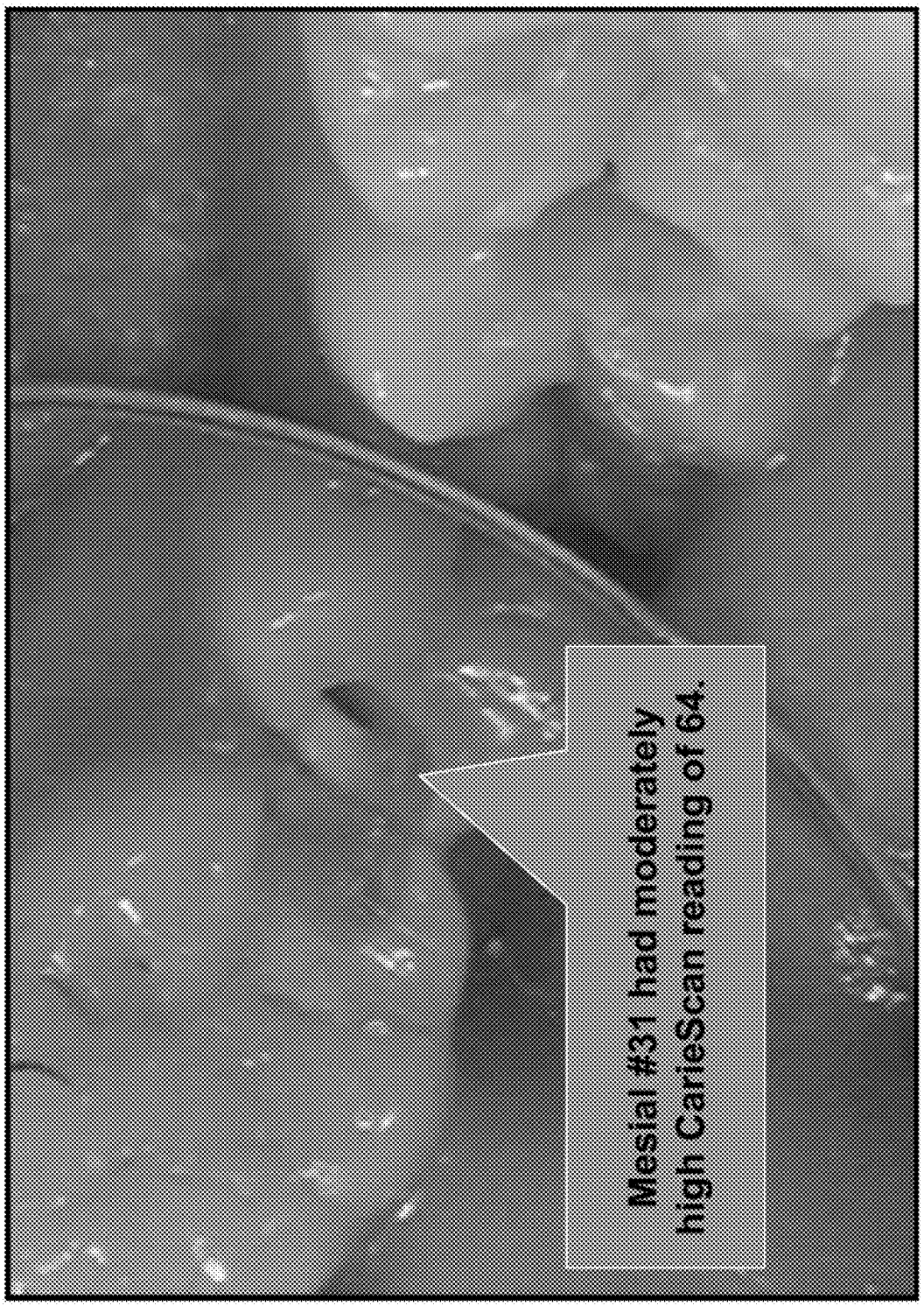
FIGS. 39-42 are photographs and a radiograph illustrating the clinical findings and treatment corresponding to the dental x-ray images of FIGS. 25-30 and the analysis of FIGS. 31-38.
Figure 40:
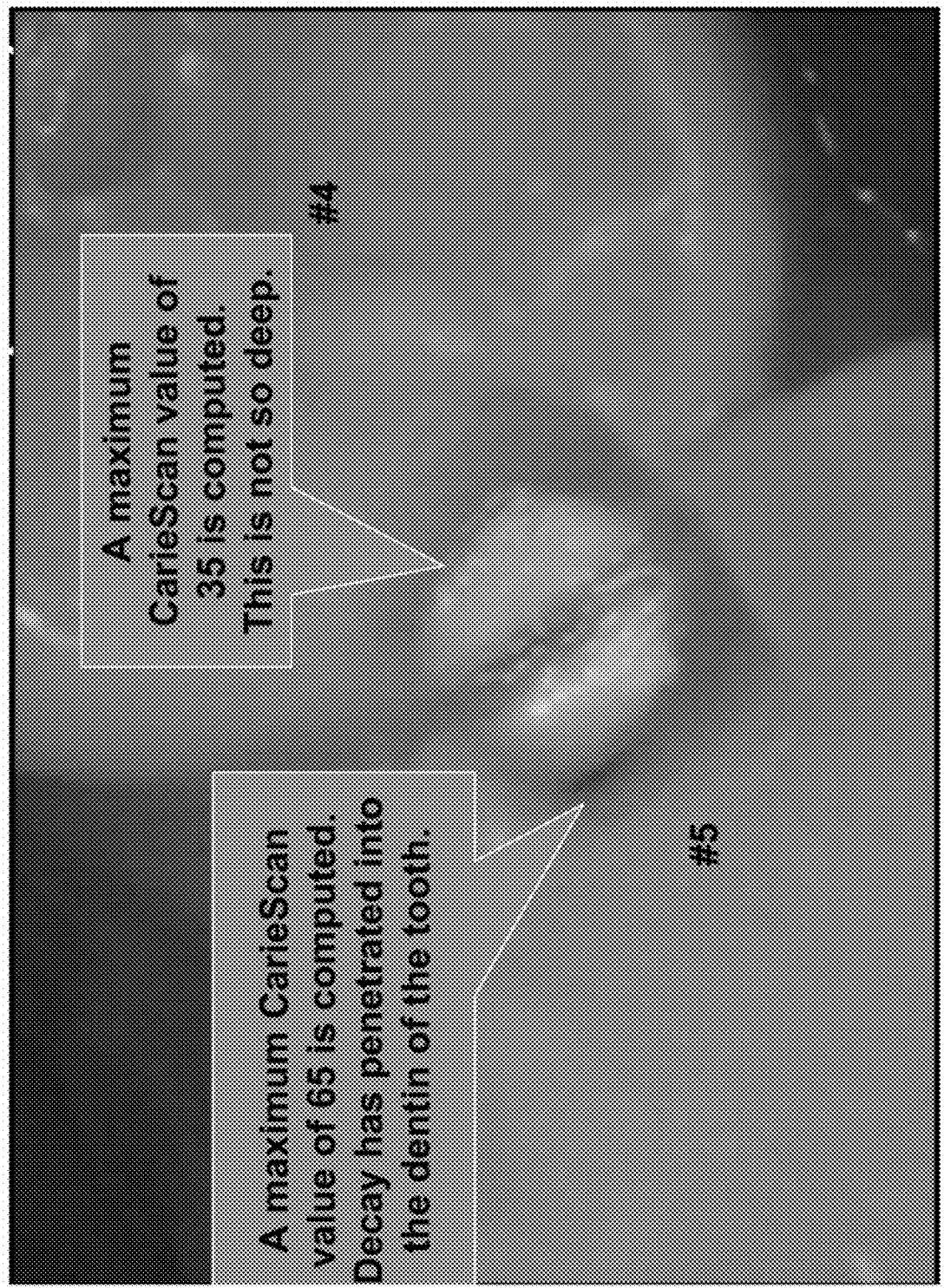
Figure 41:
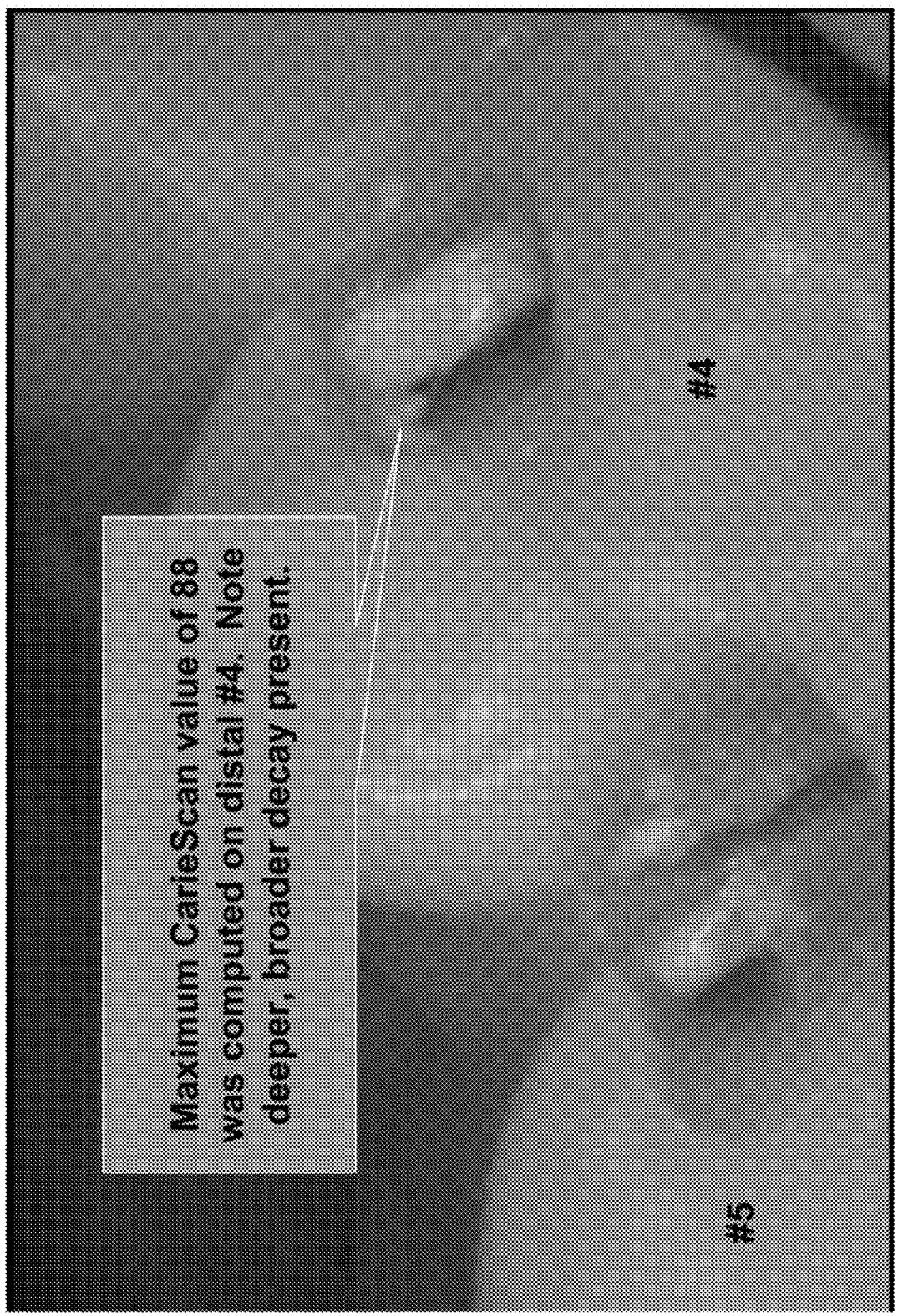
Figure 42:
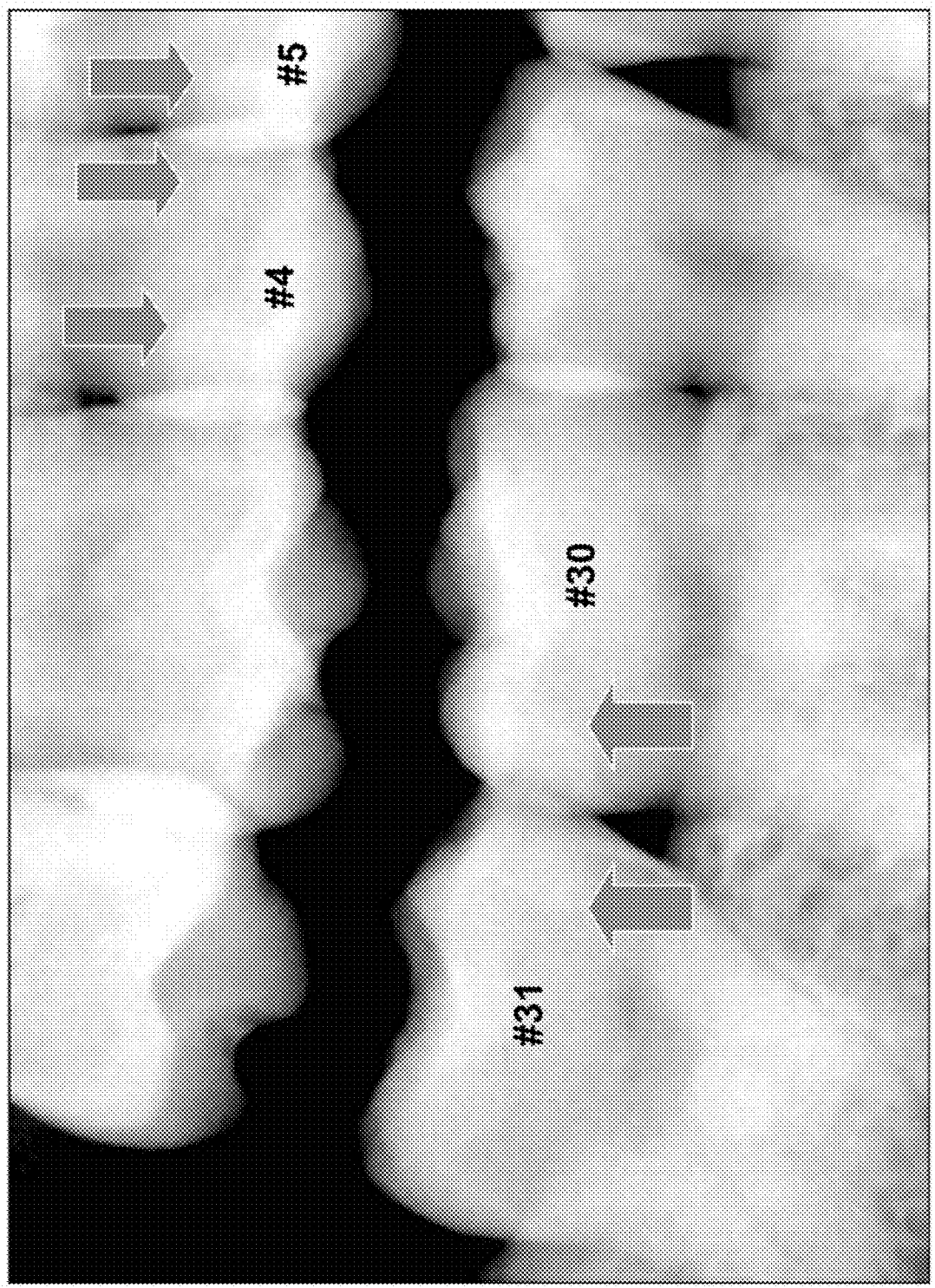
Figure 43:
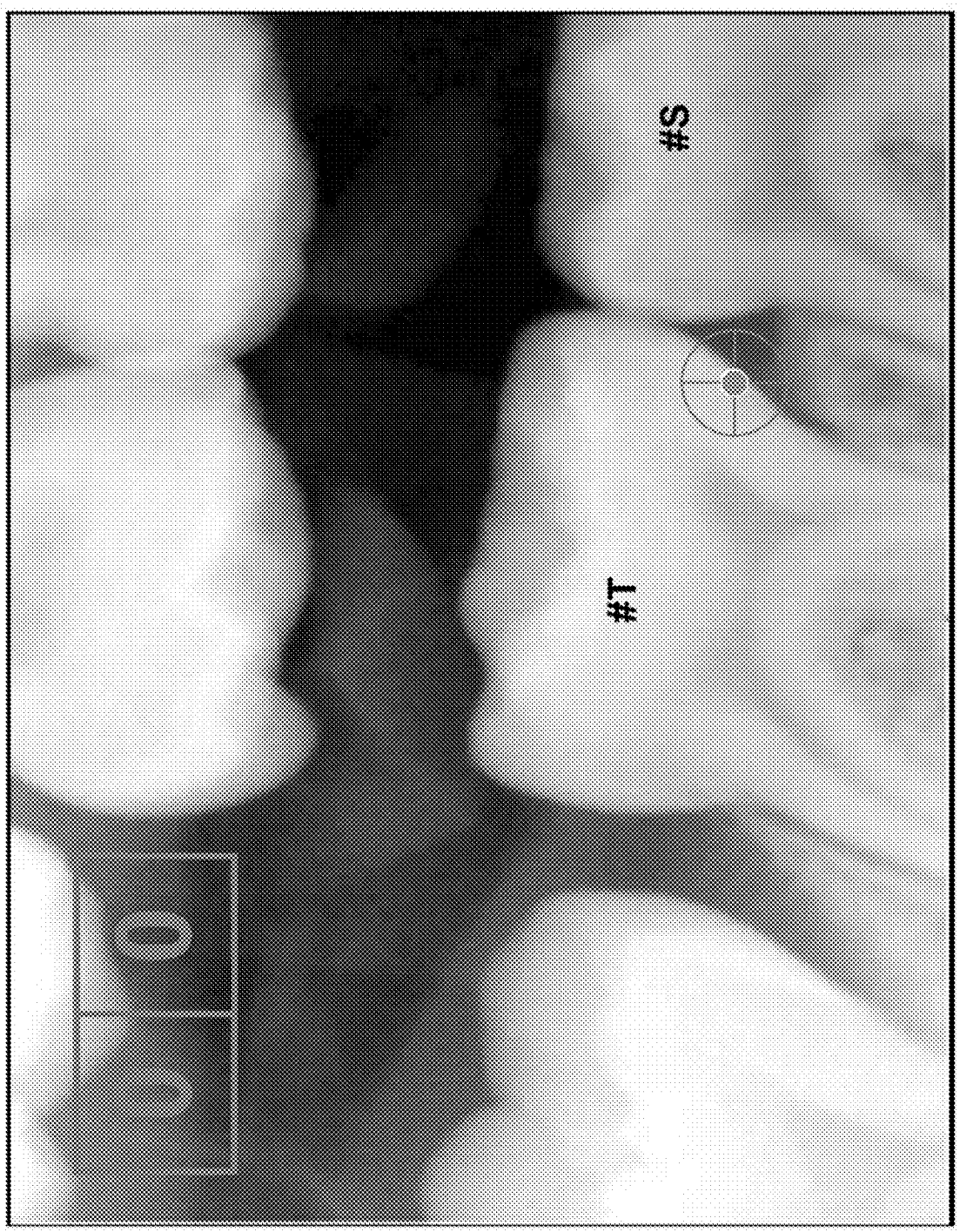
FIGS. 43-51 are images and charts that illustrate selection and analysis of areas of a dental x-ray image.
Figure 44:
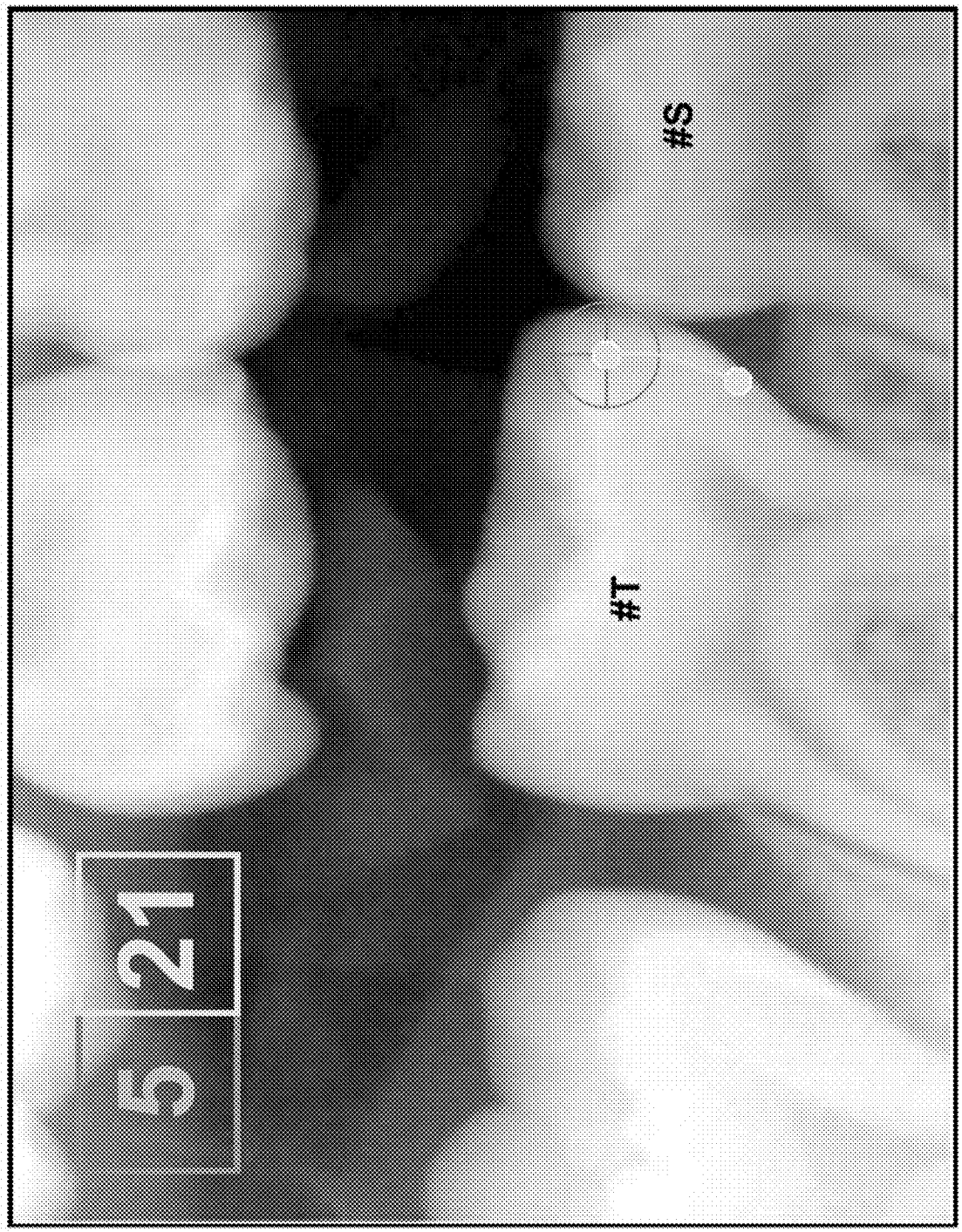
Figure 45:
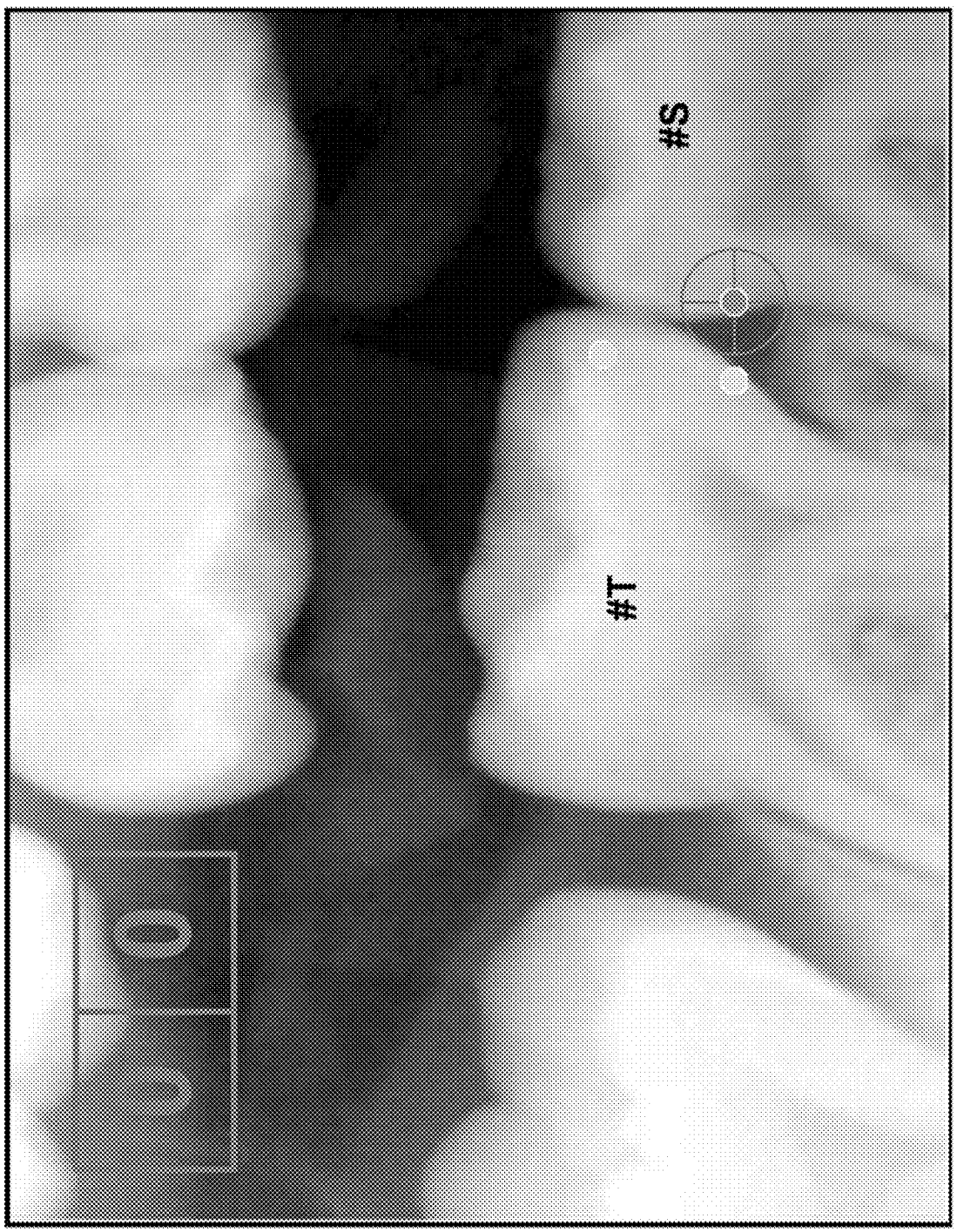
Figure 46:
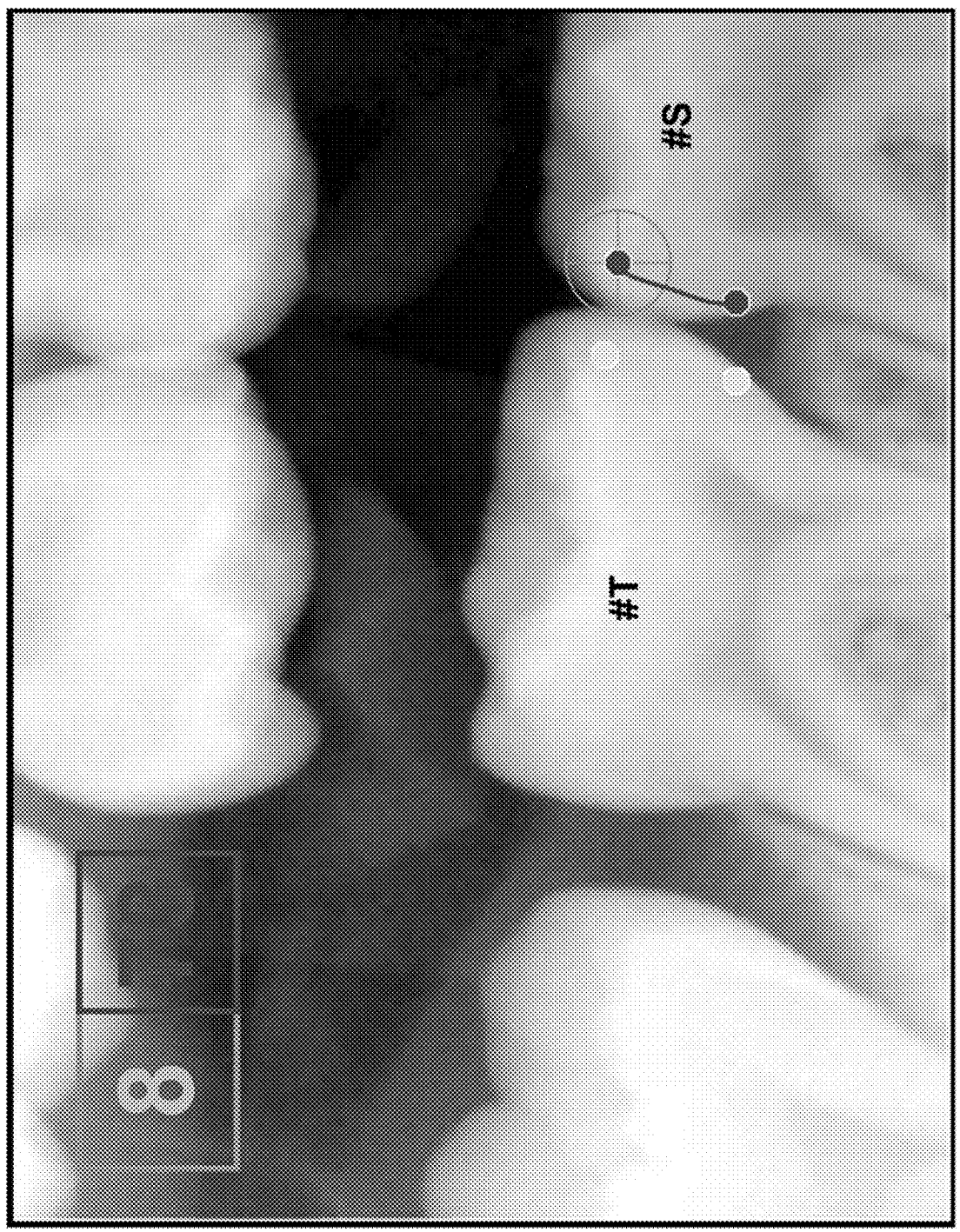
Figure 47:
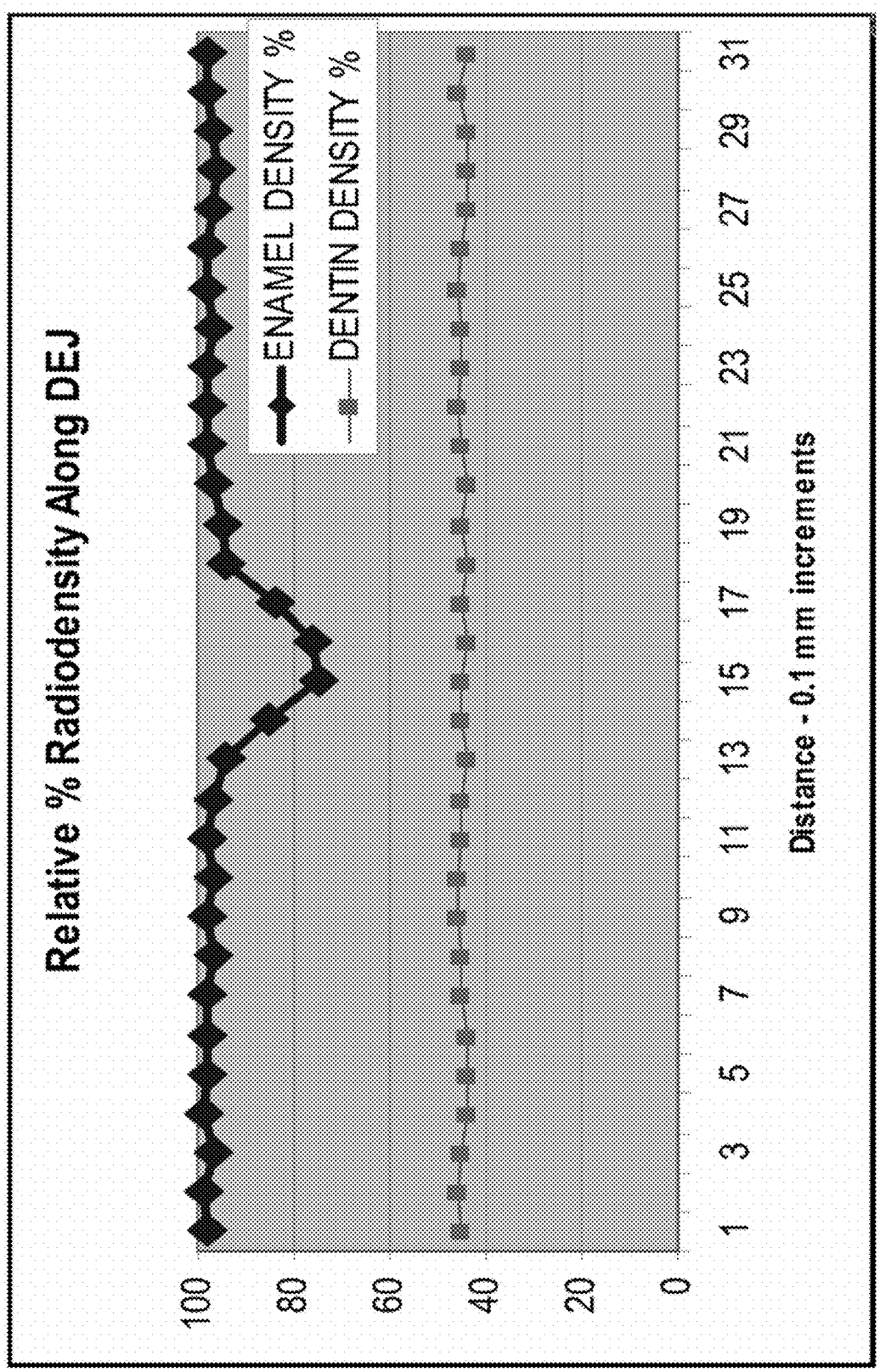
Figure 48:
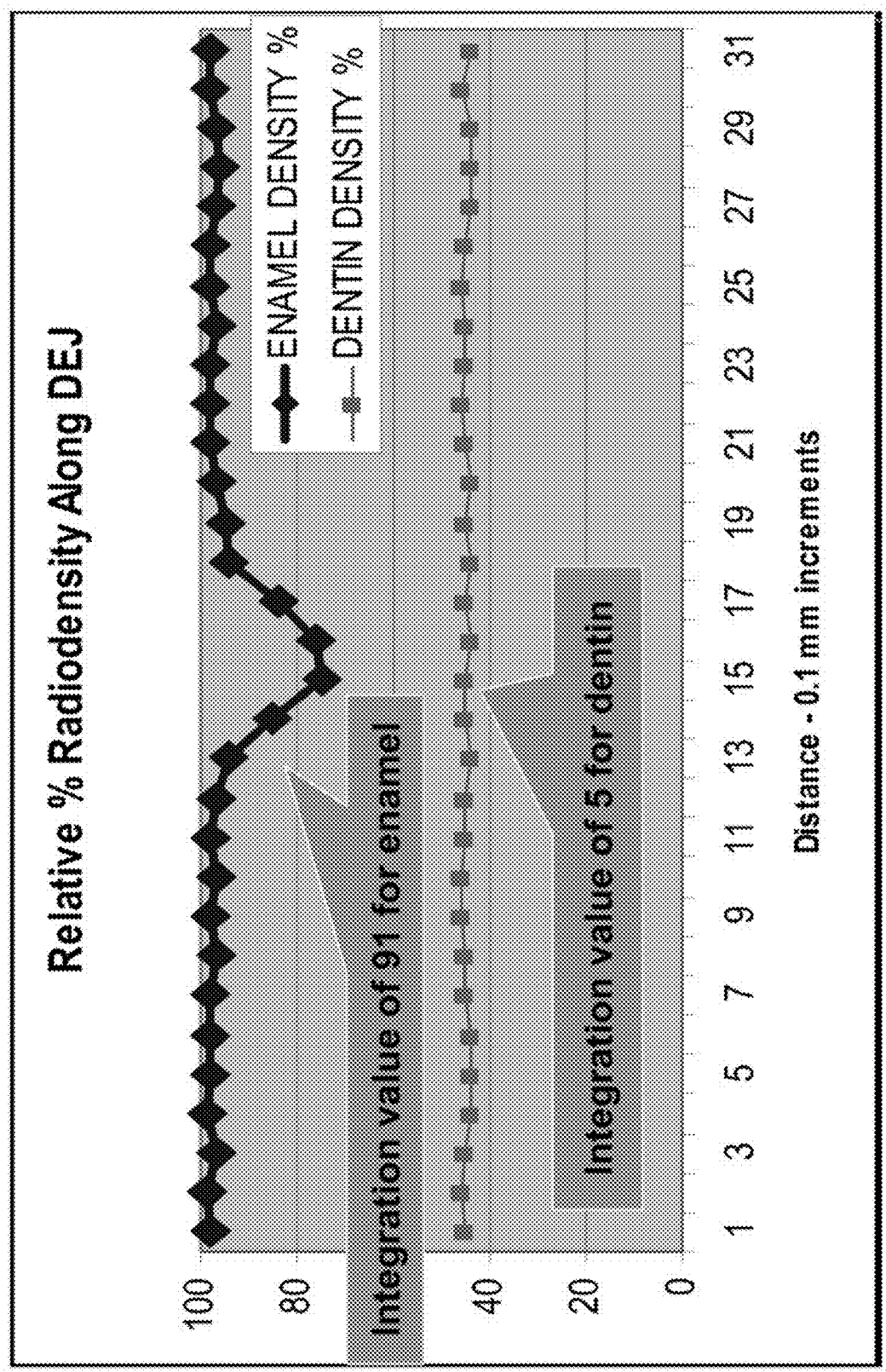
Figure 49:
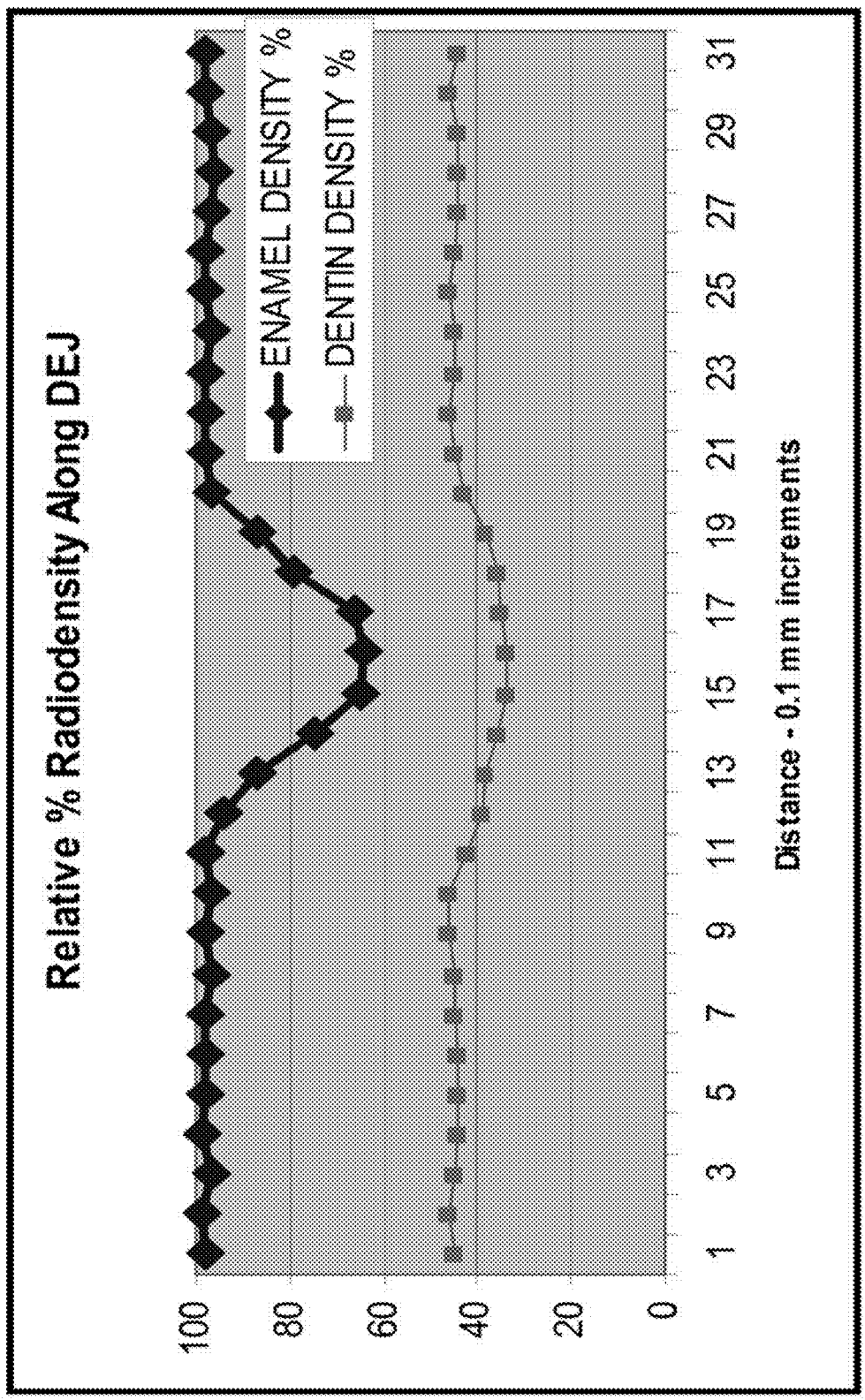
Figure 50:
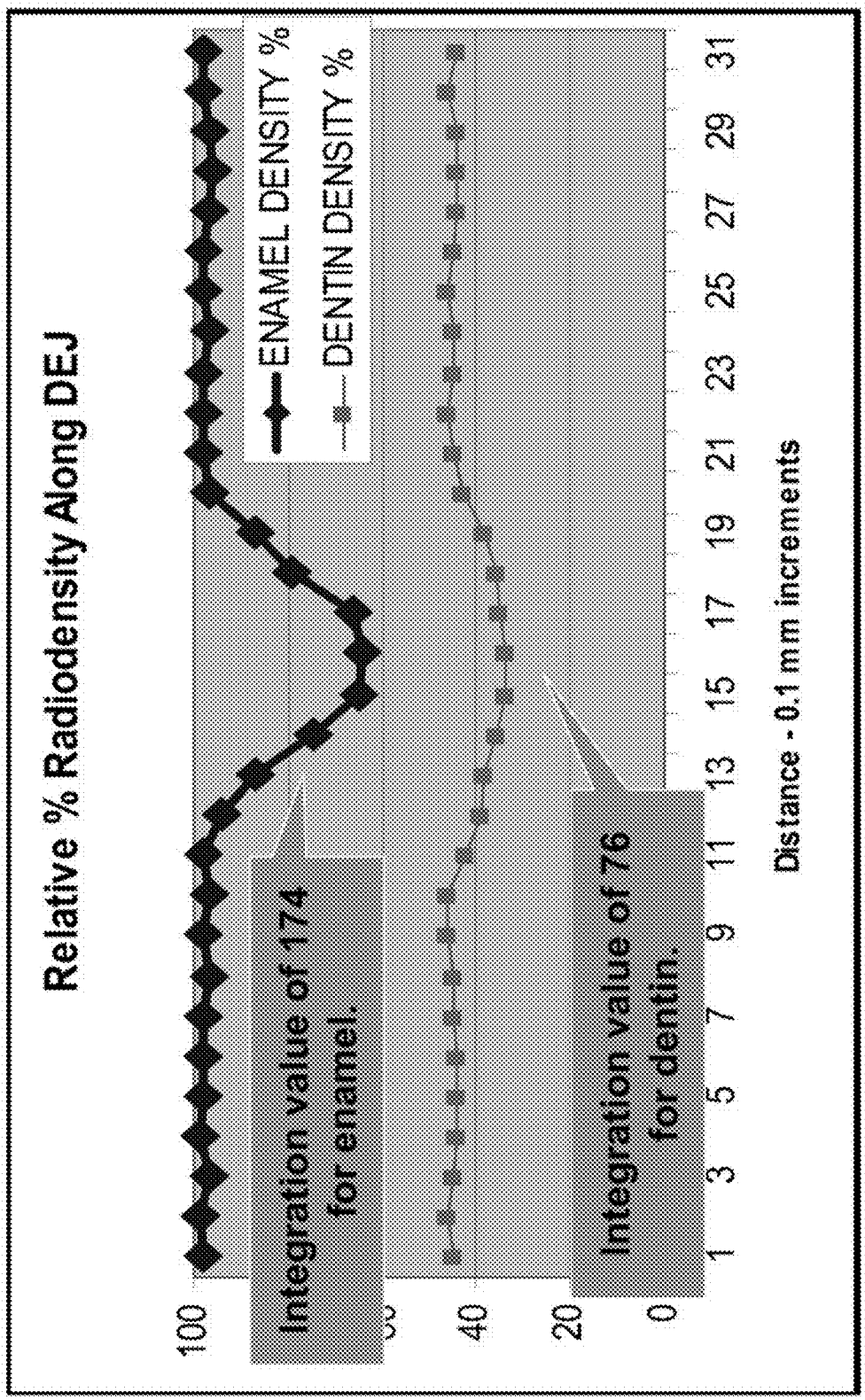
Figure 51:
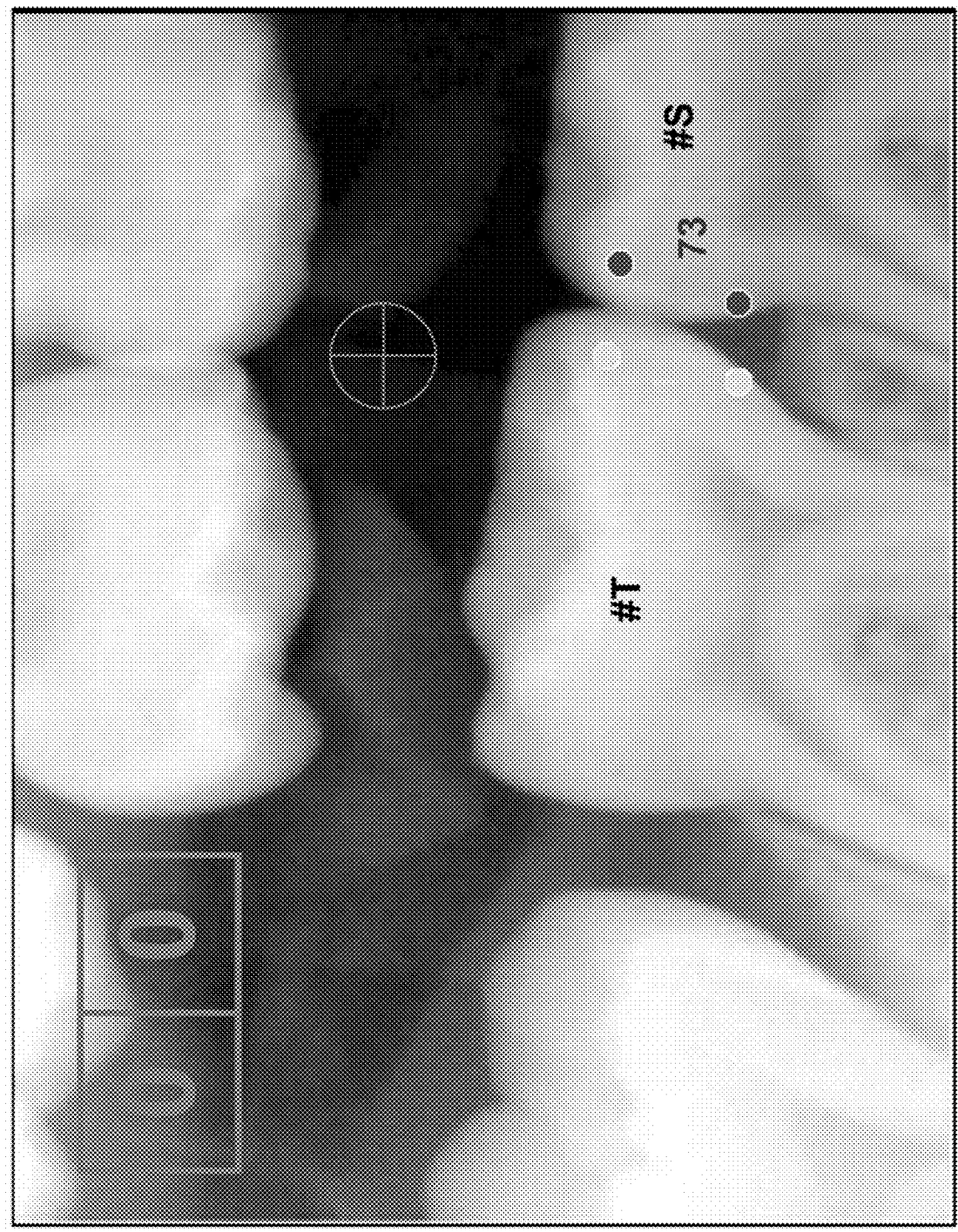

FIGS. 25-30 illustrate a remaining portion of the procedure for analyzing the entire x-ray image. The user clicks twice on each DEJ segment to be analyzed and, upon the second click, the software (in the background and as described hereinabove) locates the DEJ, plots the enamel and dentin densities along contours substantially parallel to and bracketing the DEJ, integrates any dips in the plots, calculates numerical decay values as a function of position along the DEJ, and displays the local numerical value (in the left display box) and the maximum numerical decay value (right display box). This is repeated for each DEJ segment to be analyzed. Once the desired DEJ segments have been marked and analyzed, the user may move the cursor over the image to display the numerical decay values obtained, as in FIGS. 31-37. Functionality may be added for enabling display of maximum numerical decay values for each analyzed DEJ segment, as shown in FIG. 38. Based on the maximum numerical decay values calculated, it is determined that #4, #5, #30, and #31 are in need of treatment. The actual clinical findings and treatment are illustrated in FIGS. 39-42.

It should be noted that the specific numerical values obtained upon integration of the areas of any dips in the density curves are unit-dependent. Appropriate weighting and scaling factors are chosen, based at least in part on the units employed in the optical density plots, to yield numerical decay values falling within a desired range of values. Any suitable unit and scaling scheme may be employed and shall fall within the scope of the present disclosure.

Each tooth has a specific decay pattern, influenced by tooth location, enamel thickness, enamel geometry, adult versus pediatric teeth, and so forth. The software algorithm may be adapted to account for such influences. For example, weighting or scaling factors may differ depending on these various influences so as to accordingly alter the calculated numerical decay values. Such influences may be incorporated by manual identification (tooth number, patient age, DEJ contour, and so on manually entered by user), or may be incorporated automatically by the software through optical pattern recognition, edge detection of all or part of DEJ, previously measured and stored calibration standards, statistical analysis, or through other means.

Figure 52:
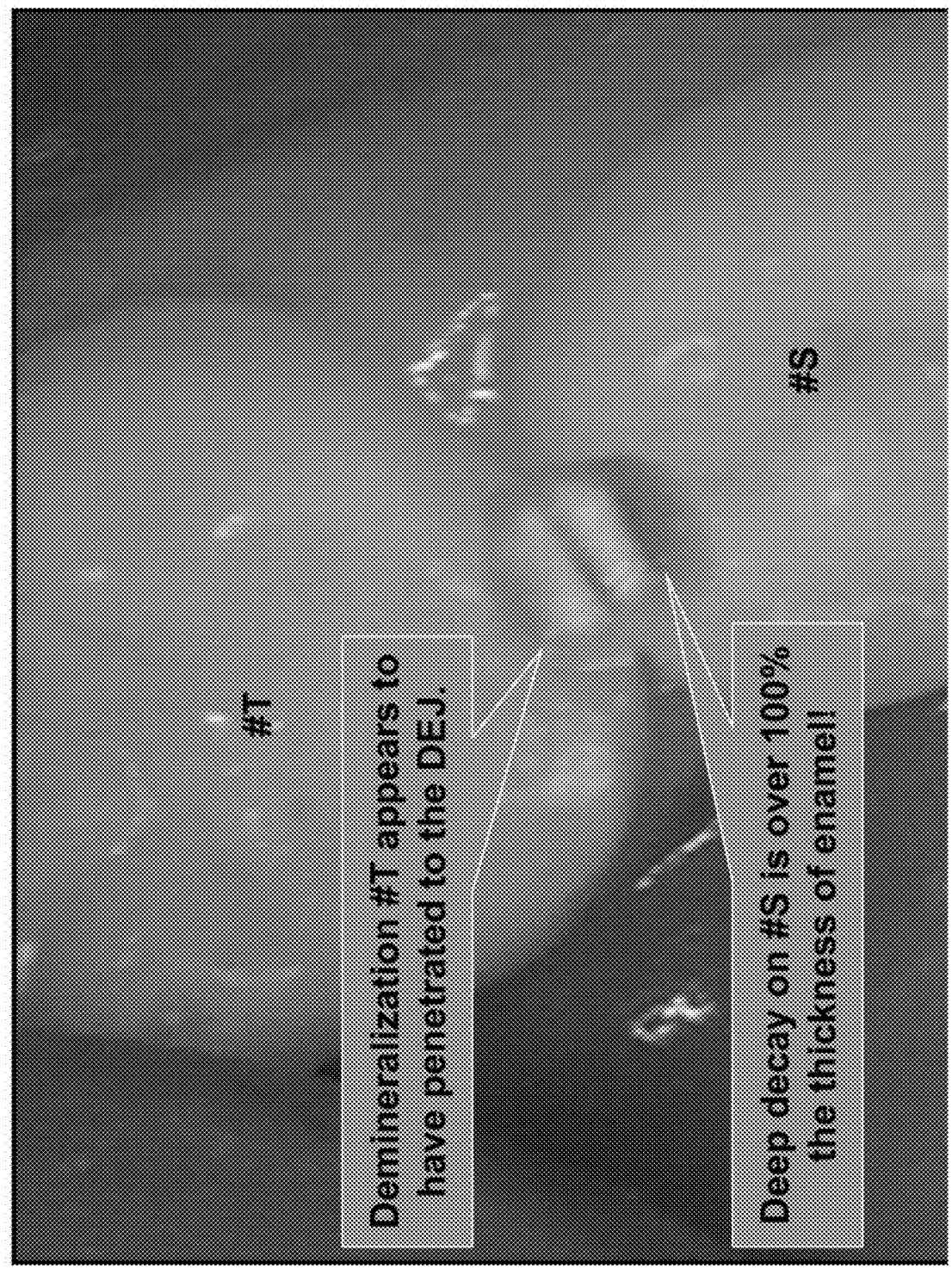
FIG. 52 is a photograph illustrating the clinical findings and treatment corresponding to the dental x-ray images and analysis of FIGS. 43-51.

An example of analysis of an x-ray of pediatric teeth is illustrated in FIGS. 43-51. Different scaling factors of 2 and 5 are used for multiplying the integrated areas of the enamel and dentin traces, respectively. These larger factors reflect the smaller size and thinner enamel characteristic of pediatric teeth, and the need for earlier detection and intervention. From the traces for #S is calculated (174×2+76×5)/10=73, and for #T is calculated (91×2+5×5)/10=21. Different levels may be assigned for color coding or audible alarms for pediatric teeth versus adult teeth. For example, for pediatric teeth: i) green indicates decay that has not yet penetrated through enamel; ii) yellow indicates decay that has penetrated through enamel to level of dentin less than about 0.25 mm or less than about 50% of enamel thickness; iii) orange indicates decay that has penetrated into dentin greater than about 0.25 mm and less than about 0.5 mm or greater than about 50% and less than about 100% of enamel thickness; and iv) red indicates decay that has penetrated into the dentin more than about 0.5 mm or more than about 100% of enamel thickness. The corresponding clinical presentation is shown in FIG. 52.

Figure 53:
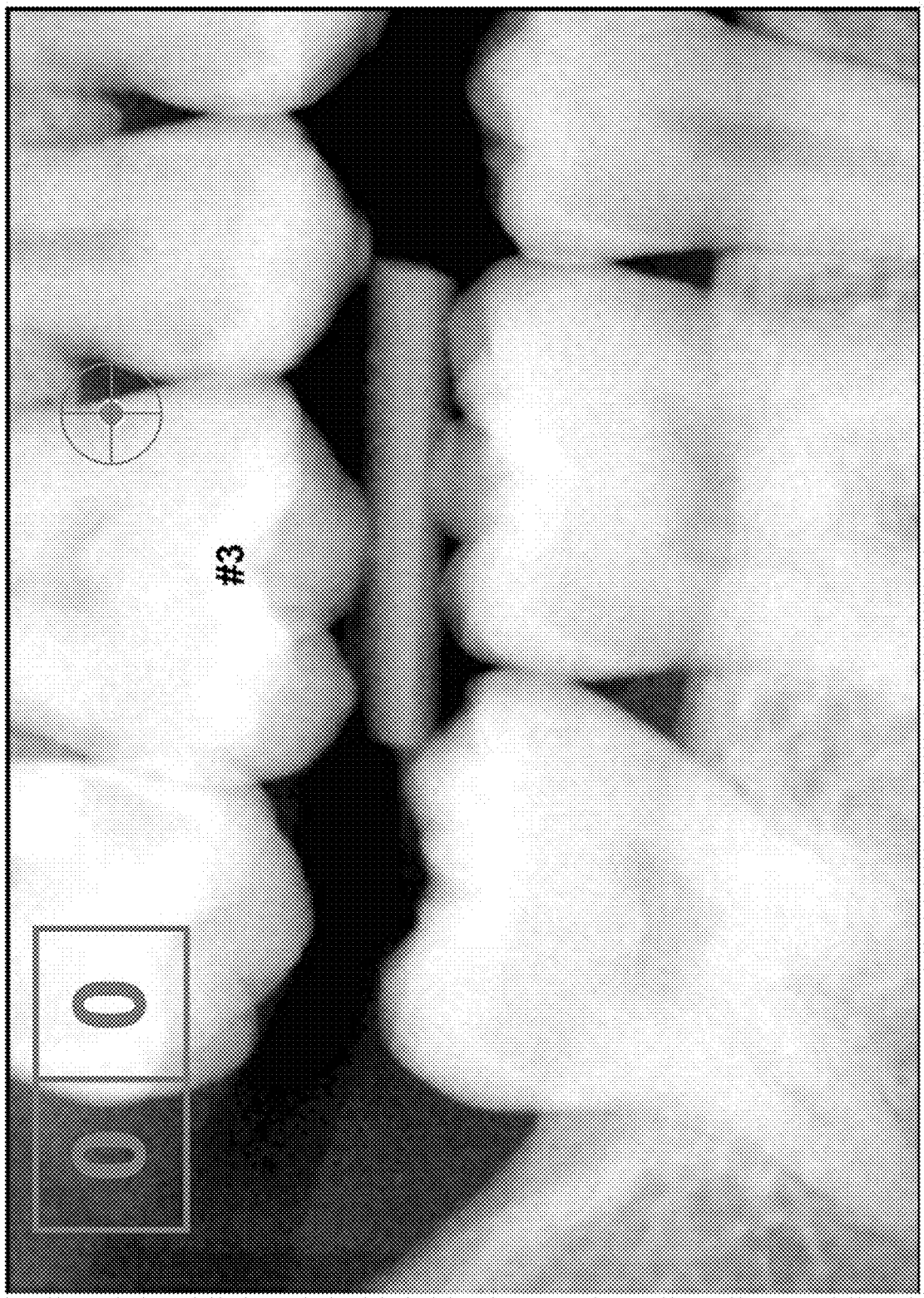
FIGS. 53-60 are images that illustrate use of a software algorithm for diagnosing and evaluating decay from the digital dental x-ray image.
Figure 54:
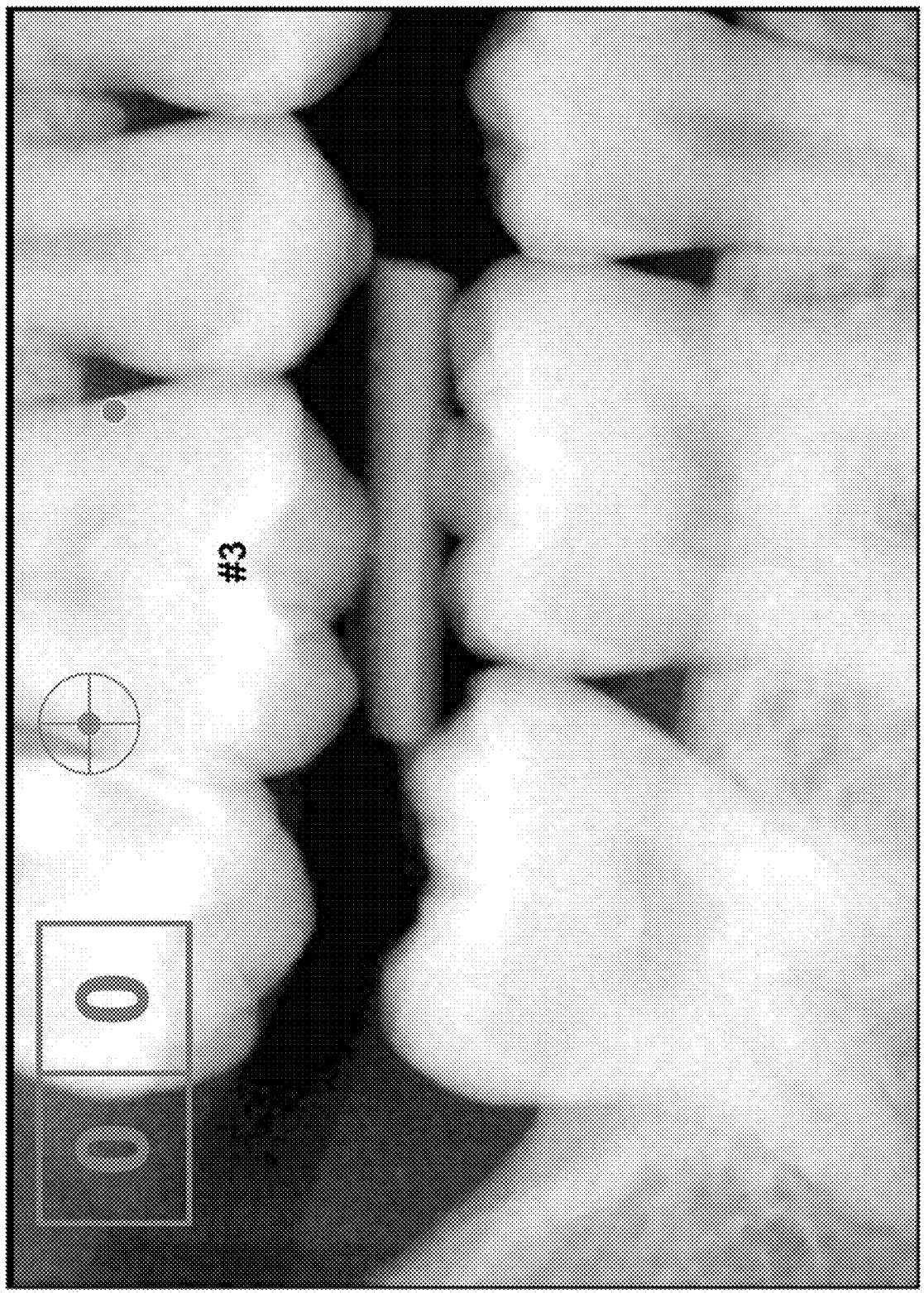
Figure 55:
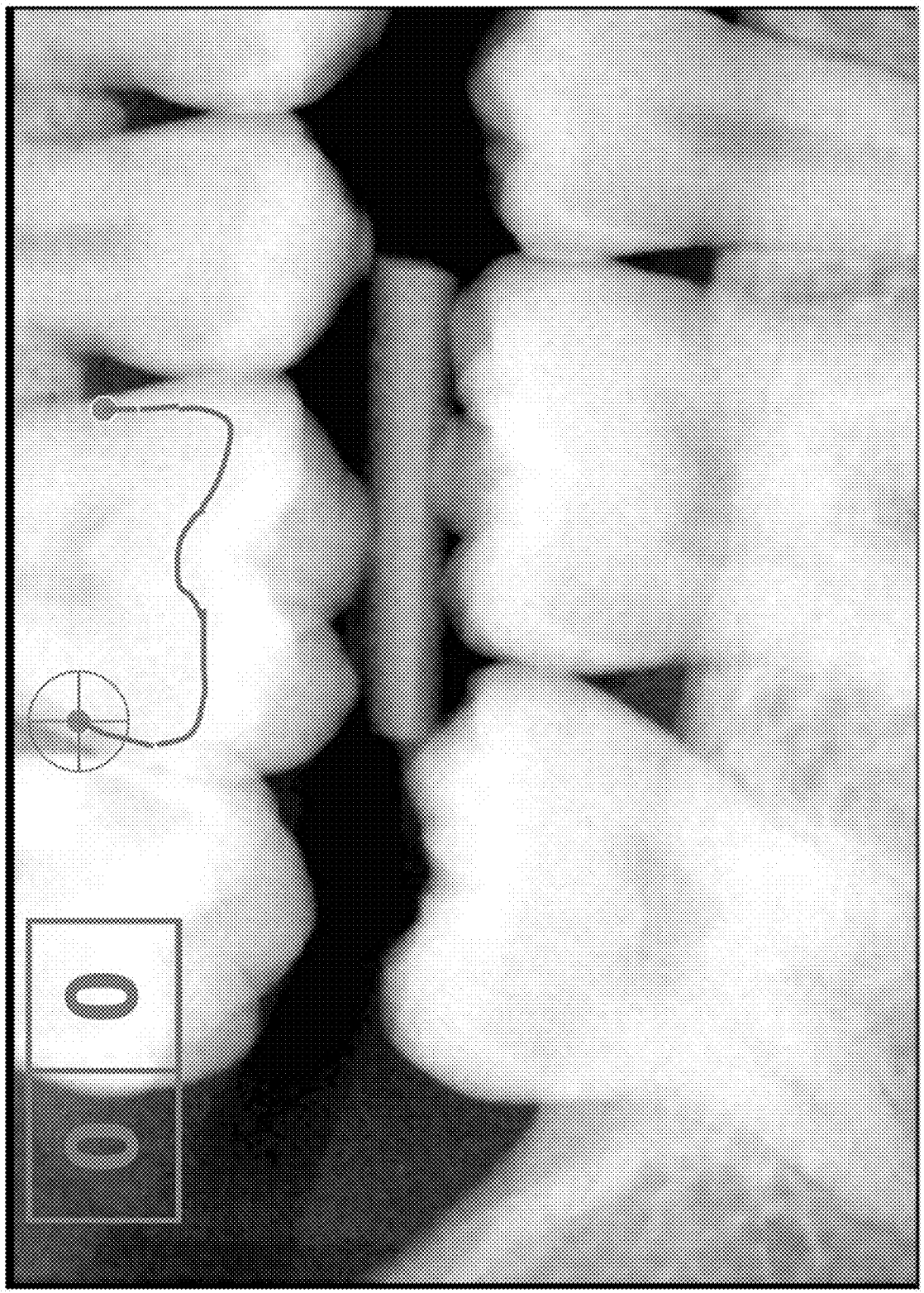
Figure 56:
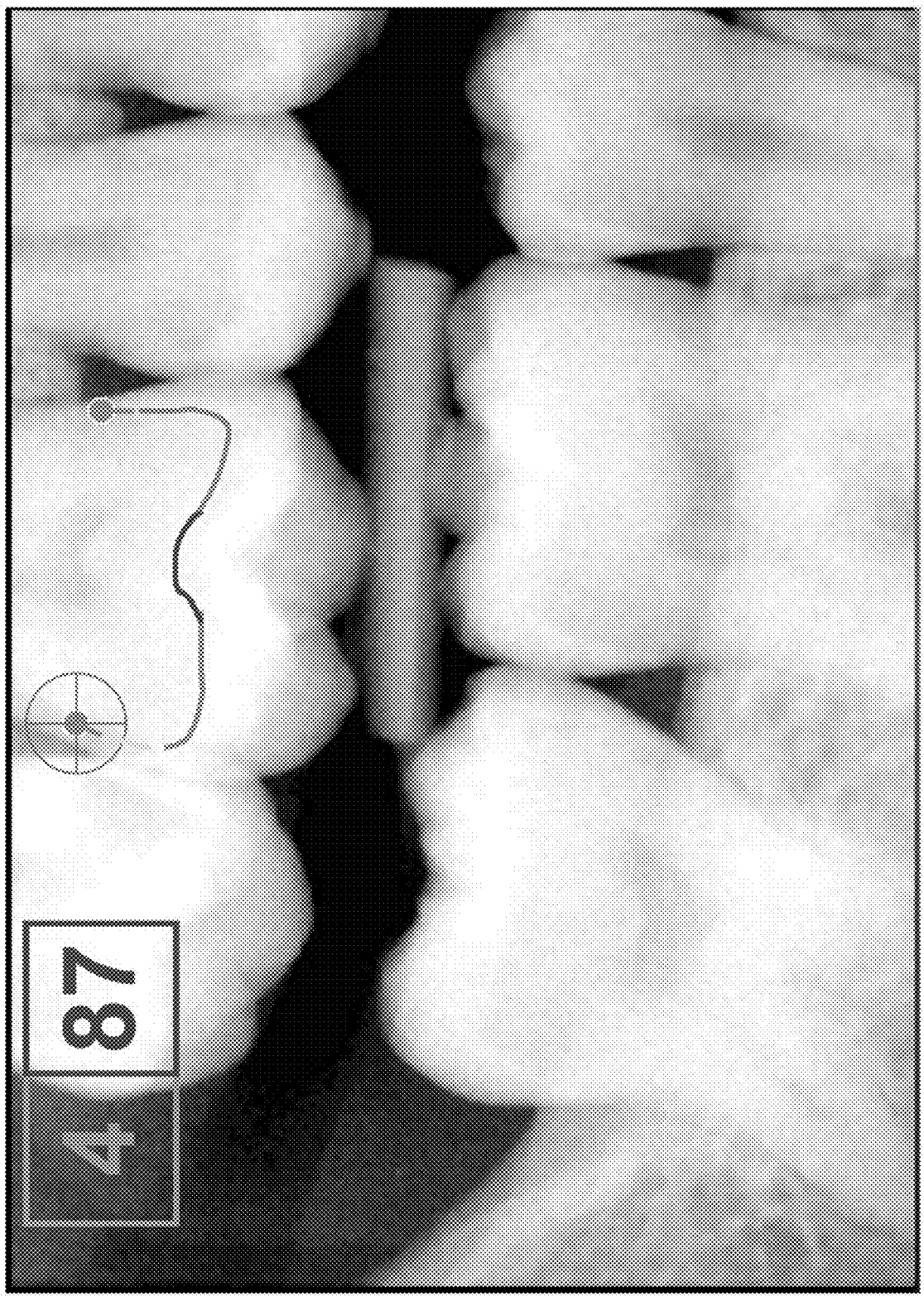
Figure 57:
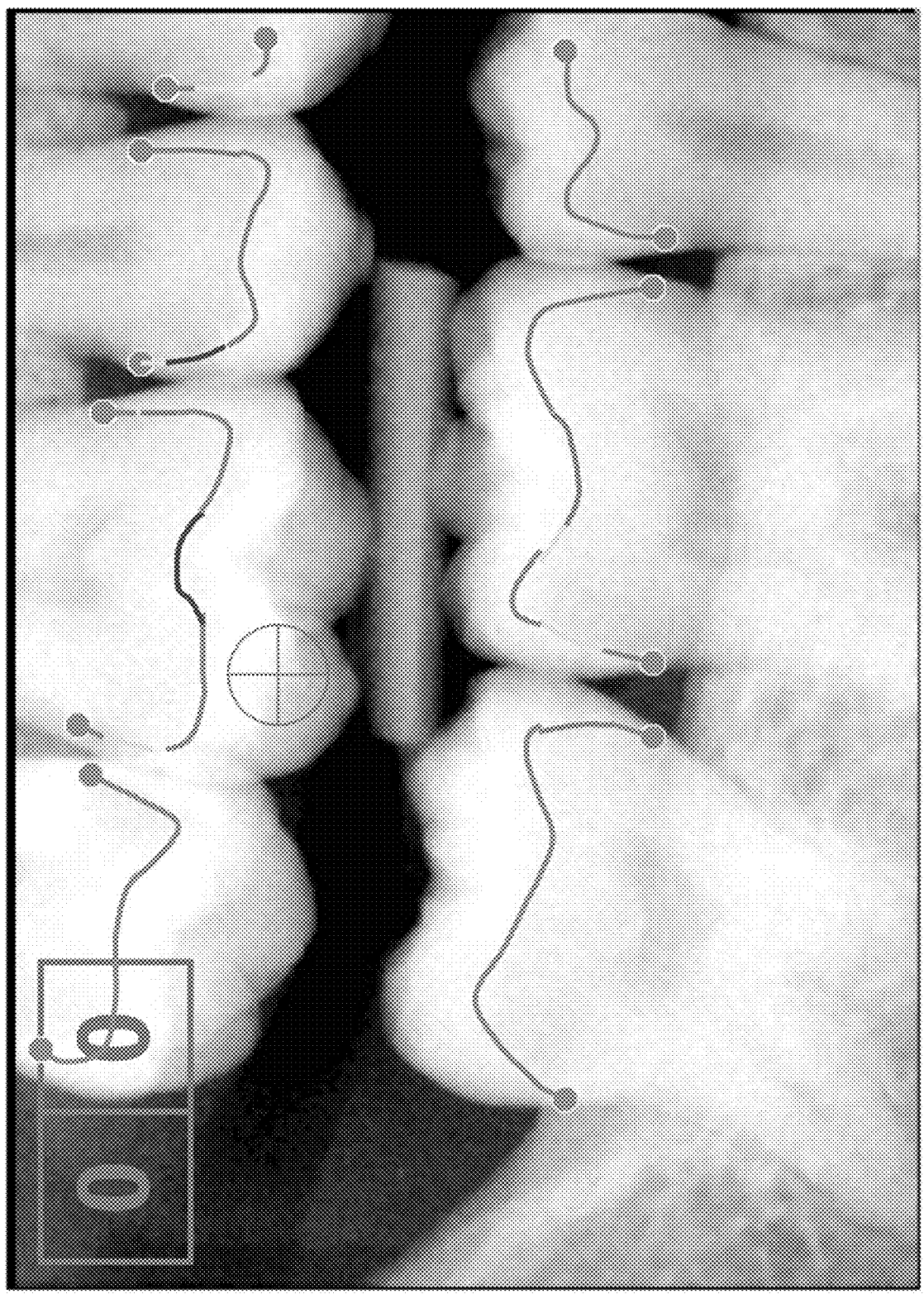
Figure 58:
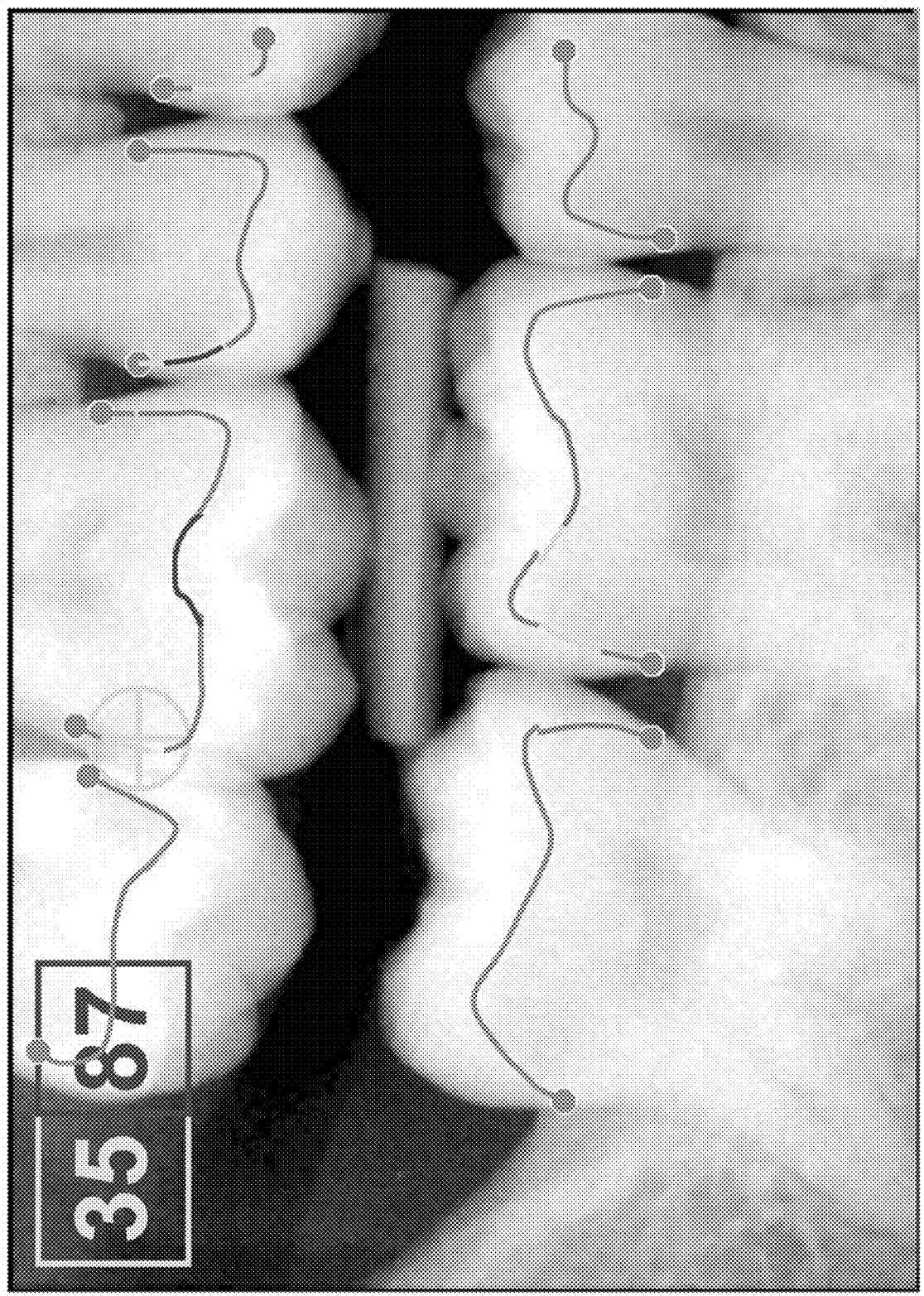
Figure 59:
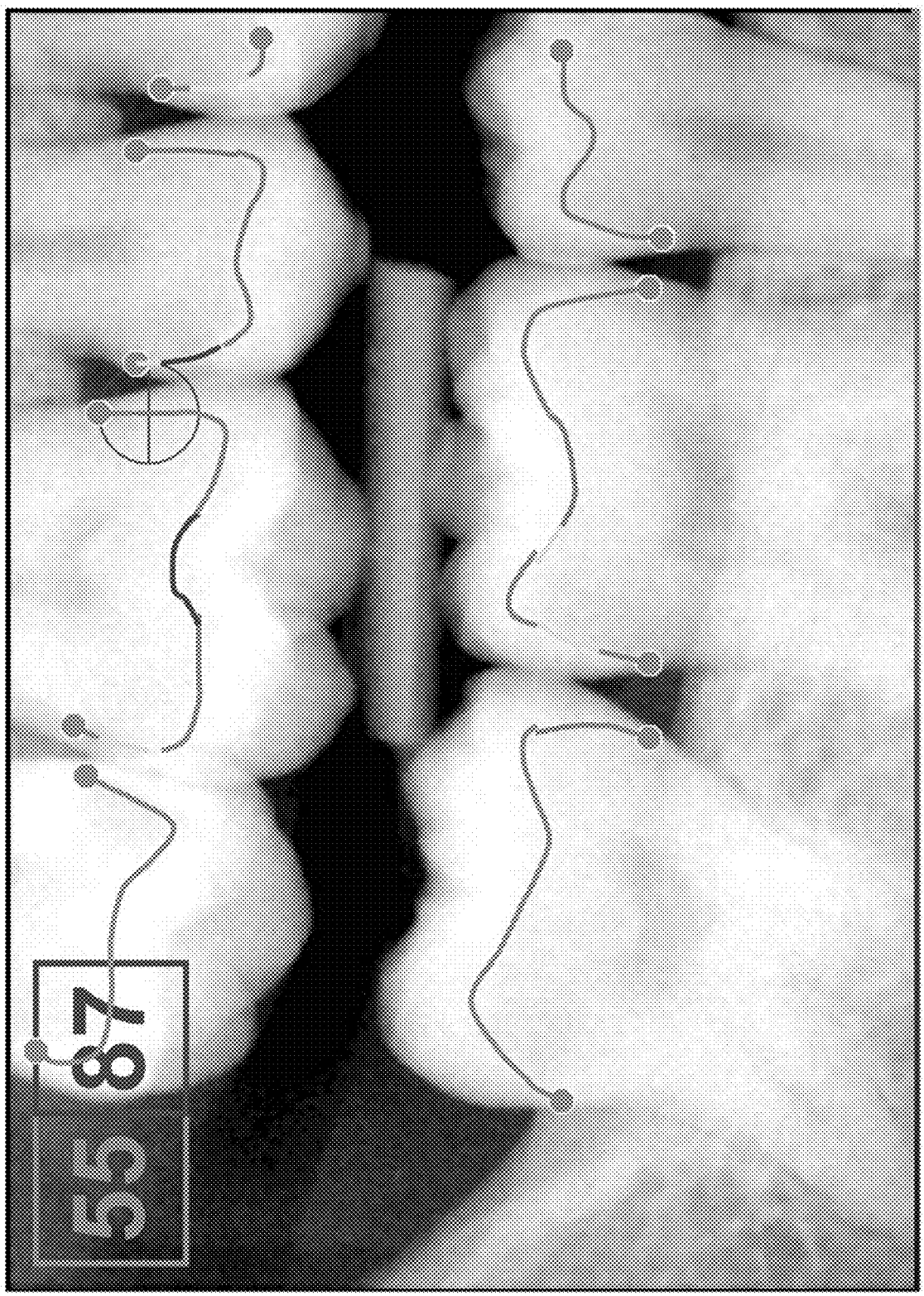
Figure 60:
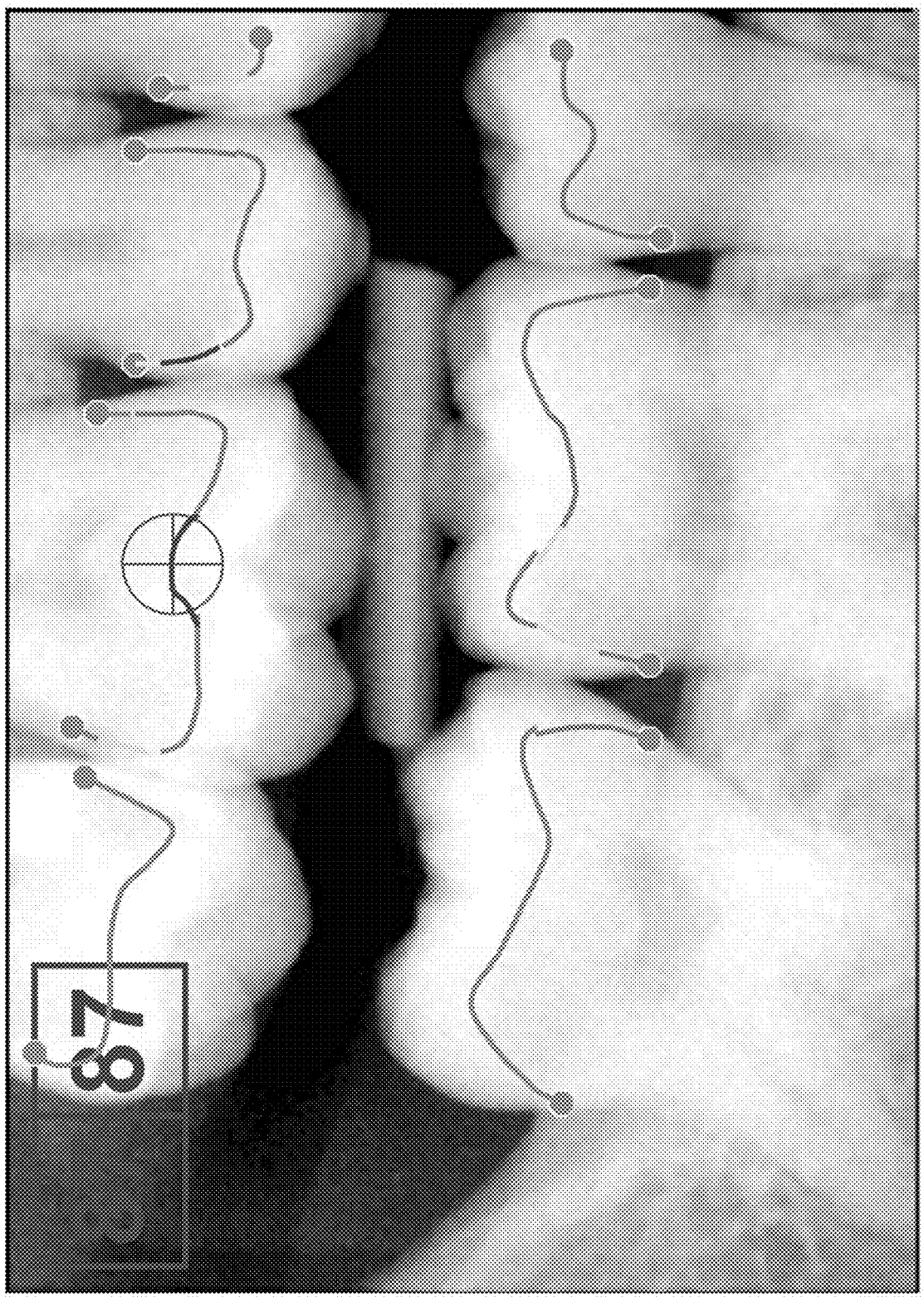

In another embodiment of a software algorithm for diagnosis of tooth decay, use of edge detection algorithms in combination with pattern recognition functions for mapping the entire DEJ contour is illustrated in FIGS. 53-60. Two points near the DEJ are marked by the user (FIGS. 53 and 54). The software algorithm then locates the DEJ contour (FIG. 55), and computes numerical decay values along the DEJ (FIG. 56). This is repeated for other teeth in the x-ray image (FIG. 57). Once the analysis is complete, numerical decay values are displayed as the user moves a cursor over the image (FIGS. 58-60). Other approaches may be employed as well. For example, the DEJ could be manually traced by a user.

The successful implementation of software algorithms disclosed herein depends to some extent on suitable calibration of the optical densities of the acquired images. Dental digital x-ray imaging processes are subject to multiple variables, including but not limited to: i) intensity variation among different x-ray sources (or just the aging of individual x-ray sources); ii) sensitivity variation among different x-ray imaging sensors, and with aging of individual x-ray sensors; iii) variations arising from different image processing algorithms or protocols; iv) variation among different display devices (or just the aging of individual display devices); v) subjective operator judgment in the final interpretation of x-ray images; and vi) other variables. Calibration "blocks," or standards, are used to try to at least partially correct for some of these variations.

Figure 61A:
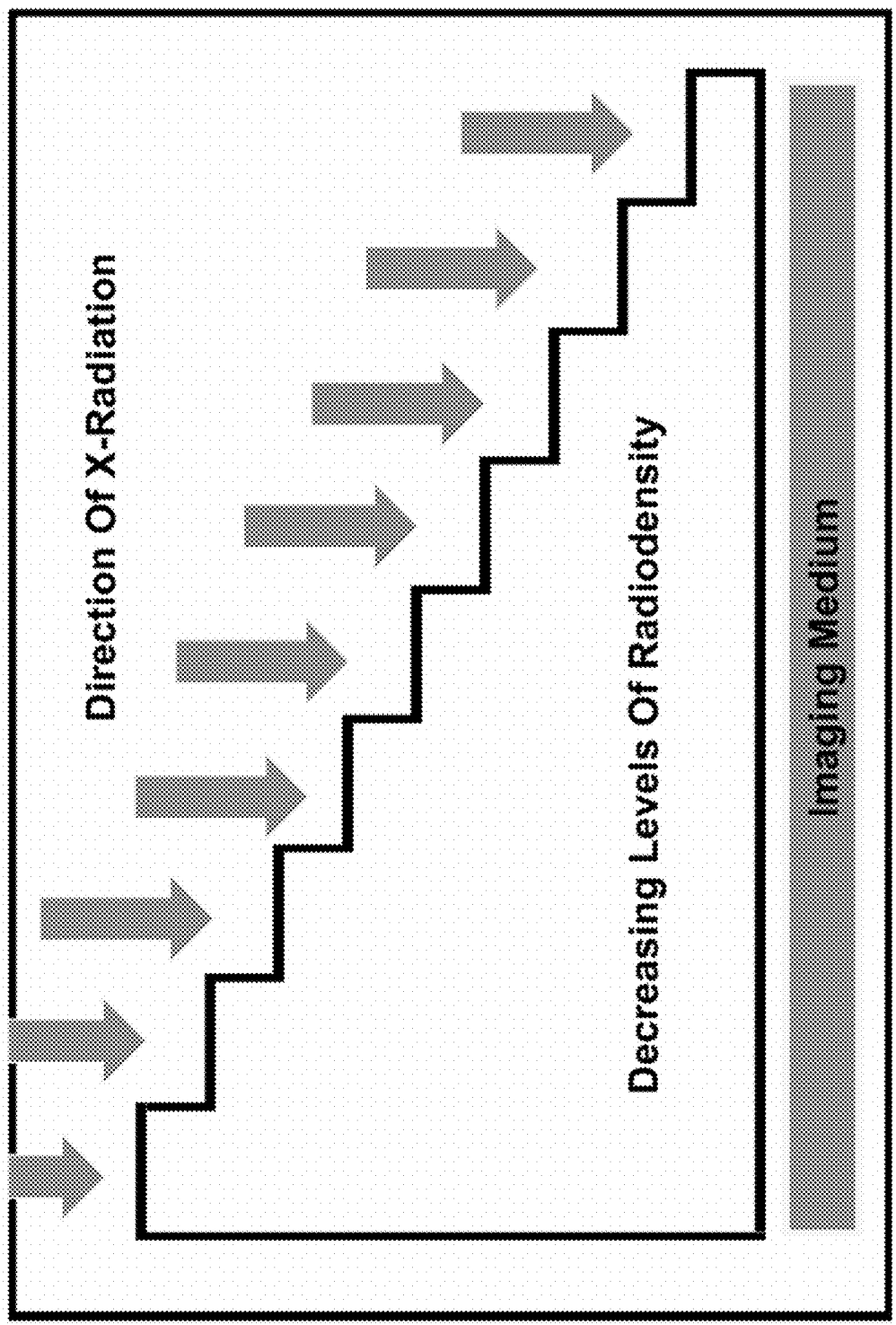
FIGS. 61A and 61B illustrate aluminum step wedge radiographic calibration blocks.
Figure 61B:
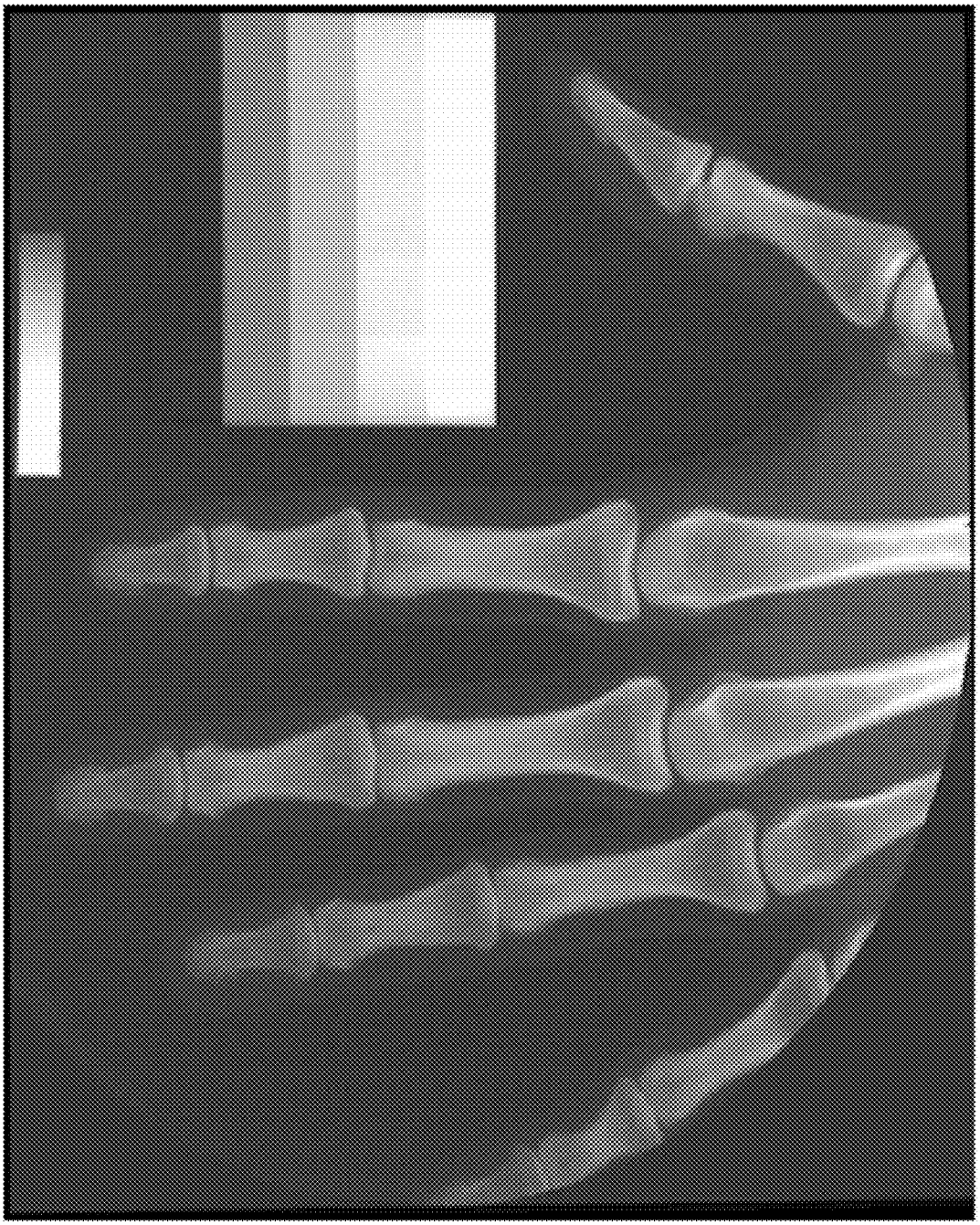
Figure 62:
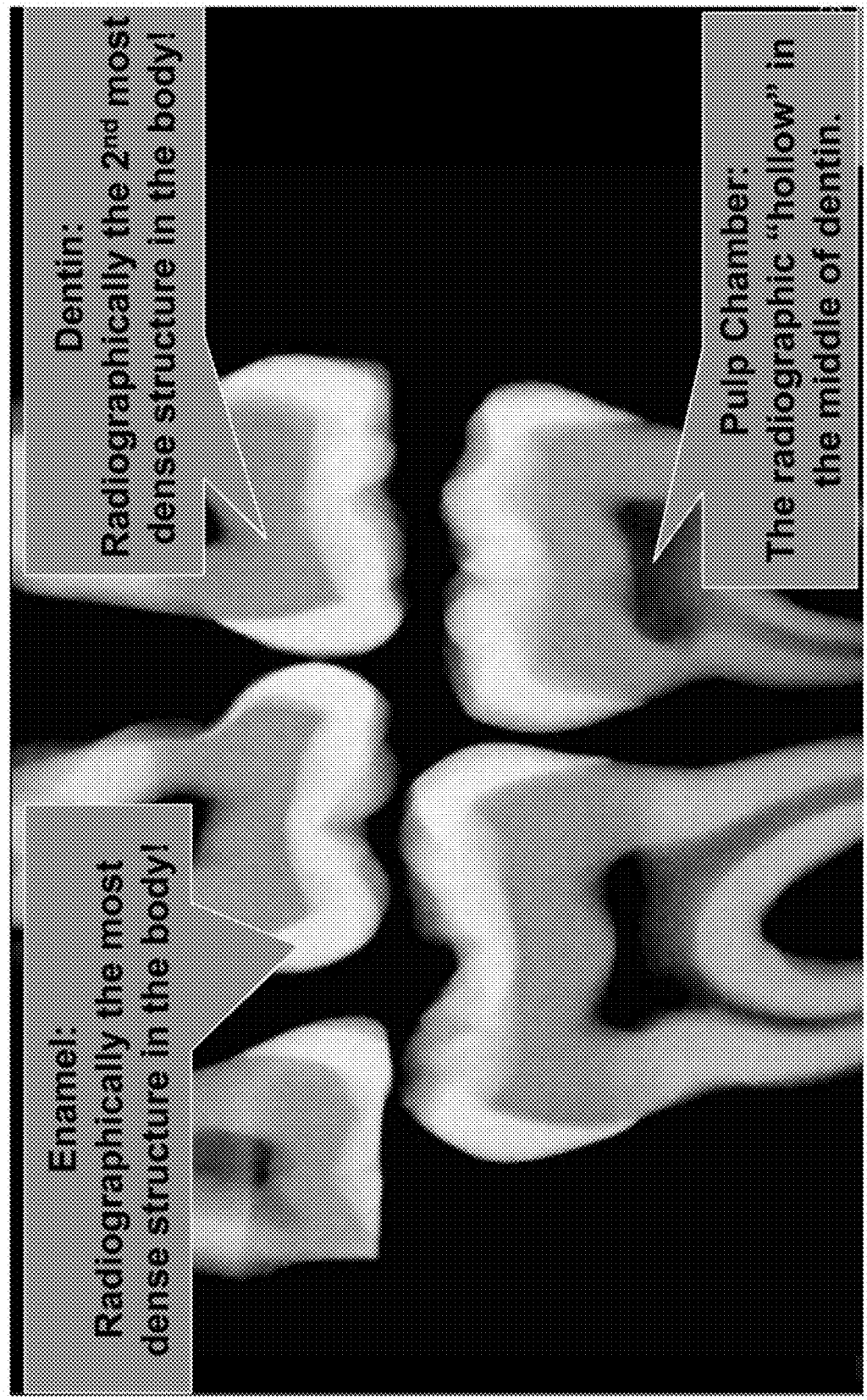
FIG. 62 is a radiograph illustrating the composite structure of teeth.

One example of an existing calibration block is an aluminum "step wedge," as illustrated in FIGS. 61A and 61B. Linear angled wedges are sometimes employed as well. However, current calibration methodologies do not typically account for tooth size, tooth location, tooth distance from the imaging plane, intervening layers of tissue, the composite structure of teeth, or the effect these factors have on clinical diagnostics. A dental diagnosis needs a calibration standard that simulates dental tissues and diseases of those tissues. Such a calibration standard should radiographically simulate the true composite structure of teeth (i.e. enamel plus dentin plus pulp; FIG. 62), should geometrically and dimensionally simulate the structure of teeth, and should simulate dental pathology, both in size and location. Such realistic calibration devices could be used in conjunction with image analysis, edge detection, or pattern recognition algorithms to achieve a far higher level of accuracy in clinical diagnosis. Accordingly, dental x-ray calibration methodologies disclosed herein simulate dental pathology in simulated teeth, factoring in pathology size, radiodensity, and location through the radiodense layers of the teeth. A rectangular (or other suitable cross-sectional shape) composite calibration structure is fabricated for simulating enamel, dentin, and various dental pathologies, and then an x-ray image of the composite calibrations structure is analyzed as described hereinabove.

Figure 63:
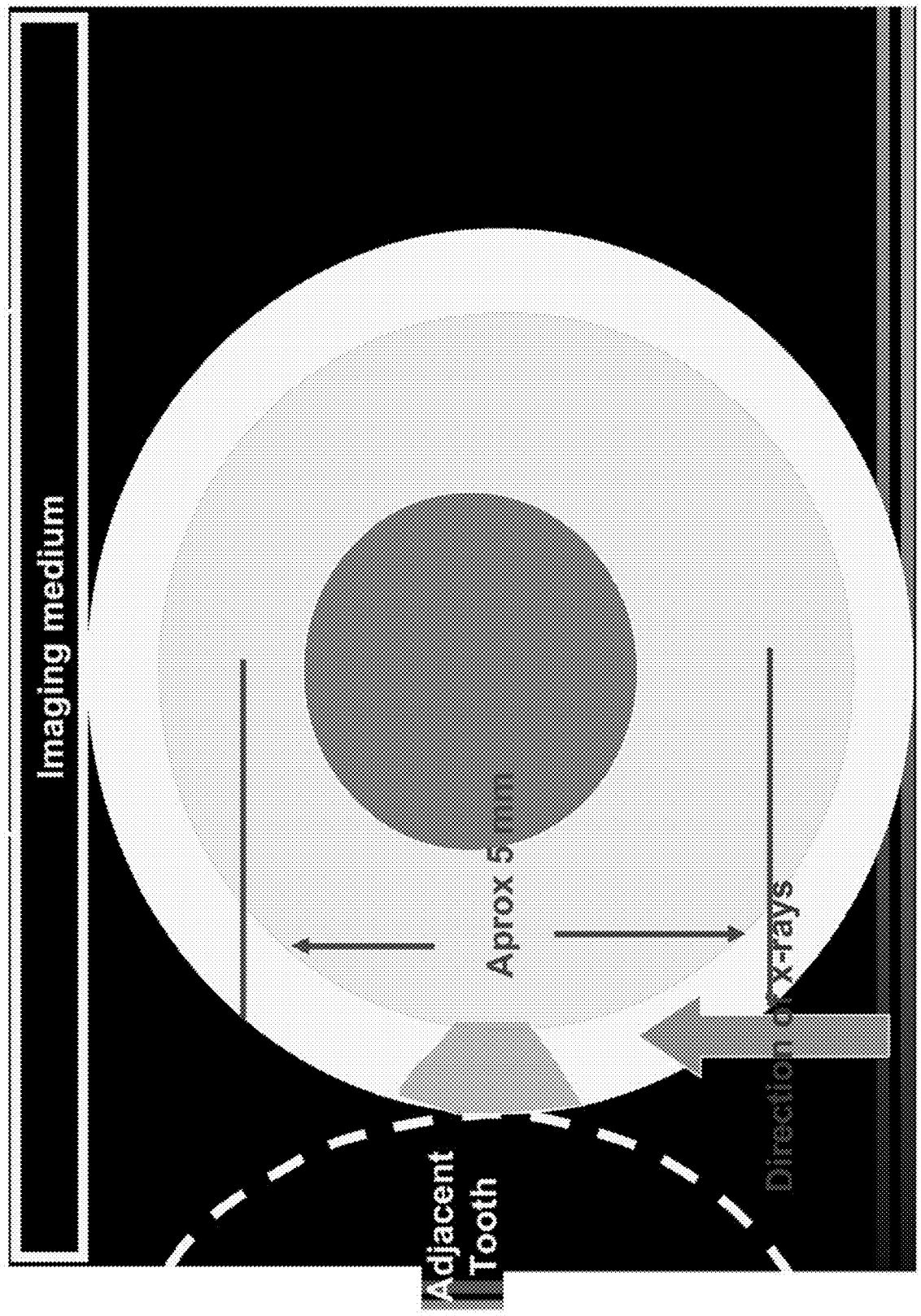
FIGS. 63 and 64 are schematic cross sectional diagrams of a tooth with decay.
Figure 64:
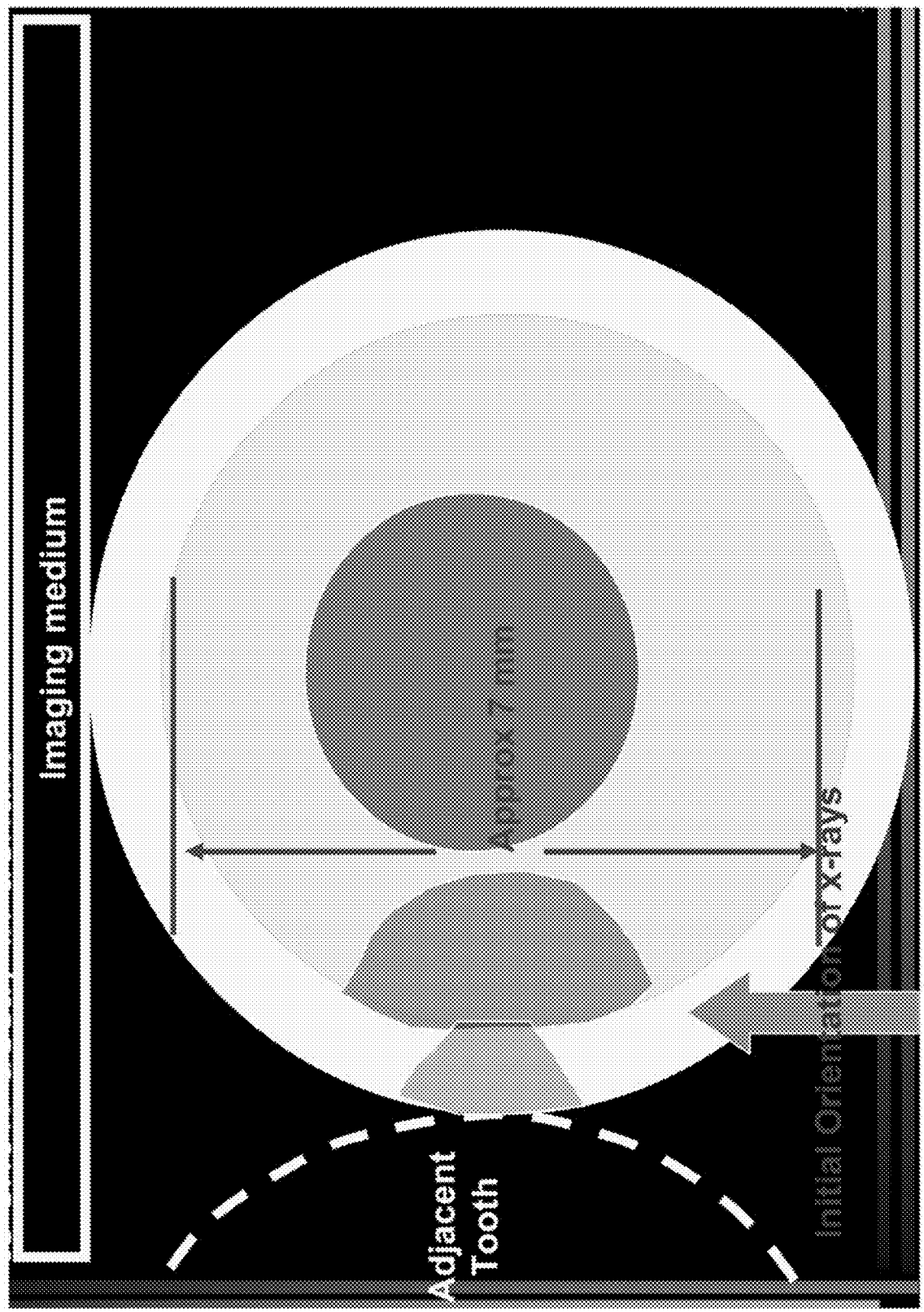
Figure 65:
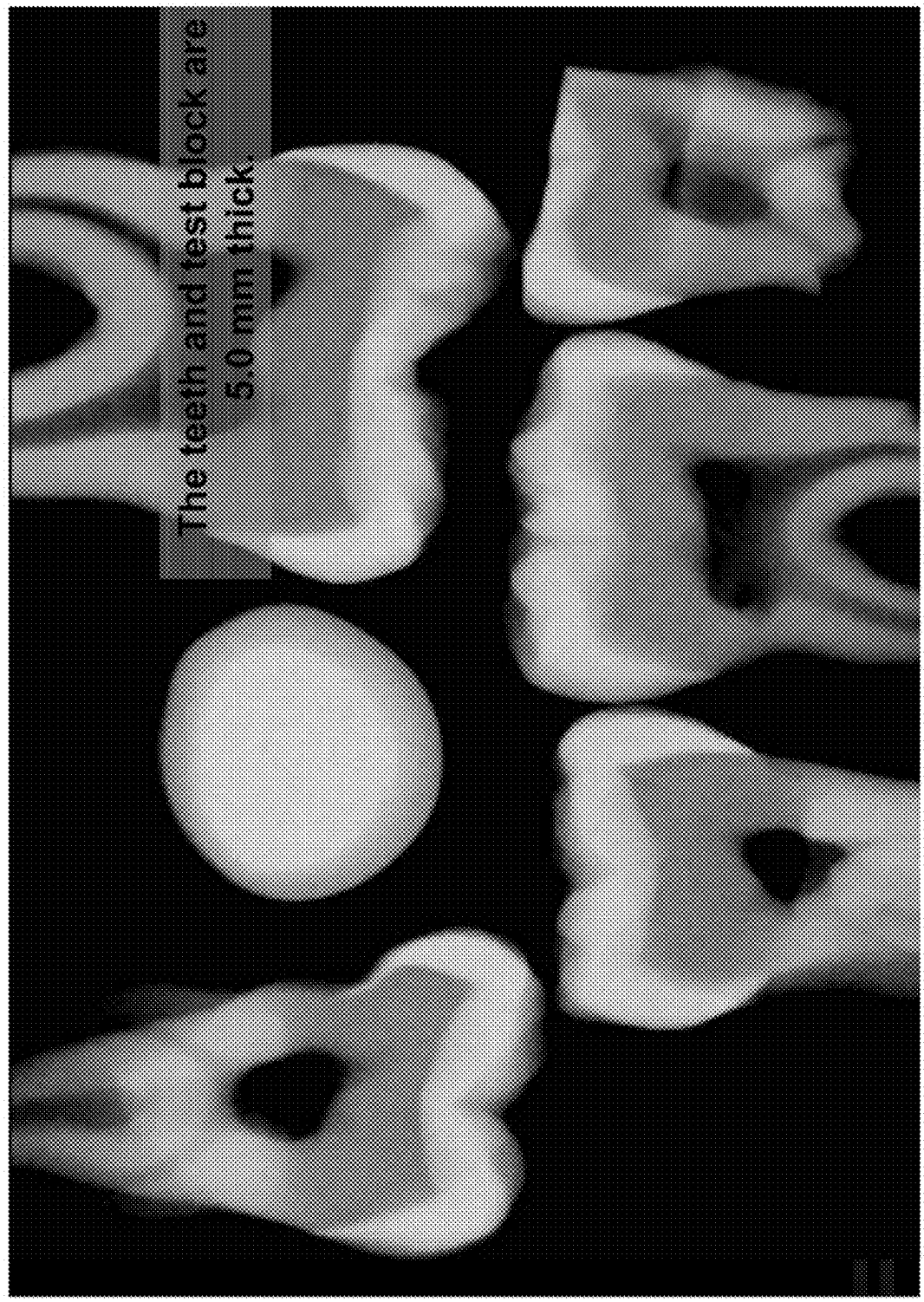
FIGS. 65 and 66 are radiographs showing samples of materials for simulating enamel and dentin, respectively.
Figure 66:
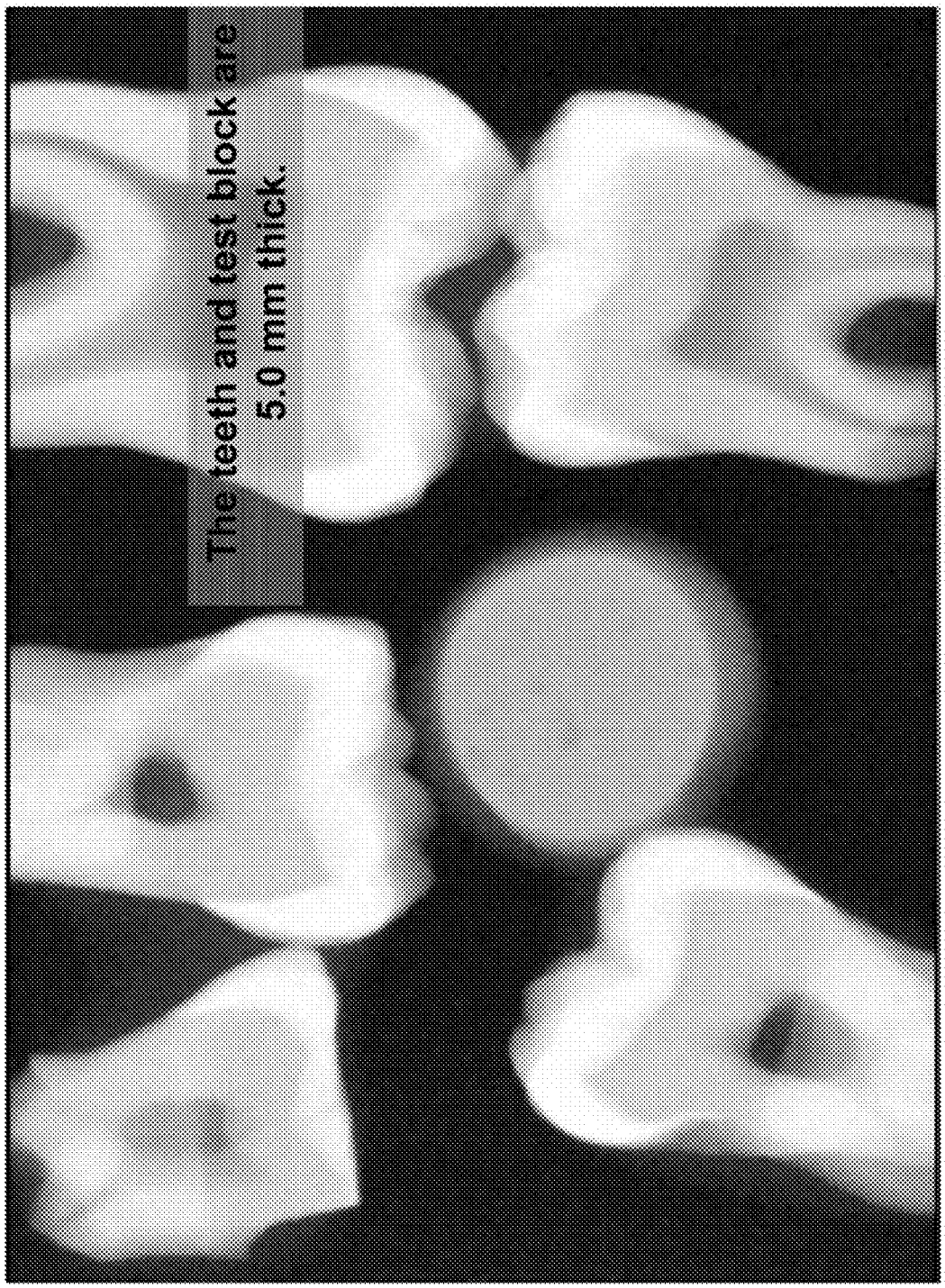
Figure 67:
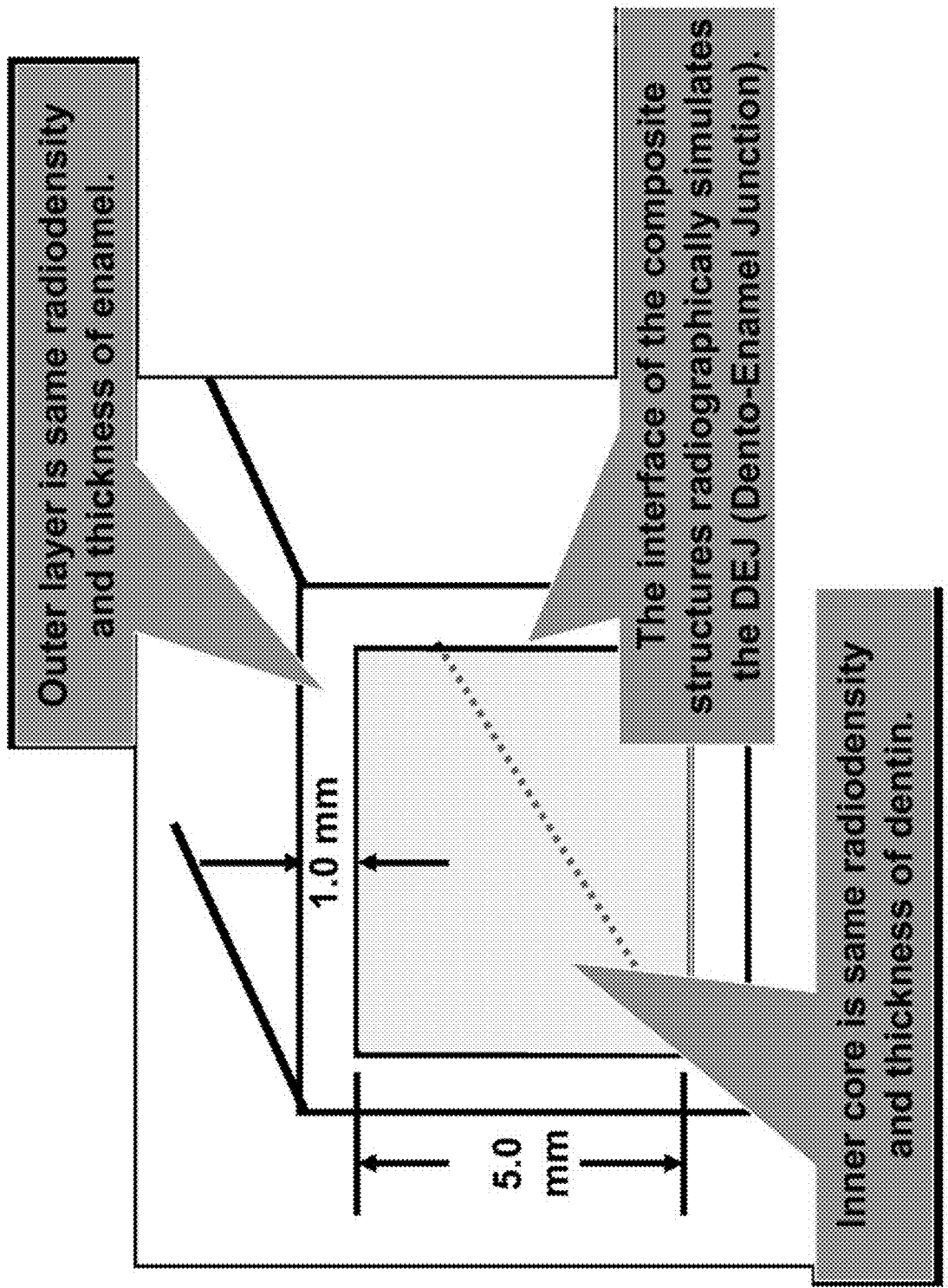
FIG. 67 is a schematic diagram of a composite calibration block.
Figure 68:
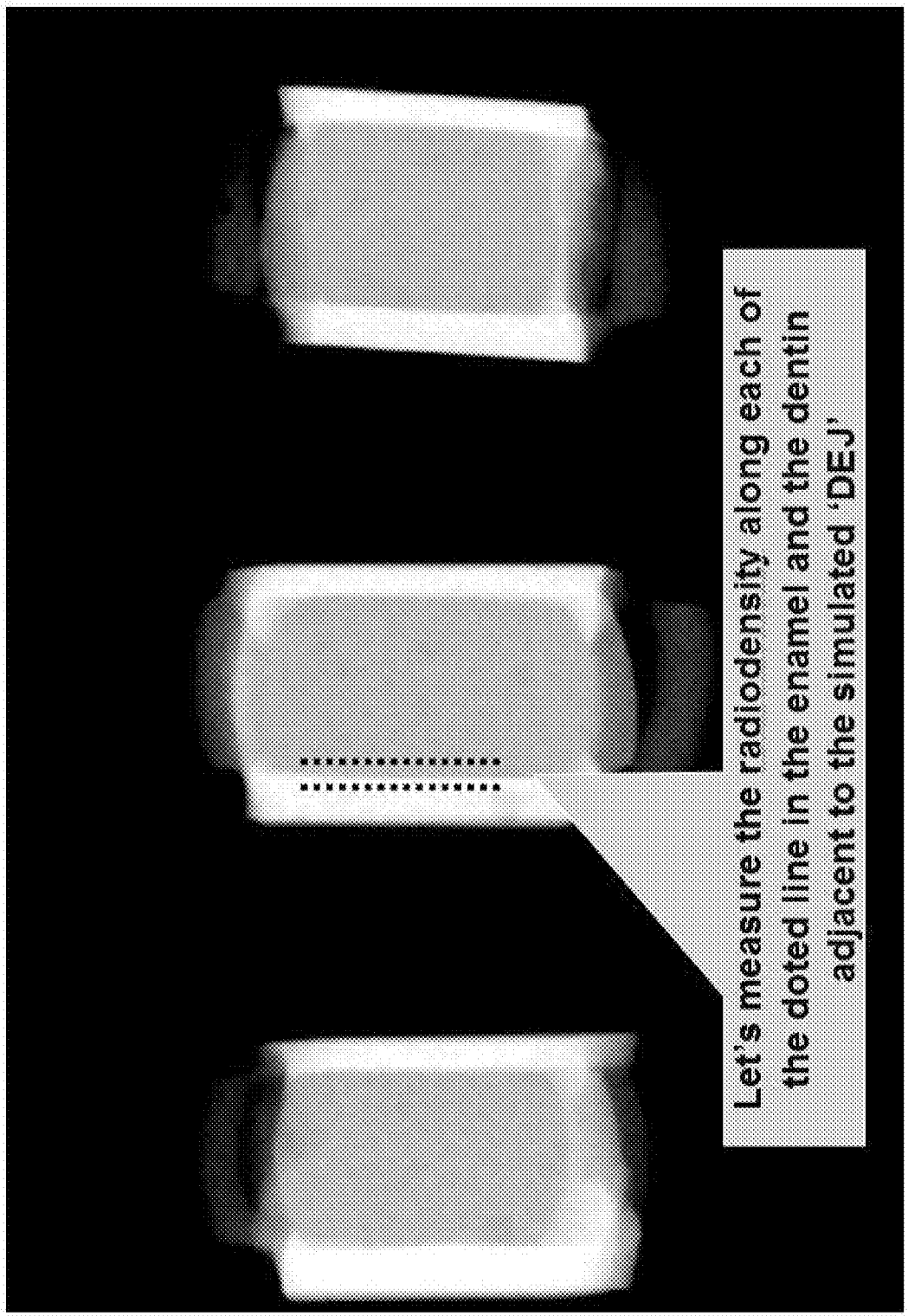
FIG. 68 is a radiograph showing composite calibration blocks.
Figure 69:
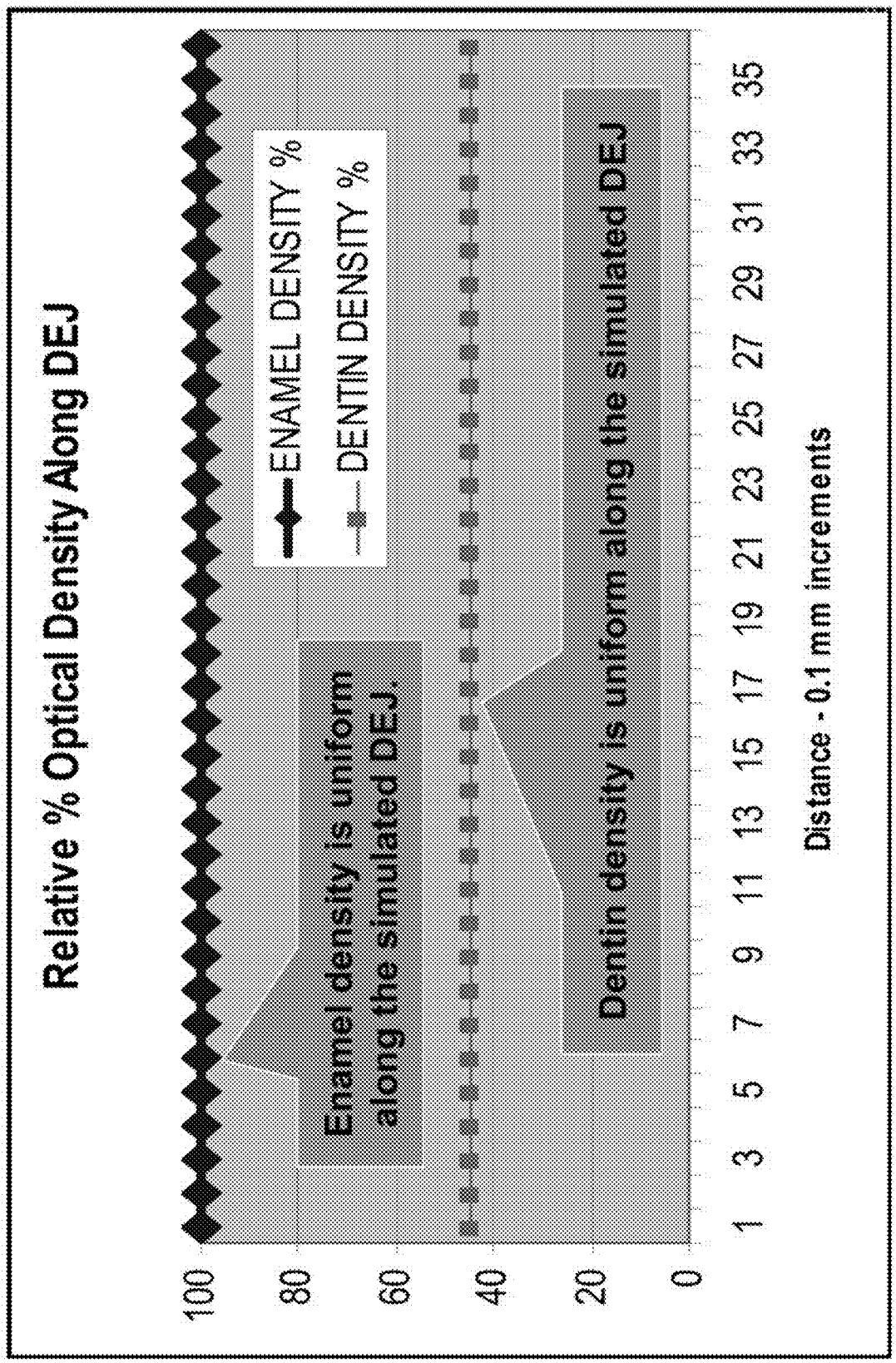
FIG. 69 shows optical density curves measured from the radiograph of FIG. 68.

As shown in the schematic cross-sectional diagram of a tooth in FIG. 63, x-rays pass through about 7 mm of enamel to show decay in the enamel near the DEJ near the proximal contact point with an adjacent tooth. In the schematic cross-sectional diagram of a tooth in FIG. 64, it is seen that x-rays pass through about 2 mm of enamel and about 5 mm of dentin to show decay in the dentin. Materials are chosen that simulate the radiodensity of enamel (FIG. 65; radiographically the most dense material in the human body) and the radiodensity of dentin (FIG. 66; radiographically the second most dense material in the human body). Examples of suitable materials that can be used are plastics impregnated with defined levels of radiopaque compounds (such as barium) to simulate enamel or dentin or the use of light-activated dental filling materials that contain varying levels of radiopaque compounds. A rectangular composite block is fabricated from simulating materials as shown in FIG. 67, with 1 mm of the enamel-density material surrounding a 5 mm thick layer of the dentin-density material. X-ray images of such blocks are shown in FIG. 68, and the optical densities measured along either side of the simulated DEJ are shown in FIG. 69. The curves of FIG. 69 resemble those curves extracted from the actual patient x-ray and shown in FIGS. 19 and 22.

Figure 70:
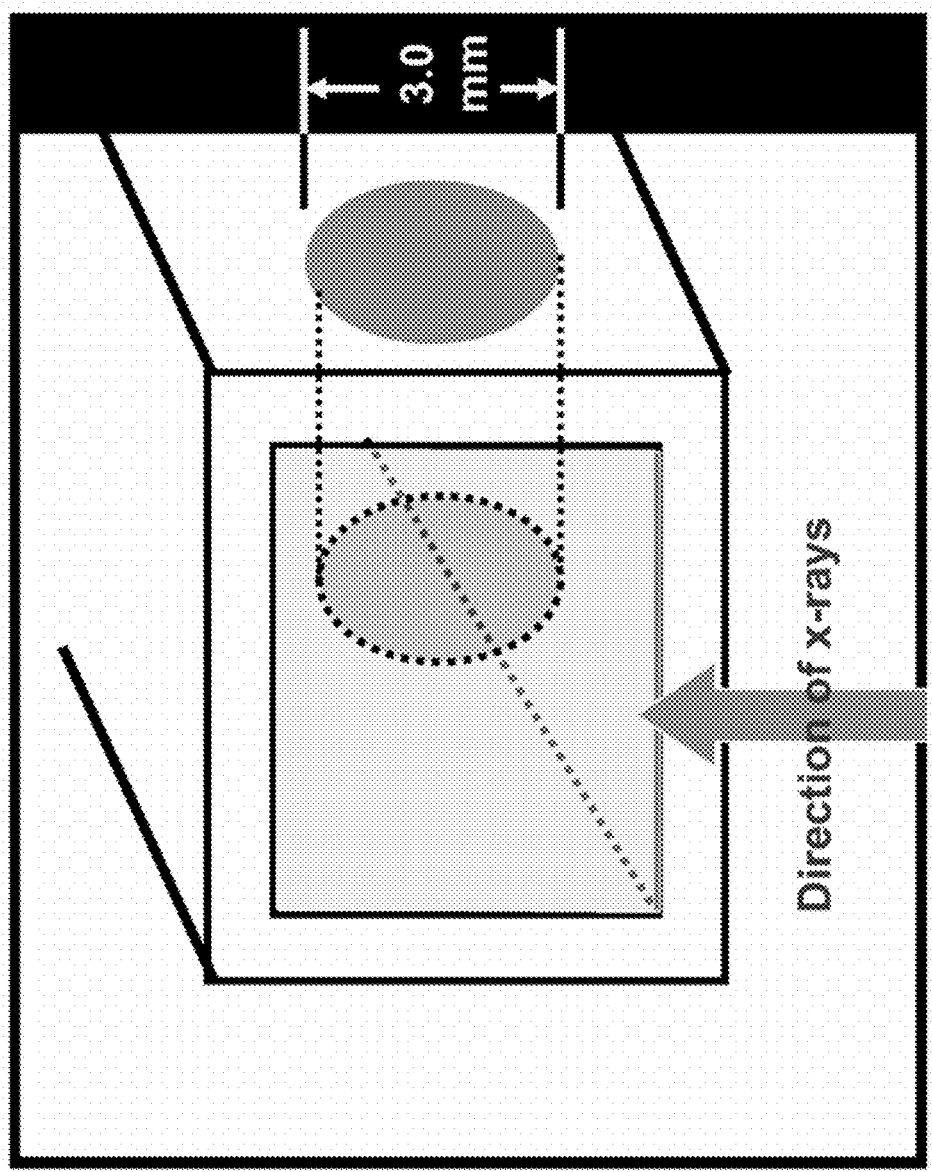
FIG. 70 is a schematic diagram of a composite calibration block with a defect.
Figure 71:
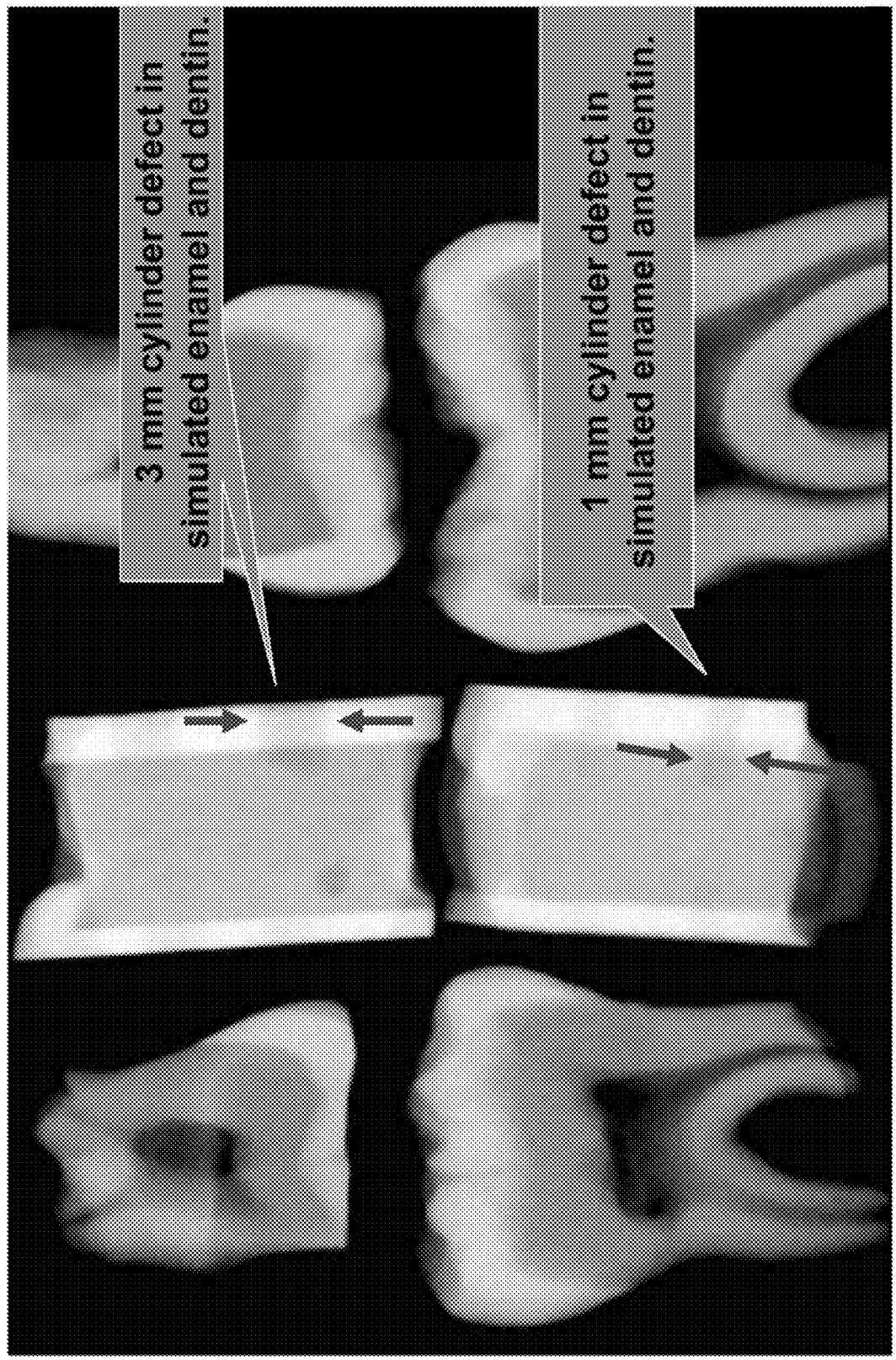
FIGS. 71 and 72 are radiographs showing composite calibration blocks with defects.
Figure 72:
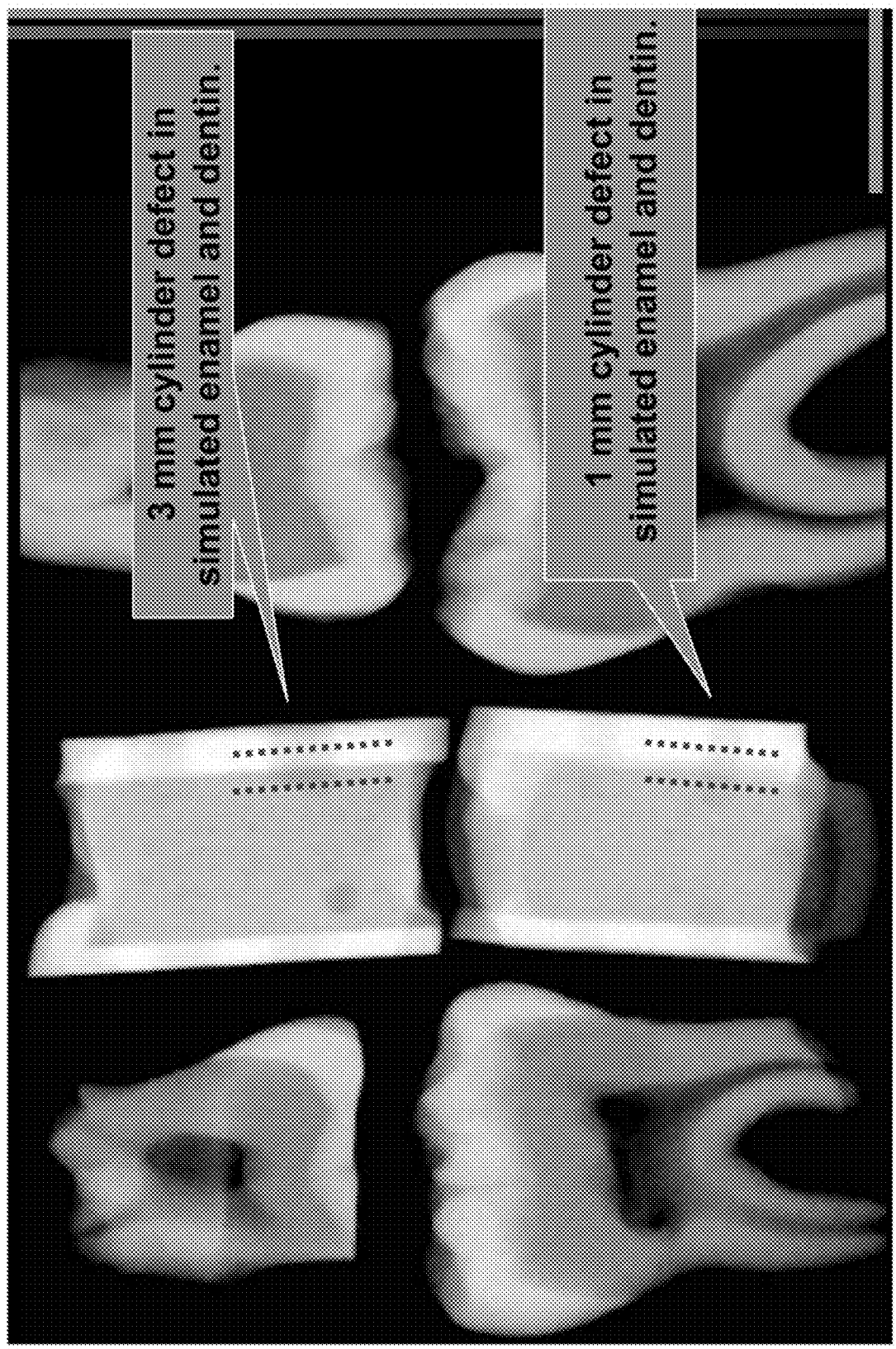
Figure 73:
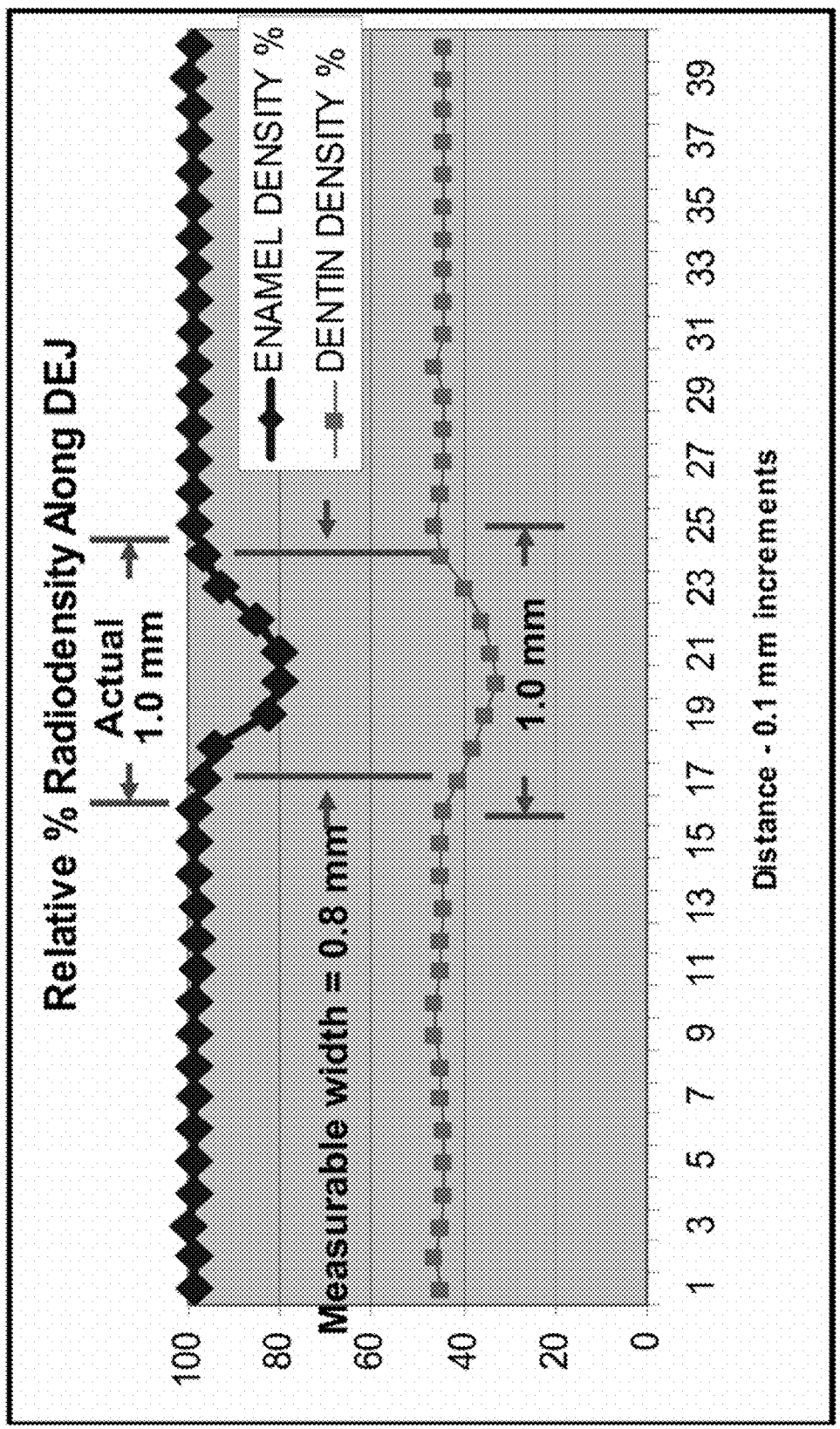
FIGS. 73 and 74 are charts that show optical density curves measured from the radiographs of FIG. 72.
Figure 74:
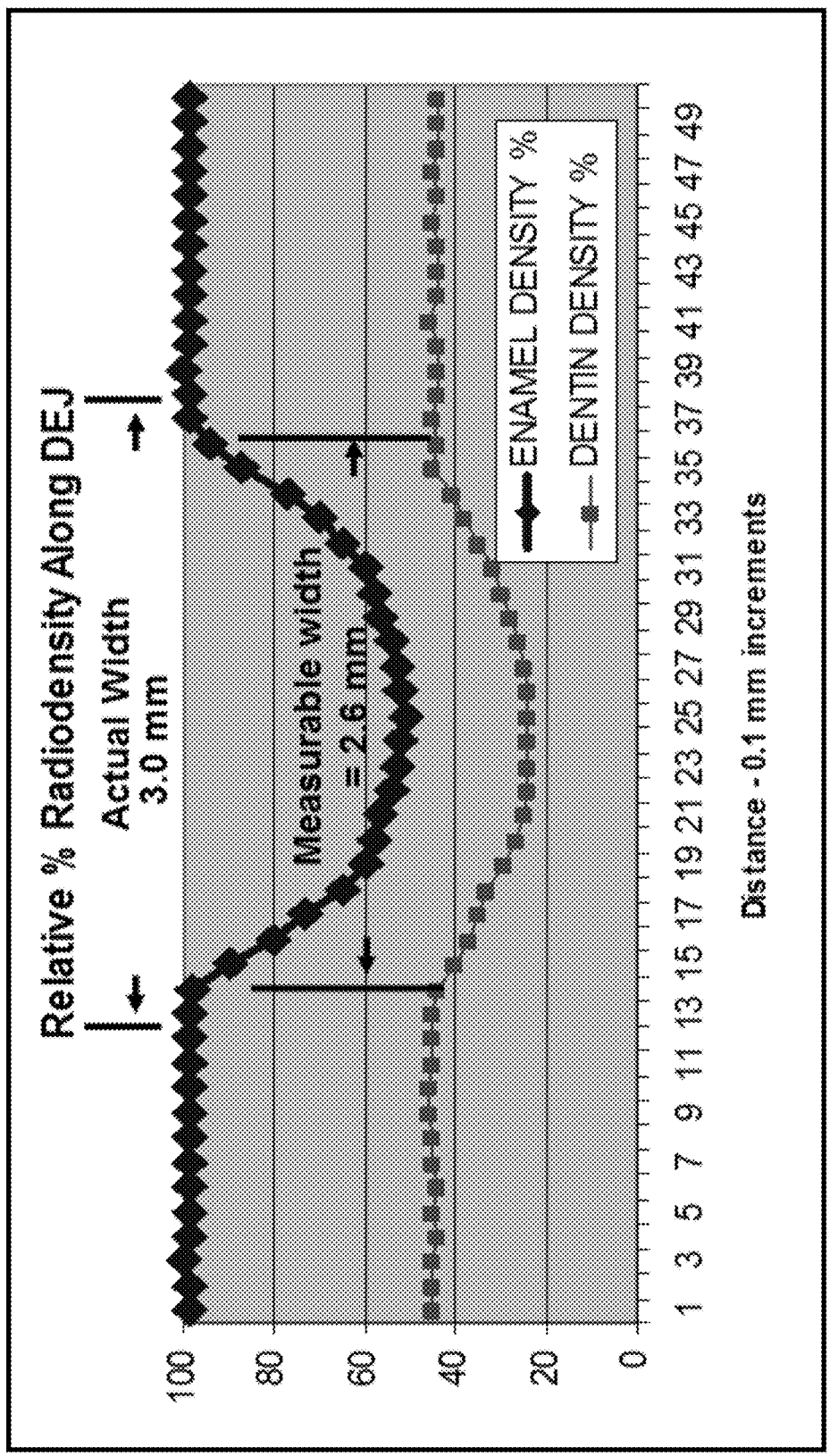

Defects of various sizes may be cut into the composite calibration blocks to simulate tooth decay or caries. A composite simulation block is shown in FIG. 70 with a 3 mm diameter cylindrical defect penetrating the enamel and entering the dentin. Simulated defects of various sizes may be employed. FIG. 71 shows x-rays of a composite calibration block with a 1 mm cylindrical defect and a composite calibration block with a 3 mm cylindrical defect. The optical densities are measured from the image along the lines parallel to the simulated DEJ in the composite calibration structure as shown in FIG. 72, and the results are plotted in FIGS. 73 and 74. The 1 mm defect yields a directly measurable width of about 0.8 mm in both the enamel and the dentin. The integrated dip in the enamel curve yields a value of 41, while the integrated dip in the dentin curve yields a value of 73. The 3 mm defect yields a directly measurable width of about 2.6 mm in both the enamel and the dentin. The integrated dip in the enamel curve yields a value of 714, while the integrated dip in the dentin curve yields a value of 305. These values may be used to construct standard calibration curves for the width of defects in enamel and dentin, assuming a sharp boundary between decayed and normal tooth structure. Revisiting the curves of FIGS. 21 and 24 (extracted from an actual patient x-ray), measurable defect widths of 1.4 mm in the enamel and 1.9 for the dentin are obtained, along with integrated areas of 285 for the enamel and 299 for the dentin. By comparison with the composite calibration structure, defect widths of 1.9 mm for the enamel and 2.3 mm for the dentin may be inferred or estimated. The integrated values correspond to a calibrated defect between about 1.5 and about 2.0 mm in width.

The calibration apparatus and methods described hereinabove may be modified in a number of ways for improving diagnostic accuracy. For example, instead of void defects, the defects in the composite calibration structure may be filled with a material simulating the radiodensity of partially decayed enamel or partially decayed dentin. In another example, the composite calibration structure may be made into a more realistic tooth shape, instead of a simple rectangle. Specific composite calibration structures may be made specific to each tooth, or specific to the location of the decay on the tooth. The composite calibration structure may be employed to optimize x-ray image acquisition conditions (by analyzing images of the composite calibration(s) structure(s) at varying exposure times, exposure intensities, and so on) to yield the best contrast between normal tooth structure and diseased or decayed tooth structure. Optimized settings thus determined may be stored for repeated use, and may be periodically re-determined and refreshed to compensate for aging of the x-ray source or x-ray imaging sensor.

Other dental pathologies may be simulated by suitably configured composite calibration structures. Such other dental pathologies include but are not limited to periodontal disease, endodontic disease, bone densities around implants or implant failures, progression of diseases by comparing prior images and data derived from those images, and potentially the identification of tumors or lesions that might contain cancer in the bone around teeth.

Software algorithms may also be employed for radiographic diagnosis or evaluation of periodontal disease. One example of such a software algorithm may be designated for convenience as PerioScan CADD.

Figure 75:
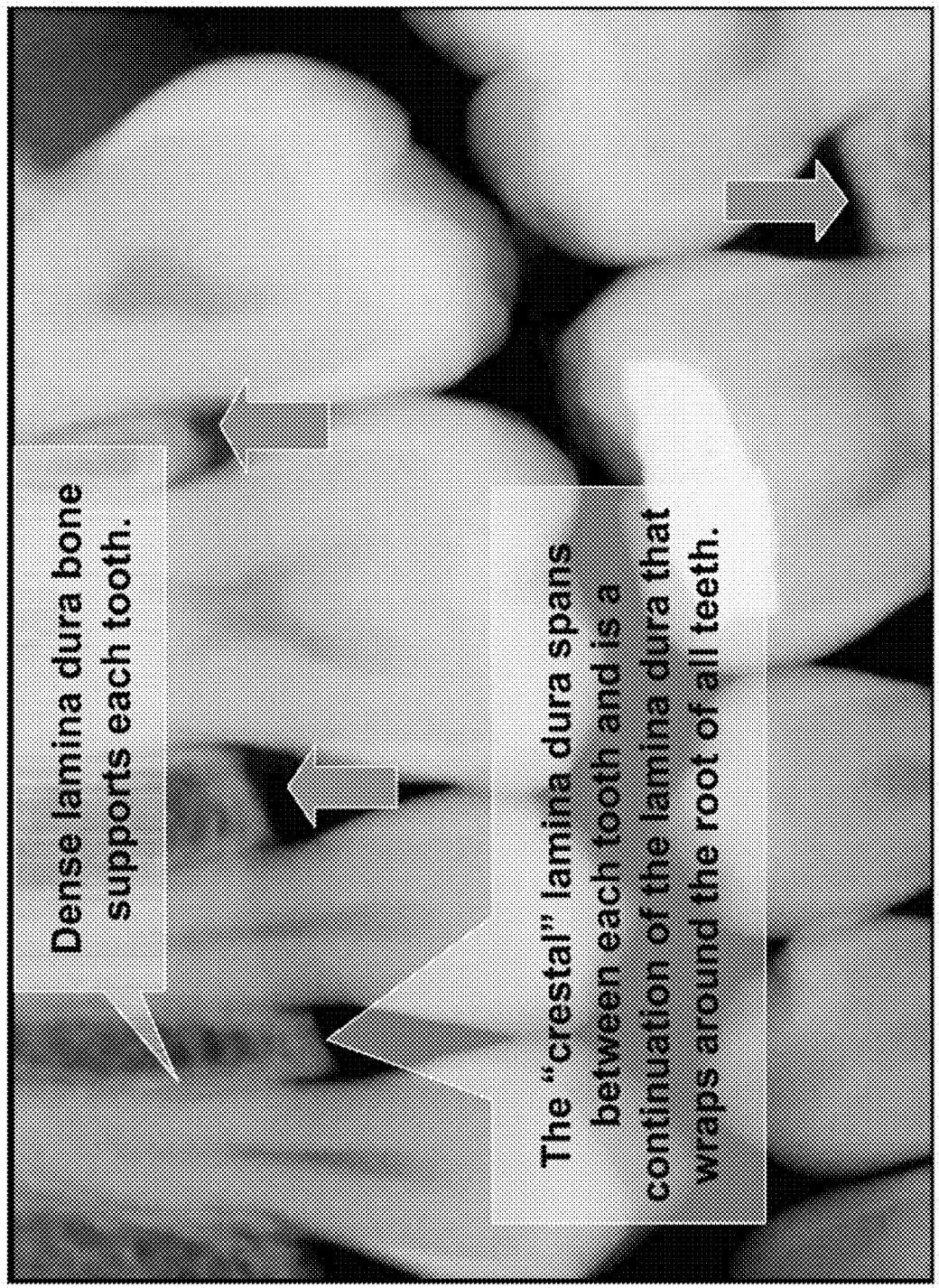
FIGS. 75 and 76 are radiographs showing healthy lamina dura bone.
Figure 76:
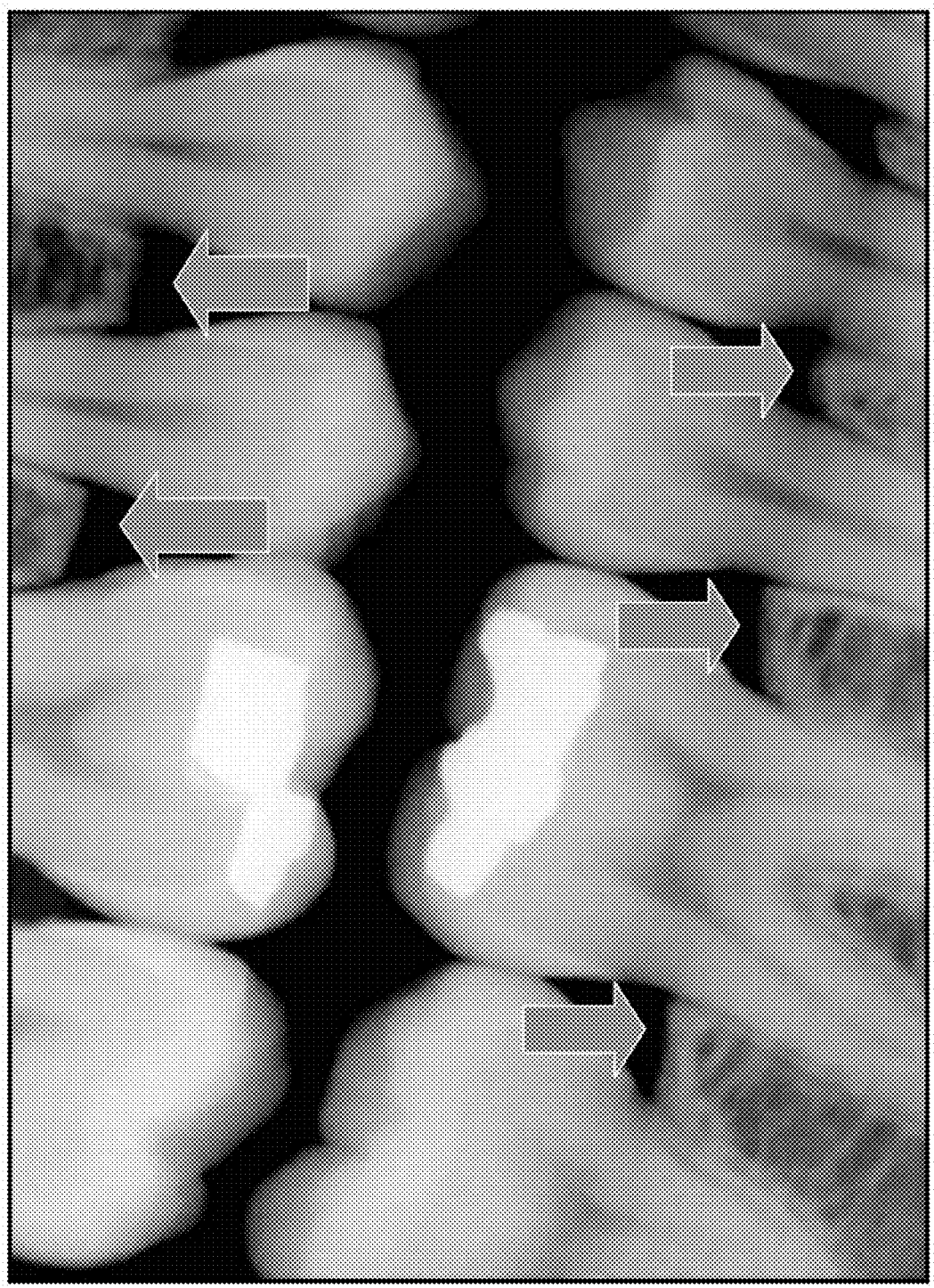
Figure 77:
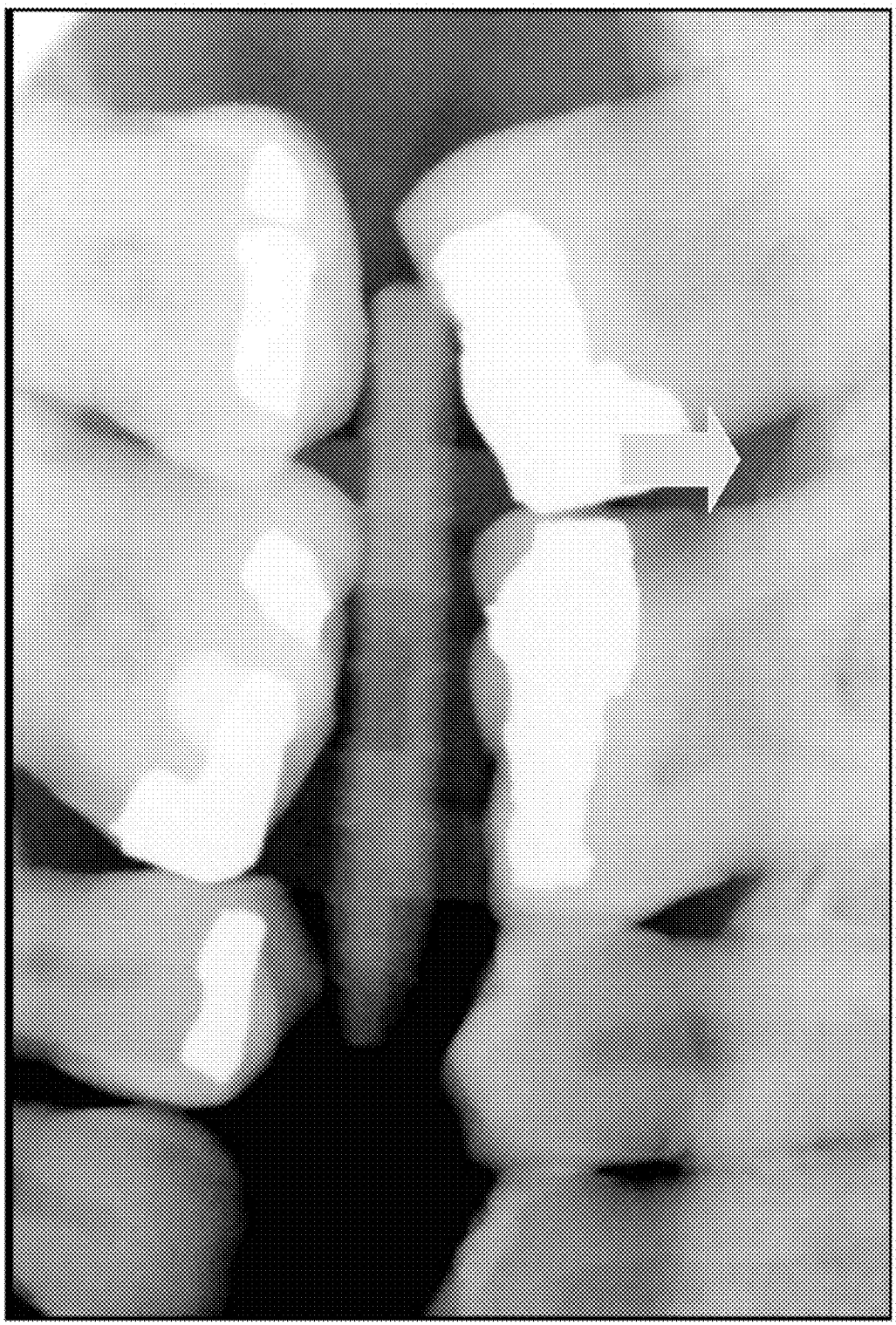
FIGS. 77-80 are radiographs showing examples of lamina dura bone damaged by periodontal disease.
Figure 78:
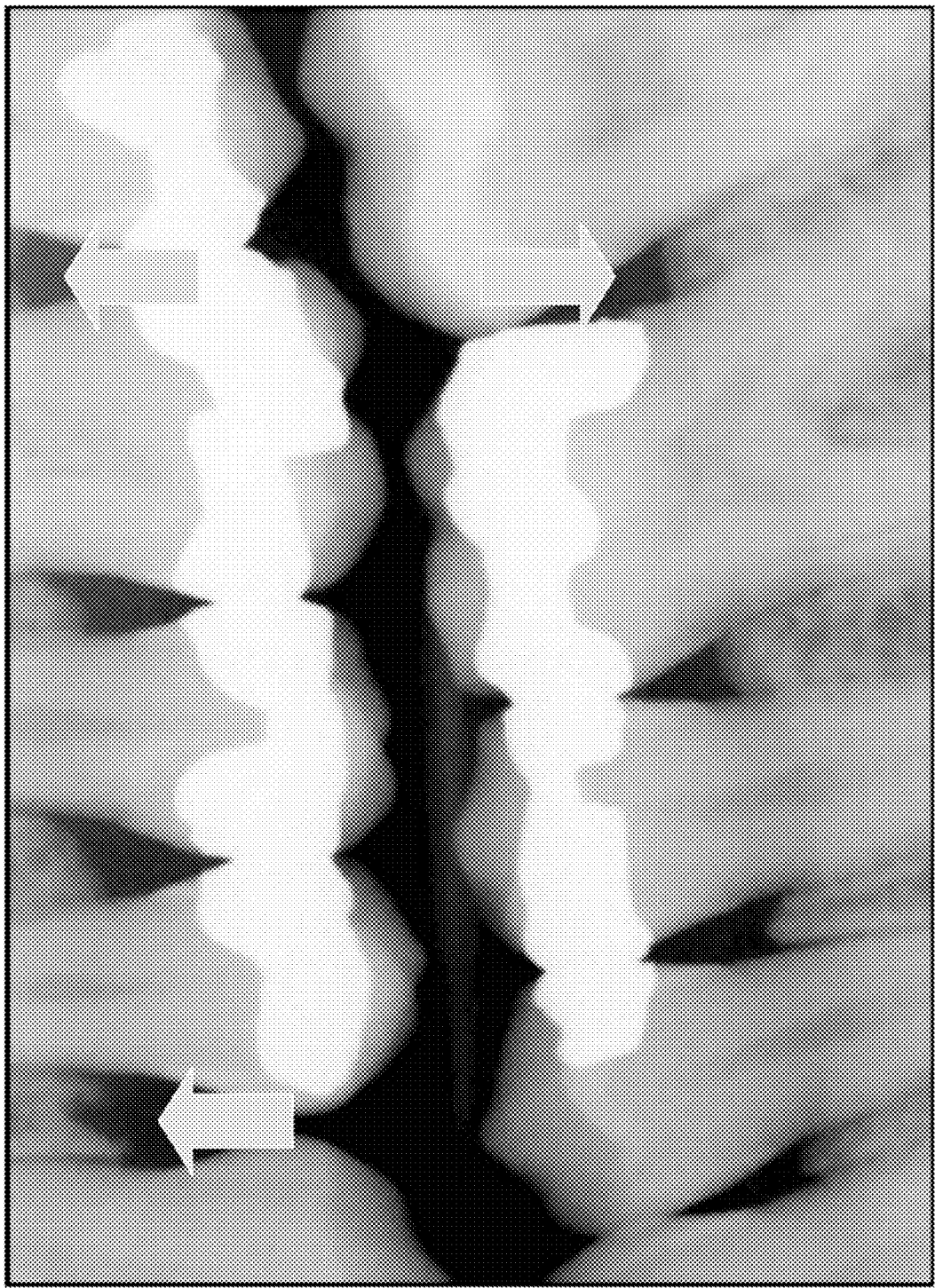
Figure 79:
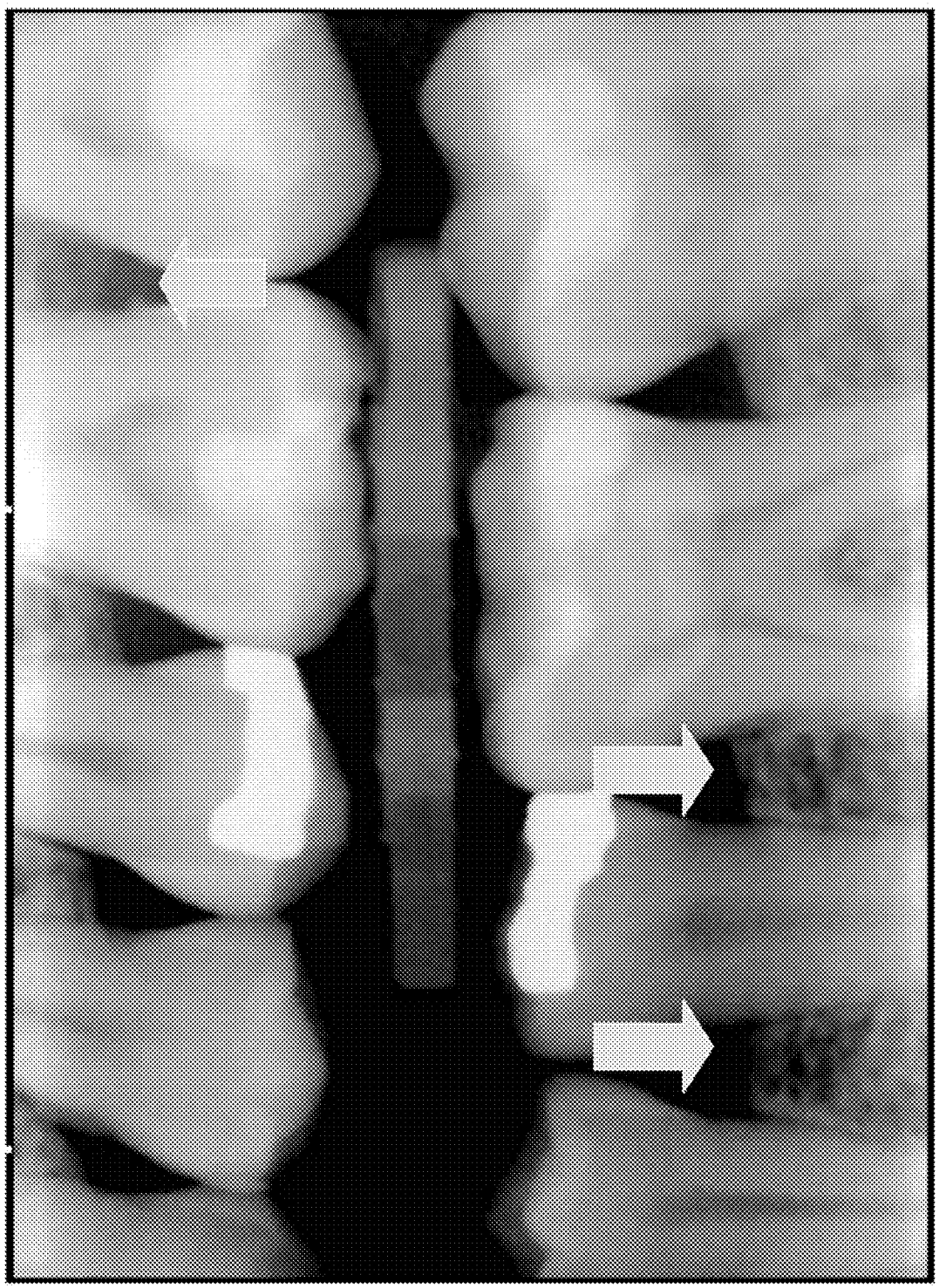
Figure 80:
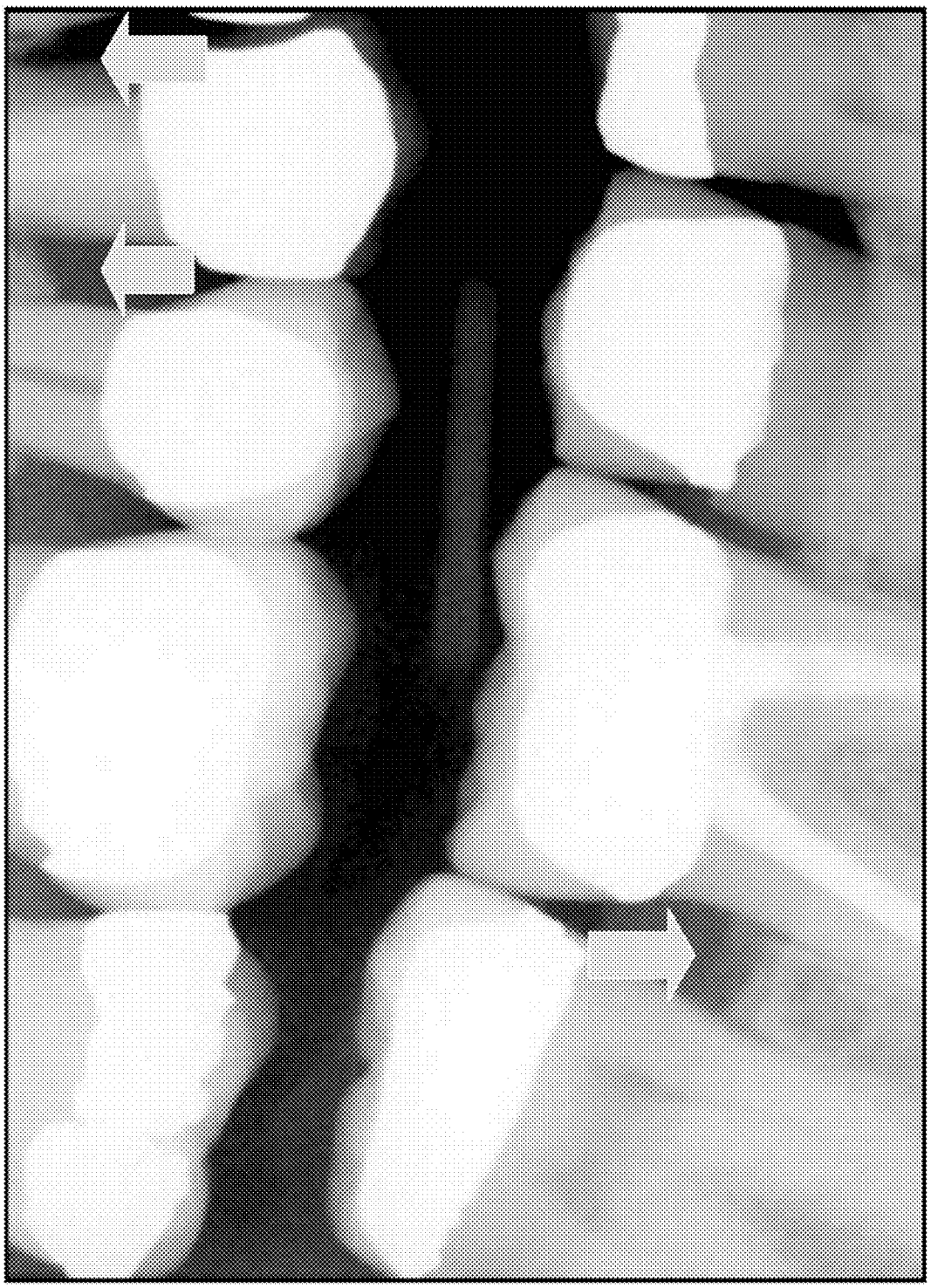

Periodontal disease (PD) is a tooth-born infection of a portion of the gums surrounding the teeth. Bacteria on the surface of teeth trigger an inflammatory response in the gum tissue around the teeth that may eventually destroy the underlying crestal lamina dura bone around the teeth (FIGS. 75 and 76). Periodontal infections may contribute to other serious diseases such as heart disease, implant infections, and strokes. However, early detection and treatment are effective means for preventing these undesirable sequelae.

A main target market for treatment of periodontal disease is among people age 40 and older. The potential market for treating periodontal disease in the U.S. may range between $15 billion and $30 billion annually. A diagnostic system that encourages earlier and more accurate detection will lead to higher levels of patient agreement to treatment, thus improving patient care as well as enhancing the dentist's revenue stream.

Currently, the most widely used assessment of periodontal disease is manual probing of the gum tissue. The "probe" typically comprises a metal or plastic instrument between about 0.5 mm and about 1 mm in diameter that is manually inserted into the patient's gums around each tooth. This is generally an uncomfortable or even painful procedure, and is also inherently inaccurate, since it is only an indirect assessment of the underlying bone condition and is highly subjective (varying with both clinician and patient). Subjective reading of dental x-ray or radiographs is often used to confirm periodontal disease, but typically bone loss must be fairly far advanced (i.e. bone must be destroyed) before the damage can be readily seen upon visual inspection (FIGS. 77-80). Unfortunately, bone destruction that has reached this stage is typically irreversible, again emphasizing the desirability of early, objective detection.

A software algorithm for analyzing digital dental radiographs may provide a more objective and more accurate means for diagnosing and evaluating periodontal disease. By providing objective numerical values for characterizing periodontal disease, the software algorithm may enable the clinician to make more appropriate treatment recommendations, and may elicit more ready acceptance of those treatment recommendations by the patient.

In order to accurately diagnose and treat periodontal disease, a clinician must ascertain, inter alias whether the disease is currently active; if active, how aggressive is the infection; how much bone damage has occurred; what is the prognosis if the disease is effectively eliminated. Further, the clinician must attempt to induce the patient to visualize, comprehend, and concur with the findings and recommended treatment of the clinician. An objective two-number numerical scoring system provided by software analysis of digital radiographic images may be employed to meet these requirements.

The first numerical value employed is the bone depth (BD). Patients are already generally aware of "pocket depths" used for evaluating periodontal disease; these are the values obtained by manual probing of gum tissue. Painless radiographic determination of bone depth is a desirable replacement for often painful manual probing, especially since manual probing to the full pocket depth in an area of disease can only be accurately determined when the patient is anesthetized in that area. The BD is typically expressed in mm from the cemento-enamel junction (CEJ), which may be readily identified and accurately located in an x-ray. A BD value of about 3 mm is desirable for an adult. Changes in BD can be readily tracked over time to detect low-level chronic bone loss. A measured BD value over 4 mm is a direct indication that bone damage has occurred, especially if the patient previously had a lower BD value determined.

The second numerical value employed is Crestal Density (CD), which may be used to detect and quantify the presence of active periodontal disease. In the current example, CD is expressed on a 1 to 10+ scale (1 indicating no periodontal disease with upper values ranging up to 15 or even higher; any other desired scale range could be used). CD values are determined relative to healthy lamina dura around teeth and relative to normal intramedullary bone density. Changes in CD may be readily tracked over time to detect periodontal disease in its earliest stages. On the scale used in this example, CD values of 1 to 3 are normal for healthy adults, CD values of 4 to 7 indicate thinning of crestal bone that may still be halted with proper treatment, and CD values of 8 or more indicate aggressive bone loss resulting in increased bone depth (BD) measurements.

Figure 81:
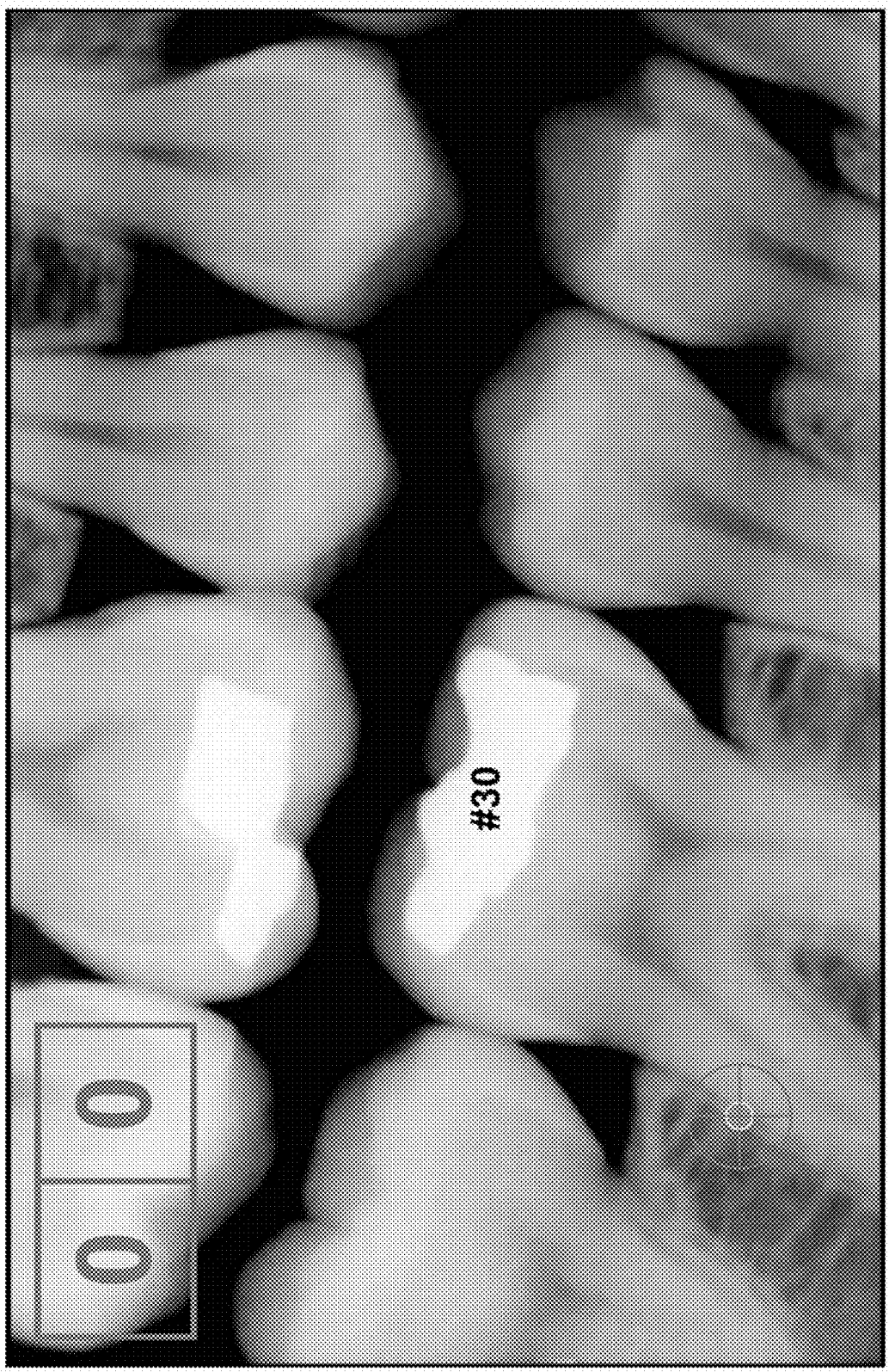
FIGS. 81-87 illustrate use of a software algorithm for diagnosing and evaluating periodontal disease from the digital dental x-ray image.
Figure 82:
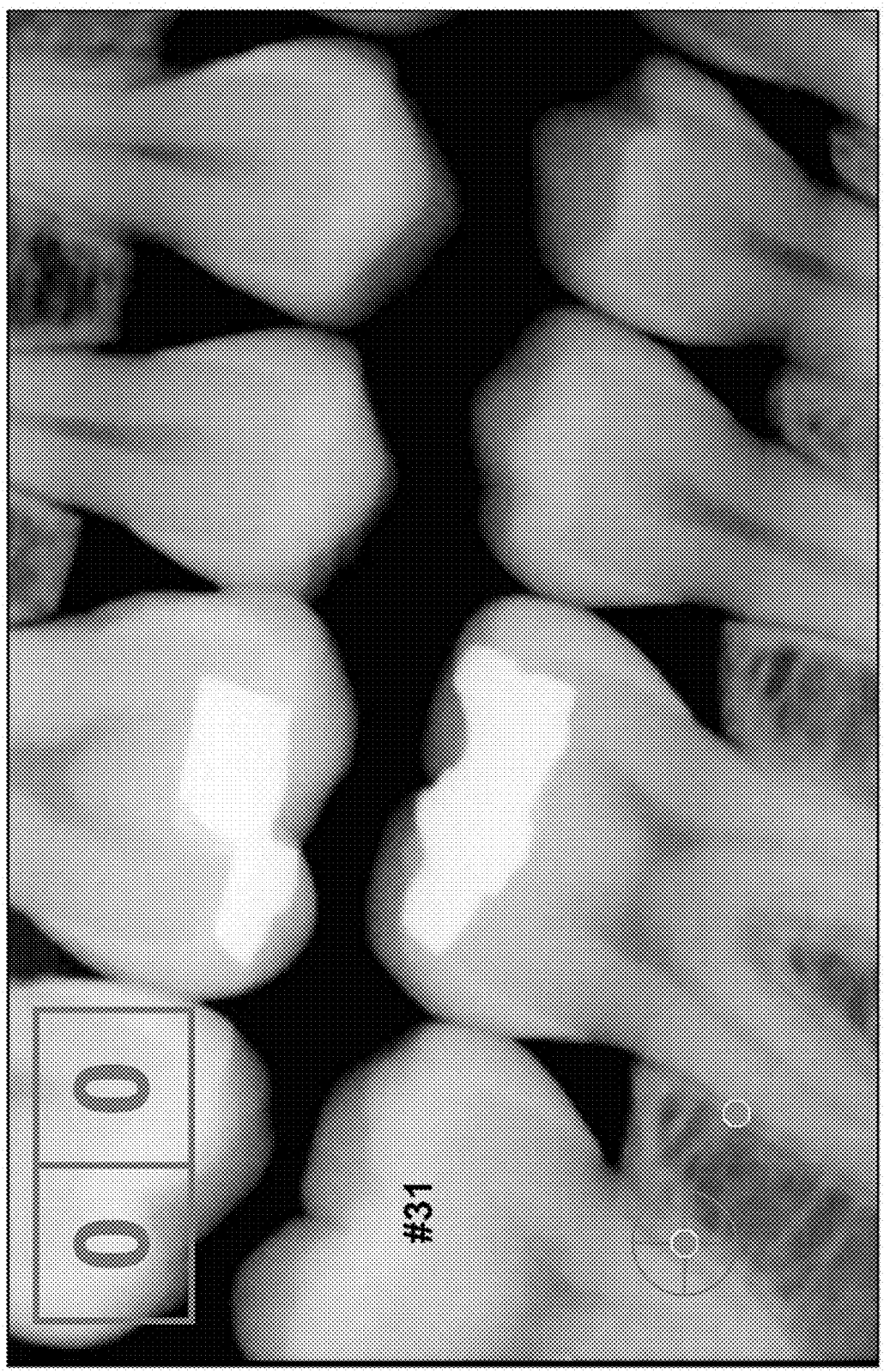
Figure 83:
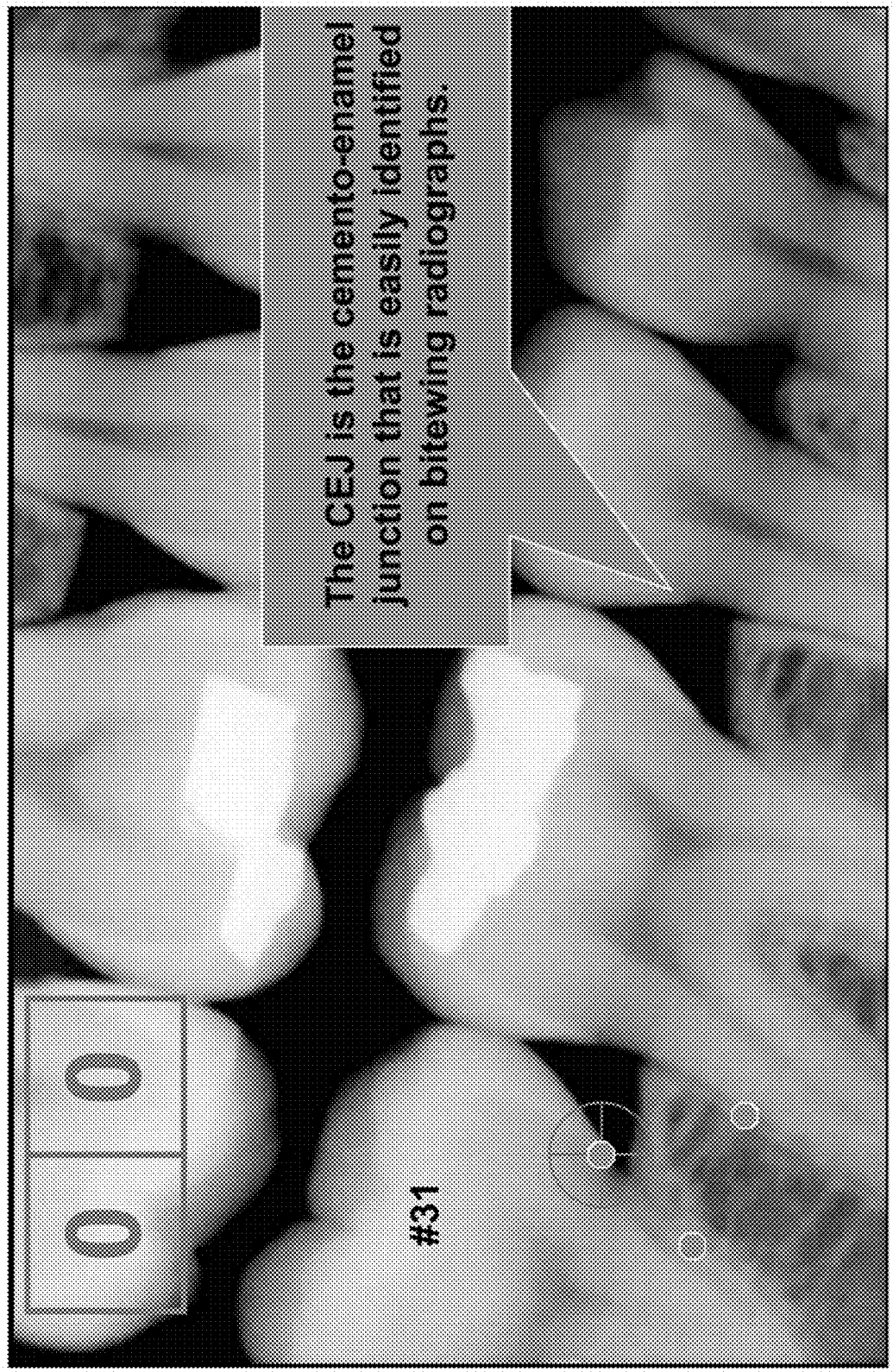
Figure 84:
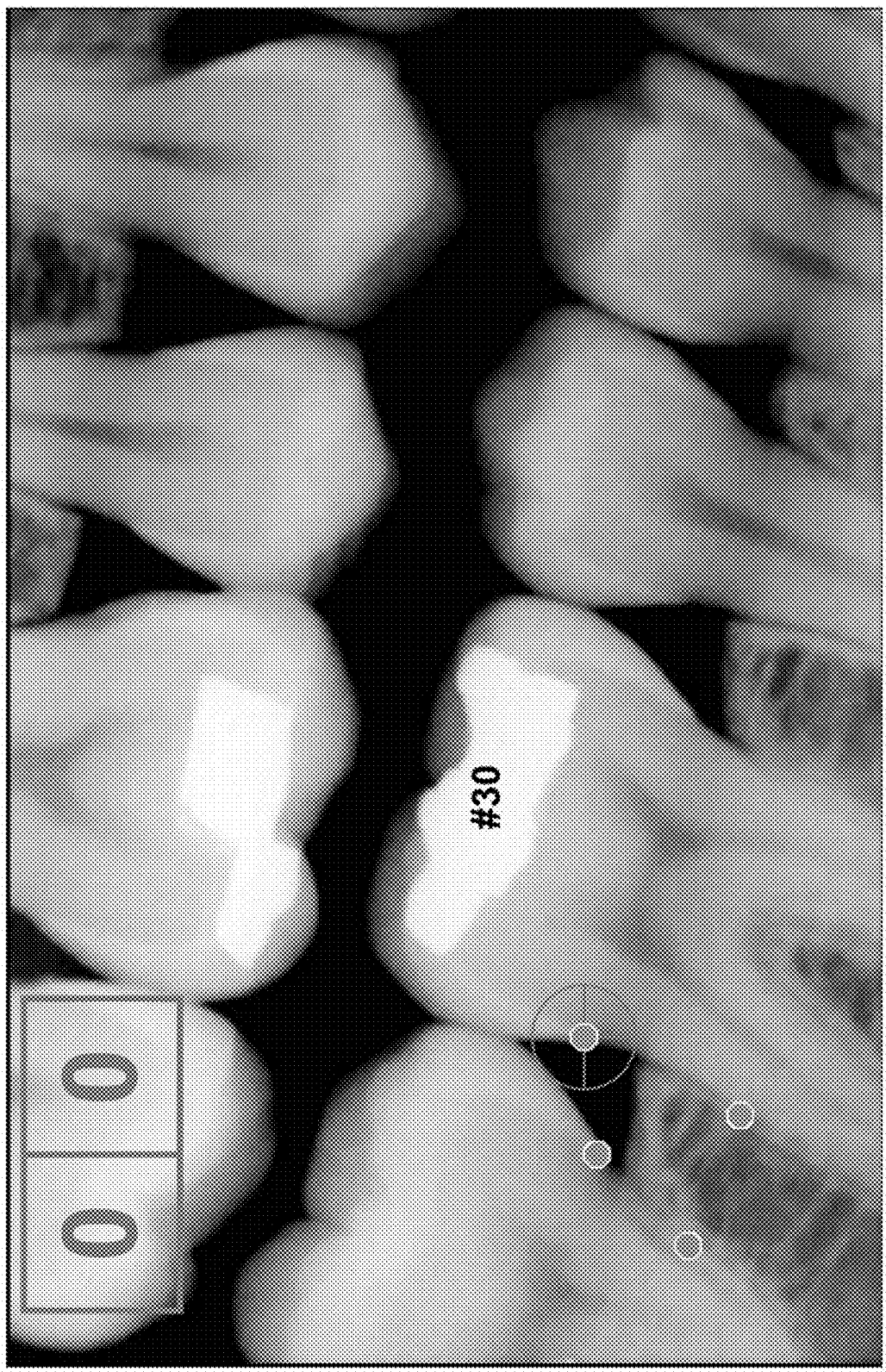
Figure 85:
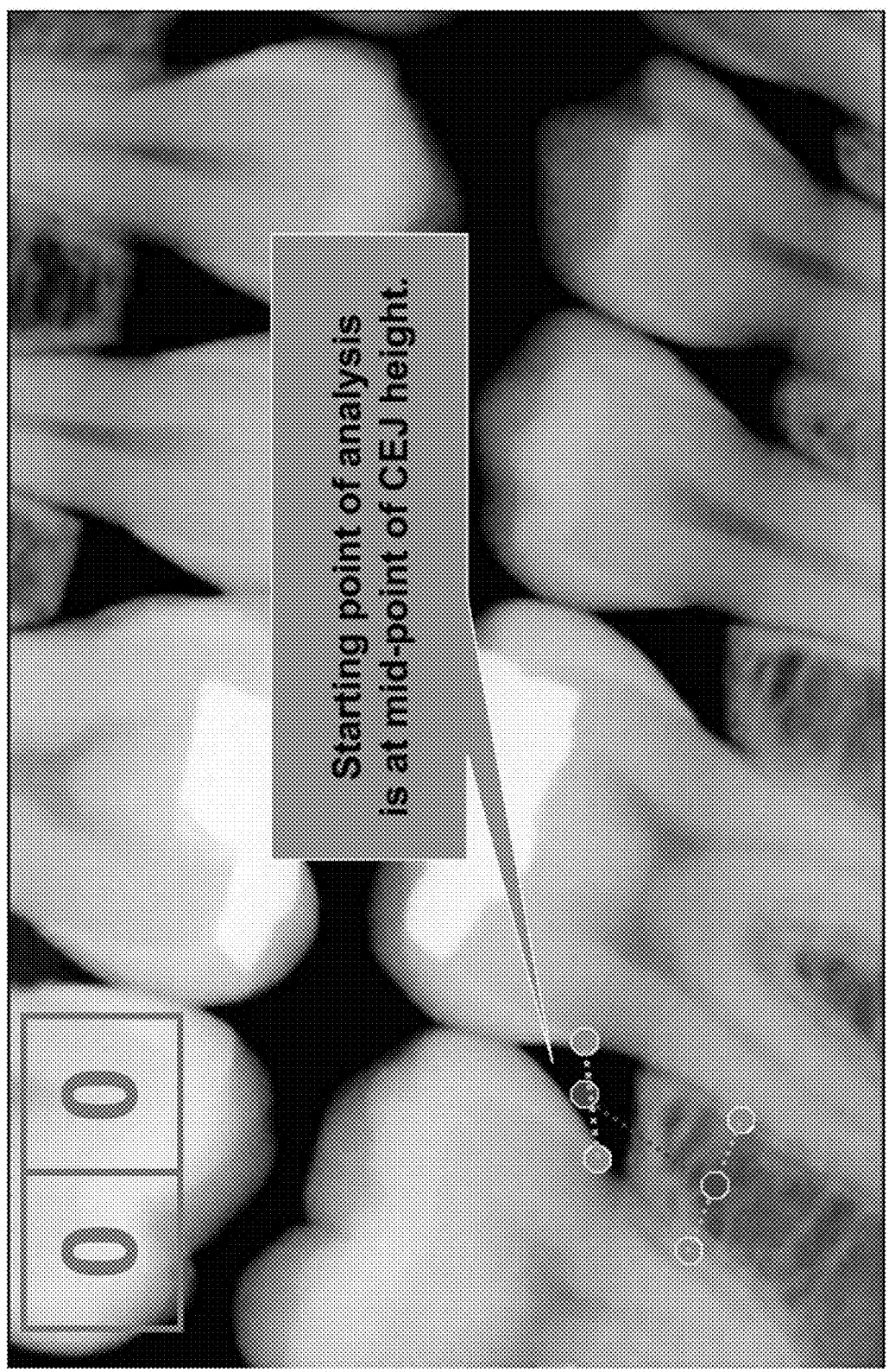
Figure 86:
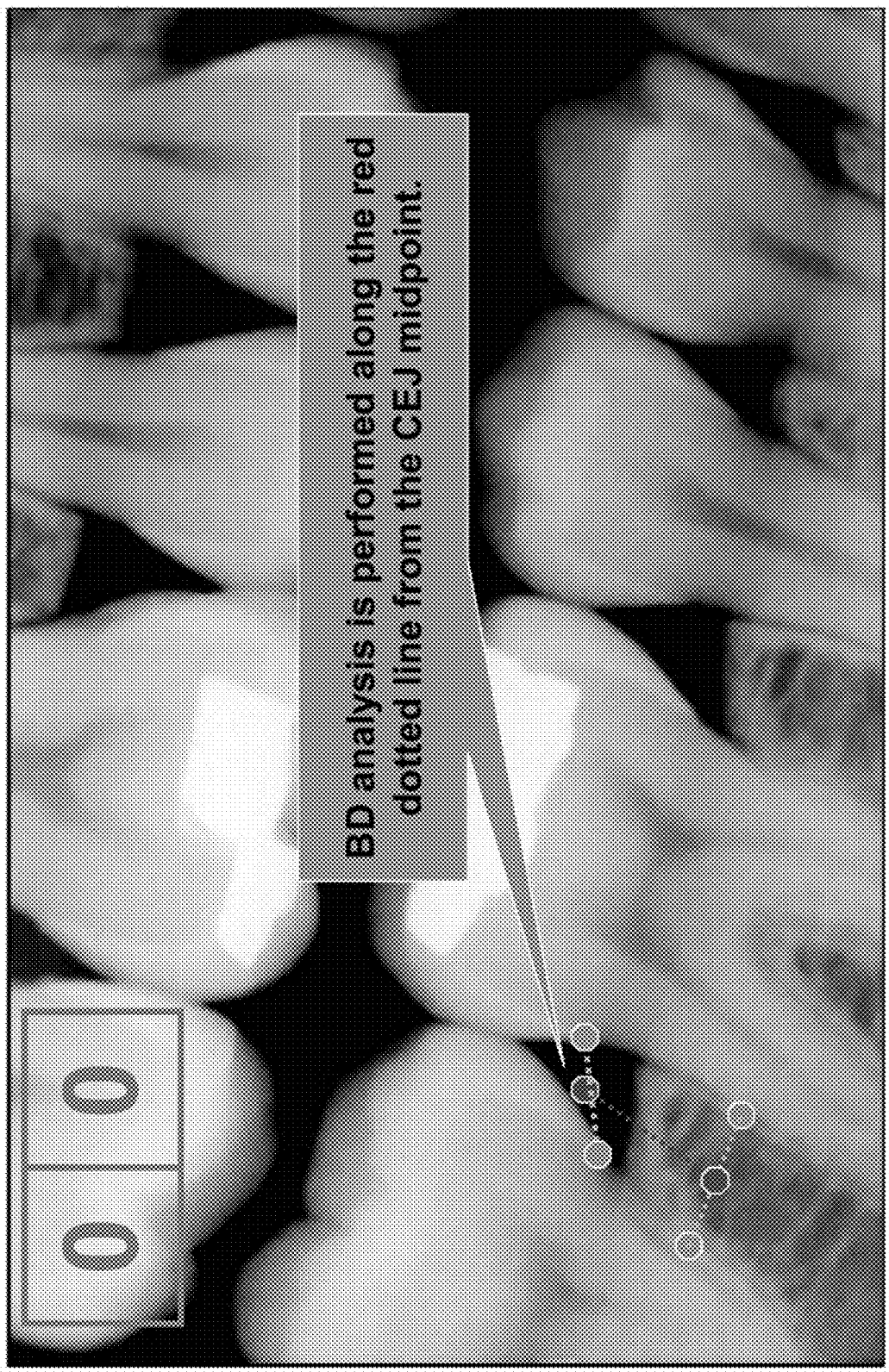
Figure 87:
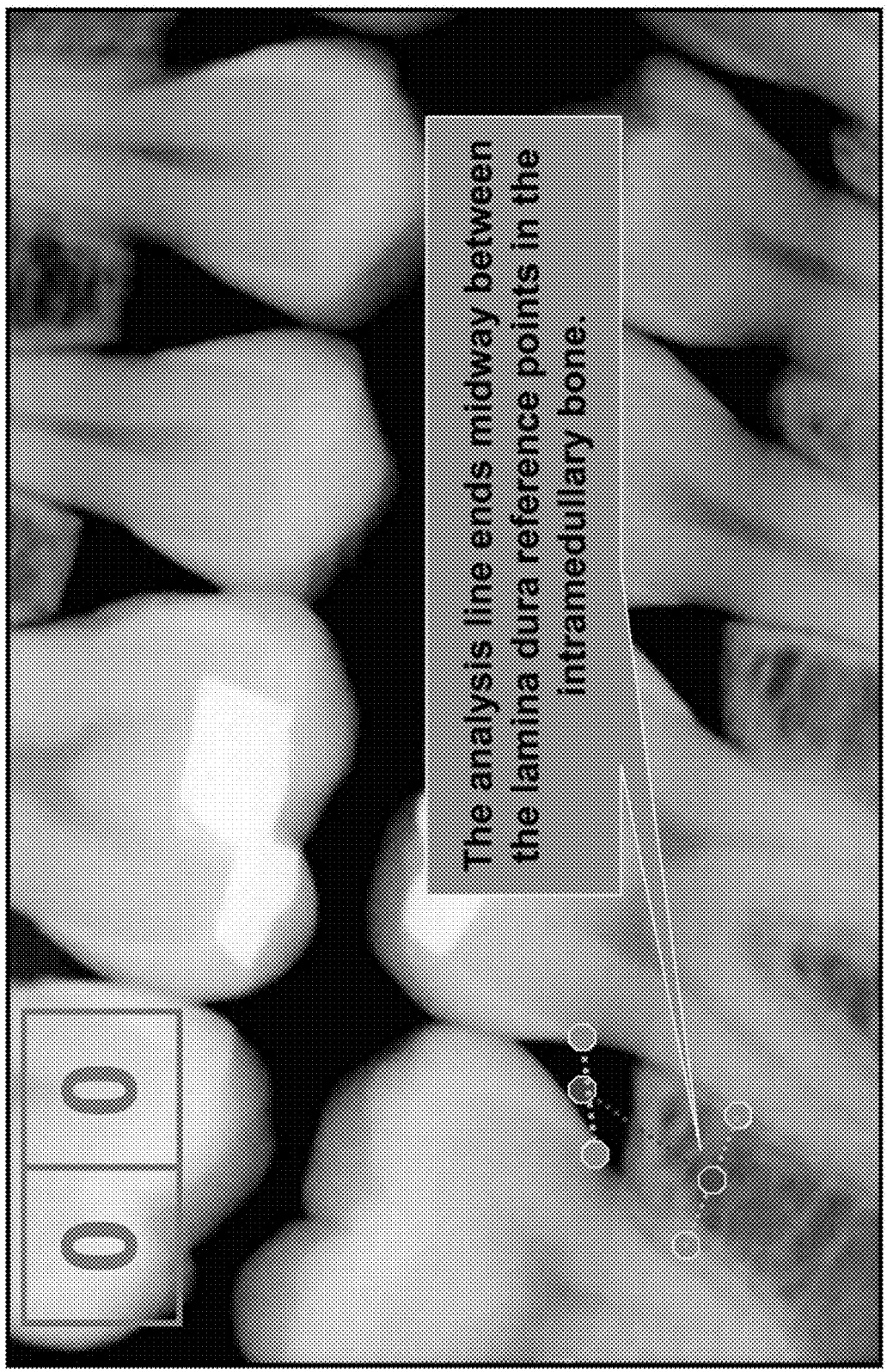
Figure 88:
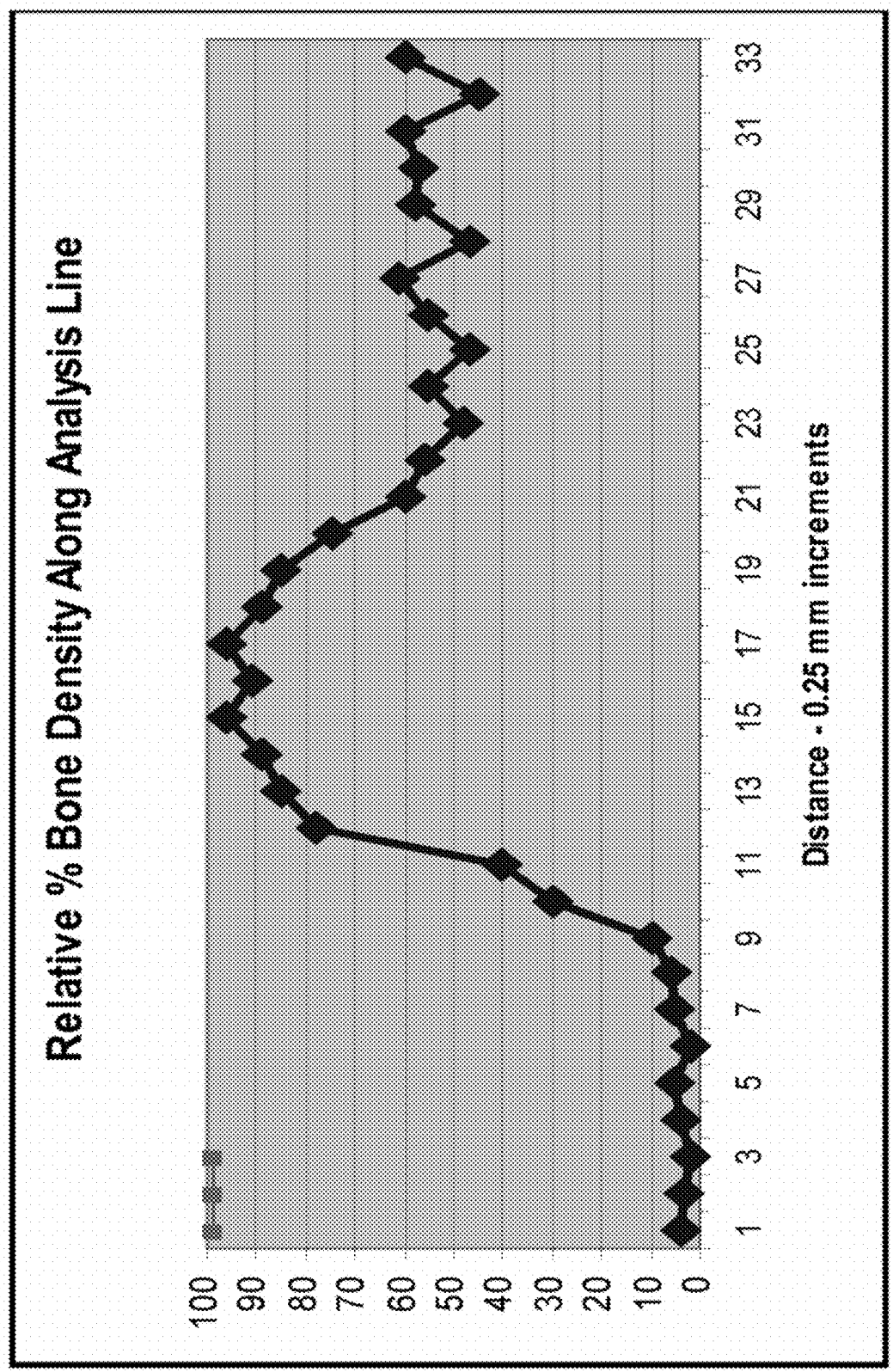
FIGS. 88 and 89 are optical density traces from the radiographs of FIGS. 81-87.
Figure 89:
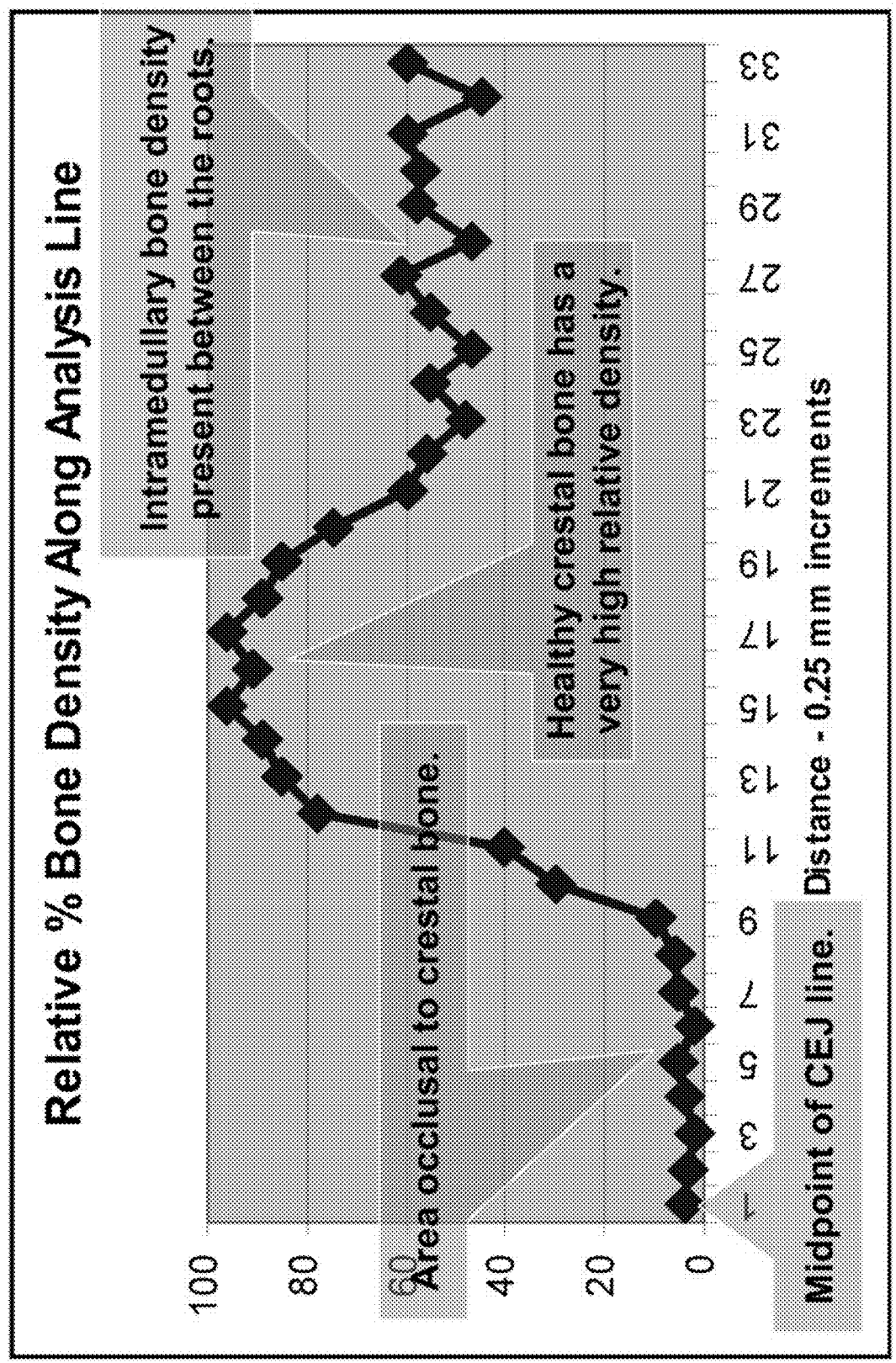

Use of the software algorithm for measuring bone depth and crestal density from an x-ray is illustrated in FIGS. 81-89. First, the user marks the image at the lamina dura on the facing surfaces of adjacent teeth (#30 and #31 in this example; FIGS. 81 and 82). Next, the user marks opposing cemento-enamel junctions (CEJs) on the same teeth (FIGS. 83 and 84). The line along which the software analyzes the crestal bone density runs between the midpoints of the segment connecting the lamina dura of the adjacent teeth and the segment connecting the CEJs of the adjacent teeth (FIGS. 85-87). FIGS. 88 and 89 show a plot of bone density (i.e. radiographic density) along this analysis line, with the maximum density normalized to 100.

Figure 90:
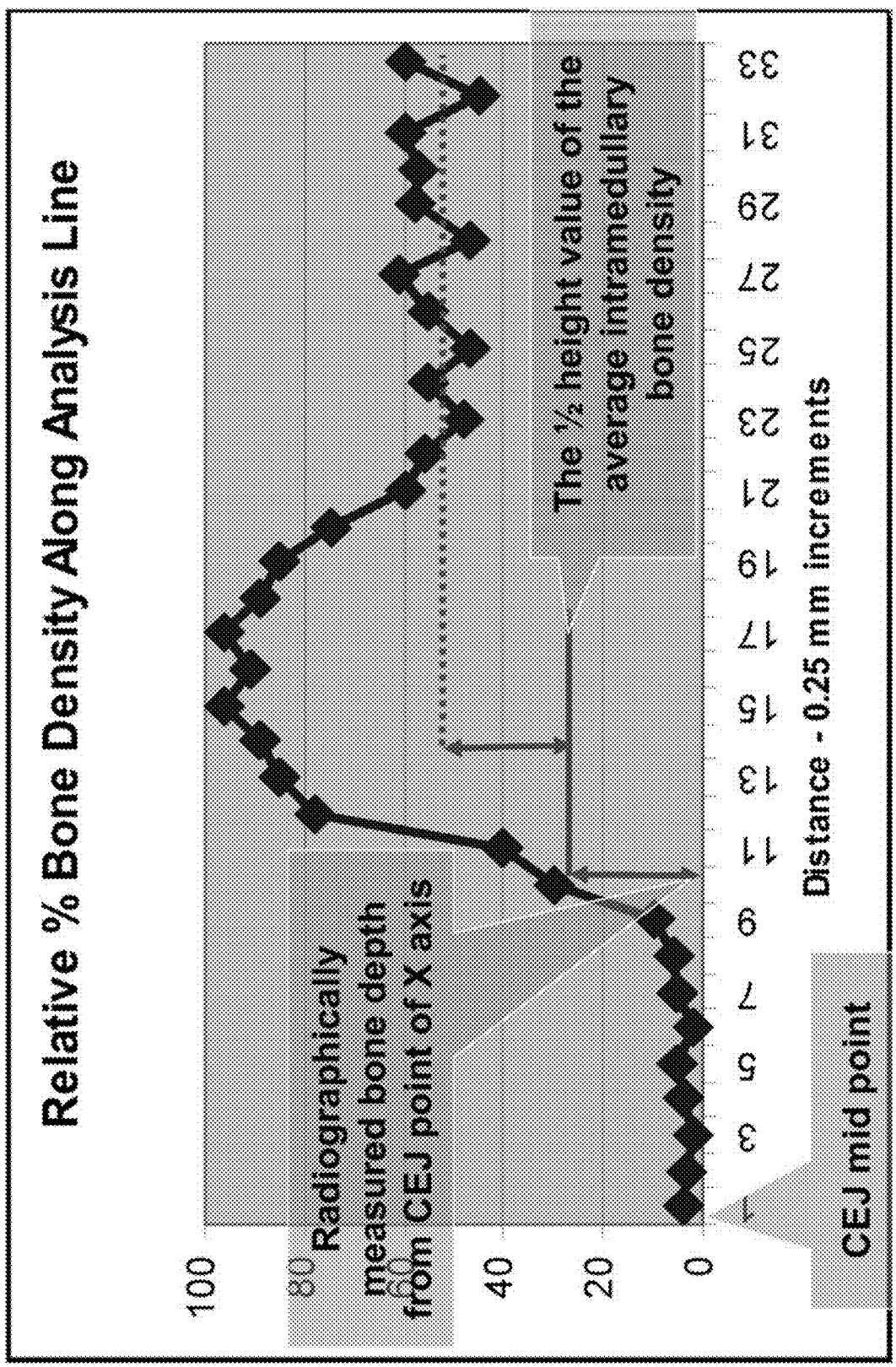
FIG. 90 is a chart that illustrates calculation of crestal bone depth from an optical density trace.

The bone depth (BD) may be extracted from the plot of FIG. 89 as follows. The midpoint of the CEJ height line is the starting point for analysis. The intramedullary bone density at the other end of the analysis line is used as a reference density. Intramedullary bone density is averaged over a small area (several mm square, for example) to average out variation on small length scales. The bone depth is defined as the distance along the analysis line from CEJ mid-point to a point where the bone density has reached ½ of the intramedullary bone density (FIG. 90). In the example illustrated in FIGS. 81-89, a BD value of about 2.5 mm is obtained, which indicates no present or past periodontal disease at this location.

Figure 91:
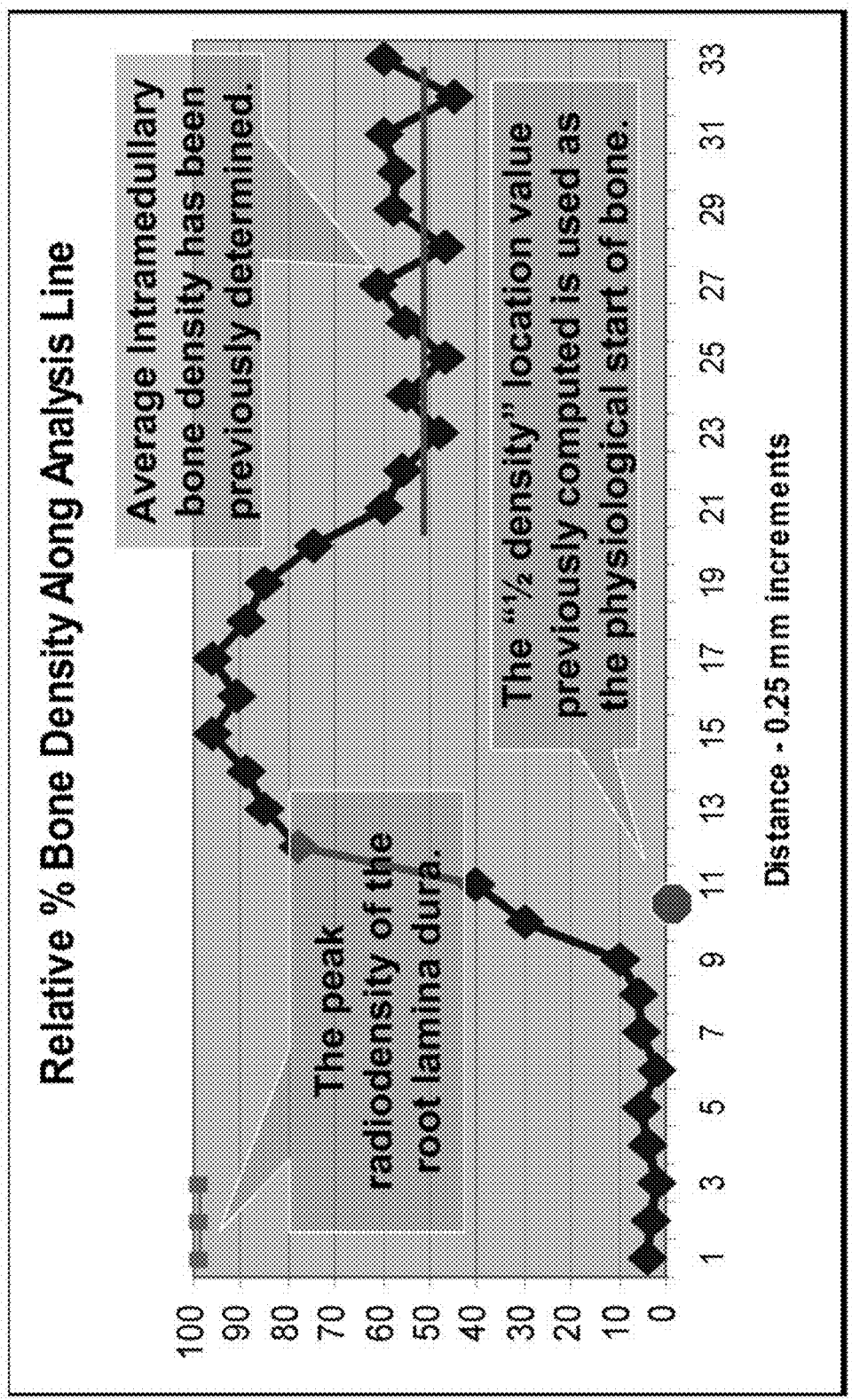
FIGS. 91 and 92 are charts that illustrate calculation of crestal bone density from an optical density trace.
Figure 92:
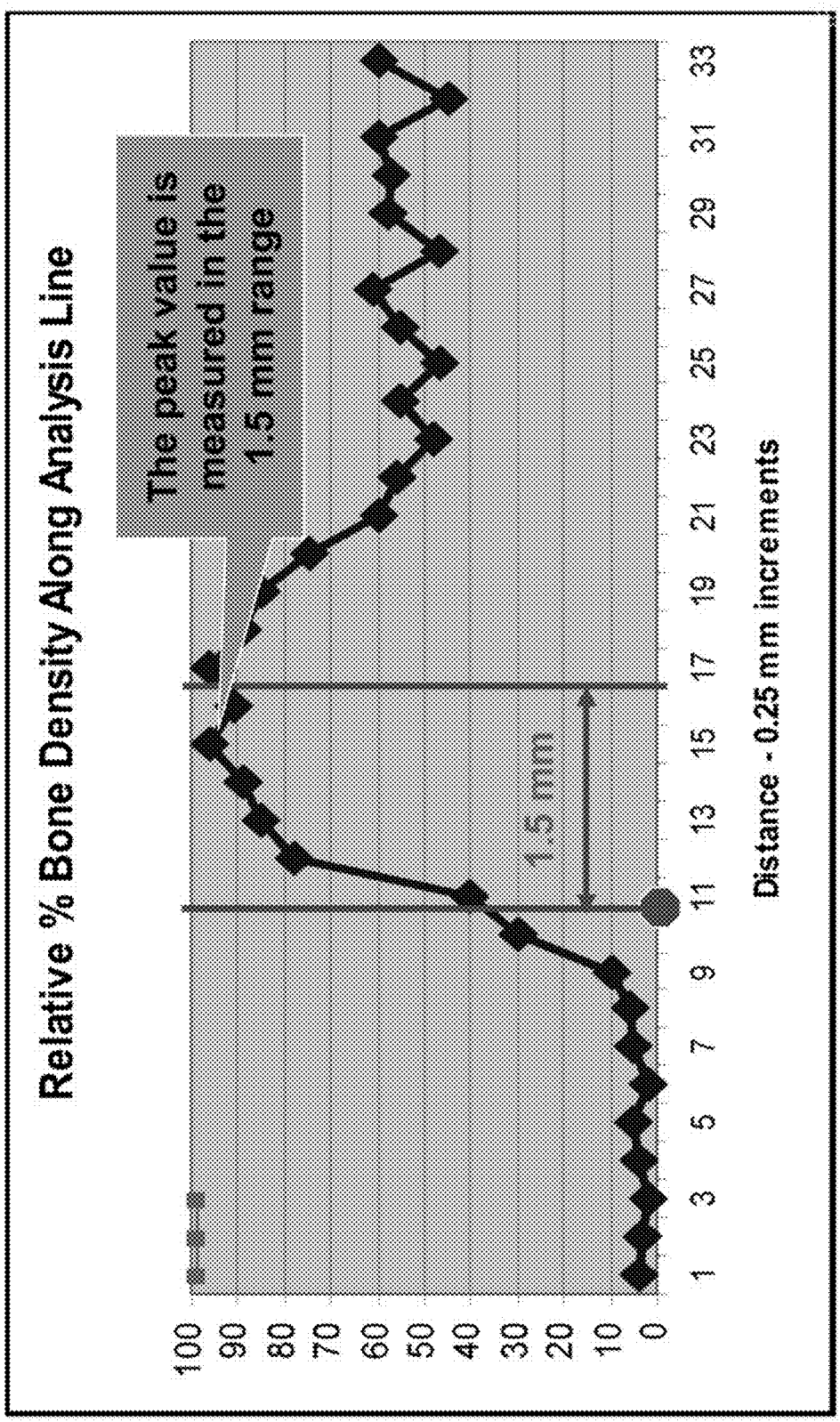
Figure 93:
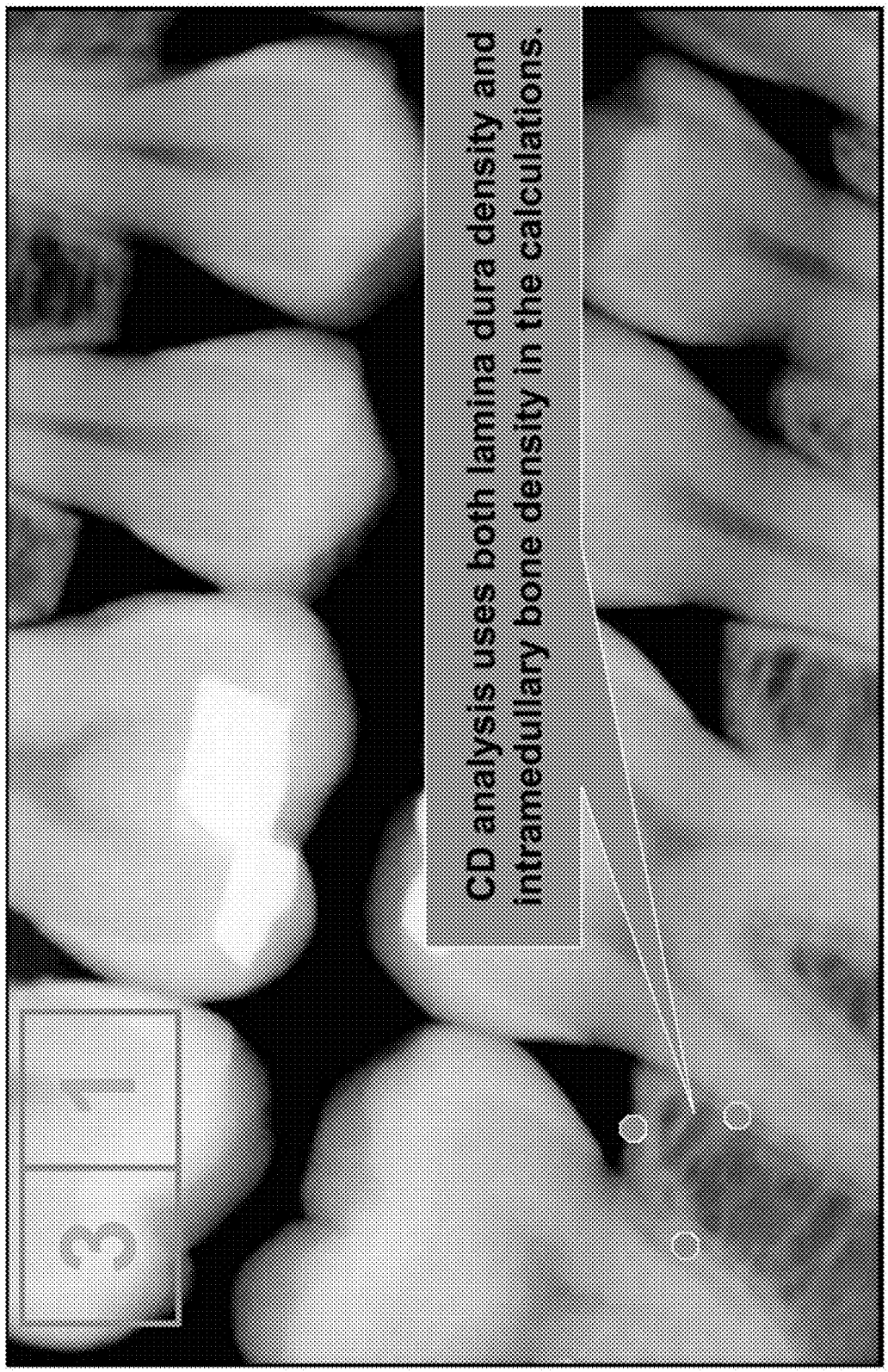
FIGS. 93 and 94 are images that illustrate crestal bone depth and bone density obtained using the software algorithm.
Figure 94:
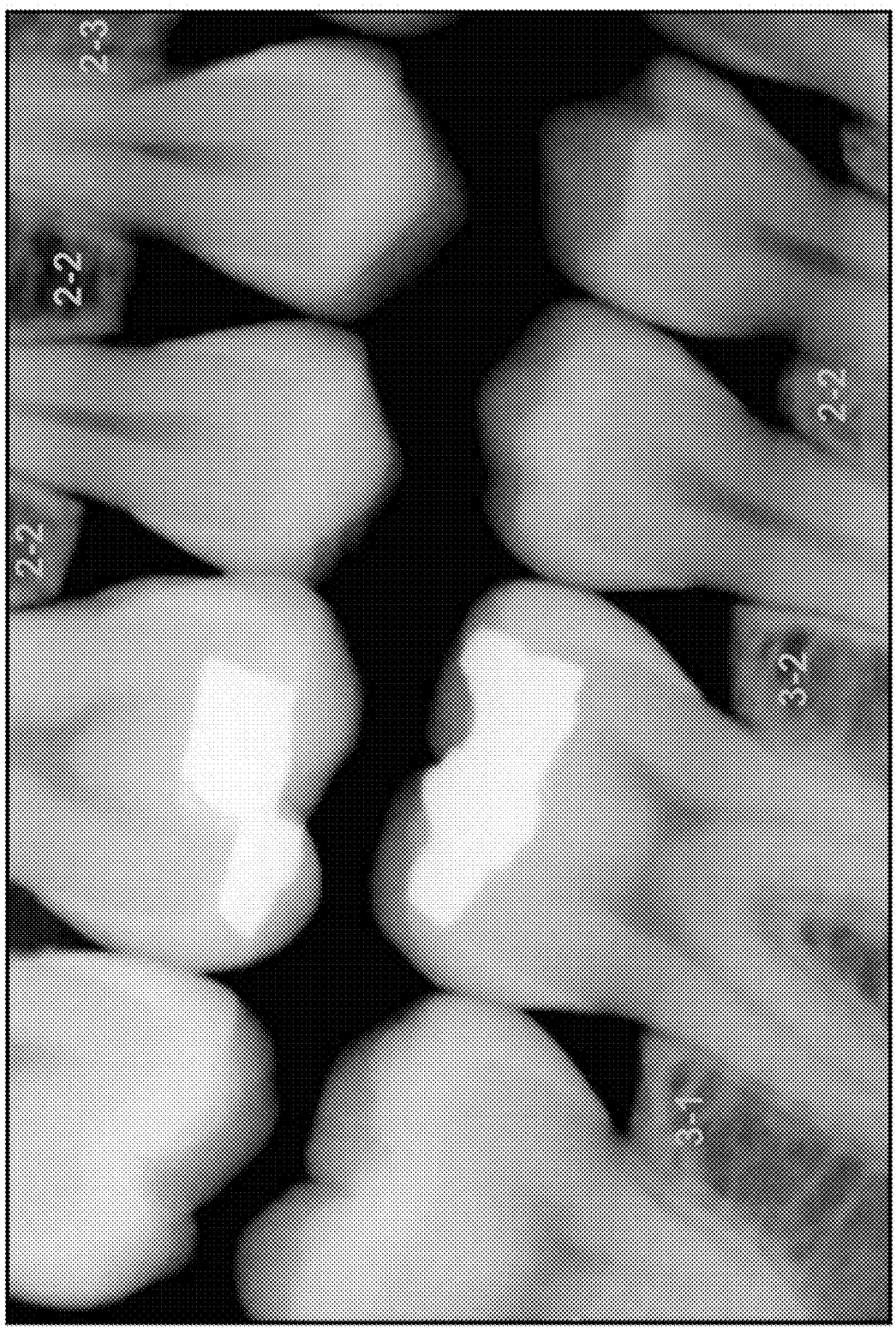

The crestal density (CD) may be extracted from the plot of FIG. 89 as follows. The bone depth point (the point where the plot reaches ½ of the intramedullary bone density) from the BD measurement serves as the starting point for the analysis (FIG. 91). Peak bone density within the next 1.5 mm along the analysis line starting at the ½ height intramedullary density location is measured (FIG. 92). Peak lamina dura density from the first two clicks (FIGS. 81 and 82) is measured from the image and arbitrarily assigned a value of 1. The intramedullary bone density previously calculated (FIGS. 90 and 91) is arbitrarily assigned a value of 10. The peak density measured in the first 1.5 mm of crestal bone (FIG. 92) is scaled by comparison to the maximum density of the lamina dura (e.g., "1") and the intramedullary bone density (e.g., "10") to determine a relative CD value. Where no periodontal disease has been present, the CD value obtained is 1 (FIG. 93). Both the BD and CD values are displayed for each location analyzed. The entire radiograph may be quickly analyzed as the operator clicks on the desired analysis locations, and the software performs the calculations described above in the background (FIG. 94).

Figure 95:
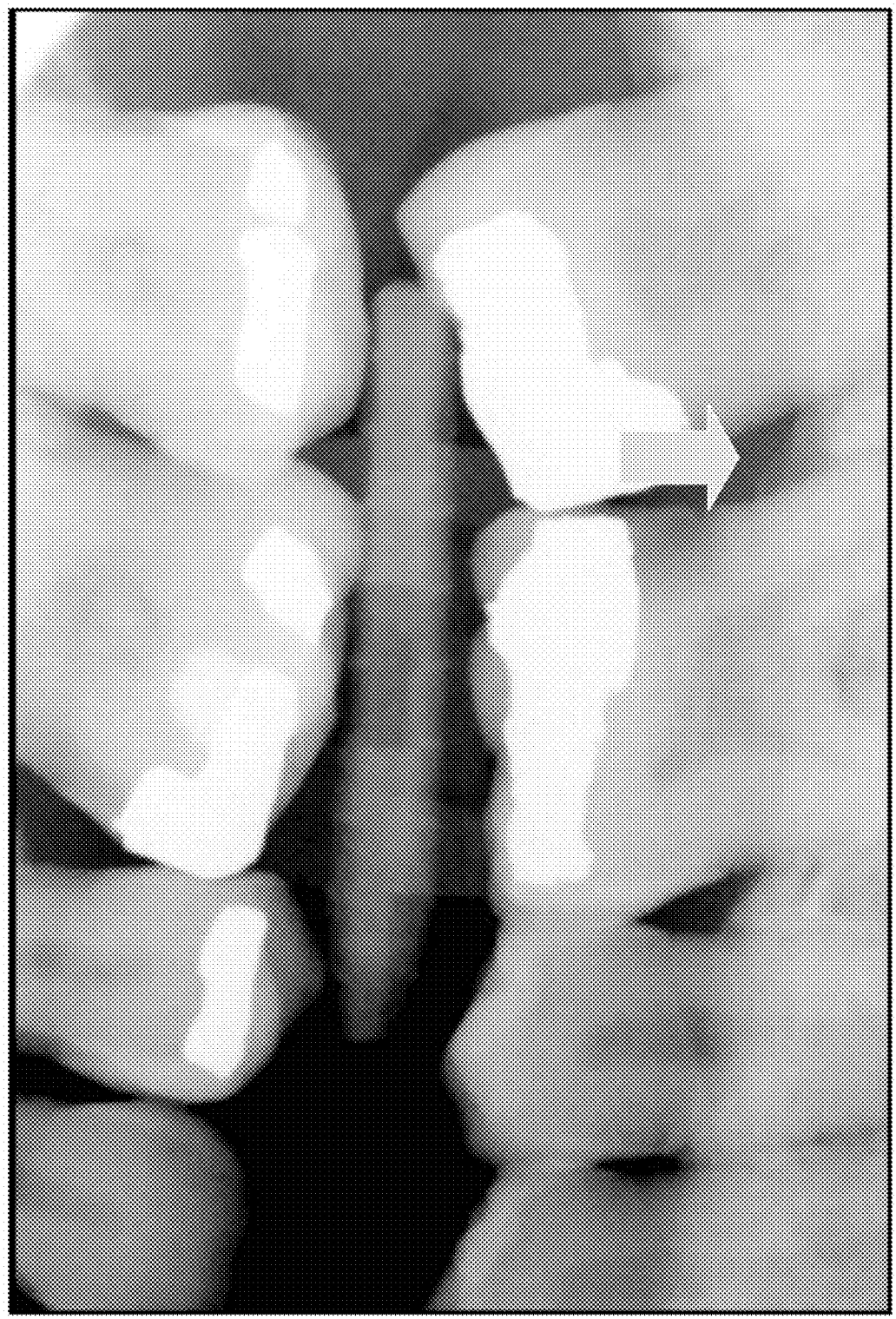
FIG. 95 is a radiograph with a site of suspected periodontal disease indicated.
Figure 96:
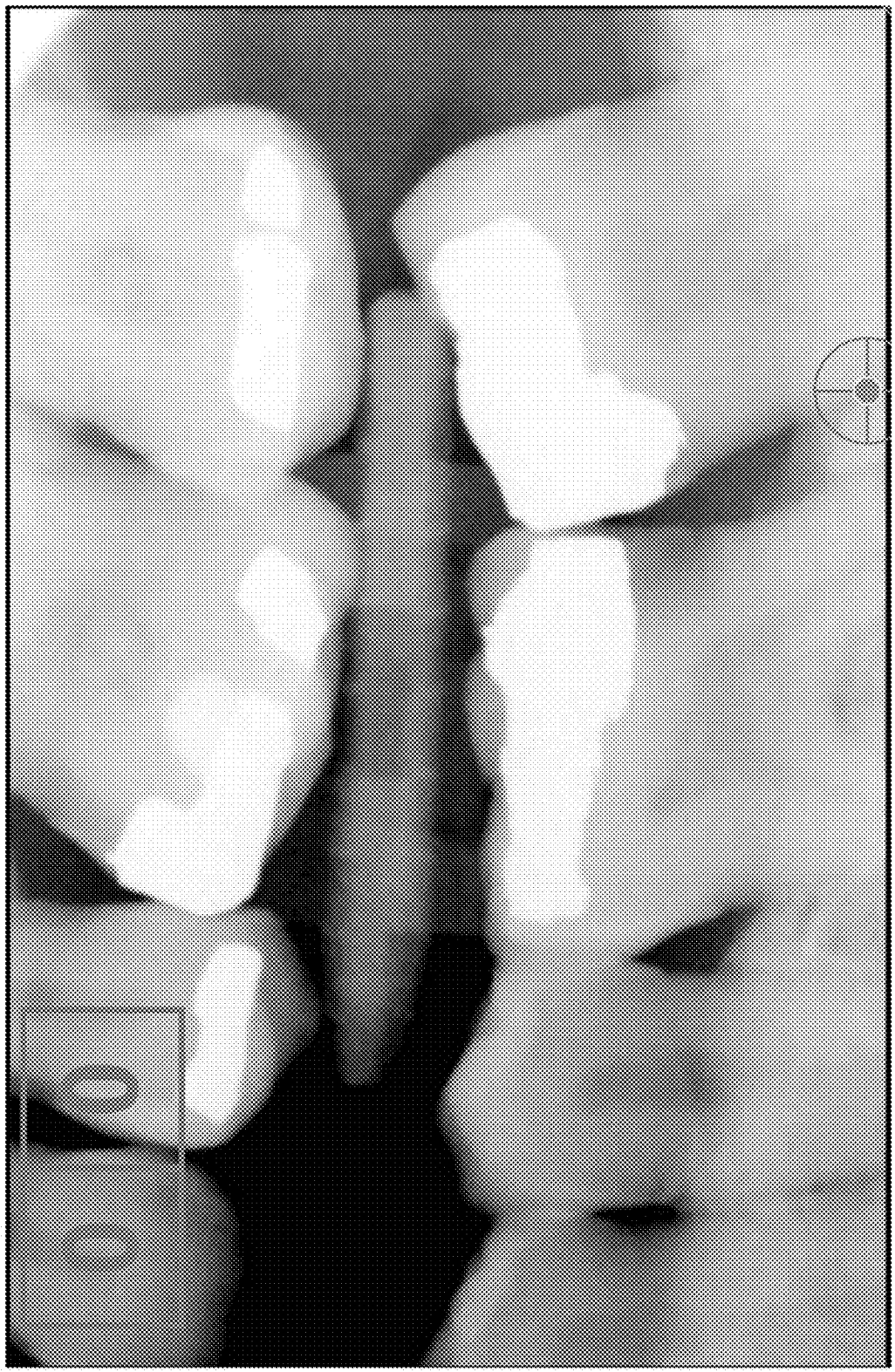
FIGS. 96-99 are images that illustrate use of a software algorithm for diagnosing and evaluating periodontal disease from a digital dental x-ray image.
Figure 97:
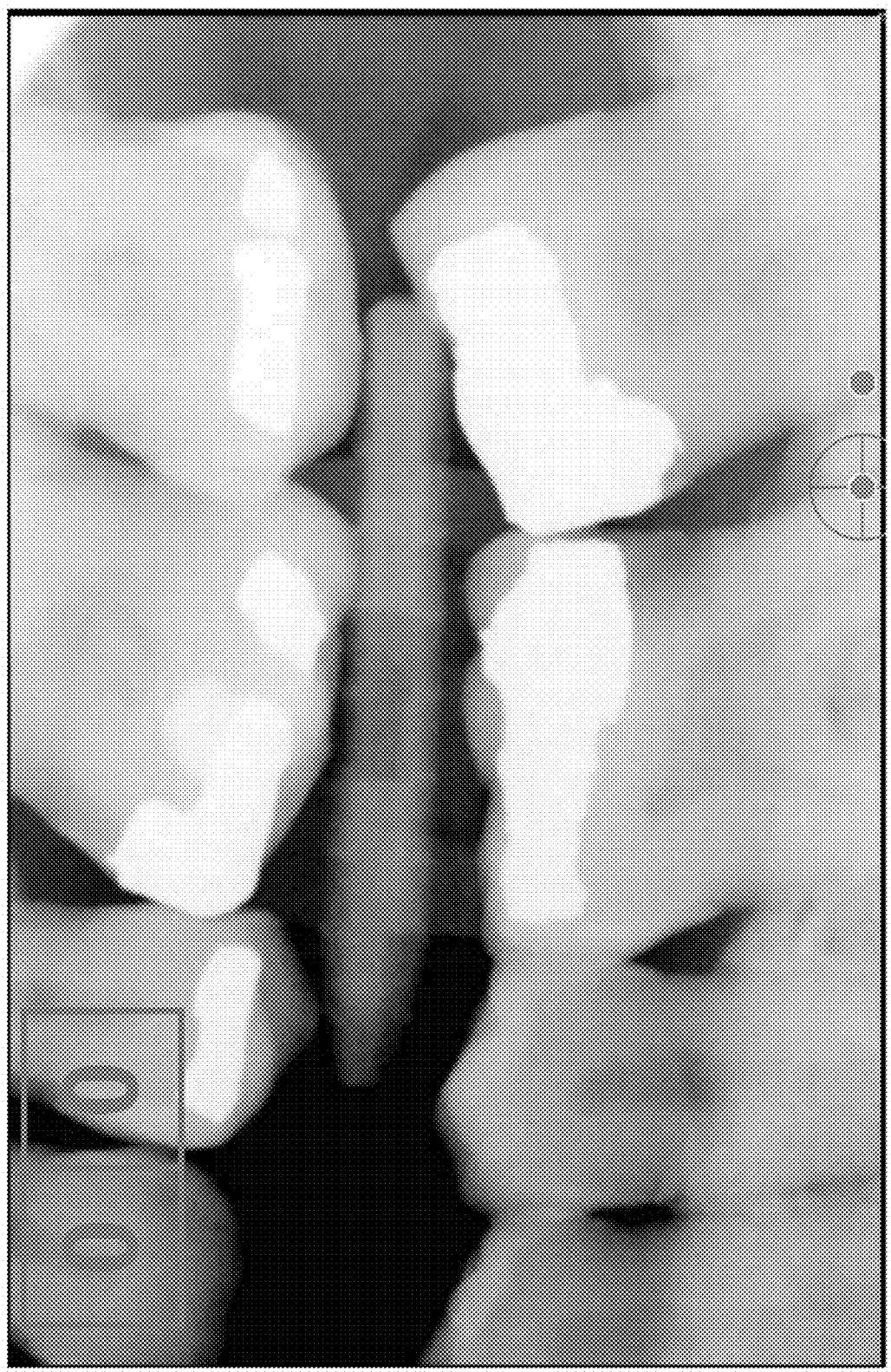
Figure 98:
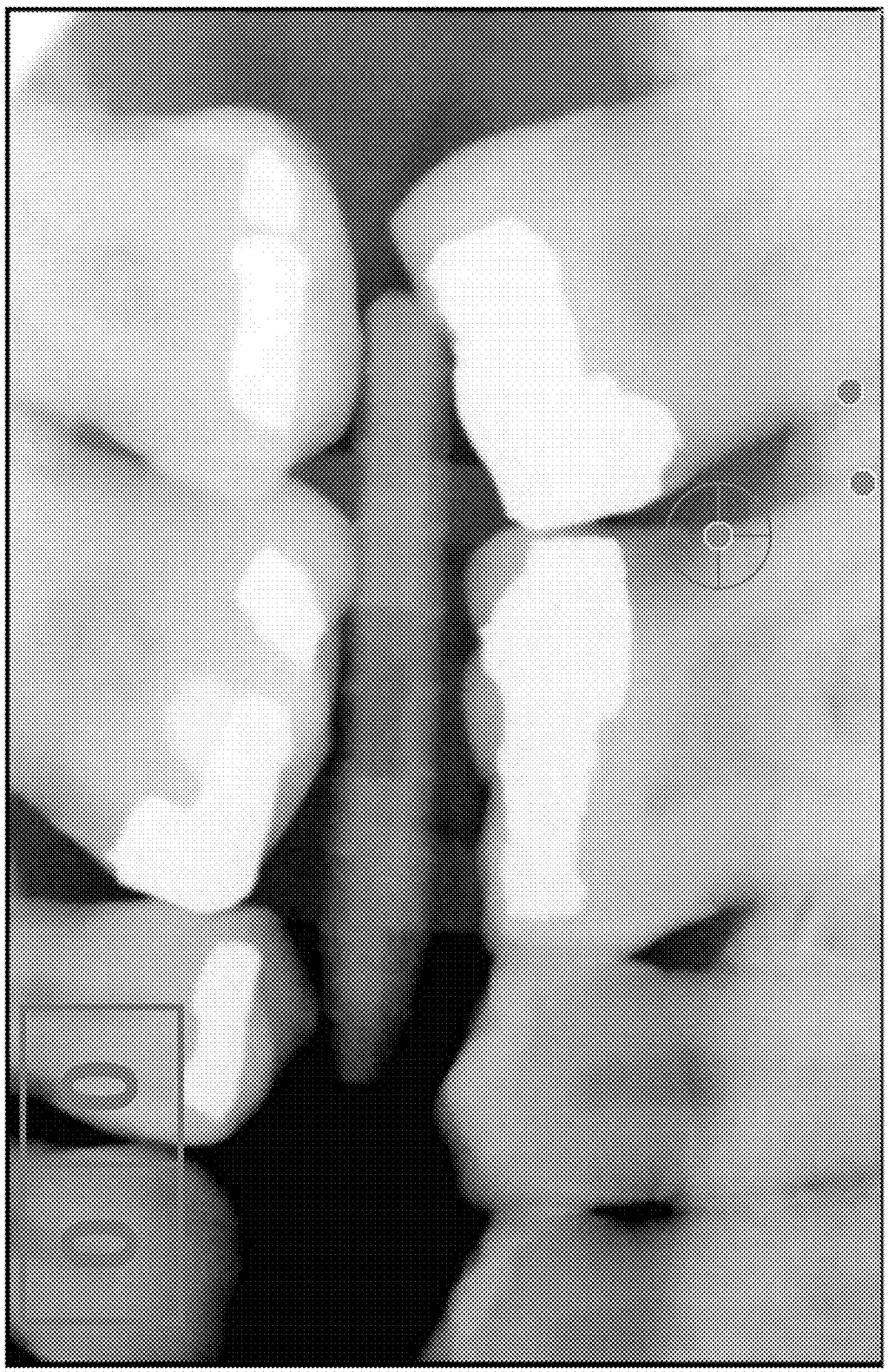
Figure 99:
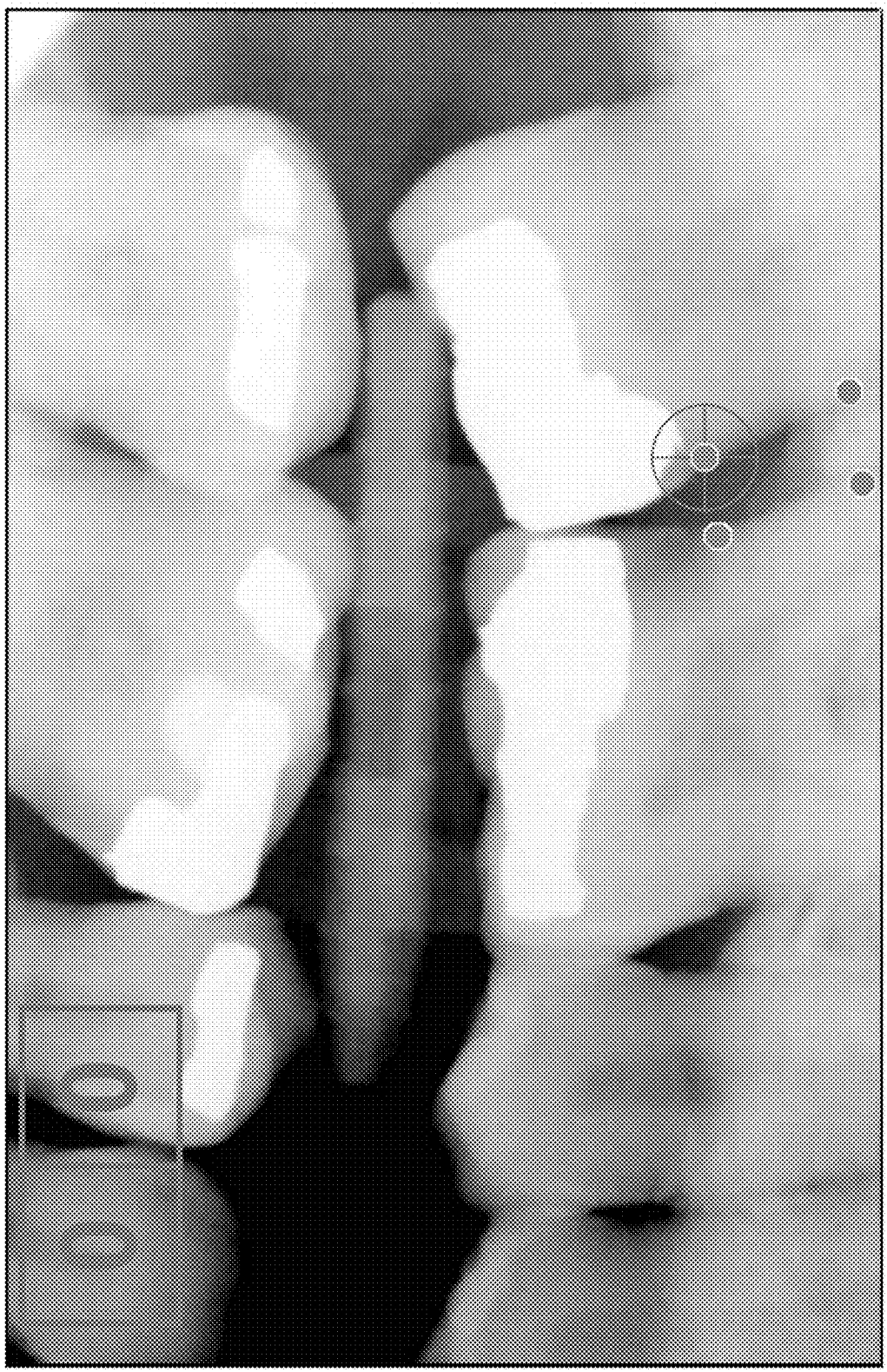
Figure 100:
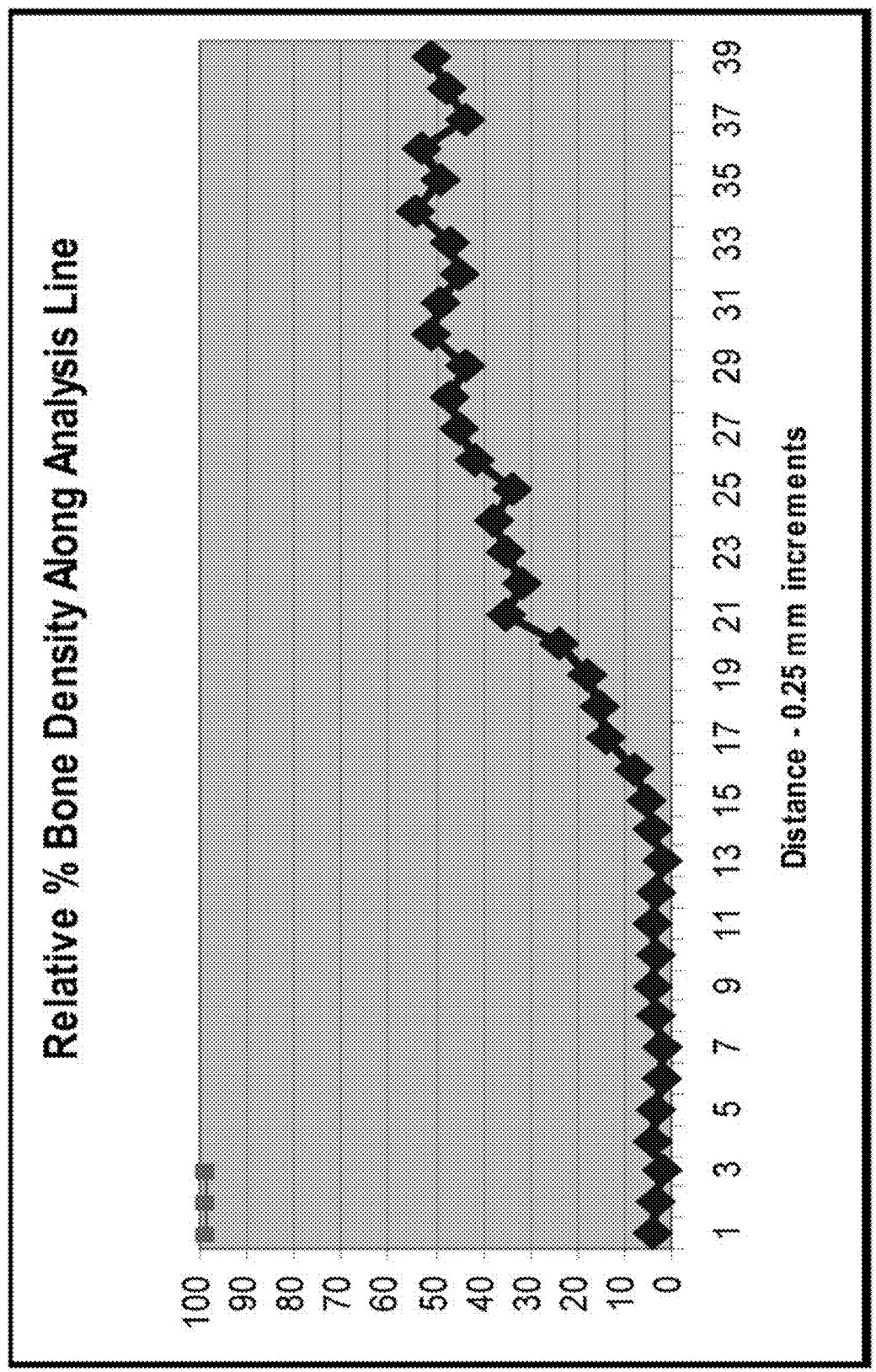
FIG. 100 is a density plot measured from the radiograph of FIGS. 95-99.
Figure 101:
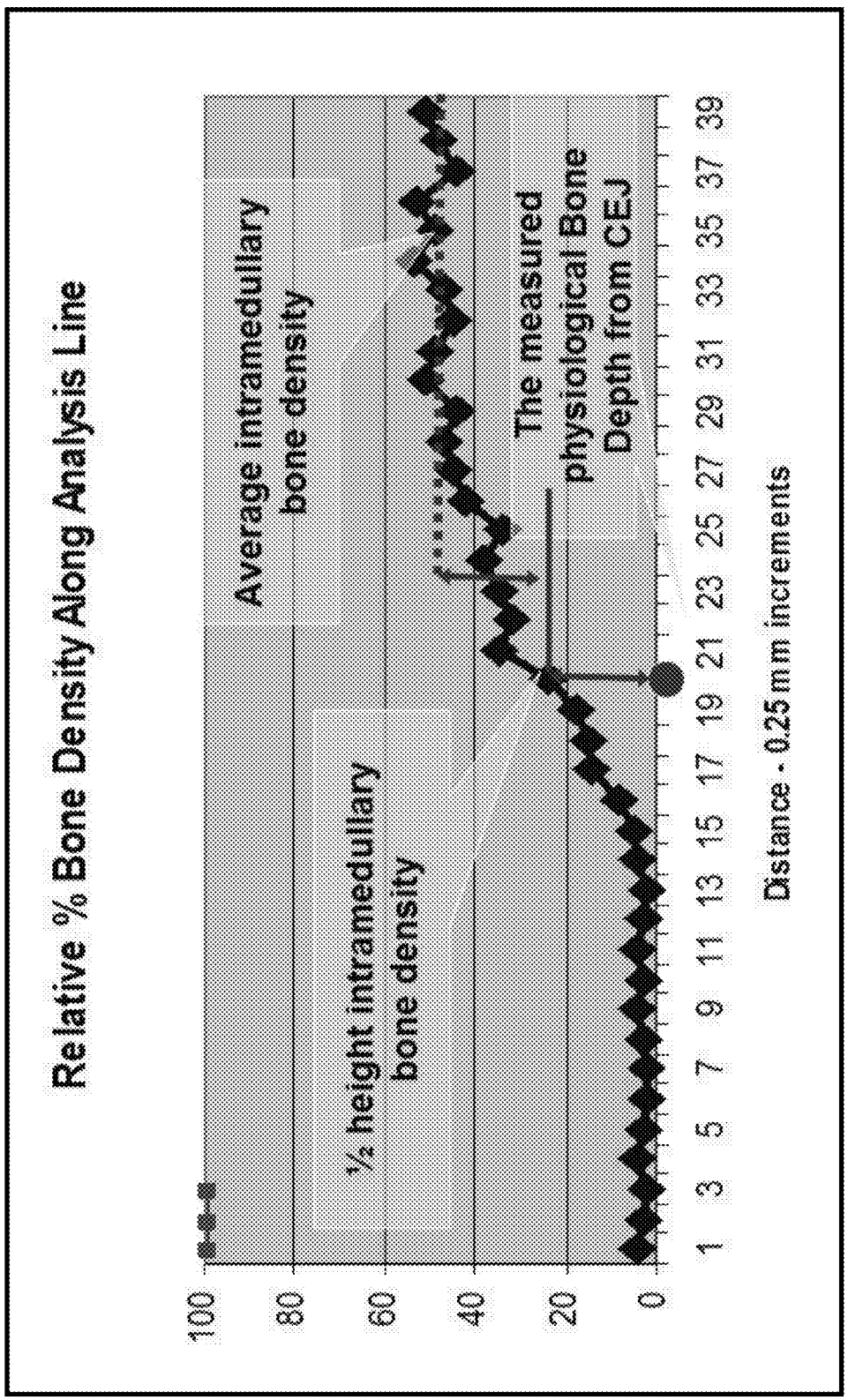
FIGS. 101 and 102 are charts that illustrate calculation of bone depth and bone density from the plot of FIG. 100.
Figure 102:
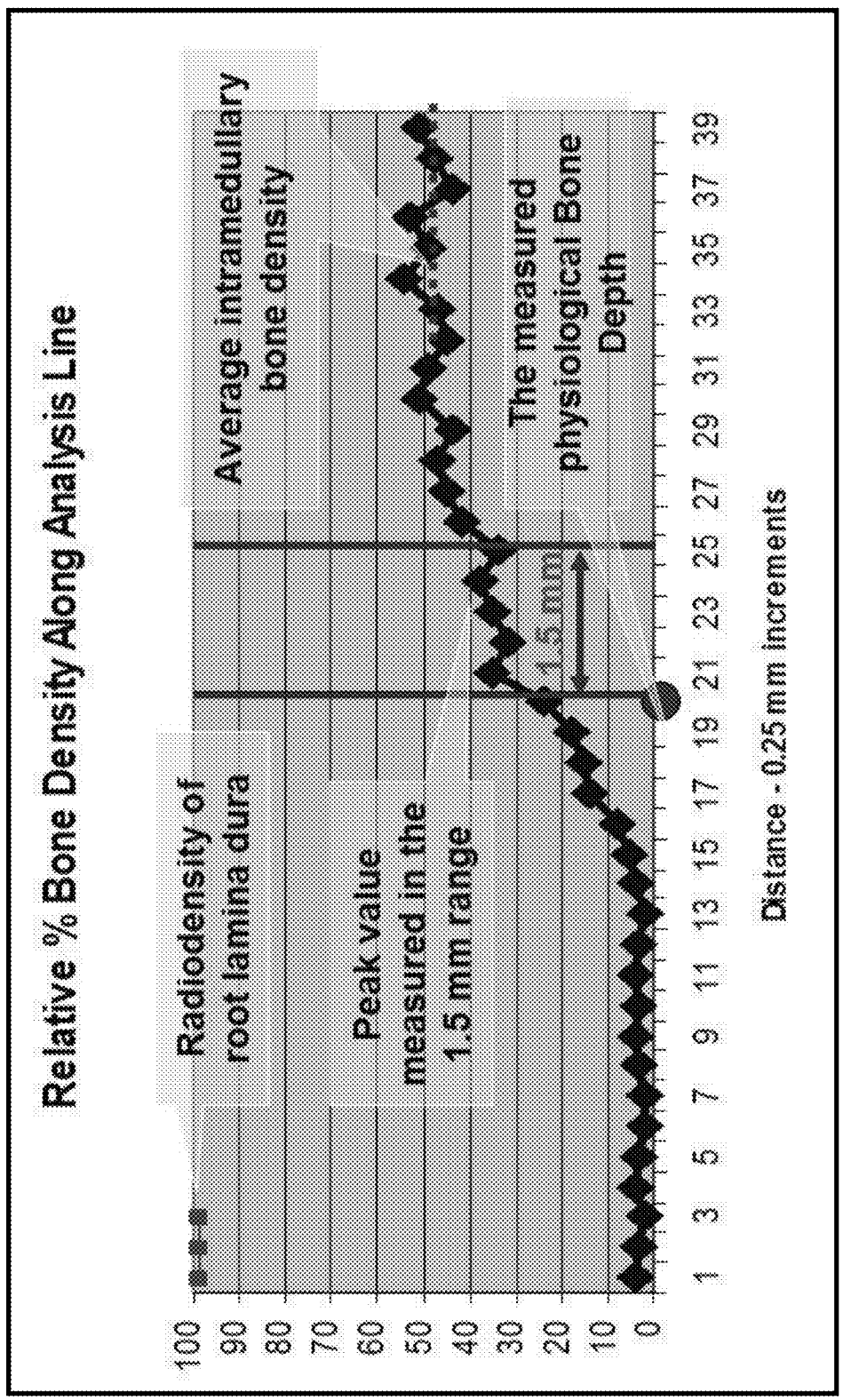
Figure 103:
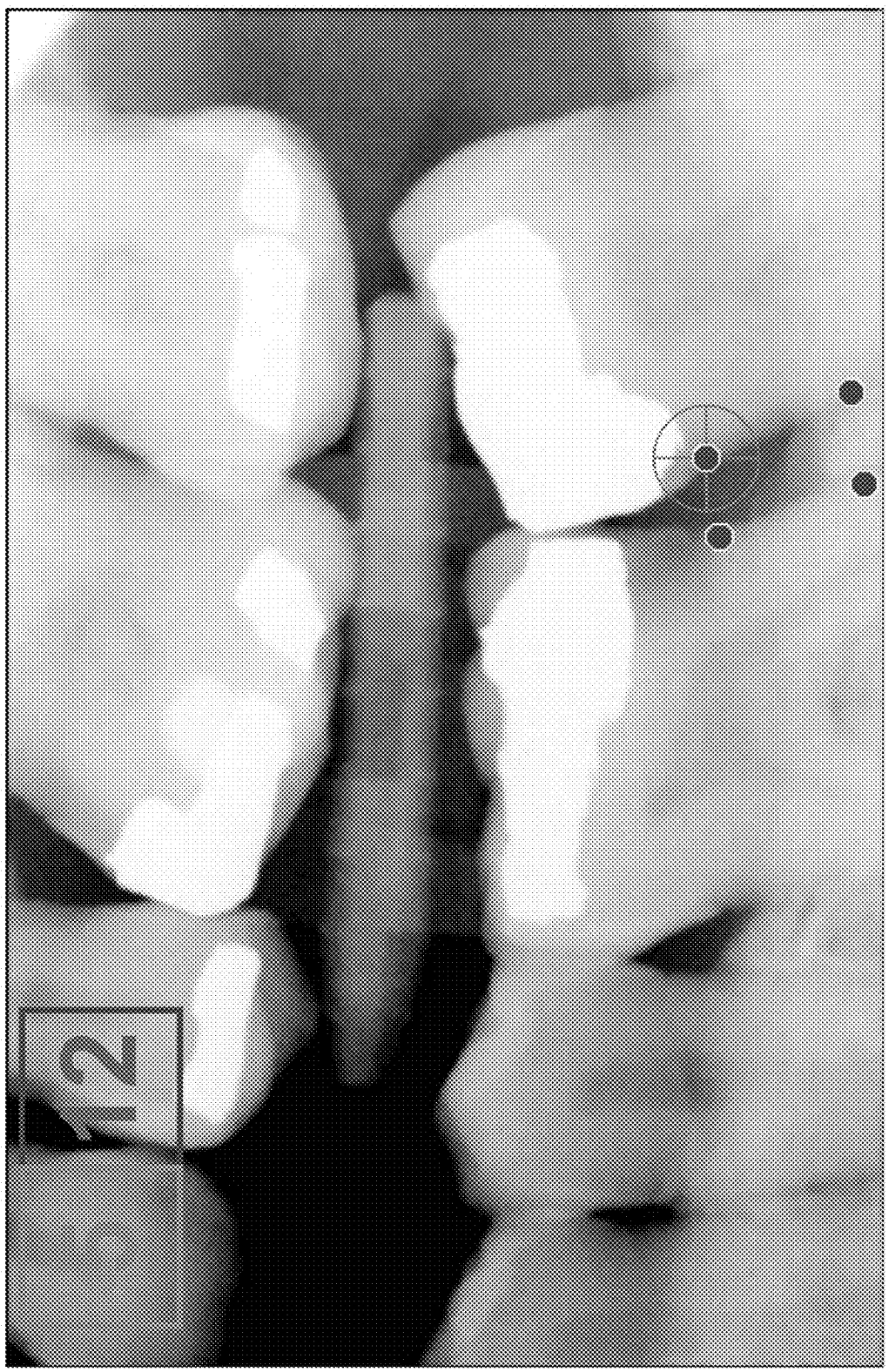
FIG. 103 is a radiograph with calculated bone depth and bone density values displayed.
Figure 104:
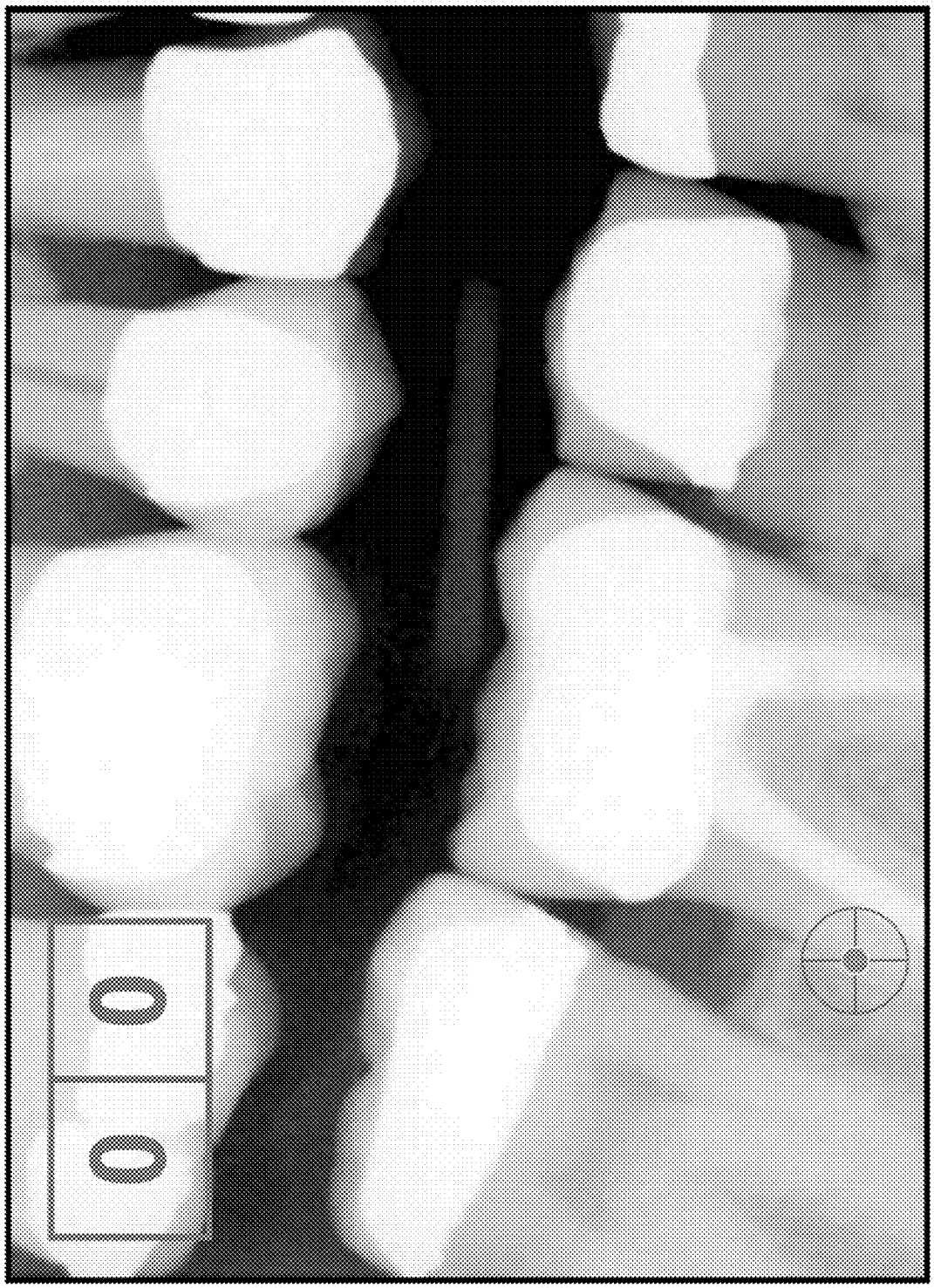
FIGS. 104-108 are radiographs illustrating use of the software algorithm for evaluating periodontal disease.
Figure 105:
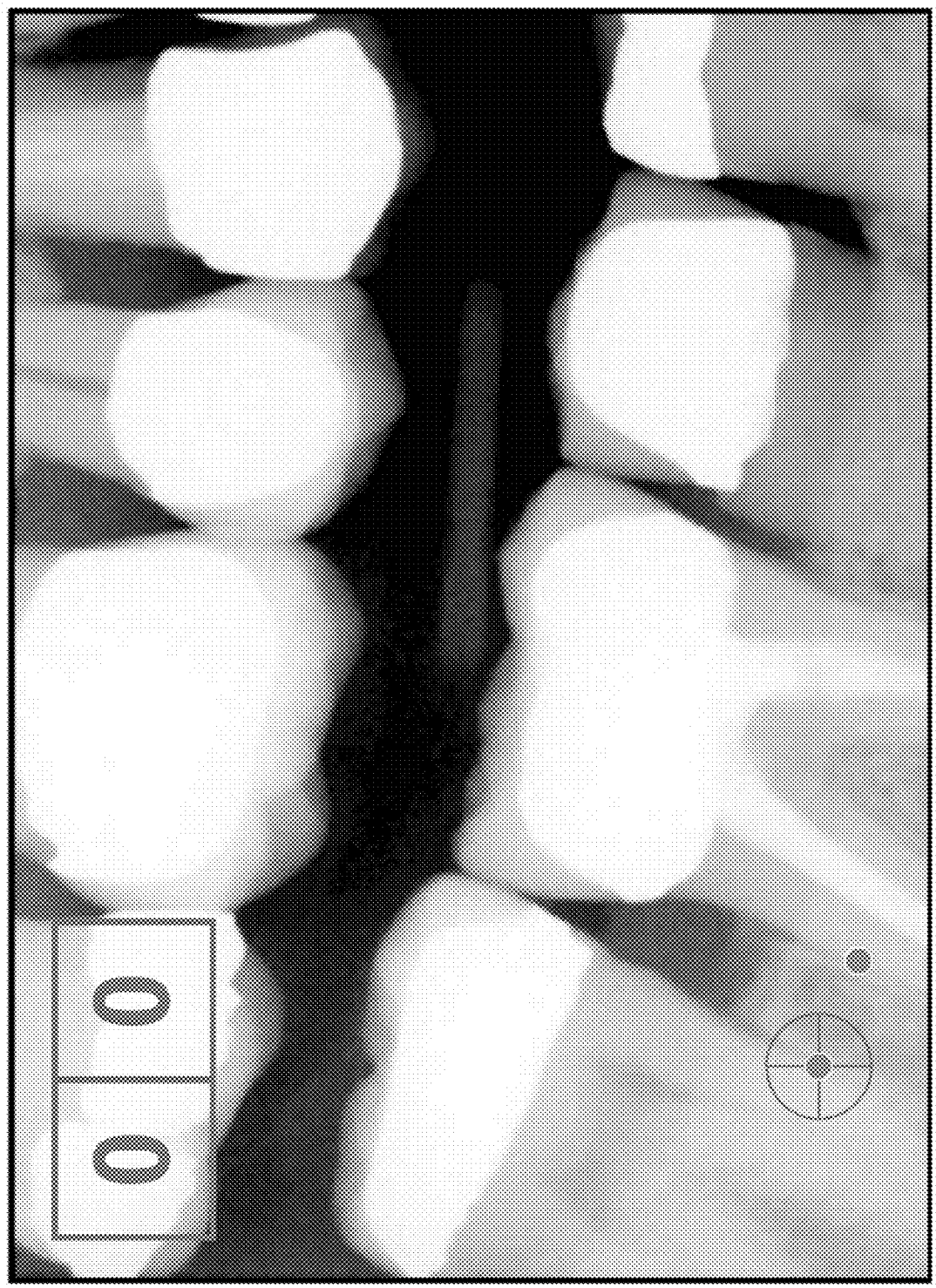
Figure 106:
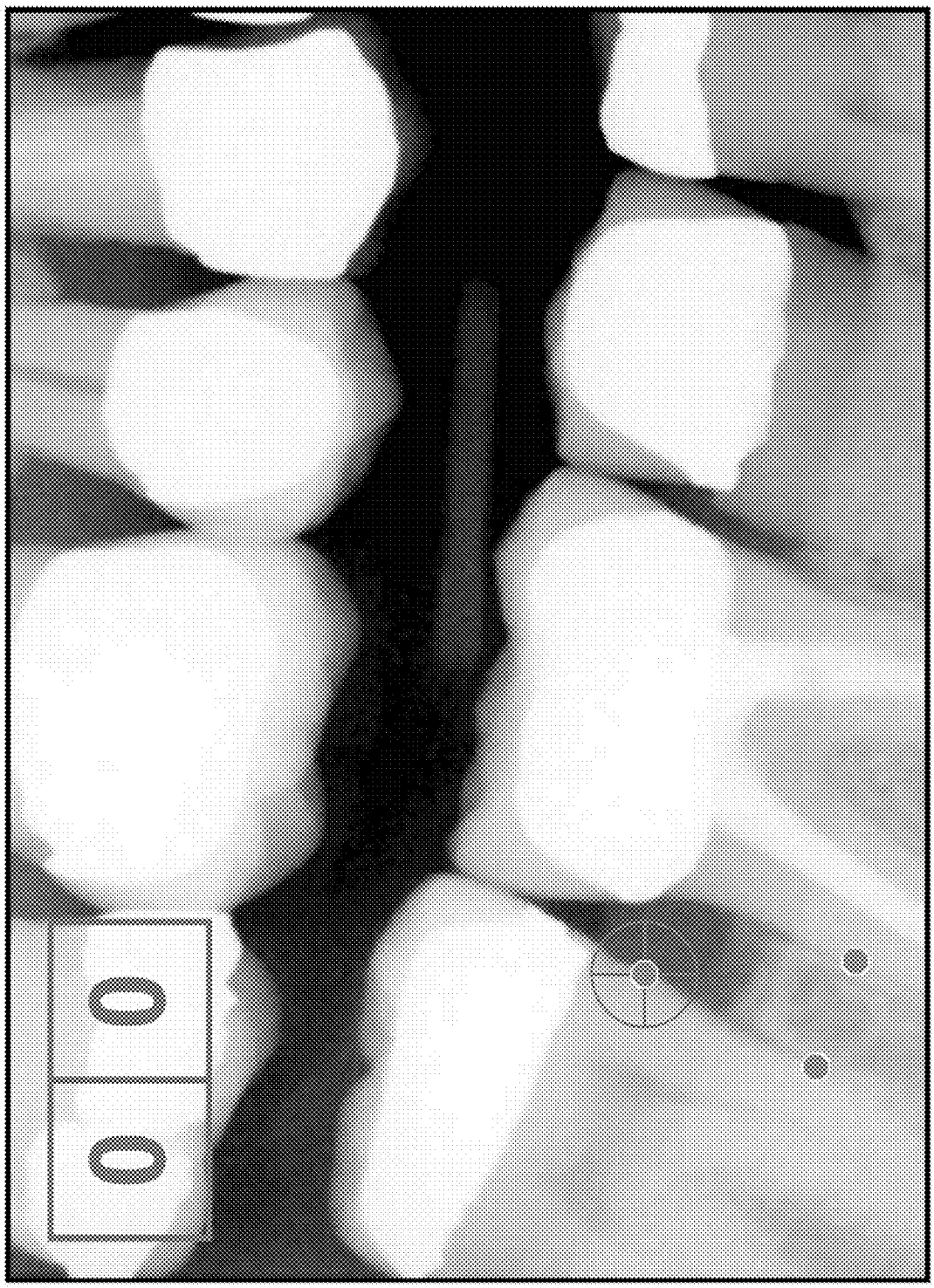
Figure 107:
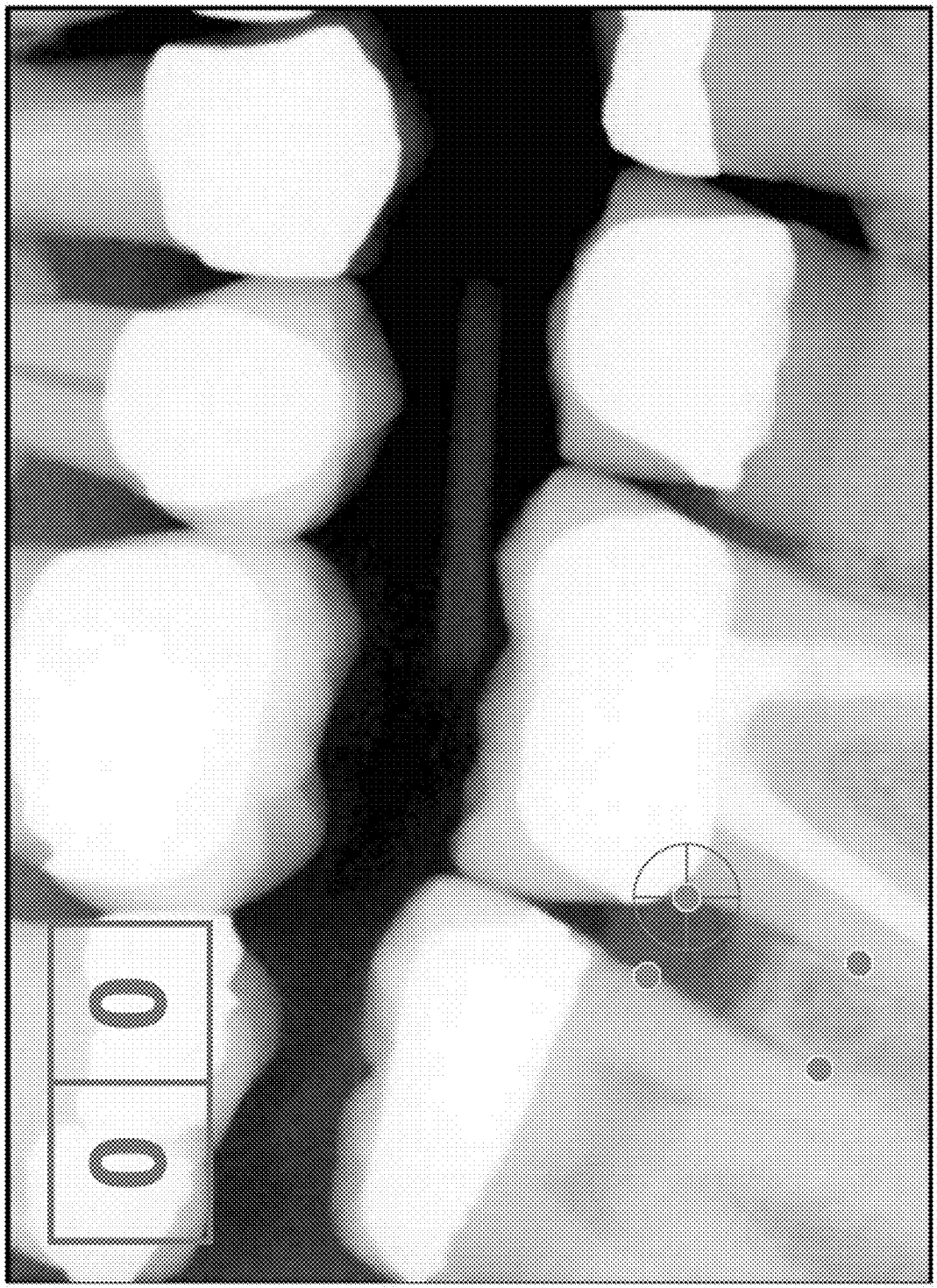
Figure 108:
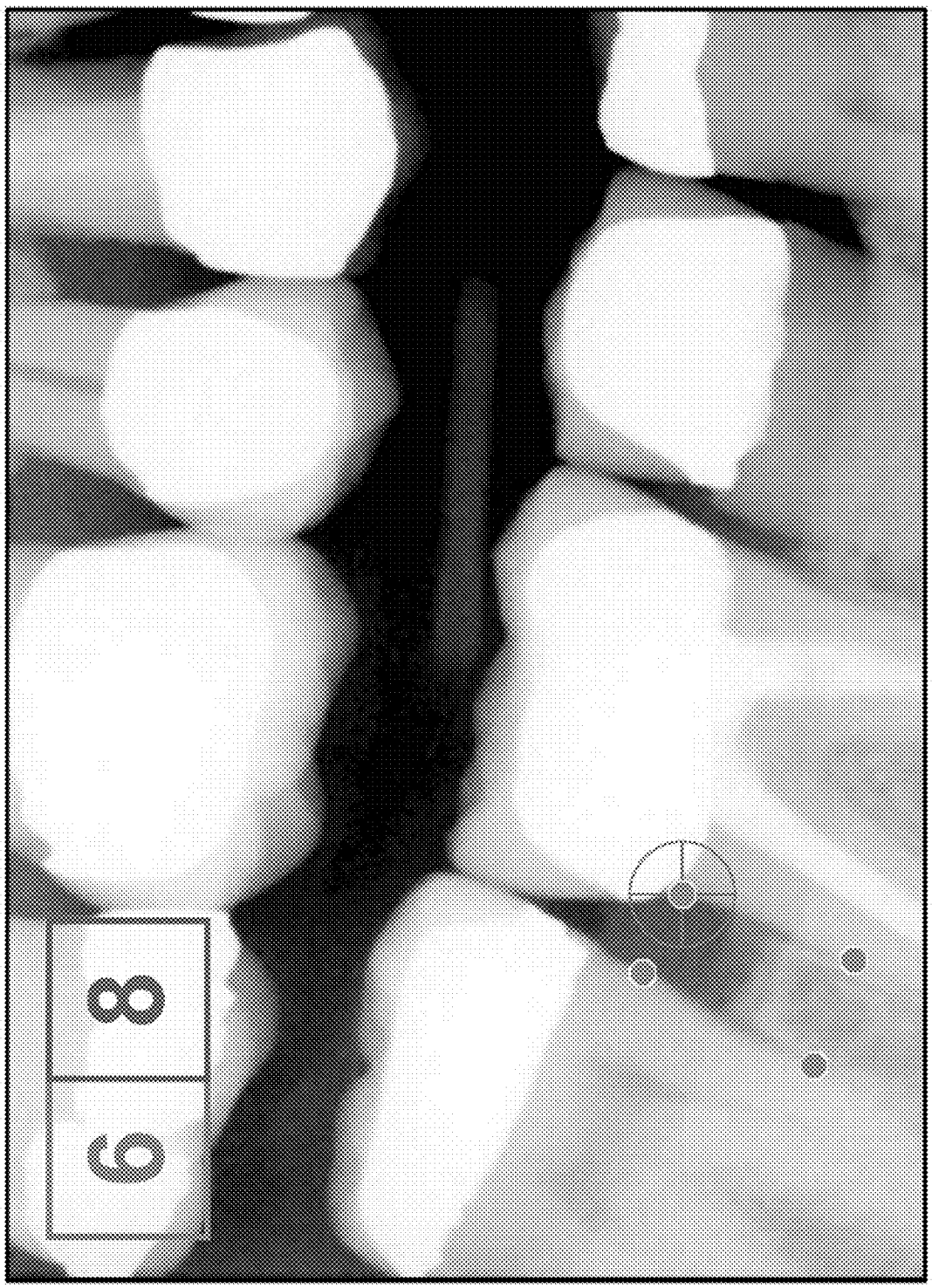

A site is indicated in FIG. 95 where there has been bone loss due to periodontal disease. The procedure described above is followed for obtaining BD and CD values. The lamina dura locations and CEJ locations are marked (FIGS. 96-99) and used to define the analysis line, along which the bone density is plotted (FIG. 100). The bone depth (BD; measured from the CEJ segment midpoint to the ½ intramedullary density point; FIG. 101) is about 5 mm, indicating significant bone loss has likely already occurred. The peak bone depth within 1.5 mm of the BD position is not as large as the intramedullary bone density (FIG. 102), yielding a CD value of about 12. This is indicative of active disease at this location. Both BD and CD values may be displayed together superimposed on the image, if desired (FIG. 103). Audible alarms or color-coded text or indicators may be employed in any desired manner to indicate the severity of disease. FIGS. 104-108 illustrate analysis of another site having active periodontal disease.

Reliability of the software algorithm for assessing periodontal disease is enhanced by use of reference points within the image. The density of the lamina dura is used as a high-density reference point, while the intramedullary bone is used as a low-density reference point. These densities should generally be relatively unaffected by periodontal disease. Since they are acquired in the same image as the disease location, these densities provide a degree of normalization against variations of x-ray source, imaging x-ray sensor, exposure time or intensity, and so on.

While the values obtained for bone depth (BD) and crestal density (CD) provide accurate diagnosis and evaluation of periodontal disease, proper treatment of the disease also depends on the overall clinical setting, including the age of the patient. It may be desirable to factor the patient's age directly into the calculation of the CD value. It also (or in the alternative) may be desirable for the clinician to determine treatment for the patient based on age-neutral CD values while independently considering the patent's age.

Figure 109:
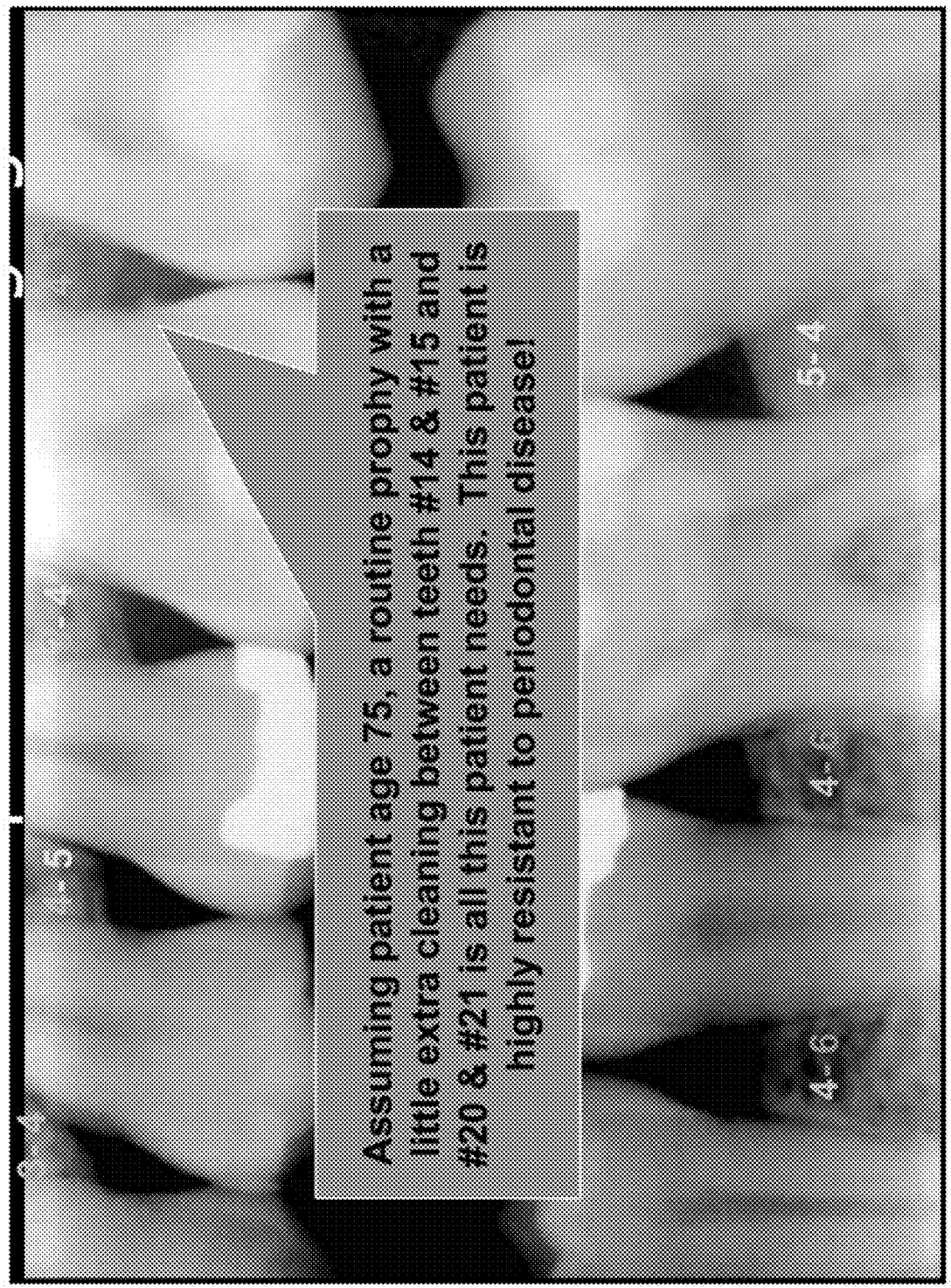
Figure 110:
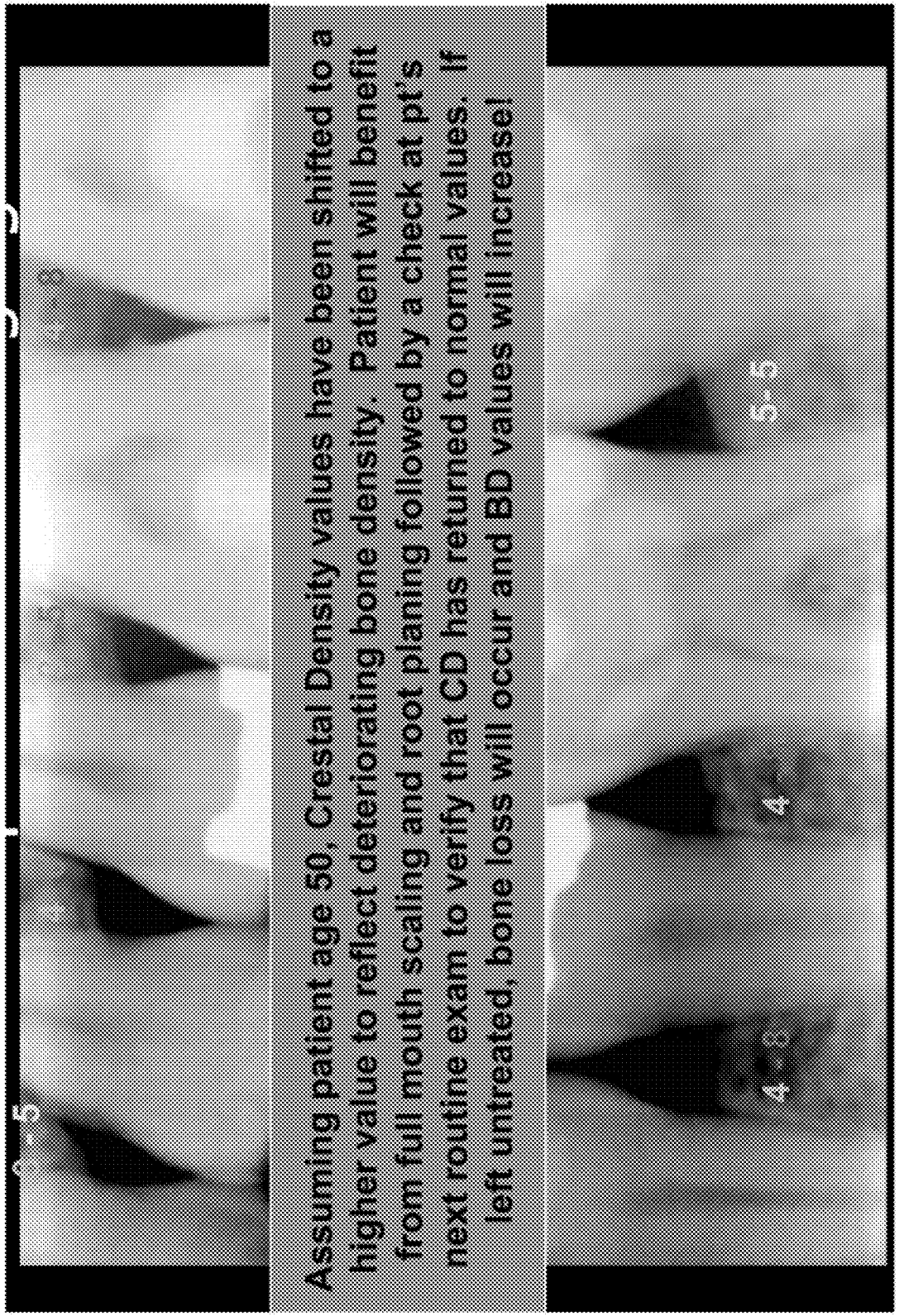

For example, a 75-year-old patient presenting with the analyzed radiograph of FIG. 109 would typically require only routine prophylactic treatment with some extra cleaning between #14 & #15 and #20 & #21. FIG. 110 shows the same radiograph analyzed as if obtained from a 50-year-old patient, with the CD values adjusted upward to reflect the patient's age. The 50-year-old patient would benefit from full mouth scaling and root planing followed by a check at the next routine exam to verify that CD had at least begun to return to normal values. If left untreated, bone loss will occur and BD values will increase for this patient. FIG. 111 shows the same radiograph analyzed as if obtained from a 25-year-old patient, with the CD values adjusted upward accordingly. This patient requires immediate interventional therapy and very close monitoring for the next 12 to 18 months to determine if the infection has been eliminated. Laser therapy or scaling, root planing, and antibiotics are indicated in this situation. Failure to treat this patient is likely to result in early tooth loss. The adjustment of CD value upwards or downward with age may be implemented in any suitable way that provides a rational correlation between the CD value and the treatment indicated for a particular clinical presentation. By having such an adjustment for risk factors (including but not limited to age), objective measurement of disease and more uniform treatment recommendations by doctors may be made to the patient based upon treatment modalities that may optimally benefit the patient.

The described procedure may be modified or adapted in a variety of ways. For example, image analysis, edge detection, or pattern recognition may be used to locate the lamina dura locations or the CEJ locations. A simplified "two-click" approach might be employed to create the analysis line: the CEJ height (click #1) and the intramedullary bone location (click #2). Rather than using the root lamina dura as a reference point in the "4-click approach," the rate of density change along the analysis line in combination with the average density of intramedullary bone may be employed instead for calculating a CD value.

Figure 112:
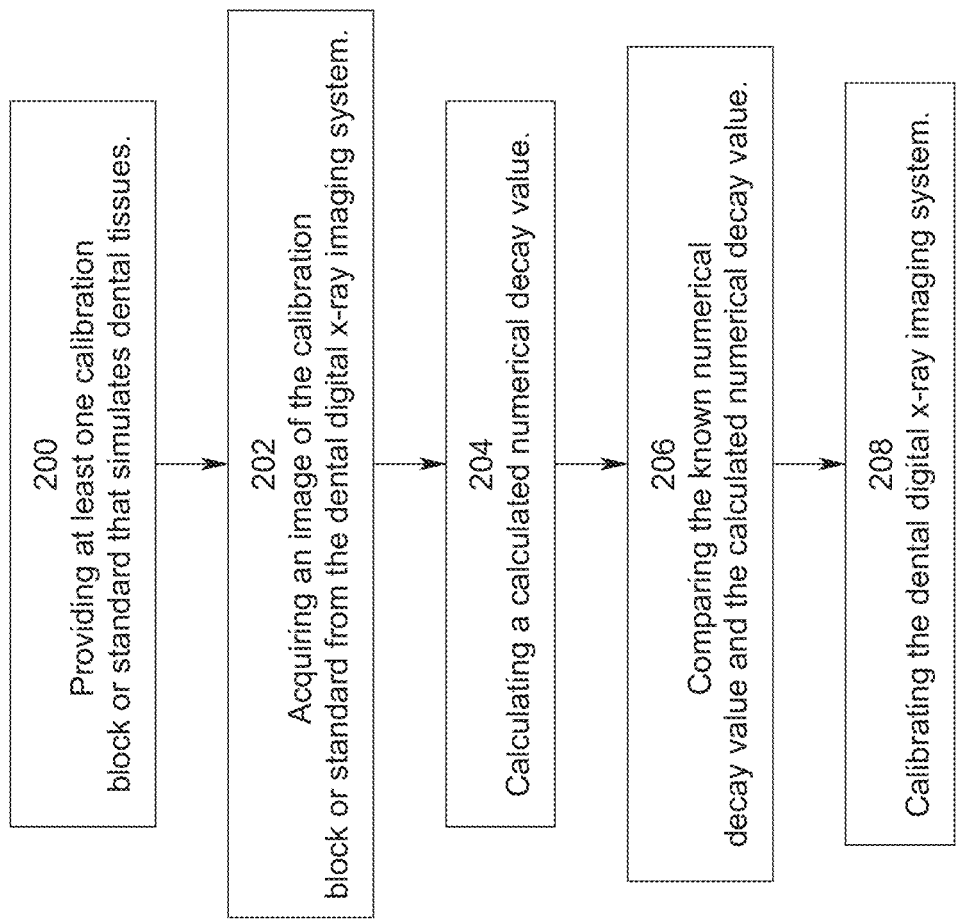
FIG. 112 is a flow chart showing a simplified exemplary embodiment of a dental digital x-ray imaging calibration method of the present invention.

The present invention is also directed to a dental digital x-ray imaging calibration method for at least partly correcting for variations of the optical densities of images acquired from the dental digital x-ray imaging system. A simplified flow chart of the invention is shown in FIG. 112.

The calibration method of the present invention may include five exemplary basic steps.

As shown in block 200, the first step is providing at least one calibration block or standard that simulates dental tissues. Preferably the calibration block or standard has at least one simulated defect having a known numerical decay value pre-calculated from measured optical densities that correlate with the extent of the at least one simulated defect. The numerical decay value can be pre-calculated by the supplier (a provided known numerical decay value) or it can be obtained upon initial acquisition of the calibration block or standard when it is in pristine condition. The calibration block or standard may be a composite calibration block or standard. The calibration block or standard may be real teeth with known levels of a particular defect. The calibration block or standard preferably simulates the true composite structure of teeth including enamel, dentin, and pulp. The calibration block or standard preferably has a simulated defect that simulates tooth decay or caries. The calibration block or standard preferably has at least one simulated defect that simulates dental pathology in both size and location. The calibration block or standard preferably has at least one simulated defect that is filled with a material simulating the radiodensity of partially decayed enamel or partially decayed dentin. In one preferred embodiment a plurality of calibration blocks or standards are provided, each calibration block or standard having a different simulated defect.

As shown in block 202, the second step is acquiring an image of the calibration block or standard from the dental digital x-ray imaging system.

As shown in block 204, the third step is calculating a calculated numerical decay value from measured optical densities that correlate with the extent of the simulated defect of the calibration block or standard from which the image is acquired. In one preferred embodiment of the present invention, the step of calculating a calculated numerical decay value is performed using a software algorithm.

As shown in block 206, the fourth step is comparing the known numerical decay value and the calculated numerical decay value. In one preferred embodiment of the present invention, the step of comparing the known numerical decay value and the calculated numerical decay value is performed using a software algorithm.

As shown in block 208, the fifth step is calibrating the dental digital x-ray imaging system by adjusting the dental digital x-ray imaging system so that the calculated numerical decay value approaches the known numerical decay value. It should be noted that the calibration may be made using any known correction technique including, but not limited to mechanical adjustments (e.g. focusing), software adjustments (e.g. using software algorithms to virtually make corrections), electrical adjustments (e.g. providing more or less power).

The calibration method of the present invention may be performed to optimize x-ray image acquisition conditions including, but not limited to exposure times, exposure intensities, protocols of image acquisition, and image processing algorithms.

The calibration method of the present invention may be performed whenever there is a possible change in x-ray image acquisition conditions. These changes include, but are not limited to: (a) aging, degradation, or change of the x-ray source; (b) aging, degradation, or change of the x-ray imaging sensor; (c) aging, degradation, or change of the display monitor; (d) change in the protocol of image acquisition; (e) change in the image processing algorithm; and (d) at periodic intervals (e.g. every week, every year).

For the various procedures and algorithms described herein, the digital images analyzed are described as being acquired using a direct digital imaging x-ray sensor. However, traditional film x-rays may be analyzed as well, by first scanning the film x-rays into a digital form. Additional variations may arise due to variability in the film, the film development procedures, and the scanning process. Calibration procedures described herein may be employed to correct for these variations.

The various analysis procedures, calibrations procedures, or software algorithms disclosed herein for dental or periodontal diagnosis may provide multiple benefits. Early diagnosis and accurate assessment of disease enable the clinician to recommend appropriate treatment in a timely fashion. Patients benefit from uniform, objective diagnostic standards, thereby protecting them from under- or over-diagnosis. The presentation of simple, numeric diagnostic values enables patients to constructively participate in their diagnosis and treatment planning. Insurance companies benefit from uniform, objective diagnostic standards to assure appropriate treatment and for screening for fraud by care providers.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: i) it is explicitly stated otherwise, e.g., by use of "either . . . or," "only one of . . . ," or similar language; or ii) two or more of the listed alternatives are mutually exclusive within the particular context, in which case "or" would encompass only those combinations involving non-mutually-exclusive alternatives. It is intended that equivalents of the disclosed exemplary embodiments and methods shall fall within the scope of the present disclosure and/or appended claims. It is intended that the disclosed exemplary embodiments and methods, and equivalents thereof, may be modified while remaining within the scope of the present disclosure or appended claims.

The terms and expressions that have been employed in the foregoing specification are used as terms of description and not of limitation, and are not intended to exclude equivalents of the features shown and described or portions of them. The scope of the invention is defined and limited only by the claims that follow.

What is claimed is:

1. A method for diagnosis and evaluation of dental disease of teeth in a mouth, said method comprising the steps of:
   (a) using a cursor, locating in an X-ray image a local location on a tooth;
   (b) measuring in said X-ray image bone density at said local location, said bone density being variable with the position of said cursor; and
   (c) calculating at least one local density value from the measured bone density at said local location, said at least one local density value being variable with the position of said cursor;
   (d) calculating at least one maximum density value from the measured bone density surrounding said local location, said at least one maximum density value being variable with the position of said cursor; and
   (e) displaying said local density value and said maximum density value, said local density value related to the extent of dental disease present at said local location, and said maximum density value being the maximum density value calculated for the density surrounding said local location;
   (f) wherein said displayed values are suitable for the diagnosis and evaluation of dental disease.

2. The method of claim 1, wherein said dental disease is dental caries.

3. The method of claim 1, wherein said dental disease is dental abscesses.

4. The method of claim 1, wherein said dental disease is dental abscesses.

5. The method of claim 1, further comprising the step of dynamically displaying said displayed values.

6. The method of claim 1, further comprising the step of dynamically displaying said displayed values in response to the position of said cursor, said cursor being a user-movable cursor.

7. A method for diagnosis and evaluation of dental disease of teeth in a mouth, said method comprising the steps of:
   (a) using a cursor, locating in an X-ray image a local location on a tooth;
   (b) measuring in said X-ray image a bone depth (BD) at said local location, said bone depth (BD) being variable with the position of said cursor;
   (c) measuring in said X-ray image a bone density at said local location, said bone density being variable with the position of said cursor; and
   (d) calculating at least one local density value from the measured bone density at said local location, said at least one local density value being variable with the position of said cursor; and
   (e) displaying said local density value and said bone depth (BD), said local density value related to the extent of dental disease present at said local location;
   (f) wherein the displayed values are suitable for the diagnosis and evaluation of dental disease.

8. The method of claim 7, wherein said dental disease is dental caries.

9. The method of claim 7, wherein said dental disease is periodontal disease.

10. The method of claim 7, wherein said dental disease is dental abscesses.

11. The method of claim 7, further comprising the step of dynamically displaying said displayed values.

12. The method of claim 7 further comprising the step of dynamically displaying said displayed values in response to the position of said cursor, said cursor being a user-movable cursor.

13. A method for diagnosis and evaluation of dental abscesses of teeth in a mouth, said method comprising the steps of:
   (a) using a cursor, locating in an X-ray image a lamina dura local location on a tooth;
   (b) measuring in an X-ray image a lamina dura bone density of a tooth, and further measuring in said X-ray image bone density at said lamina dura local location, said lamina dura bone density being variable with the position of said cursor; and
   (c) calculating a density value from the measured lamina dura bone density, and further calculating at least one lamina dura local density value from the measured bone density at said lamina dura local location, said at least one lamina dura local density value being variable with the position of said cursor;
   (d) calculating at least one lamina dura maximum density value from the measured bone density surrounding said lamina dura local location, said at least one lamina dura maximum density value being variable with the position of said cursor; and
   (e) displaying said lamina dura local density value and said lamina dura maximum density value, said lamina dura local density value related to the extent of dental abscesses present at said lamina dura local location, and said lamina dura maximum density value being the maximum lamina dura density value calculated for the lamina dura density surrounding said lamina dura local location;
   (f) wherein said displayed values are suitable for the diagnosis and evaluation of dental abscesses.

14. The method of claim 13, further comprising the step of displaying said density value.

15. The method of claim 13, further comprising the step of dynamically displaying said density value.

16. The method of claim 13, further comprising the step of dynamically displaying said density value in response to a position of a user-movable cursor.

* * * * *